US012214055B2

(12) United States Patent
Cotta-Ramusino et al.

(10) Patent No.: US 12,214,055 B2
(45) Date of Patent: Feb. 4, 2025

(54) SYSTEMS AND METHODS FOR TREATING HYPER-IGM SYNDROME

(71) Applicants: EDITAS MEDICINE, INC., Cambridge, MA (US); FONDAZIONE TELETHON ETS, Rome (IT); OSPEDALE SAN RAFFAELE, Milan (IT)

(72) Inventors: Cecillia Cotta-Ramusino, Cambridge, MA (US); Carrie M. Margulies, Waban, MA (US); Luigi Naldini, Milan (IT); Pietro Genovese, Milan (IT)

(*) Notice: Subject to any disclaimer, the term of this patent is extended or adjusted under 35 U.S.C. 154(b) by 1292 days.

(21) Appl. No.: 16/758,752

(22) PCT Filed: Oct. 24, 2018

(86) PCT No.: PCT/US2018/057354
§ 371 (c)(1),
(2) Date: Apr. 23, 2020

(87) PCT Pub. No.: WO2019/084168
PCT Pub. Date: May 2, 2019

(65) Prior Publication Data
US 2020/0338213 A1    Oct. 29, 2020

Related U.S. Application Data

(60) Provisional application No. 62/746,900, filed on Oct. 17, 2018, provisional application No. 62/690,284, filed on Jun. 26, 2018, provisional application No. 62/673,039, filed on May 17, 2018, provisional application No. 62/664,800, filed on Apr. 30, 2018, provisional application No. 62/576,277, filed on Oct. 24, 2017.

(51) Int. Cl.
*A61K 48/00* (2006.01)
*A61K 39/00* (2006.01)
*A61P 37/02* (2006.01)
*C07K 14/475* (2006.01)
*C07K 14/705* (2006.01)
*C12N 15/10* (2006.01)
*C12N 15/113* (2010.01)
*C12N 15/86* (2006.01)
*C12N 15/90* (2006.01)
*A61K 35/17* (2015.01)

(52) U.S. Cl.
CPC .......... *A61K 48/005* (2013.01); *A61K 39/461* (2023.05); *A61K 39/4611* (2023.05); *A61K 39/464411* (2023.05); *A61P 37/02* (2018.01); *C07K 14/475* (2013.01); *C07K 14/70575* (2013.01); *C07K 14/70578* (2013.01); *C12N 15/102* (2013.01); *C12N 15/113* (2013.01); *C12N 15/86* (2013.01); *C12N 15/907* (2013.01); *C12N 2750/14143* (2013.01); *C12N 2830/50* (2013.01); *C12N 2840/203* (2013.01)

(58) Field of Classification Search
None
See application file for complete search history.

(56) References Cited

U.S. PATENT DOCUMENTS 9,499,847 B2    11/2016    Porter et al.

FOREIGN PATENT DOCUMENTS

| WO | 2015070083 A1 | 5/2015 |
| WO | 2015138510 A1 | 9/2015 |
| WO | 2016073990 A2 | 5/2016 |
| WO | 2016/183345 | 11/2016 |
| WO | 2019014564 A1 | 1/2019 |

OTHER PUBLICATIONS

Bak RO, Porteus MH. CRISPR-Mediated Integration of Large Gene Cassettes Using AAV Donor Vectors. Cell Rep. Jul. 18, 2017;20(3):750-756. doi: 10.1016/j.celrep.2017.06.064. PMID: 28723575; PMCID: PMC5568673. (Year: 2017).*
Laura Page. Express yourself: Gene Co-Expression in Bicistronic Constructs. Bitesize Bio. 2015, retrieved from URL: https://bitesizebio.com/24492/express-yourself-gene-co-expression-in-bicistronic-constructs/ (Year: 2015).*
Anders, C. et al. Structural basis of PAM-dependent target DNA recognition by the Cas9 endonuclease. Nature. Sep. 25, 2014;513(7519):569-73. doi: 10.1038/nature13579. Epub Jul. 27, 2014. PMID: 25079318; PMCID: PMC4176945.
Bae, S. et al. Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014. PMID: 24463181; PMCID: PMC4016707.
Briner A. E. et al. Guide RNA functional modules direct Cas9 activity and orthogonality. Mol Cell. Oct. 23, 2014;56(2):333-339. doi: 10.1016/j.molcel.2014.09.019. Epub Oct. 16, 2014. PMID: 25373540.
Cong, L. et al. Multiplex genome engineering using CRISPR/Cas systems. Science. Feb. 15, 2013;339(6121):819-23. doi: 10.1126/science.1231143. Epub Jan. 3, 2013. PMID: 23287718; PMCID: PMC3795411.
Cornish-Bowden, A. Nomenclature for incompletely specified bases in nucleic acid sequences: recommendations 1984. Nucleic Acids Res. May 10, 1985;13(9):3021-30. doi: 10.1093/nar/13.9.3021. PMID: 2582368; PMCID: PMC341218.

(Continued)

*Primary Examiner* — Allison M Fox
*Assistant Examiner* — Qinhua Gu
(74) *Attorney, Agent, or Firm* — McDonnell Boehnen Hulbert & Berghoff

(57) ABSTRACT

Disclosed herein are genome editing systems and related methods which allow for treatment of Hyper IgM Syndrome, a group of disorders characterized by defective CD40 signaling. The compositions and methods described herein rely on the use of donor templates comprising a CD40L exons to restore proper CD40 signaling and B cell class switch recombination.

20 Claims, 54 Drawing Sheets

Specification includes a Sequence Listing.

(56) References Cited

OTHER PUBLICATIONS

Davis, L. and Maizels, N. Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014. PMID: 24556991; PMCID: PMC3956201.
Fine E. J. et al. Trans-spliced Cas9 allows cleavage of HBB and CCR5 genes in human cells using compact expression cassettes. Sci Rep. Jul. 1, 2015;5:10777. doi: 10.1038/srep10777. PMID: 26126518; PMCID: PMC4486982.
Frit, P. et al. Alternative end-joining pathway(s): bricolage at DNA breaks. DNA Repair (Amst). May 2014;17:81-97. doi: 10.1016/j.dnarep.2014.02.007. Epub Mar. 6, 2014. PMID: 24613763.
Fu, Y. et al. Improving CRISPR-Cas nuclease specificity using truncated guide RNAs. Nat Biotechnol. Mar. 2014;32(3):279-284. doi: 10.1038/nbt.2808. Epub Jan. 26, 2014. PMID: 24463574; PMCID: PMC3988262.
Guilinger, J. P. et al. Fusion of catalytically inactive Cas9 to FokI nuclease improves the specificity of genome modification. Nat Biotechnol. Jun. 2014;32(6):577-582. doi: 10.1038/nbt.2909. Epub Apr. 25, 2014. PMID: 24770324; PMCID: PMC4263420.
Heigwer, F. et al. E-CRISP: fast CRISPR target site identification. Nat Methods. Feb. 2014;11(2):122-3. doi: 10.1038/nmeth.2812. PMID: 24481216.
Hsu, P. D. et al. DNA targeting specificity of RNA-guided Cas9 nucleases. Nat Biotechnol. Sep. 2013;31(9):827-32. doi: 10.1038/nbt.2647. Epub Jul. 21, 2013. PMID: 23873081; PMCID: PMC3969858.
Iyama, T. and Wilson, D. M. 3rd. DNA repair mechanisms in dividing and non-dividing cells. DNA Repair (Amst). Aug. 2013;12(8):620-36. doi: 10.1016/j.dnarep.2013.04.015. Epub May 16, 2013. PMID: 23684800; PMCID: PMC3720834.
Jiang, W. et al. RNA-guided editing of bacterial genomes using CRISPR-Cas systems. Nat Biotechnol 31, 233-239 (2013). https://doi.org/10.1038/nbt.2508.
Jinek, M. et al. A programmable dual-RNA-guided DNA endonuclease in adaptive bacterial immunity. Science. Aug. 17, 2012;337(6096):816-21. doi: 10.1126/science.1225829. Epub Jun. 28, 2012. PMID: 22745249; PMCID: PMC6286148.
Kleinstiver, B. P. et al. Broadening the targeting range of Staphylococcus aureus CRISPR-Cas9 by modifying PAM recognition. Nat Biotechnol 33, 1293-1298 (2015). https://doi.org/10.1038/nbt.3404.
Kleinstiver, B. P. et al. Engineered CRISPR-Cas9 nucleases with altered PAM specificities. Nature. Jul. 23, 2015;523(7561):481-5. doi: 10.1038/nature14592. Epub Jun. 22, 2015. PMID: 26098369; PMCID: PMC4540238.
Kleinstiver, B. P. et al. High-fidelity CRISPR-Cas9 nucleases with no detectable genome-wide off-target effects. Nature. Jan. 28, 2016;529(7587):490-5. doi: 10.1038/nature16526. Epub Jan. 6, 2016. PMID: 26735016; PMCID: PMC4851738.
Komor, A. et al. Programmable editing of a target base in genomic DNA without double-stranded DNA cleavage. Nature 533, 420-424 (2016). https://doi.org/10.1038/nature17946.
Makarova, K. S. et al. Evolution and classification of the CRISPR-Cas systems. Nat Rev Microbiol. Jun. 2011;9(6):467-77. doi: 10.1038/nrmicro2577. Epub May 9, 2011. PMID: 21552286; PMCID: PMC3380444.
Mali, P. et al. RNA-guided human genome engineering via Cas9. Science. Feb. 15, 2013;339(6121):823-6. doi: 10.1126/science.1232033. Epub Jan. 3, 2013. PMID: 23287722; PMCID: PMC3712628.
Nishimasu, H. et al. Crystal Structure of Staphylococcus aureus Cas9. Cell. Aug. 27, 2015;162(5):1113-26. doi: 10.1016/j.cell.2015.08.007. PMID: 26317473; PMCID: PMC4670267.
Nishimasu H. et al. Crystal structure of Cas9 in complex with guide RNA and target DNA. Cell. Feb. 27, 2014;156(5):935-49. doi: 10.1016/j.cell.2014.02.001. Epub Feb. 13, 2014. PMID: 24529477; PMCID: PMC4139937.
Ran F. A. et al. Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013. Erratum in: Cell. Oct. 10, 2013;155(2):479-80. PMID: 23992846; PMCID: PMC3856256.
Richardson, C. D. et al. Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016. PMID: 26789497.
Seyama, K. et al. Mutations of the CD40 ligand gene and its effect on CD40 ligand expression in patients with X-linked hyper IgM syndrome. Blood. Oct. 1, 1998;92(7):2421-34. PMID: 9746782.
Shmakov, S. et al. Discovery and Functional Characterization of Diverse Class 2 CRISPR-Cas Systems. Mol Cell. Nov. 5, 2015;60(3):385-97. doi: 10.1016/j.molcel.2015.10.008. Epub Oct. 22, 2015. PMID: 26593719; PMCID: PMC4660269.
Suzuki, Y. et al. Poly(A)-dependent Post-transcriptional Regulations. BSJ-review, 2017, 8:110. DOI:10.24480/bsj-review.8b8.00118.
Tahara, M. et al. Trans-splicing repair of CD40 ligand deficiency results in naturally regulated correction of a mouse model of hyper-IgM X-linked immunodeficiency. Nat Med. Aug. 2004;10(8):835-41. doi: 10.1038/nm1086. Epub Jul. 25, 2004. PMID: 15273748.
Tsai, S. Q. et al. Open-source guideseq software for analysis of GUIDE-seq data. Nat Biotechnol. May 6, 2016;34(5):483. doi: 10.1038/nbt.3534. PMID: 27153277.
Tsai, S. Q. et al. GUIDE-seq enables genome-wide profiling of off-target cleavage by CRISPR-Cas nucleases. Nat Biotechnol. Feb. 2015;33(2):187-197. doi: 10.1038/nbt.3117. Epub Dec. 16, 2014. PMID: 25513782; PMCID: PMC4320685.
Wang, H. et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013. PMID: 23643243; PMCID: PMC3969854.
Xiao, A. et al. CasOT: a genome-wide Cas9/gRNA off-target searching tool. Bioinformatics. Apr. 15, 2014;30(8):1180-1182. doi: 10.1093/bioinformatics/btt764. Epub Jan. 2, 2014. PMID: 24389662.
Yamano, T. et al. Crystal Structure of Cpf1 in Complex with Guide RNA and Target DNA. Cell. May 5, 2016;165(4):949-62. doi: 10.1016/j.cell.2016.04.003. Epub Apr. 21, 2016. PMID: 27114038; PMCID: PMC4899970.
Zetsche, B. et al. Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015. PMID: 26422227; PMCID: PMC4638220.
Zetsche, B. et al. A split-Cas9 architecture for inducible genome editing and transcription modulation. Nat Biotechnol. Feb. 2015;33(2):139-42. doi: 10.1038/nbt.3149. PMID: 25643054; PMCID: PMC4503468.
The International Search Report (ISR) with Written Opinion for PCT/US201/057354 dated Feb. 11, 2019, paes 1-18.
Caroline Kuo et al. "Targeted Gene Therapy in the Treatment of X-L inked Hyper IgM Syndrome" CDI Symposium 2016, May 2016 (May 2016), XP055554527, Retrieved from the Internet: URL:https://www.uclahealth.orgjmatteljcdi/workfilesjSymposium/2016/CKuo-CDI-Symposium-2016.pdf [retrieved on Feb. 11, 2019].
Nicholas Hubbard et al. "Targeted gene editing restores regulated CD40L function in X-linked hyper-IgM syndrome", BLOOD,vol. 127, No. 21,Feb. 22, 2016 (Feb. 22, 2016), pp. 2513-2522.
Nicholas Hubbard et al. "Supplemental Methods", Blood, Feb. 22, 2016 (Feb. 22, 2016), XP55554515, Retrieved from the Internet: URL:http://www.bloodjournal.org/content/bloodjournalfsuppl/2016/02/22/blood-2015-11-683235.DC1/blood-2015-11-683235-1.pdf [retrieved on Feb. 11, 2019] p. 1-p. 3.
Daisuke Tomizawa et al. "Allogeneic hematopoietic stem cell transplantationfor seven children with X-linked hyper-IgM syndrome: A single center experience", American Journal of Hematology, vol. 76, No. 1, May 20, 2004 (May 20, 2004), pp. 33-39.
Caroline Kuo et al. "Targeted Gene Therapy in the Treatment of X-Linked Hyper IgM Syndrome", Molecular Therapy: the Journal of the American Society of Gene Therapy, vol. 23, May 2015 (May 2015), p. S50.
Caroline Kuo et al. "Site Specific Gene Correction of Defects in CD40 Ligand Using the CrisprjCas9 Genome Editing Plat form",

(56) References Cited

OTHER PUBLICATIONS

Journal of Allergy and Clinical Immunology, vo 1 • 135, No. 2, Feb. 2, 2015 (Feb. 2, 2015), p. AB17.

Caroline Kuo et al. "Patient Specific Targeted Gene Therapy In The Treatment Of X-Linked Hyper-IgM Syndrome", Journal of Allergy and Clinical Immunology, vol. 133, No. 2, Jan. 23, 2014 (Jan. 23, 2014), p. AB162.

Matthew H. Porteus "Knock-in editing: it functionally corrects!", Blood, vol. 127, No. 21, May 26, 2016 (May 26, 2016) pp. 2507-2509.

Ashish Jain et al. "Partial inmune reconstitution of X-linked hyper IgM syndrome with recombinant CD40 ligand" Blood vol. 118, No. 14, Aug. 12, 2011 (Aug. 12, 2011), pp. 3811-381.

Juliette M. K. M. Delhove et al."Genome-Edited T Cell Therapies", Current Stem Cell Reports, vol. 3, No. 2, Apr. 18, 2017 (Apr. 18, 2017), pp. 124-136.

Caroline Kuo et al. "Site-Specific Gene Editing of Human Hematopoietic Stem Cells for X-Linked Hyper-IgM Syndrome" Cell Reports, vol. 23, No. 9, May 29, 2018 (May 29, 2018), pp. 2606-2616.

\* cited by examiner

A. HA + cDNA + GFP + Stuffers

B. HA + cDNA + GFP - Stuffers

C. HA + cDNA - GFP + Stuffers

D. HA + cDNA - GFP - Stuffers

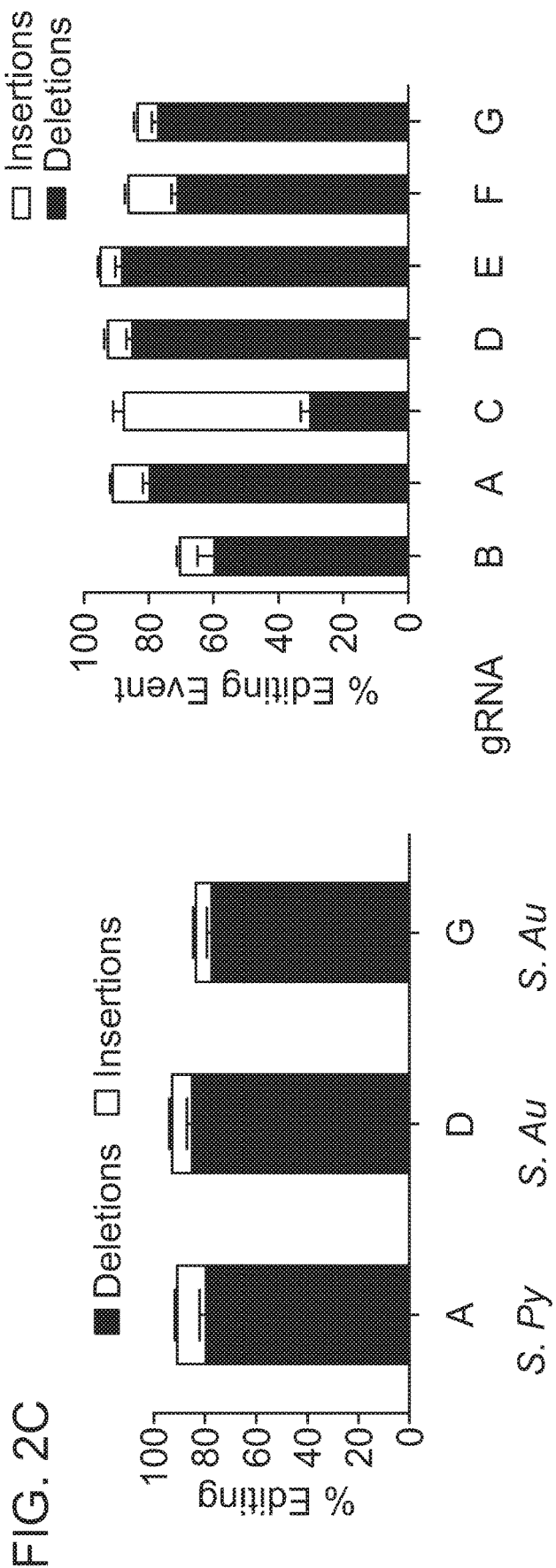
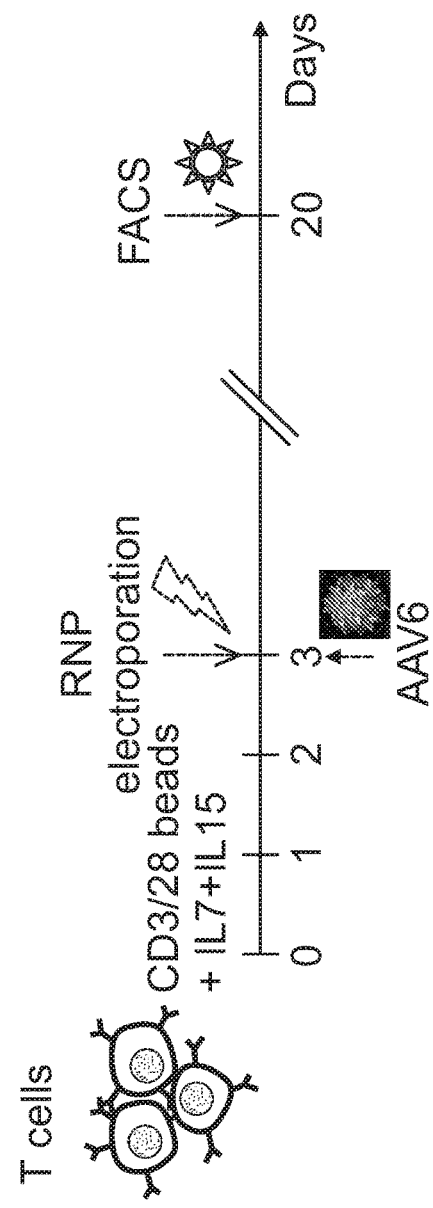

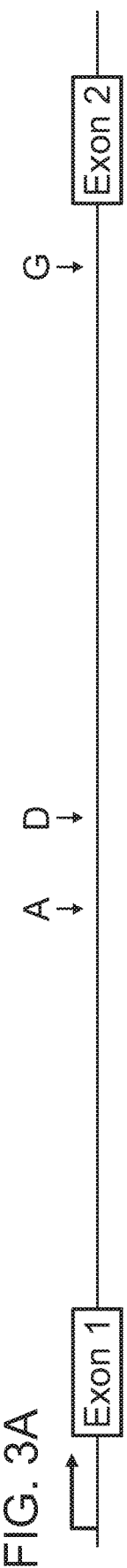
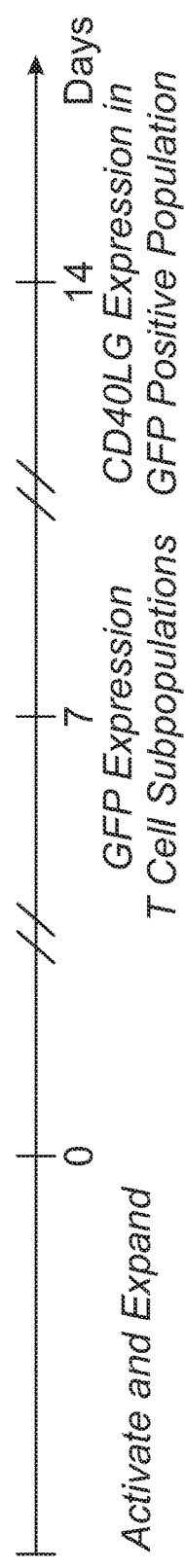
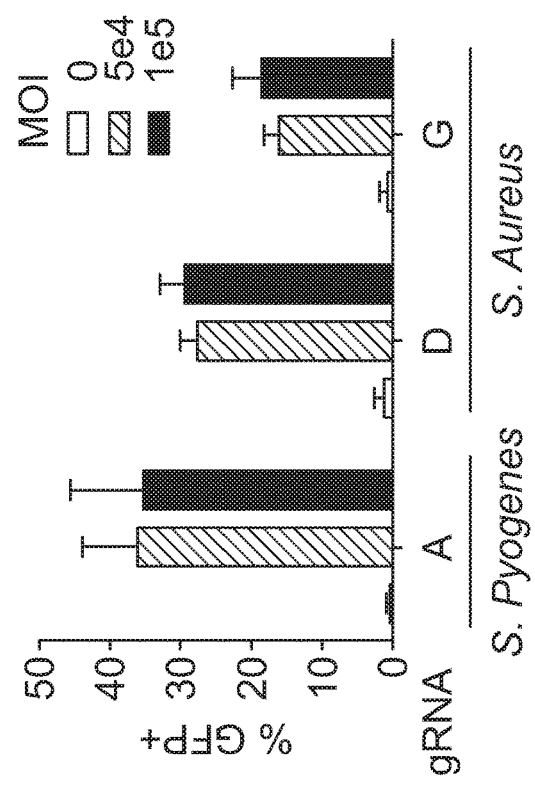
FIG. 3A
FIG. 3B
FIG. 3C

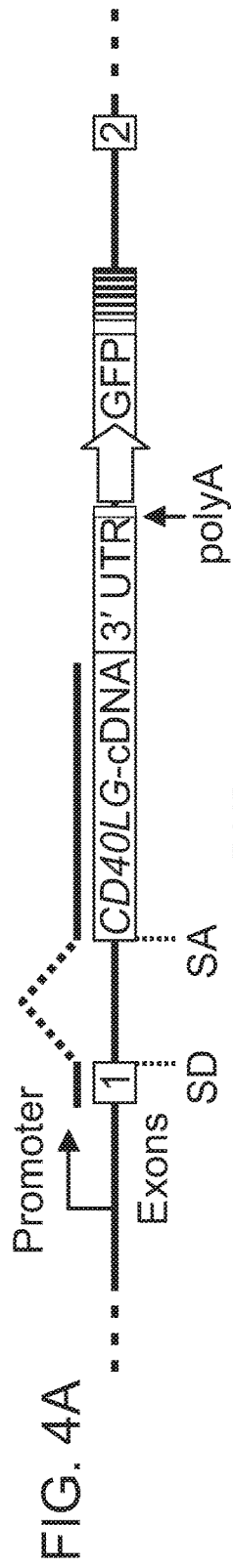
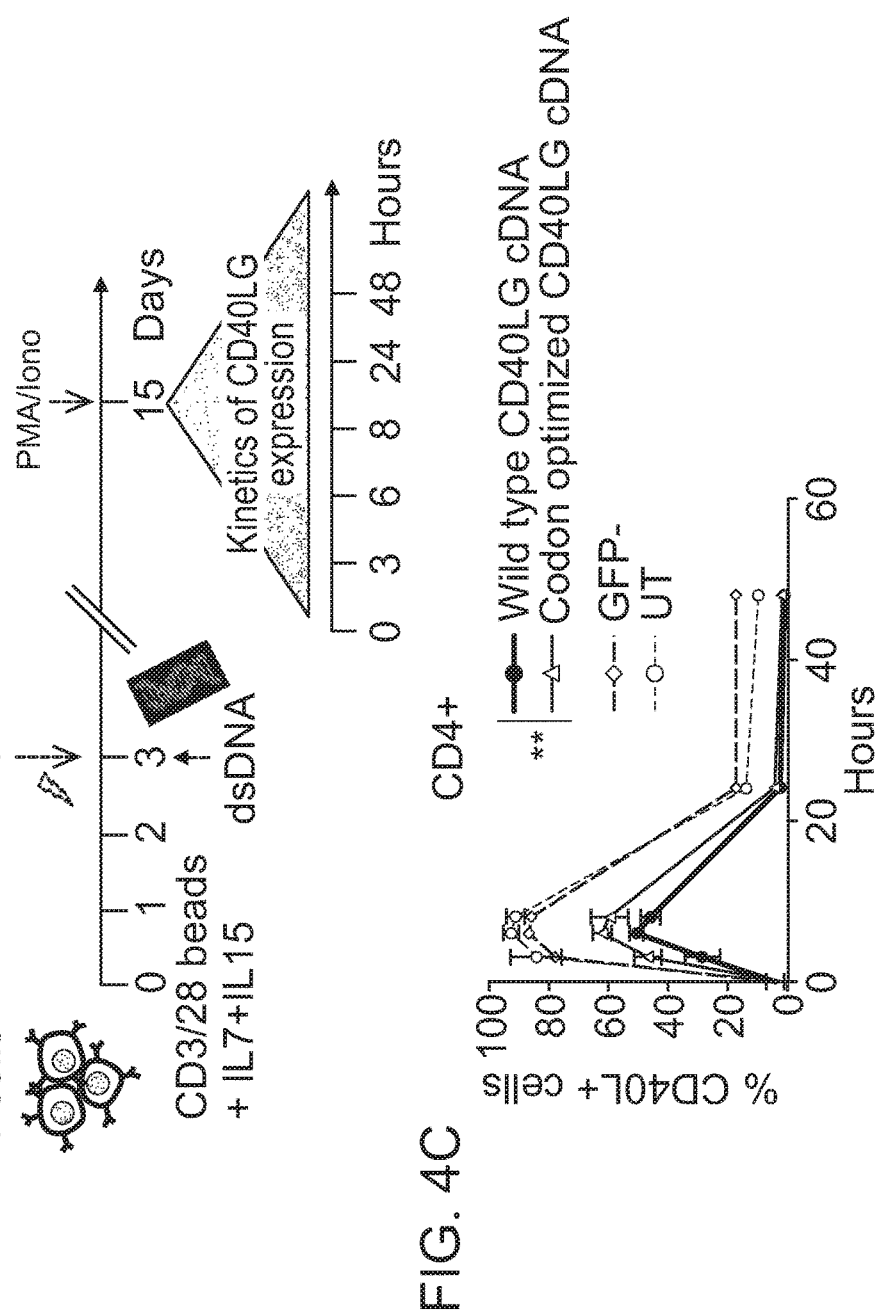
FIG. 4A
FIG. 4B
FIG. 4C

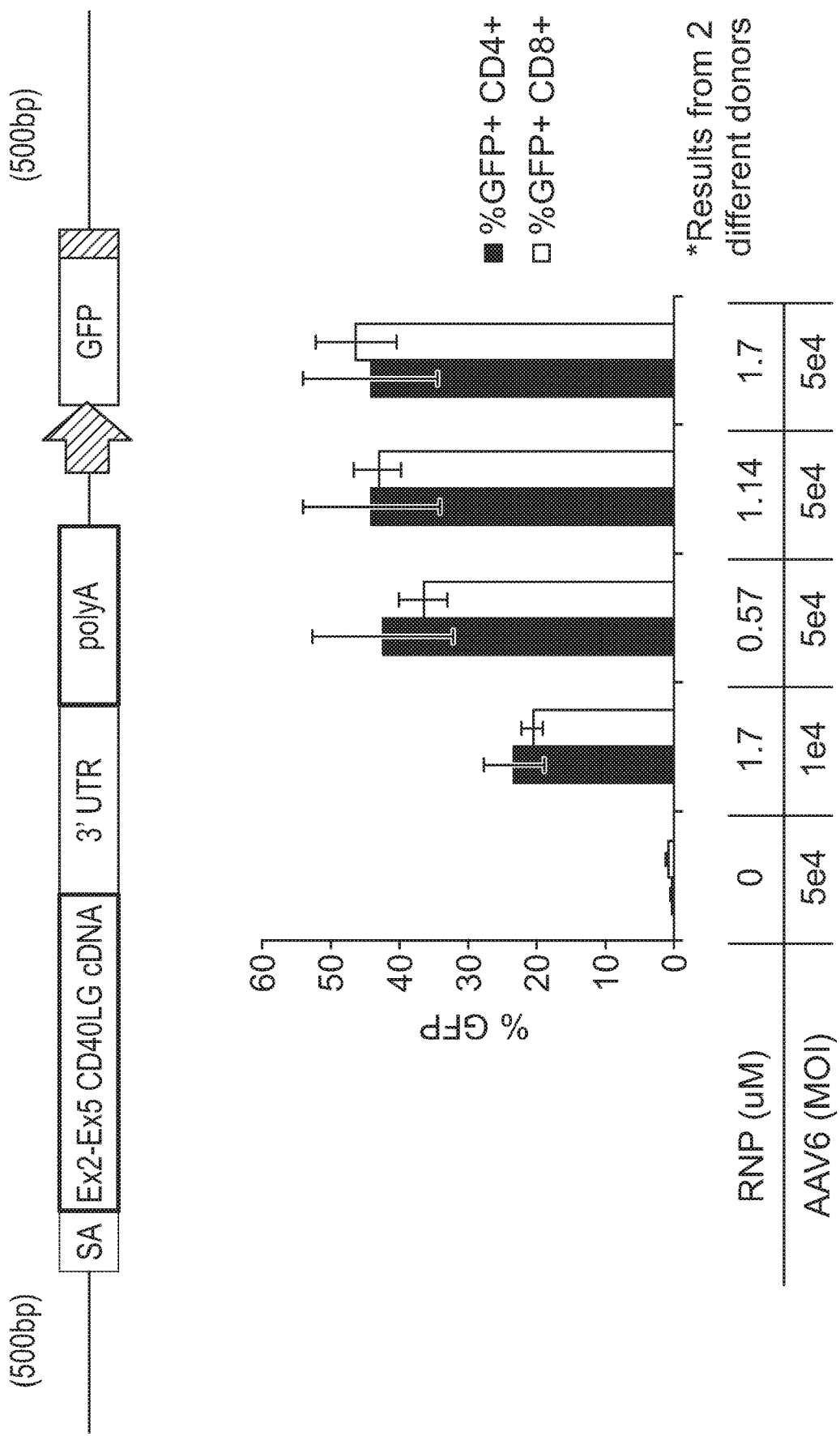

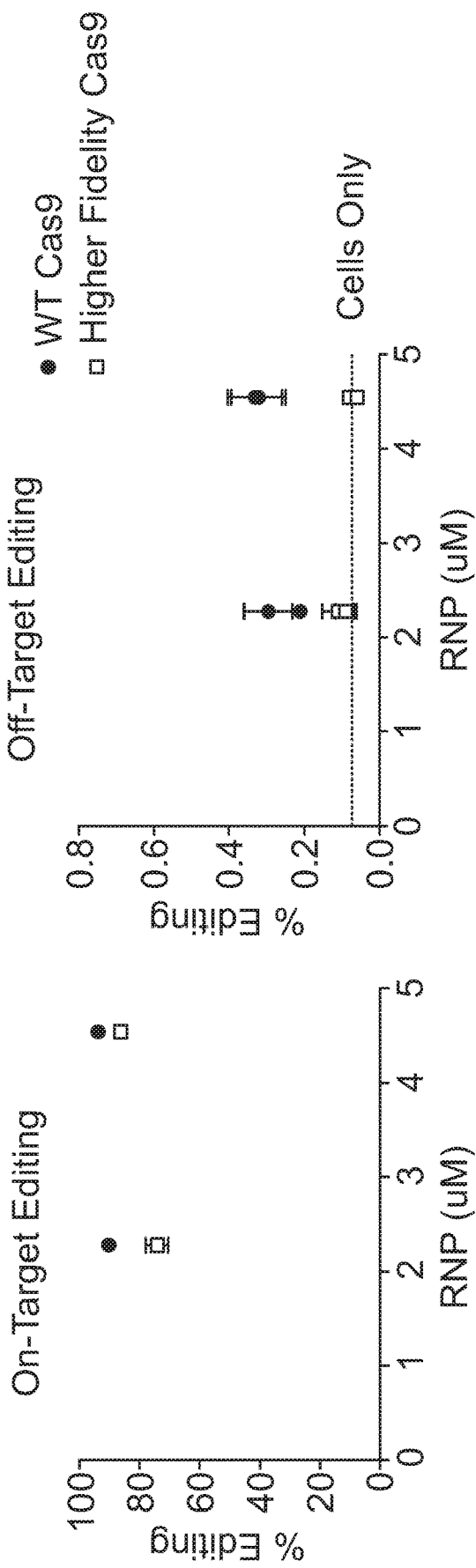

FIG. 15A Immunohistochemistry of GC B Cells in Spleen sections of TNP-KLH-immunized Mice
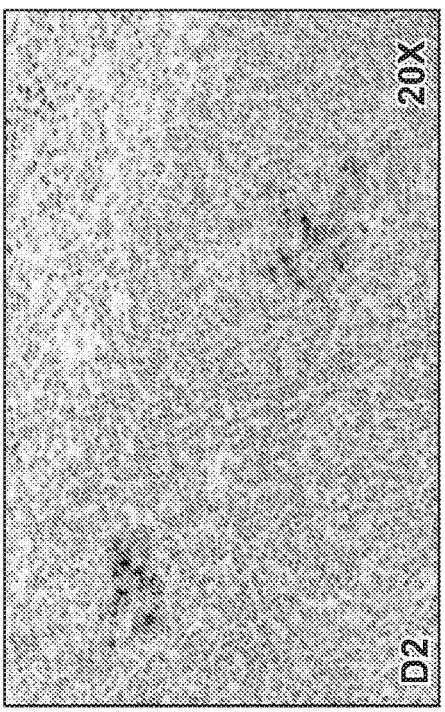
CD40L−/−
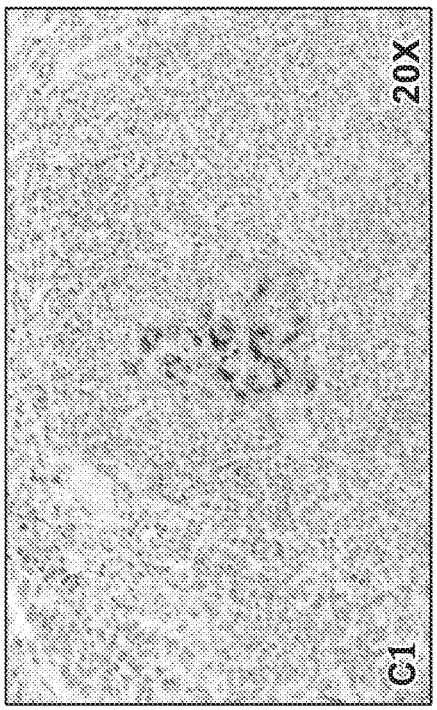
WT
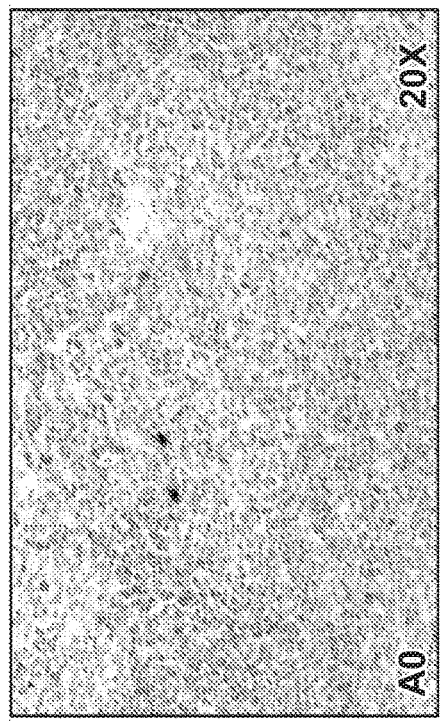
CD40L−/− + T cell transplant
(3 out of 9 mice positive for GC formation)
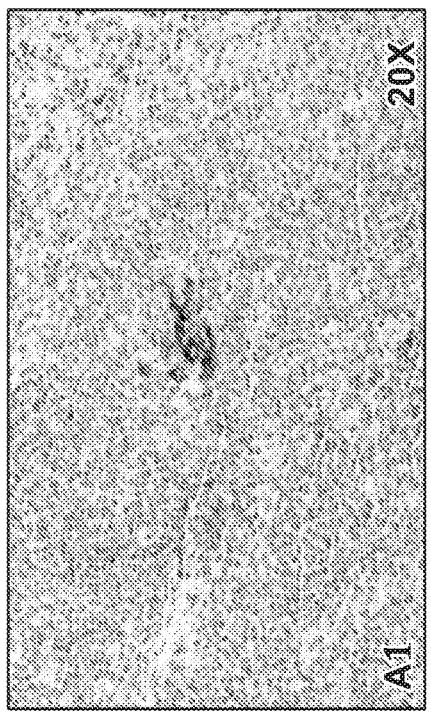
CD40L−/− + Cyclo + T cell transplant
(4 out of 4 mice positive for GC formation)
*PNA (Peanut agglutinin) staining is shown in brown and hematoxylin counterstaining in blue*

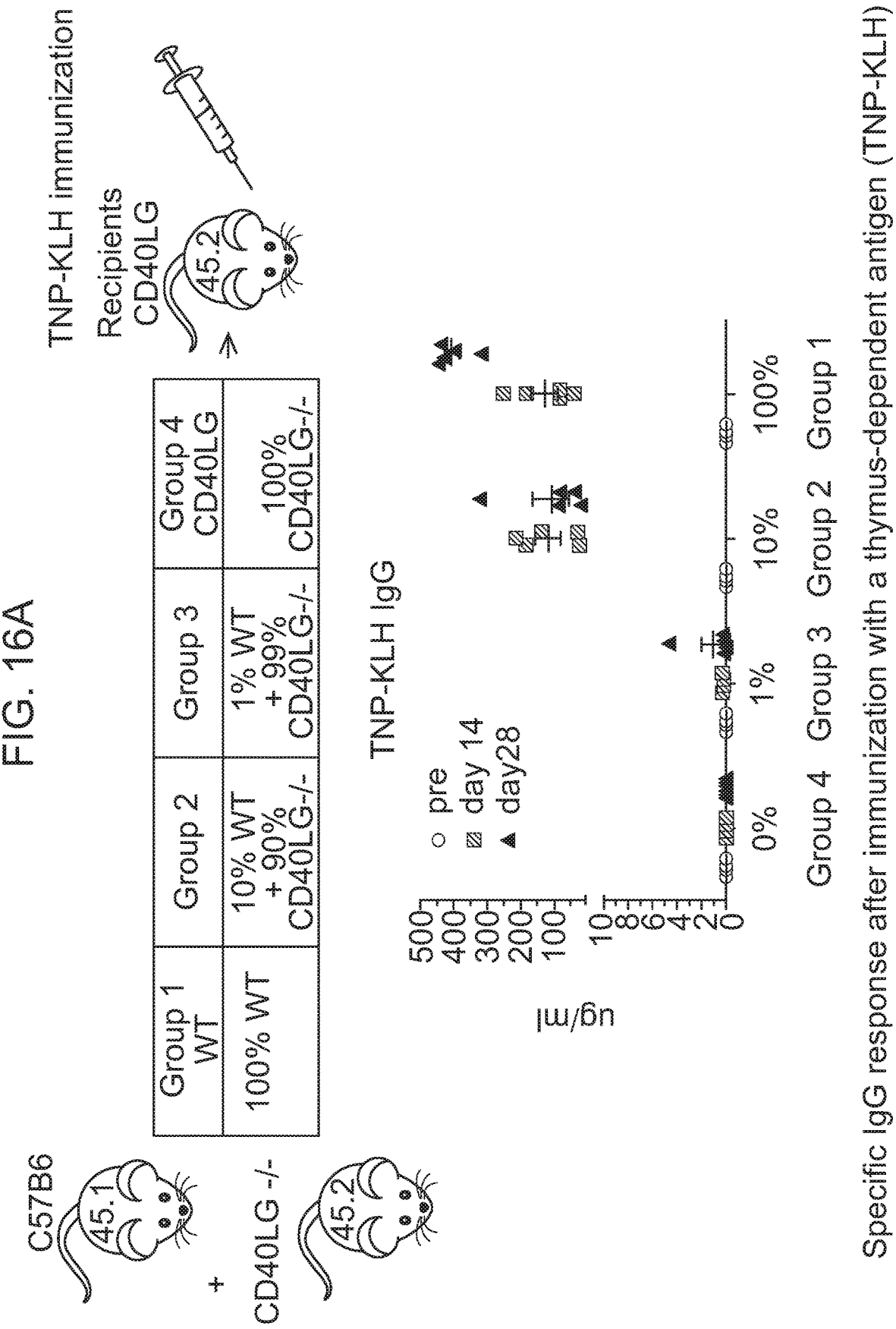

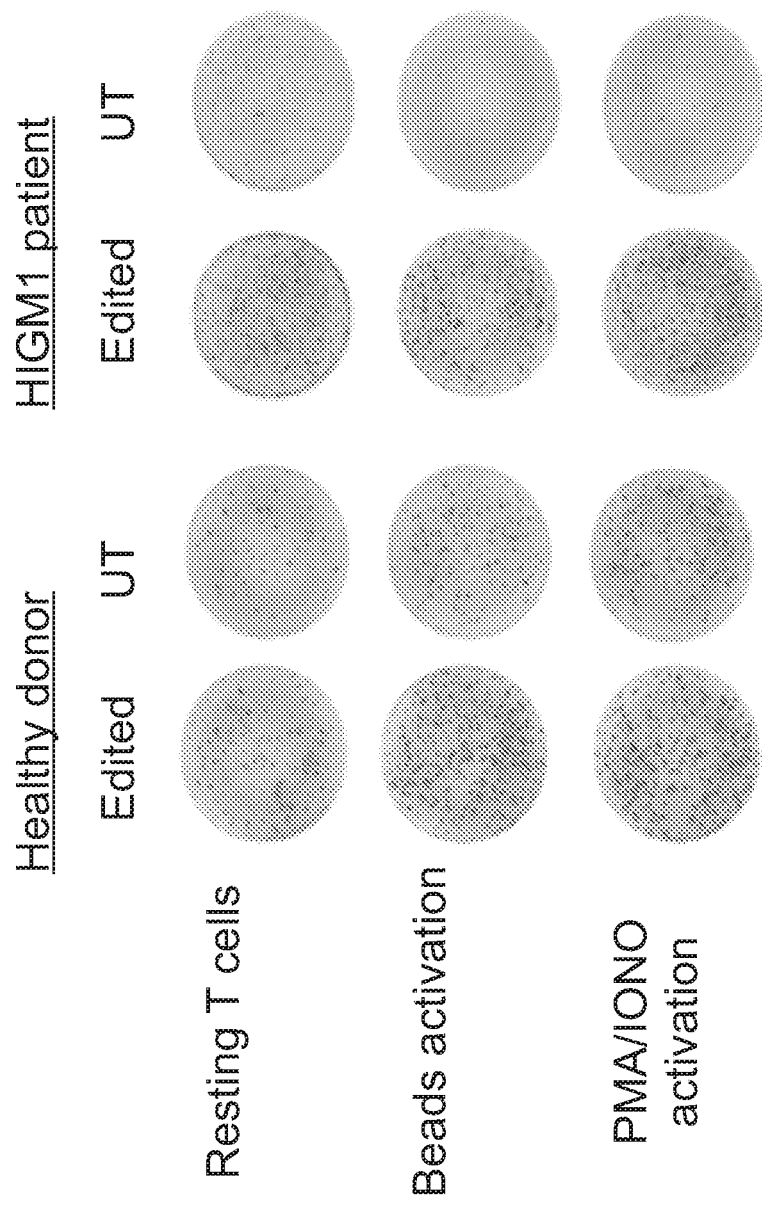

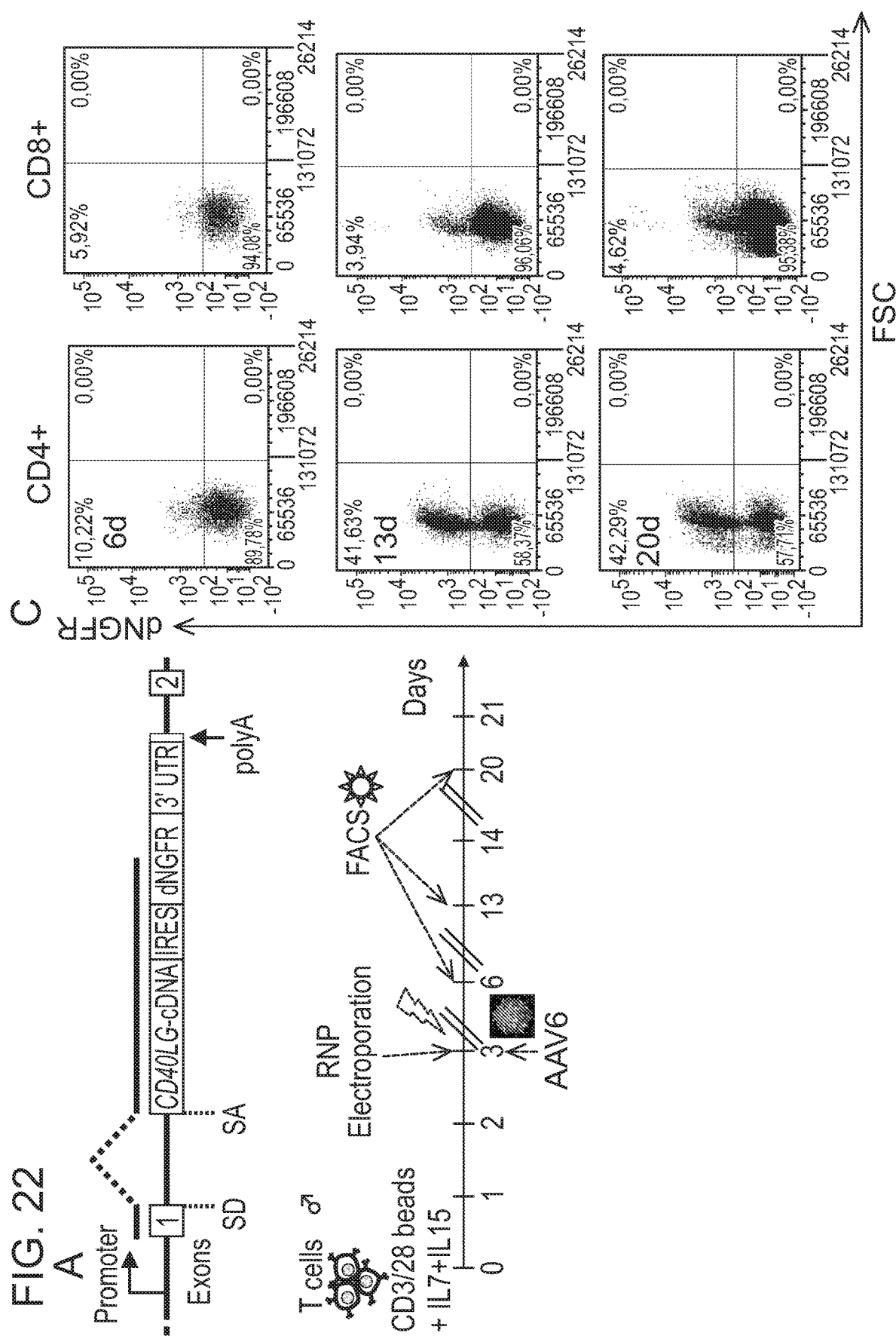

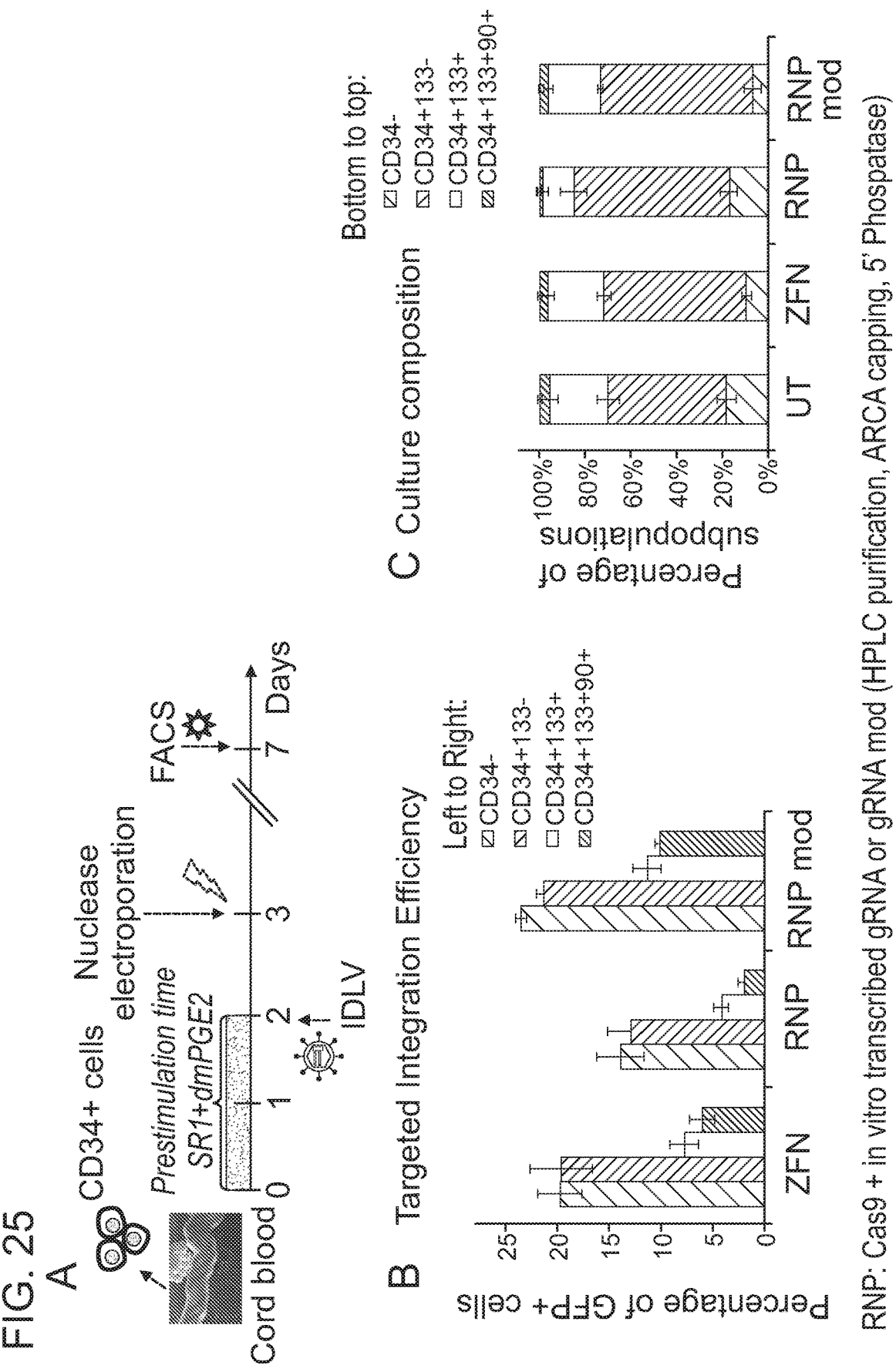

SEQUENCE LISTING

<160> NUMBER OF SEQ ID NOS: 48

<210> SEQ ID NO 1
<211> LENGTH: 1834
<212> TYPE: DNA
<213> ORGANISM: Homo sapiens

<400> SEQUENCE: 1

```
actttgacag tcttctcatg ctgcctctgc caccttctct gccagaagat accatttcaa      60
ctttaacaca gcatgatcga aacatacaac caaacttctc cccgatctgc ggccactgga     120
ctgcccatca gcatgaaaat ttttatgtat ttacttactg tttttcttat cacccagatg     180
attgggtcag cactttttgc tgtgtatctt catagaaggt tggacaagat agaagatgaa     240
aggaatcttc atgaagattt tgtattcatg aaaacgatac agagatgcaa cacaggagaa     300
agatccttat ccttactgaa ctgtgaggag attaaaagcc agtttgaagg ctttgtgaag     360
gatataatgt taaacaaaga ggagacgaag aaagaaaaca gctttgaaat gcaaaaaggt     420
gatcagaatc ctcaaattgc ggcacatgtc ataagtgagg ccagcagtaa aacaacatct     480
gtgttacagt gggctgaaaa aggatactac accatgagca caacttggt  aaccctggaa     540 aatgggaaac agctgaccgt taaaagacaa ggactctatt atatctatgc ccaagtcacc     600
ttctgttcca atcgggaagc ttcgagtcaa gctccattta tagccagcct ctgcctaaag     660
tcccccggta gattcgagag aatcttactc agagctgcaa atacccacag ttccgccaaa     720
ccttgcgggc aacaatccat tcacttggga ggagtatttg aattgcaacc aggtgcttcg     780
gtgtttgtca atgtgactga tccaagccaa gtgagccatg gcactggctt cacgtccttt     840
ggcttactca aactctgaac agtgtcacct tgcaggctgt ggtggagctg acgctgggag     900
tcttcataat acagcacagc ggttaagccc accccctgtt aactgcctat ttataaccct     960
aggatcctcc ttatggagaa ctatttatta tacactccaa ggcatgtaga actgtaataa    1020
gtgaattaca ggtcacatga aaccaaaacg ggccctgctc cataagagct tatatatctg    1080
aagcagcaac cccactgatg cagacatcca gagagtccta tgaaaagaca aggccattat    1140
gcacaggtta aattctgagt aaacagcaga taacttgcca agttcagttt tgtttctttg    1200
cgtgcagtgt ctttccatgg ataatgcatt tgatttatca gtgaagatgc agaagggaaa    1260
```

```
tggggagcct cagctcacat tcagttatgg ttgactctgg gttcctatgg ccttgttgga    1320
gggggccagg ctctagaacg tctaacacag tggagaaccg aaacccccc ccccccccg      1380 ccaccctctc ggacagttat tcattctctt tcaatctctc tctctccatc tctctctttc    1440
agtctctctc tctcaacctc tttcttccaa tctctctttc tcaatctctc tgtttccctt    1500
tgtcagtctc ttccctcccc cagtctctct tctcaatccc cctttctaac acacacacac    1560
acacacacac acacacacac acacacacac acacacacac agagtcaggc cgttgctagt    1620
cagttctctt ctttccaccc tgtccctatc tctaccacta tagatgaggg tgaggagtag    1680
ggagtgcagc cctgagcctg cccactcctc attacgaaat gactgtattt aaaggaaatc    1740
tattgtatct acctgcagtc tccattgttt ccagagtgaa cttgtaatta tcttgttatt    1800
tattttttga ataataaaga cctcttaaca ttaa                                1834

<210> SEQ ID NO 2
<211> LENGTH: 20
<212> TYPE: DNA
<213> ORGANISM: Artificial Sequence
<220> FEATURE:
<223> OTHER INFORMATION: Protospacer sequence (Guide RNA (gRNA) A)

<400> SEQUENCE: 2
tggatgattg cactttatca                                                  20

<210> SEQ ID NO 3
<211> LENGTH: 20
<212> TYPE: DNA
<213> ORGANISM: Artificial Sequence
<220> FEATURE:
<223> OTHER INFORMATION: Protospacer sequence (gRNA B)

<400> SEQUENCE: 3
ttttctaaca ggataaggtg                                                  20

<210> SEQ ID NO 4
<211> LENGTH: 20
<212> TYPE: DNA
<213> ORGANISM: Artificial Sequence
<220> FEATURE:
<223> OTHER INFORMATION: Protospacer sequence (gRNA C)

<400> SEQUENCE: 4
cggtaaatat cagtccactg                                                  20

<210> SEQ ID NO 5
<211> LENGTH: 21
<212> TYPE: DNA
<213> ORGANISM: Artificial Sequence
<220> FEATURE:
<223> OTHER INFORMATION: Protospacer sequence (gRNA D)

<400> SEQUENCE: 5
agtgagggct gaagtcatcc a                                                21

<210> SEQ ID NO 6
<211> LENGTH: 21
<212> TYPE: DNA
<213> ORGANISM: Artificial Sequence
<220> FEATURE:
<223> OTHER INFORMATION: Protospacer sequence (gRNA E)

<400> SEQUENCE: 6
acctaatatt tggataaccc a                                                21
```

<210> SEQ ID NO 7
<211> LENGTH: 21
<212> TYPE: DNA
<213> ORGANISM: Artificial Sequence
<220> FEATURE:
<223> OTHER INFORMATION: Protospacer sequence (gRNA F)

<400> SEQUENCE: 7
caatgagaaa tgtgacaatt a                                              21

<210> SEQ ID NO 8
<211> LENGTH: 21
<212> TYPE: DNA
<213> ORGANISM: Artificial Sequence
<220> FEATURE:
<223> OTHER INFORMATION: Protospacer sequence (gRNA G)

<400> SEQUENCE: 8
agaatagctc tgatttctac c                                              21

<210> SEQ ID NO 9
<211> LENGTH: 21
<212> TYPE: DNA
<213> ORGANISM: Artificial Sequence
<220> FEATURE:
<223> OTHER INFORMATION: Protospacer sequence (gRNA H)

<400> SEQUENCE: 9
gaggactttc aggcataaat g                                              21

<210> SEQ ID NO 10
<211> LENGTH: 3
<212> TYPE: DNA
<213> ORGANISM: Artificial Sequence
<220> FEATURE:
<223> OTHER INFORMATION: Protospacer adjacent motif (PAM) sequence (gRNA
      A)

<400> SEQUENCE: 10 ggg                                                                   3

<210> SEQ ID NO 11
<211> LENGTH: 3
<212> TYPE: DNA
<213> ORGANISM: Artificial Sequence
<220> FEATURE:
<223> OTHER INFORMATION: PAM sequence (gRNA B)

<400> SEQUENCE: 11 agg                                                                   3

<210> SEQ ID NO 12
<211> LENGTH: 3
<212> TYPE: DNA
<213> ORGANISM: Artificial Sequence
<220> FEATURE:
<223> OTHER INFORMATION: PAM sequence (gRNA C)

<400> SEQUENCE: 12 agg                                                                   3

<210> SEQ ID NO 13
<211> LENGTH: 6
<212> TYPE: DNA
<213> ORGANISM: Artificial Sequence

```
<220> FEATURE:
<223> OTHER INFORMATION: PAM sequence (gRNA D)

<400> SEQUENCE: 13 ctgggt                                                                        6

<210> SEQ ID NO 14
<211> LENGTH: 6
<212> TYPE: DNA
<213> ORGANISM: Artificial Sequence
<220> FEATURE:
<223> OTHER INFORMATION: PAM sequence (gRNA E)

<400> SEQUENCE: 14 gtggat                                                                        6

<210> SEQ ID NO 15
<211> LENGTH: 6
<212> TYPE: DNA
<213> ORGANISM: Artificial Sequence
<220> FEATURE:
<223> OTHER INFORMATION: PAM sequence (gRNA F)

<400> SEQUENCE: 15 cagaat                                                                        6

<210> SEQ ID NO 16
<211> LENGTH: 6
<212> TYPE: DNA
<213> ORGANISM: Artificial Sequence
<220> FEATURE:
<223> OTHER INFORMATION: PAM sequence (gRNA G)

<400> SEQUENCE: 16 tggagt                                                                        6

<210> SEQ ID NO 17
<211> LENGTH: 6
<212> TYPE: DNA
<213> ORGANISM: Artificial Sequence
<220> FEATURE:
<223> OTHER INFORMATION: PAM sequence (gRNA H)

<400> SEQUENCE: 17 gagaat                                                                        6

<210> SEQ ID NO 18
<211> LENGTH: 20
<212> TYPE: RNA
<213> ORGANISM: Artificial Sequence
<220> FEATURE:
<223> OTHER INFORMATION: gRNA sequence (gRNA A)

<400> SEQUENCE: 18
uggaugauug cacuuuauca                                                        20

<210> SEQ ID NO 19
<211> LENGTH: 20
<212> TYPE: RNA
<213> ORGANISM: Artificial Sequence
<220> FEATURE:
<223> OTHER INFORMATION: gRNA sequence (gRNA B)

<400> SEQUENCE: 19
uuuucuaaca ggauaaggug                                                        20
```

```
<210> SEQ ID NO 20
<211> LENGTH: 20
<212> TYPE: RNA
<213> ORGANISM: Artificial Sequence
<220> FEATURE:
<223> OTHER INFORMATION: gRNA sequence (gRNA C)

<400> SEQUENCE: 20
cgguaaauau caguccacug                                                   20

<210> SEQ ID NO 21
<211> LENGTH: 21
<212> TYPE: RNA
<213> ORGANISM: Artificial Sequence
<220> FEATURE:
<223> OTHER INFORMATION: gRNA sequence (gRNA D)

<400> SEQUENCE: 21
agugagggcu gaagucaucc a                                                 21

<210> SEQ ID NO 22
<211> LENGTH: 21
<212> TYPE: RNA
<213> ORGANISM: Artificial Sequence
<220> FEATURE:
<223> OTHER INFORMATION: gRNA sequence (gRNA E)

<400> SEQUENCE: 22
accuaauauu uggauaaccc a                                                 21

<210> SEQ ID NO 23
<211> LENGTH: 21
<212> TYPE: RNA
<213> ORGANISM: Artificial Sequence
<220> FEATURE:
<223> OTHER INFORMATION: gRNA sequence (gRNA F)

<400> SEQUENCE: 23
caaugagaaa ugugacaauu a                                                 21

<210> SEQ ID NO 24
<211> LENGTH: 21
<212> TYPE: RNA
<213> ORGANISM: Artificial Sequence
<220> FEATURE:
<223> OTHER INFORMATION: gRNA sequence (gRNA G)

<400> SEQUENCE: 24
agaauagcuc ugauuucuac c                                                 21

<210> SEQ ID NO 25
<211> LENGTH: 21
<212> TYPE: DNA
<213> ORGANISM: Artificial Sequence
<220> FEATURE:
<223> OTHER INFORMATION: gRNA sequence (gRNA H)

<400> SEQUENCE: 25
gaggactttc aggcataaat g                                                 21

<210> SEQ ID NO 26
<211> LENGTH: 3
<212> TYPE: DNA
<213> ORGANISM: Artificial Sequence
<220> FEATURE:
<223> OTHER INFORMATION: PAM sequence (gRNA A)
```

```
<400> SEQUENCE: 26 ggg                                                                       3

<210> SEQ ID NO 27
<211> LENGTH: 3
<212> TYPE: DNA
<213> ORGANISM: Artificial Sequence
<220> FEATURE:
<223> OTHER INFORMATION: PAM sequence (gRNA B)

<400> SEQUENCE: 27 agg                                                                       3

<210> SEQ ID NO 28
<211> LENGTH: 3
<212> TYPE: DNA
<213> ORGANISM: Artificial Sequence
<220> FEATURE:
<223> OTHER INFORMATION: PAM sequence (gRNA C)

<400> SEQUENCE: 28 agg                                                                       3

<210> SEQ ID NO 29
<211> LENGTH: 6
<212> TYPE: DNA
<213> ORGANISM: Artificial Sequence
<220> FEATURE:
<223> OTHER INFORMATION: PAM sequence (gRNA D)

<400> SEQUENCE: 29 ctgggt                                                                    6

<210> SEQ ID NO 30
<211> LENGTH: 6
<212> TYPE: DNA
<213> ORGANISM: Artificial Sequence
<220> FEATURE:
<223> OTHER INFORMATION: PAM sequence (gRNA E)

<400> SEQUENCE: 30 gtggat                                                                    6

<210> SEQ ID NO 31
<211> LENGTH: 6
<212> TYPE: DNA
<213> ORGANISM: Artificial Sequence
<220> FEATURE:
<223> OTHER INFORMATION: PAM sequence (gRNA F)

<400> SEQUENCE: 31 cagaat                                                                    6

<210> SEQ ID NO 32
<211> LENGTH: 6
<212> TYPE: DNA
<213> ORGANISM: Artificial Sequence
<220> FEATURE:
<223> OTHER INFORMATION: PAM sequence (gRNA G)

<400> SEQUENCE: 32 tggagt                                                                    6

<210> SEQ ID NO 33
```

```
<211> LENGTH: 6
<212> TYPE: DNA
<213> ORGANISM: Artificial Sequence
<220> FEATURE:
<223> OTHER INFORMATION: PAM sequence (gRNA H)

<400> SEQUENCE: 33 gagaat                                                              6

<210> SEQ ID NO 34
<211> LENGTH: 3956
<212> TYPE: DNA
<213> ORGANISM: Artificial Sequence
<220> FEATURE:
<223> OTHER INFORMATION: Donor sequence, donor 1 gRNA-A_HA + cDNA +
      GFP + Stuffer

<400> SEQUENCE: 34
tgttttgcat tcttaggaaa agaaaaccat caggacttat tttgttttca tgtattttt       60 cacttccact gaggagtata attggctggt gttgacaaaa taccaatcat agatgtaaag     120
gagaaagttg attagttttc tggctgttcc taaaattctg gatgcaggaa ctgtggctag     180
aaagcatctg gatgattgca ctttatactc ttaattcatt acatattgtg cggtcgaatt     240
cagggagccg ataatgcggt tacaataatt cctatactta aatatacaaa gatttaaaat     300
ttcaaaaaat ggttaccagc atcgttagtg cgtatacatc aagaggcacg tgccccggag     360
acagcaagta agctctttaa acacctgatg tgctctgtca atcaaatgta aagcttcctt     420
aggtttacat gtgctcttaa ttacagcaga accggtctga cctcttctct tcctcccaca     480
gatcgaggac gagagaaacc tgcacgagga cttcgtgttc atgaagacca ccagcggtg     540 caacaccggc gagagaagtc tgagcctgct gaactgcgag gaaatcaaga gccagttcga     600
gggcttcgtg aaggacatca tgctgaacaa agaggaaacg aagaaagaaa actccttcga     660
gatgcagaag ggcgaccaga tcctcagat cgccgctcac gtgatcagcg aggccagcag     720
caagacaaca agcgtgctgc agtgggccga aagggctac tacaccatga gcaacaacct     780
ggtcaccctg aaaacggca agcagctgac agtgaagcgg cagggcctgt actacatcta     840
cgcccaagtg accttctgca gcaacagaga ggccagctct caggcccctt ttatcgccag     900
cctgtgcctg aagtcccctg gcagattcga gcggattctg ctgagagccg ccaacacaca     960
cagcagcgcc aaaccttgtg gccagcagtc tattcacctc ggcggagtgt ttgagctgca    1020
gcctggcgca agcgtgttcg tgaatgtgac agaccctagc caggtgtccc acggcaccgg    1080
ctttacatct ttcggactgc tgaagctgtg aacagtgtca ccttgcaggc tgtggtggag    1140
ctgacgctgg gagtcttcat aatacagcac agcggttaag cccaccccct gttaactgcc    1200
tatttataac cctaggatcc tccttatgga gaactattta ttatacactc caaggcatgt    1260
agaactgtaa taagtgaatt acaggtcaca tgaaaccaaa acgggccctg ctccataaga    1320
gcttatatat ctgaagcagc aaccccactg atgcagacat ccagagagtc ctatgaaaag    1380
acaaggccat tatgcacagg ttgaattctg agtaaacagc agataacttg ccaagttcag    1440
ttttgtttct ttgcgtgcag tgtctttcca tggataatgc atttgattta tcagtgaaga    1500
tgcagaaggg aaatggggag cctcagctca cattcagtta tggttgactc tgggttccta    1560
tggccttgtt ggagggggcc aggctctaga acgtctaaca cagtggagaa ccgaaacccc    1620 cccccccgc caccctctcg gacagttatt cattctcttt caatctctct ctctccatct    1680
ctctctttca gtctctctct ctcaacctct ttcttccaat ctctctttct caatctctct    1740
```

|  |  |  |  |  |  |
|---|---|---|---|---|---|
| gtttcccttt | gtcagtctct | tccctcccc | agtctctctt | ctcaatcccc | ctttctaaca | 1800 |
| cacacacaca | cacacacaca | cacacacaca | cacacacaca | cacacacaca | gagtcaggcc | 1860 |
| gttgctagtc | agttctcttc | tttccaccct | gtccctatct | ctaccactat | agatgagggt | 1920 |
| gaggagtagg | gagtgcagcc | ctgagcctgc | ccactcctca | ttacgaaatg | actgtattta | 1980 |
| aaggaaatct | attgtatcta | cctgcagtct | ccattgtttc | cagagtgaac | ttgtaattat | 2040 |
| cttgttattt | attttttgaa | taataaagac | ctcttaacat | tacgcgctta | acattatcgt | 2100 |
| tgttgtttga | gtacctaaag | ctcccagcca | ggttggggaa | agaggaagca | tttggaggga | 2160 |
| attttcccaa | cctttgtgat | gttttcataa | actttgttct | caagctactt | acattacgcg | 2220 |
| tactagttgg | ctccggtgcc | cgtcagtggg | cagagcgcac | atcgcccaca | gtccccgaga | 2280 |
| agttgggggg | aggggtcggc | aattgaaccg | gtgcctagag | aaggtggcgc | ggggtaaact | 2340 |
| gggaaagtga | tgtcgtgtac | tggctccgcc | tttttcccga | gggtggggga | gaaccgtata | 2400 |
| taagtgcagt | agtcgccgtg | aacgttcttt | ttcgcaacgg | gtttgccgcc | agaacacagg | 2460 |
| tgtcgtgacg | cggatcgtac | ccgggttaag | ggcgaattcc | agcacactgg | cggccgttac | 2520 |
| tagtggatcc | accggtcgcc | accatggtga | gcaagggcga | ggagctgttc | accggggtgg | 2580 |
| tgcccatcct | ggtcgagctg | gacggcgacg | taaacggcca | caagttcagc | gtgtccggcg | 2640 |
| agggcgaggg | cgatgccacc | tacggcaagc | tgaccctgaa | gttcatctgc | accaccggca | 2700 |
| agctgcccgt | gccctggccc | accctcgtga | ccaccctgac | ctacggcgtg | cagtgcttca | 2760 |
| gccgctaccc | cgaccacatg | aagcagcacg | acttcttcaa | gtccgccatg | cccgaaggct | 2820 |
| acgtccagga | gcgcaccatc | ttcttcaagg | acgacggcaa | ctacaagacc | cgcgccgagg | 2880 |
| tgaagttcga | gggcgacacc | ctggtgaacc | gcatcgagct | gaagggcatc | gacttcaagg | 2940 |
| aggacggcaa | catcctgggg | cacaagctgg | agtacaacta | caacagccac | aacgtctata | 3000 |
| tcatggccga | caagcagaag | aacggcatca | aggtgaactt | caagatccgc | cacaacatcg | 3060 |
| aggacggcag | cgtgcagctc | gccgaccact | accagcagaa | cacccccatc | ggcgacggcc | 3120 |
| ccgtgctgct | gcccgacaac | cactacctga | gcacccagtc | cgccctgagc | aaagacccca | 3180 |
| acgagaagcg | cgatcacatg | gtcctgctgg | agttcgtgac | cgccgccggg | atcactctcg | 3240 |
| gcatggacga | gctgtacaag | taaagcggcc | gcgtcgagtc | tagagggccc | gtttaaaccc | 3300 |
| gctgatcagc | ctcgactgtg | ccttctagtt | gccagccatc | tgttgtttgc | ccctcccccg | 3360 |
| tgccttcctt | gaccctggaa | ggtgccactc | ccactgccct | ttcctaataa | aatgaggaaa | 3420 |
| ttgcatcgca | ttgtctgagt | aggtgtcatt | ctattctggg | gggtggggtg | gggcaggaca | 3480 |
| gcaaggggga | ggattgggaa | gacaatagca | ggcatgctgg | ggatgcggtg | ggctctatgg | 3540 |
| taccagctta | aagagcagag | taacttagta | ggctgctttg | acatacgatt | tttaataaaa | 3600 |
| catgagcatt | tgaataaaaa | cgacttcctc | atactgtaaa | catcacgcat | gcacattaga | 3660 |
| caataatcca | gtaacgaaac | ggcttcagtc | gtaatcgccc | atatagttgg | ctacagaatg | 3720 |
| ttggatagag | aacttaagta | cgctaaggcg | gcgtattttc | ttaatattta | ggggtatttc | 3780 |
| agggatactt | gagtgtcctc | tcttaggatc | tggacctaga | attaatgtca | tgagattttt | 3840 |
| ctaacaggat | aaggtgaggt | agtgagggct | gaagtcatcc | actgggttat | ccaaatatta | 3900 |
| ggtttcactg | ctgacaaaag | aggggcttc | tggtctggtt | ggttatttgt | gtttgg | 3956 |

<210> SEQ ID NO 35
<211> LENGTH: 3573
<212> TYPE: DNA
<213> ORGANISM: Artificial Sequence
<220> FEATURE:
<223> OTHER INFORMATION: Donor sequence, donor 2 gRNA-A_HA + cDNA + GFP - Stuffer

<400> SEQUENCE: 35

| | | | | | |
|---|---|---|---|---|---|
| tgttttgcat | tcttaggaaa | agaaaaccat | caggacttat | tttgttttca | tgtattttt | 60 |
| cacttccact | gaggagtata | attggctggt | gttgacaaaa | taccaatcat | agatgtaaag | 120 |
| gagaaagttg | attagttttc | tggctgttcc | taaaattctg | gatgcaggaa | ctgtggctag | 180 |
| aaagcatctg | gatgattgca | ctttacctga | tgtgctctgt | caatcaaatg | taaagcttcc | 240 |
| ttaggtttac | atgtgctctt | aattacagca | gaaccggtct | gacctcttct | cttcctccca | 300 |
| cagatcgagg | acgagagaaa | cctgcacgag | gacttcgtgt | tcatgaagac | catccagcgg | 360 |
| tgcaacaccg | gcgagagaag | tctgagcctg | ctgaactgcg | aggaaatcaa | gagccagttc | 420 |
| gagggcttcg | tgaaggacat | catgctgaac | aaagaggaaa | cgaagaaaga | aaactccttc | 480 |
| gagatgcaga | agggcgacca | gaatcctcag | atcgccgctc | acgtgatcag | cgaggccagc | 540 |
| agcaagacaa | caagcgtgct | gcagtgggcc | gagaagggct | actacaccat | gagcaacaac | 600 |
| ctggtcaccc | tggaaaacgg | caagcagctg | acagtgaagc | ggcagggcct | gtactacatc | 660 |
| tacgcccaag | tgaccttctg | cagcaacaga | gaggccagct | ctcaggcccc | ttttatcgcc | 720 |
| agcctgtgcc | tgaagtcccc | tggcagattc | gagcggattc | tgctgagagc | cgccaacaca | 780 |
| cacagcagcc | ccaaaccttg | tggccagcag | tctattcacc | tcggcggagt | gtttgagctg | 840 |
| cagcctggcg | caagcgtgtt | cgtgaatgtg | acagaccta | gccaggtgtc | ccacggcacc | 900 |
| ggctttacat | ctttcggact | gctgaagctg | tgaacagtgt | caccttgcag | gctgtggtgg | 960 |
| agctgacgct | gggagtcttc | ataatacagc | acagcggtta | agcccacccc | ctgttaactg | 1020 |
| cctatttata | accctaggat | cctccttatg | gagaactatt | tattatacac | tccaaggcat | 1080 |
| gtagaactgt | aataagtgaa | ttacaggtca | catgaaacca | aaacgggccc | tgctccataa | 1140 |
| gagcttatat | atctgaagca | gcaaccccac | tgatgcagac | atccagagag | tcctatgaaa | 1200 |
| agacaaggcc | attatgcaca | ggttgaattc | tgagtaaaca | gcagataact | tgccaagttc | 1260 |
| agttttgttt | ctttgcgtgc | agtgtctttc | catggataat | gcatttgatt | tatcagtgaa | 1320 |
| gatgcagaag | ggaaatgggg | agcctcagct | cacattcagt | tatggttgac | tctgggttcc | 1380 |
| tatgccttg | ttgaggggg | ccaggctcta | gaacgtctaa | cacagtggag | aaccgaaacc | 1440 |
| cccccccccc | gccaccctct | cggacagtta | ttcattctct | ttcaatctct | ctctctccat | 1500 |
| ctctctcttt | cagtctctct | ctccaacct | cttttcttcca | atctctcttt | ctcaatctct | 1560 |
| ctgtttccct | ttgtcagtct | cttccctccc | ccagtctctc | ttctcaatcc | ccttttctaa | 1620 |
| cacacacaca | cacacacaca | cacacacaca | cacacacaca | cacacacaca | cagagtcagg | 1680 |
| ccgttgctag | tcagttctct | tctttccacc | ctgtccctat | ctctaccact | atagatgagg | 1740 |
| gtgaggagta | gggagtgcag | ccctgagcct | gcccactcct | cattacgaaa | tgactgtatt | 1800 |
| taaaggaaat | ctattgtatc | tacctgcagt | ctccattgtt | tccagagtga | acttgtaatt | 1860 |
| atcttgttat | ttatttttg | aataataaag | acctcttaac | attacgcgct | taacattatc | 1920 |
| gttgttgttt | gagtacctaa | agctcccagc | caggttgggg | aaagaggaag | catttggagg | 1980 |
| gaattttccc | aacctttgtg | atgttttcat | aaactttgtt | ctcaagctac | ttacattacg | 2040 |
| cgtactagtt | ggctccggtg | cccgtcagtg | ggcagagcgc | acatcgccca | cagtcccga | 2100 |
| gaagttgggg | ggaggggtcg | gcaattgaac | cggtgcctag | agaaggtggc | gcggggtaaa | 2160 |
| ctgggaaagt | gatgtcgtgt | actggctccg | cctttttccc | gagggtgggg | gagaaccgta | 2220 |

```
tataagtgca gtagtcgccg tgaacgttct ttttcgcaac gggtttgccg ccagaacaca    2280
ggtgtcgtga cgcggatcgt acccgggtta agggcgaatt ccagcacact ggcggccgtt    2340
actagtggat ccaccggtcg ccaccatggt gagcaagggc gaggagctgt tcaccggggt    2400
ggtgcccatc ctggtcgagc tggacggcga cgtaaacggc cacaagttca gcgtgtccgg    2460
cgagggcgag ggcgatgcca cctacggcaa gctgaccctg aagttcatct gcaccaccgg    2520
caagctgccc gtgccctggc ccaccctcgt gaccaccctg acctacggcg tgcagtgctt    2580
cagccgctac cccgaccaca tgaagcagca cgacttcttc aagtccgcca tgcccgaagg    2640
ctacgtccag gagcgcacca tcttcttcaa ggacgacggc aactacaaga cccgcgccga    2700
ggtgaagttc gagggcgaca ccctggtgaa ccgcatcgag ctgaagggca tcgacttcaa    2760
ggaggacggc aacatcctgg ggcacaagct ggagtacaac tacaacagcc acaacgtcta    2820
tatcatggcc gacaagcaga agaacggcat caaggtgaac ttcaagatcc gccacaacat    2880
cgaggacggc agcgtgcagc tcgccgacca ctaccagcag aacaccccca tcggcgacgg    2940
ccccgtgctg ctgcccgaca accactacct gagcacccag tccgccctga gcaaagaccc    3000
caacgagaag cgcgatcaca tggtcctgct ggagttcgtg accgccgccg ggatcactct    3060
cggcatggac gagctgtaca gtaaagcgg ccgcgtcgag tctagagggc cgtttaaac    3120 ccgctgatca gcctcgactg tgccttctag ttgccagcca tctgttgttt gcccctcccc    3180
cgtgccttcc ttgaccctgg aaggtgccac tcccactgcc ctttcctaat aaaatgagga    3240
aattgcatcg cattgtctga gtaggtgtca ttctattctg gggggtgggg tgggcagga    3300 cagcaagggg gaggattggg aagacaatag caggcatgct ggggatgcgg tgggctctat    3360
ggtaccagct taaagagcag agtaacttag taggctcagg gatacttgag tgtcctctct    3420
taggatctgg acctagaatt aatgtcatga gattttttcta acaggataag gtgaggtagt    3480
gagggctgaa gtcatccact gggttatcca aatattaggt ttcactgctg acaaagagg    3540 gggcttctgg tctggttggt tatttgtgtt tgg                                  3573
```

<210> SEQ ID NO 36
<211> LENGTH: 2643
<212> TYPE: DNA
<213> ORGANISM: Artificial Sequence
<220> FEATURE:
<223> OTHER INFORMATION: Donor sequence, donor 3 gRNA-A_HA + cDNA -
      GFP + stuffer

<400> SEQUENCE: 36

```
tgttttgcat tcttaggaaa agaaaaccat caggacttat tttgttttca tgtatttttt    60
cacttccact gaggagtata attggctggt gttgacaaaa taccaatcat agatgtaaag    120
gagaaagttg attagttttc tggctgttcc taaaattctg gatgcaggaa ctgtggctag    180
aaagcatctg gatgattgca ctttatactc ttaattcatt acatattgtg cggtcgaatt    240
cagggagccg ataatgcggt tacaataatt cctatactta aatatacaaa gatttaaaat    300
ttcaaaaaat ggttaccagc atcgttagtg cgtatacatc aagaggcacg tgccccggag    360
acagcaagta agctctttaa acaccctgat gctctgtca atcaaatgta agcttccttt    420
aggtttacat gtgctcttaa ttacagcaga accggtctga cctcttctct tcctcccaca    480
gatcgaggac gagagaaacc tgcacgagga cttcgtgttc atgaagacca tccagcggtg    540
caacaccggc gagagaagtc tgagcctgct gaactgcgag gaaatcaaga gccagttcga    600
gggcttcgtg aaggacatca tgctgaacaa agaggaaacg aagaaagaaa actccttcga    660
```

```
gatgcagaag ggcgaccaga atcctcagat cgccgctcac gtgatcagcg aggccagcag    720
caagacaaca agcgtgctgc agtgggccga aagggctac tacaccatga gcaacaacct    780
ggtcaccctg aaaacggca agcagctgac agtgaagcgg cagggcctgt actacatcta    840
cgcccaagtg accttctgca gcaacagaga ggccagctct caggccccctt ttatcgccag    900
cctgtgcctg aagtcccctg gcagattcga gcggattctg ctgagagccg ccaacacaca    960
cagcagcgcc aaaccttgtg gccagcagtc tattcacctc ggcggagtgt ttgagctgca   1020
gcctggcgca agcgtgttcg tgaatgtgac agaccctagc caggtgtccc acggcaccgg   1080
ctttacatct ttcggactgc tgaagctgtg aacagtgtca ccttgcaggc gtggtggag   1140
ctgacgctgg gagtcttcat aatacagcac agcggttaag cccaccccct gttaactgcc   1200
tatttataac cctaggatcc tccttatgga gaactattta ttatacactc caaggcatgt   1260
agaactgtaa taagtgaatt acaggtcaca tgaaaccaaa acgggccctg ctccataaga   1320
gcttatatat ctgaagcagc aaccccactg atgcagacat ccagagagtc ctatgaaaag   1380
acaaggccat tatgcacagg ttgaattctg agtaaacagc agataacttg ccaagttcag   1440
ttttgtttct ttgcgtgcag tgtctttcca tggataatgc atttgattta tcagtgaaga   1500
tgcagaaggg aaatggggag cctcagctca cattcagtta tggttgactc tgggttccta   1560
tggccttgtt ggaggggggcc aggctctaga acgtctaaca cagtggagaa ccgaaacccc   1620
cccccccgc caccctctcg gacagttatt cattctcttt caatctctct ctctccatct   1680
ctctcttcca gtctctctct ctcaacctct ttcttccaat ctctcttctt caatctctct   1740
gtttcccttt gtcagtctct tccctccccc agtctctctt ctcaatcccc cttttctaaca   1800
cacacacaca cacacacaca cacacacaca cacacacaca cacacacaca gagtcaggcc   1860
gttgctagtc agttctcttc tttccaccct gtccctatct ctaccactat agatgagggt   1920
gaggagtagg gagtgcagcc ctgagcctgc ccactcctca ttacgaaatg actgtattta   1980
aaggaaatct attgtatcta cctgcagtct ccattgtttc cagagtgaac ttgtaattat   2040
cttgttattt attttttgaa taataaagac ctcttaacat tacgcgctta acattatcgt   2100
tgttgtttga gtacctaaag ctcccagcca ggttggggaa agaggaagca tttggaggga   2160
attttcccaa cctttgtgat gttttcataa actttgttct caagctactt acattacgcg   2220
tactagttac cagcttaaag agcagagtaa cttagtaggc tgctttgaca tacgattttt   2280
aataaaacat gagcatttga ataaaaacga cttcctcata ctgtaaacat cacgcatgca   2340
cattagacaa taatccagta acgaaacggc ttcagtcgta atcgcccata tagttggcta   2400
cagaatgttg gatagagaac ttaagtacgc taaggcggcg tatttctta atatttaggg   2460
gtatttcagg gatacttgag tgtcctctct taggatctgg acctagaatt aatgtcatga   2520
gatttttcta acaggataag gtgaggtagt gagggctgaa gtcatccact gggttatcca   2580
aatattaggt ttcactgctg acaaaagagg gggcttctgg tctggttggt tatttgtgtt   2640
tgg                                                                  2643
```

<210> SEQ ID NO 37
<211> LENGTH: 2260
<212> TYPE: DNA
<213> ORGANISM: Artificial Sequence
<220> FEATURE:
<223> OTHER INFORMATION: Donor sequence, donor 4 gRNA-A_HA + cDNA - GFP - stuffer

<400> SEQUENCE: 37

```
tgttttgcat tcttaggaaa agaaaaccat caggacttat tttgttttca tgtattttt     60 cacttccact gaggagtata attggctggt gttgacaaaa taccaatcat agatgtaaag    120
gagaaagttg attagttttc tggctgttcc taaaattctg gatgcaggaa ctgtggctag    180
aaagcatctg gatgattgca cttacctga tgtgctctgt caatcaaatg taaagcttcc     240
ttaggtttac atgtgctctt aattacagca gaaccggtct gacctcttct cttcctccca    300
cagatcgagg acgagagaaa cctgcacgag gacttcgtgt tcatgaagac catccagcgg    360
tgcaacaccg gcgagagaag tctgagcctg ctgaactgcg aggaaatcaa gagccagttc    420
gagggcttcg tgaaggacat catgctgaac aaagaggaaa cgaagaaaga aaactccttc    480
gagatgcaga agggcgacca gaatcctcag atcgccgctc acgtgatcag cgaggccagc    540
agcaagacaa caagcgtgct gcagtgggcc gagaagggcc actacaccat gagcaacaac    600
ctggtcaccc tggaaaacgg caagcagctg acagtgaagc ggcagggcct gtactacatc    660
tacgcccaag tgaccttctg cagcaacaga gaggccagct ctcaggcccc ttttatcgcc    720
agcctgtgcc tgaagtcccc tggcagattc gagcggattc tgctgagagc cgccaacaca    780
cacagcagcg ccaaaccttg tggccagcag tctattcacc tcggcggagt gtttgagctg    840
cagcctggcg caagcgtgtt cgtgaatgtg acagaccta gccaggtgtc ccacggcacc     900
ggctttacat ctttcggact gctgaagctg tgaacagtgt caccttgcag gctgtggtgg    960
agctgacgct gggagtcttc ataatacagc acagcggtta agcccacccc ctgttaactg   1020
cctatttata accctaggat cctccttatg gagaactatt tattatacac tccaaggcat   1080
gtagaactgt aataagtgaa ttacaggtca catgaaacca aaacgggccc tgctccataa   1140
gagcttatat atctgaagca gcaaccccac tgatgcagac atccagagag tcctatgaaa   1200
agacaaggcc attatgcaca ggttgaattc tgagtaaaca gcagataact tgccaagttc   1260
agttttgttt ctttgcgtgc agtgtctttc catggataat gcatttgatt tatcagtgaa    1320
gatgcagaag ggaaatgggg agcctcagct cacattcagt tatggttgac tctgggttcc    1380
tatggccttg ttggagggg ccaggctcta gaacgtctaa cacagtggag aaccgaaacc     1440
cccccccccc gccaccctct cggacagtta ttcattctct ttcaatctct ctctctccat   1500
ctctctcttt cagtctctct ctctcaacct ctttcttcca atctctcttt ctcaatctct   1560
ctgtttccct ttgtcagtct cttccctccc ccagtctctc ttctcaatcc cccttttctaa  1620 cacacacaca cacacacaca cacacacaca cacacacaca cacacacaca cagagtcagg   1680
ccgttgctag tcagttctct tctttccacc ctgtccctat ctctaccact atagatgagg   1740
gtgaggagta gggagtgcag ccctgagcct gcccactcct cattacgaaa tgactgtatt   1800
taaaggaaat ctattgtatc tacctgcagt ctccattgtt tccagagtga acttgtaatt   1860
atcttgttat ttattttttg aataataaag acctcttaac attacgcgct taacattatc   1920
gttgttgttt gagtacctaa agctcccagc caggttgggg aaagaggaag catttggagg   1980
gaattttccc aacctttgtg atgttttcat aaactttgtt ctcaagctac ttacattacg   2040
cgtactagtt accagcttaa agagcagagt aacttagtag gctcagggat acttgagtgt   2100
cctctcttag gatctggacc tagaattaat gtcatgagat ttttctaaca ggataaggtg   2160
aggtagtgag ggctgaagtc atccactggg ttatccaaat attaggtttc actgctgaca   2220
aaagaggggg cttctggtct ggttggttat ttgtgtttgg                         2260

<210> SEQ ID NO 38
```

<211> LENGTH: 4144
<212> TYPE: DNA
<213> ORGANISM: Artificial Sequence
<220> FEATURE:
<223> OTHER INFORMATION: Donor sequence, donor 5 gRNA-G_HA + cDNA + GFP + Stuffer

<400> SEQUENCE: 38

```
ttcttttat aaagcactgc atcacaaaca ctaaaatgaa gtgggcaaat tagctctgca      60
gaaaactatt ttctaggctg atgtttataa tgaccaatca ttactgaagc aatgagaaat    120
gtgacaatta cagaatattg ctgctatagt atgttgaaaa aatatgcatt ttgtagtgaa    180
catttagtag aatagctctg atttcttact cttaattcat tacatattgt gcggtcgaat    240
tcagggagcc gataatgcgg ttacaataat tcctatactt aaatatacaa agatttaaaa    300
tttcaaaaaa tggttaccag catcgttagt gcgtatacat caagaggcac gtgcccggga    360
gacagcaagt aagctcttta aacatgcttt gacatacgat ttttaataaa acatgagcat    420
ttgaataaaa acgacttcct catactgtaa acatcacgca tgcacattag acaatagata    480
cagagatgca acacaggaga agcttcctta ggtttacatg tgctcttaat tacagcagaa    540
ccggtctgac ctcttctctt cctcccacag atcgaggacg agagaaacct gcacgaggac    600
ttcgtgttca tgaagaccat ccagcggtgc aacaccggcg agagaagtct gagcctgctg    660
aactgcgagg aaatcaagag ccagttcgag ggcttcgtga aggacatcat gctgaacaaa    720
gaggaaacga agaaagaaaa ctccttcgag atgcagaagg gcgaccagaa tcctcagatc    780
gccgctcacg tgatcagcga ggccagcagc aagacaacaa gcgtgctgca gtgggccgag    840
aagggctact acaccatgag caacaacctg gtcaccctgg aaaacggcaa gcagctgaca    900
gtgaagcggc agggcctgta ctacatctac gcccaagtga ccttctgcag caacagagag    960
gccagctctc aggccccttt tatcgccagc ctgtgcctga agtccctgg cagattcgag    1020
cggattctgc tgagagccgc caacacacac agcagcgcca accttgtgg ccagcagtct    1080
attcacctcg gcggagtgtt tgagctgcag cctggcgcaa gcgtgttcgt gaatgtgaca    1140
gaccctagcc aggtgtccca cggcaccggc tttacatctt tcggactgct gaagctgtga    1200
acagtgtcac cttgcaggct gtggtggagc tgacgctggg agtcttcata atacagcaca    1260
gcggttaagc ccaccccctg ttaactgcct atttataacc ctaggatcct ccttatggag    1320
aactatttat tatacactcc aaggcatgta gaactgtaat aagtgaatta caggtcacat    1380
gaaaccaaaa cgggccctgc tccataagag cttatatatc tgaagcagca accccactga    1440
tgcagacatc cagagagtcc tatgaaaaga caaggccatt atgcacaggt tgaattctga    1500
gtaaacagca gataacttgc caagttcagt tttgtttctt tgcgtgcagt gtctttccat    1560
ggataatgca tttgatttat cagtgaagat gcagaaggga aatggggagc ctcagctcac    1620
attcagttat ggttgactct gggttcctat ggccttgttg gaggggccca ggctctagaa    1680
cgtctaacac agtggagaac cgaaccccc cccccccgcc accctctcgg acagttattc    1740
attctctttc aatctctctc tctccatctc tctctttcag tctctctctc tcaacctctt    1800
tcttccaatc tctctttctc aatctctctg tttccctttg tcagtctctt ccctccccca    1860
gtctctcttc tcaatccccc tttctaacac acacacacac acacacacac acacacacac    1920
acacacacac acacacacag agtcaggccg ttgctagtca gttctcttct ttccaccctg    1980
tccctatctc taccactata gatgagggtg aggagtaggg agtgcagccc tgagcctgcc    2040
cactcctcat tacgaaatga ctgtatttaa aggaaatcta ttgtatctac ctgcagtctc    2100
```

```
cattgtttcc agagtgaact tgtaattatc ttgttattta ttttttgaat aataaagacc    2160
tcttaacatt acgcgcttaa cattatcgtt gttgtttgag tacctaaagc tcccagccag    2220
gttggggaaa gaggaagcat ttggagggaa ttttcccaac ctttgtgatg ttttcataaa    2280
ctttgttctc aagctactta cattacgcgt actagttggc tccggtgccc gtcagtgggc    2340
agagcgcaca tcgcccacag tccccgagaa gttgggggga ggggtcggca attgaaccgg    2400
tgcctagaga aggtggcgcg gggtaaactg ggaaagtgat gtcgtgtact ggctccgcct    2460
ttttcccgag ggtgggggag aaccgtatat aagtgcagta gtcgccgtga acgttctttt    2520
tcgcaacggg tttgccgcca gaacacaggt gtcgtgacgc ggatcgtacc cgggttaagg    2580
gcgaattcca gcacactggc ggccgttact agtggatcca ccggtcgcca ccatggtgag    2640
caagggcgag gagctgttca ccggggtggt gcccatcctg gtcgagctgg acggcgacgt    2700
aaacggccac aagttcagcg tgtccggcga gggcgagggc gatgccacct acggcaagct    2760
gaccctgaag ttcatctgca ccaccggcaa gctgcccgtg ccctggccca ccctcgtgac    2820
caccctgacc tacggcgtgc agtgcttcag ccgctacccc gaccacatga agcagcacga    2880
cttcttcaag tccgccatgc ccgaaggcta cgtccaggag cgcaccatct tcttcaagga    2940
cgacggcaac tacaagaccc gcgccgaggt gaagttcgag ggcgacaccc tggtgaaccg    3000
catcgagctg aagggcatcg acttcaagga ggacggcaac atcctggggc acaagctgga    3060
gtacaactac aacagccaca acgtctatat catggccgac aagcagaaga acggcatcaa    3120
ggtgaacttc aagatccgcc acaacatcga ggacggcagc gtgcagctcg ccgaccacta    3180
ccagcagaac acccccatcg gcgacggccc cgtgctgctg cccgacaacc actacctgag    3240
cacccagtcc gccctgagca agacccccaa cgagaagcgc gatcacatgg tcctgctgga    3300
gttcgtgacc gccgccggga tcactctcgg catggacgag ctgtacaagt aaagcggccg    3360
cgtcgagtct agagggcccg tttaaacccg ctgatcagcc tcgactgtgc cttctagttg    3420
ccagccatct gttgtttgcc cctcccccgt gccttccttg accctggaag gtgccactcc    3480
cactgccctt tcctaataaa atgaggaaat tgcatcgcat tgtctgagta ggtgtcattc    3540
tattctgggg ggtggggtgg ggcaggacag caaggggag gattgggaag acaatagcag    3600
gcatgctggg gatgcggtgg gctctatggt accagcttaa ctcgttaact gacacattgc    3660
aaattaacat ccagtaacga aacggcttca gtcgtaatcg cccatatagt tggctacaga    3720
atgttggata gagaacttaa gtacgctaag gcggcgtatt ttcttaatat ttaggggtat    3780
tgccgcagtc attacagata accgcctatg cggccatgcc aggattatag ataactttt    3840 aacattagcc gcagaggtgg gactagcacg taatacctgg agtttctgat aacatgacat    3900
cttaattgct gtcttttata gattttaaa ctgcaaatac aaaatagcaa tcagccaata    3960
taataactta ttattctcca tttatgcctg aaagtcctcc tcttgttgat gccgtggaaa    4020
tgaatgtaga ggcagatatc attagctgta ttctccttcc gaatgacatt tatcatatcc    4080
ttgttattcc aaaatagata gaagatgaaa ggaatcttca tgaagatttt gtattcatga    4140
aaac                                                                4144
```

<210> SEQ ID NO 39
<211> LENGTH: 3668
<212> TYPE: DNA
<213> ORGANISM: Artificial Sequence
<220> FEATURE:
<223> OTHER INFORMATION: Donor sequence, donor 6 gRNA-G_HA + cDNA +
      GFP - Stuffer

<400> SEQUENCE: 39

```
ttcttttat aaagcactgc atcacaaaca ctaaaatgaa gtgggcaaat tagctctgca        60
gaaaactatt ttctaggctg atgtttataa tgaccaatca ttactgaagc aatgagaaat       120
gtgacaatta cagaatattg ctgctatagt atgttgaaaa aatatgcatt ttgtagtgaa       180
catttagtag aatagctctg atttctgata cagagatgca acacaggaga agcttcctta      240
ggtttacatg tgctcttaat tacagcagaa ccggtctgac ctcttctctt cctcccacag      300
atcgaggacg agagaaacct gcacgaggac ttcgtgttca tgaagaccat ccagcggtgc      360
aacaccggcg agagaagtct gagcctgctg aactgcgagg aaatcaagag ccagttcgag      420
ggcttcgtga aggacatcat gctgaacaaa gaggaaacga agaaagaaaa ctccttcgag      480
atgcagaagg cgaccagaa tcctcagatc gccgctcacg tgatcagcga ggccagcagc      540
aagacaacaa gcgtgctgca gtgggccgag aagggctact acaccatgag caacaacctg      600
gtcaccctgg aaaacggcaa gcagctgaca gtgaagcggc agggcctgta ctacatctac      660
gcccaagtga ccttctgcag caacagagag gccagctctc aggcccctt tatcgccagc      720
ctgtgcctga agtcccctgg cagattcgag cggattctgc tgagagccgc caacacacac      780
agcagcgcca aaccttgtgg ccagcagtct attcacctcg gcggagtgtt tgagctgcag      840
cctggcgcaa gcgtgttcgt gaatgtgaca gaccctagcc aggtgtccca cggcaccggc      900
tttacatctt tcggactgct gaagctgtga acagtgtcac cttgcaggct gtggtggagc      960
tgacgctggg agtcttcata atacagcaca gcggttaagc ccaccccctg ttaactgcct     1020
atttataacc ctaggatcct ccttatggag aactatttat tatacactcc aaggcatgta     1080
gaactgtaat aagtgaatta caggtcacat gaaaccaaaa cgggccctgc tccataagag     1140
cttatatatc tgaagcagca accccactga tgcagacatc cagagagtcc tatgaaaaga     1200
caaggccatt atgcacaggt tgaattctga gtaaacagca gataacttgc caagttcagt     1260
tttgtttctt tgcgtgcagt gtctttccat ggataatgca tttgatttat cagtgaagat     1320
gcagaaggga aatggggagc ctcagctcac attcagttat ggttgactct gggttcctat     1380
ggccttgttg gaggggggcca ggctctagaa cgtctaacac agtggagaac cgaaaccccc     1440
cccccccgcc accctctcgg acagttattc attctctttc aatctctctc tctccatctc     1500
tctctttcag tctctctctc tcaacctctt tcttccaatc tctcttctc aatctctctg      1560
tttccctttg tcagtctctt ccctccccca gtctctcttc tcaatccccc tttctaacac     1620
acacacacac acacacacac acacacacac acacacacac acacacacag agtcaggccg     1680
ttgctagtca gttctcttct ttccaccctg tccctatctc taccactata gatgagggtg     1740
aggagtaggg agtgcagccc tgagcctgcc cactcctcat tacgaaatga ctgtatttaa     1800
aggaaatcta ttgtatctac ctgcagtctc cattgtttcc agagtgaact tgtaattatc     1860
ttgttattta ttttttgaat aataaagacc tcttaacatt acgcgcttaa cattatcgtt     1920
gttgtttgag tacctaaagc tcccagccag gttgggaaa gaggaagcat ttggagggaa       1980
ttttcccaac ctttgtgatg ttttcataaa ctttgttctc aagctactta cattacgcgt     2040
actagttggc tccggtgccc gtcagtgggc agagcgcaca tcgcccacag tccccgagaa     2100
gttgggggga ggggtcggca attgaaccgg tgcctagaga aggtggcgcg ggtaaactg       2160
ggaaagtgat gtcgtgtact ggctccgcct ttttcccgag ggtgggggag aaccgtatat     2220
aagtgcagta gtcgccgtga acgttctttt tcgcaacggg tttgccgcca gaacacaggt     2280
gtcgtgacgc ggatcgtacc cgggttaagg gcgaattcca gcacactggc ggccgttact     2340
```

```
agtggatcca ccggtcgcca ccatggtgag caagggcgag gagctgttca ccggggtggt    2400
gcccatcctg gtcgagctgg acggcgacgt aaacggccac aagttcagcg tgtccggcga    2460
gggcgagggc gatgccacct acggcaagct gaccctgaag ttcatctgca ccaccggcaa    2520
gctgcccgtg ccctggccca cctcgtgac caccctgacc tacggcgtgc agtgcttcag    2580
ccgctacccc gaccacatga agcagcacga cttcttcaag tccgccatgc ccgaaggcta    2640
cgtccaggag cgcaccatct tcttcaagga cgacggcaac tacaagaccc gcgccgaggt    2700
gaagttcgag ggcgacaccc tggtgaaccg catcgagctg aagggcatcg acttcaagga    2760
ggacggcaac atcctggggc acaagctgga gtacaactac aacagccaca cgtctatat    2820 catggccgac aagcagaaga acggcatcaa ggtgaacttc aagatccgcc acaacatcga    2880
ggacggcagc gtgcagctcg ccgaccacta ccagcagaac cccccatcg cgacggccc     2940 cgtgctgctg cccgacaacc actacctgag cacccagtcc gccctgagca agacccccaa    3000
cgagaagcgc gatcacatgg tcctgctgga gttcgtgacc gccgccggga tcactctcgg    3060
catggacgag ctgtacaagt aaagcggccg cgtcgagtct agagggcccg tttaaacccg    3120
ctgatcagcc tcgactgtgc cttctagttg ccagccatct gttgtttgcc ctcccccgt     3180 gccttccttg accctggaag gtgccactcc cactgcccct tcctaataaa atgaggaaat    3240
tgcatcgcat tgtctgagta ggtgtcattc tattctgggg ggtggggtgg ggcaggacag    3300 caaggggag gattgggaag acaatagcag gcatgctggg gatgcggtgg gctctatggt     3360
accagcttaa ctcgttaact gacacattgc aaattaacac ctggagtttc tgataacatg    3420
acatcttaat tgctgtcttt tatagatttt taaactgcaa atacaaaata gcaatcagcc    3480
aatataataa cttattattc tccatttatg cctgaaagtc ctcctcttgt tgatgccgtg    3540
gaaatgaatg tagaggcaga tatcattagc tgtattctcc ttccgaatga catttatcat    3600
atccttgtta ttccaaaata gatagaagat gaaaggaatc ttcatgaaga ttttgtattc    3660
atgaaaac                                                              3668
```

<210> SEQ ID NO 40  
<211> LENGTH: 2831  
<212> TYPE: DNA  
<213> ORGANISM: Artificial Sequence  
<220> FEATURE:  
<223> OTHER INFORMATION: Donor sequence, donor 7 gRNA-G_HA + cDNA - GFP + Stuffer

<400> SEQUENCE: 40

```
ttcttttat aaagcactgc atcacaaaca ctaaaatgaa gtgggcaaat tagctctgca     60
gaaaactatt ttctaggctg atgtttataa tgaccaatca ttactgaagc aatgagaaat    120
gtgacaatta cagaatattg ctgctatagt atgttgaaaa aatatgcatt ttgtagtgaa    180
catttagtag aatagctctg atttcttact cttaattcat tacatattgt gcggtcgaat    240
tcagggagcc gataatgcgg ttacaataat tcctatactt aaatatacaa agatttaaaa    300
tttcaaaaaa tggttaccag catcgttagt gcgtatacat caagaggcac gtgccccgga    360
gacagcaagt aagctcttta acatgctttt gacatacgat ttttaataaa acatgagcat    420
ttgaataaaa acgacttcct catactgtaa acatcacgca tgcacattag acaatagata    480
cagagatgca acacaggaga agcttcctta ggtttacatg tgctcttaat tacagcagaa    540
ccggtctgac ctcttctctt cctcccacag atcgaggacg agagaaacct gcacgaggac    600
ttcgtgttca tgaagaccat ccagcggtgc aacaccggcg agagaagtct gagcctgctg    660
```

```
aactgcgagg aaatcaagag ccagttcgag ggcttcgtga aggacatcat gctgaacaaa    720
gaggaaacga agaagaaaa ctccttcgag atgcagaagg gcgaccagaa tcctcagatc     780
gccgctcacg tgatcagcga ggccagcagc aagacaacaa gcgtgctgca gtgggccgag    840
aagggctact acaccatgag caacaacctg gtcaccctgg aaaacggcaa gcagctgaca    900
gtgaagcggc agggcctgta ctacatctac gcccaagtga ccttctgcag caacagagag    960
gccagctctc aggcccctt tatcgccagc ctgtgcctga gtcccctgg cagattcgag      1020 cggattctgc tgagagccgc caacacacac agcagcgcca aaccttgtgg ccagcagtct   1080
attcacctcg gcgagtgtt tgagctgcag cctggcgcaa gcgtgttcgt gaatgtgaca    1140
gaccctagcc aggtgtccca cggcaccggc tttacatctt tcggactgct gaagctgtga   1200
acagtgtcac cttgcaggct gtggtggagc tgacgctggg agtcttcata atacagcaca   1260
gcggttaagc ccaccccctg ttaactgcct atttataacc ctaggatcct ccttatggag   1320
aactatttat tatacactcc aaggcatgta gaactgtaat aagtgaatta caggtcacat   1380
gaaaccaaaa cgggccctgc tccataagag cttatatatc tgaagcagca accccactga   1440
tgcagacatc cagagagtcc tatgaaaaga caaggccatt atgcacaggt tgaattctga   1500
gtaaacagca gataacttgc caagttcagt tttgtttctt tgcgtgcagt gtctttccat   1560
ggataatgca tttgatttat cagtgaagat gcagaaggga aatggggagc ctcagctcac   1620
attcagttat ggttgactct gggttcctat ggccttgttg gaggggggcca ggctctagaa  1680 cgtctaacac agtggagaac cgaaaccccc ccccccgcc accctctcgg acagttattc    1740
attctctttc aatctctctc tctccatctc tctctttcag tctctctctc tcaacctctt   1800
tcttccaatc tctctttctc aatctctctg tttcccttg tcagtctctt ccctccccca    1860
gtctctcttc tcaatccccc tttctaacac acacacacac acacacacac acacacacac   1920
acacacacac acacacacag agtcaggccg ttgctagtca gttctcttct ttccaccctg   1980
tccctatctc taccactata gatgagggtg aggagtaggg agtgcagccc tgagcctgcc   2040
cactcctcat tacgaaatga ctgtatttaa aggaaatcta ttgtatctac ctgcagtctc   2100
cattgtttcc agagtgaact tgtaattatc ttgttattta tttttgaat aataaagacc    2160 tcttaacatt acgcgcttaa cattatcgtt gttgtttgag tacctaaagc tcccagccag   2220 gttgggaaa gaggaagcat ttggagggaa ttttcccaac ctttgtgatg ttttcataaa    2280
ctttgttctc aagctactta cattacgcgt actagttacc agcttaactc gttaactgac   2340
acattgcaaa ttaacatcca gtaacgaaac ggcttcagtc gtaatcgccc atatagttgg   2400
ctacagaatg ttggatagag aacttaagta cgctaaggcg gcgtattttc ttaatattta   2460
ggggtattgc cgcagtcatt acagataacc gcctatgcgg ccatgccagg attatagata   2520 acttttttaac attagccgca gaggtgggac tagcacgtaa tacctggagt ttctgataac   2580 atgcatctt aattgctgtc ttttatagat ttttaaactg caaatacaaa atagcaatca    2640
gccaatataa taacttatta ttctccattt atgcctgaaa gtcctcctct tgttgatgcc   2700
gtggaaatga atgtagaggc agatatcatt agctgtattc tccttccgaa tgacatttat   2760
catatccttg ttattccaaa atagatagaa gatgaaagga atcttcatga agattttgta   2820
ttcatgaaaa c                                                         2831
```

<210> SEQ ID NO 41
<211> LENGTH: 2355
<212> TYPE: DNA

<213> ORGANISM: Artificial Sequence
<220> FEATURE:
<223> OTHER INFORMATION: Donor sequence, donor 8 gRNA-G_HA + cDNA - GFP - Stuffer

<400> SEQUENCE: 41

```
ttcttttat aaagcactgc atcacaaaca ctaaaatgaa gtgggcaaat tagctctgca      60
gaaaactatt ttctaggctg atgtttataa tgaccaatca ttactgaagc aatgagaaat    120
gtgacaatta cagaatattg ctgctatagt atgttgaaaa aatatgcatt ttgtagtgaa    180
catttagtag aatagctctg atttctgata cagagatgca acacaggaga agcttcctta    240
ggtttacatg tgctcttaat tacagcagaa ccggtctgac ctcttctctt cctcccacag    300
atcgaggacg agagaaacct gcacgaggac ttcgtgttca tgaagaccat ccagcggtgc    360
aacaccggcg agagaagtct gagcctgctg aactgcgagg aaatcaagag ccagttcgag    420
ggcttcgtga aggacatcat gctgaacaaa gaggaaacga gaaagaaaa ctccttcgag     480
atgcagaagg gcgaccagaa tcctcagatc gccgctcacg tgatcagcga ggccagcagc    540
aagacaacaa gcgtgctgca gtgggccgag aagggctact acaccatgag caacaacctg    600
gtcaccctgg aaaacggcaa gcagctgaca gtgaagcggc agggcctgta ctacatctac    660
gcccaagtga ccttctgcag caacagagag gccagctctc aggcccctt tatcgccagc     720
ctgtgcctga gtcccctgg cagattcgag cggattctgc tgagagccgc caacacacac     780
agcagcgcca aacttgtgg ccagcagtct attcacctcg gcggagtgtt tgagctgcag     840
cctggcgcaa gcgtgttcgt gaatgtgaca gaccctagcc aggtgtccca cggcaccggc    900
tttacatctt tcggactgct gaagctgtga acagtgtcac cttgcaggct gtggtggagc    960
tgacgctggg agtcttcata atacagcaca gcggttaagc ccaccccctg ttaactgcct   1020
atttataacc ctaggatcct ccttatggag aactatttat tatacactcc aaggcatgta   1080
gaactgtaat aagtgaatta caggtcacat gaaaccaaaa cgggccctgc tccataagag   1140
cttatatatc tgaagcagca accccactga tgcagacatc cagagagtcc tatgaaaaga   1200
caaggccatt atgcacaggt tgaattctga gtaaacagca gataacttgc caagttcagt   1260
tttgtttctt tgcgtgcagt gtcttttccat ggataatgca tttgatttat cagtgaagat   1320
gcagaaggga aatggggagc ctcagctcac attcagttat ggttgactct gggttcctat   1380
ggccttgttg gaggggccca ggctctagaa cgtctaacac agtggagaac cgaaaccccc   1440
ccccccgcc accctctcgg acagttattc attctctttc aatctctctc tctccatctc    1500
tctcttttcag tctctctctc tcaacctctt cttccaatc tctcttttctc aatctctctg   1560
tttcccttttg tcagtctctt ccctccccca gtctctcttc tcaatccccc tttctaacac   1620
acacacacac acacacacac acacacacac acacacacac acacacacag agtcaggccg   1680
ttgctagtca gttctcttct ttccaccctg tccctatctc taccactata gatgagggtg   1740
aggagtaggg agtgcagccc tgagcctgcc cactcctcat tacgaaatga ctgtatttaa   1800
aggaaatcta ttgtatctac ctgcagtctc cattgtttcc agagtgaact tgtaattatc   1860
ttgttattta ttttttgaat aataaagacc tcttaacatt acgcgcttaa cattatcgtt   1920
gttgtttgag tacctaaagc tcccagccag gttggggaaa gaggaagcat ttggagggaa   1980
ttttcccaac ctttgtgatg ttttcataaa ctttgttctc aagctactta cattacgcgt   2040
actagttacc agcttaactc gttaactgac acattgcaaa ttaacacctg gagtttctga   2100
taacatgaca tcttaattgc tgtctttat agatttttaa actgcaaata caaaatagca   2160
```

```
atcagccaat ataataactt attattctcc atttatgcct gaaagtcctc ctcttgttga    2220
tgccgtggaa atgaatgtag aggcagatat cattagctgt attctccttc cgaatgacat    2280
ttatcatatc cttgttattc caaaatagat agaagatgaa aggaatcttc atgaagattt    2340
tgtattcatg aaaac                                                     2355

<210> SEQ ID NO 42
<211> LENGTH: 3943
<212> TYPE: DNA
<213> ORGANISM: Artificial Sequence
<220> FEATURE:
<223> OTHER INFORMATION: Donor sequence, donor 9 gRNA-C_HA + cDNA +
      GFP + Stuffer

<400> SEQUENCE: 42
gatacttgag tgtcctctct taggatctgg acctagaatt aatgtcatga gattttcta      60 acaggataag gtgaggtagt gagggctgaa gtcatccact gggttatcca aatattaggt    120
ttcactgctg acaaaagagg gggcttctgg tctggttggt tatttgtgtt tggcctgatg    180
tgctctgtca atcaaatgta tggacatagg cctagcttct aaaggggcaa tagtgacctc    240
agtactctta attcattaca tattgtgcgg tcgaattcag ggagccgata atgcggttac    300
aataattcct atacttaaat atacaaagat ttaaaatttc aaaaaatggt taccagcatc    360
gttagtgcgt atagcaagtg aattctgtac atttaattat tctaaaagct tccttaggtt    420
tacatgtgct cttaattaca gcagaaccgg tctgacctct tctcttcctc ccacagatcg    480
aggacgagag aaacctgcac gaggacttcg tgttcatgaa gaccatccag cggtgcaaca    540
ccggcgagag aagtctgagc ctgctgaact gcgaggaaat caagagccag ttcgagggct    600
tcgtgaagga catcatgctg aacaaagagg aaacgaagaa agaaaactcc ttcgagatgc    660
agaagggcga ccagaatcct cagatcgccg ctcacgtgat cagcgaggcc agcagcaaga    720
caacaagcgt gctgcagtgg gccgagaagg gctactacac catgagcaac aacctggtca    780
ccctggaaaa cggcaagcag ctgacagtga agcggcaggg cctgtactac atctacgccc    840
aagtgacctt ctgcagcaac agagaggcca gctctcaggc ccctttttatc gccagcctgt    900 gcctgaagtc ccctggcaga ttcgagcgga ttctgctgag agccgccaac acacacagca    960
gcgccaaacc ttgtgccag cagtctattc acctcggcgg agtgtttgag ctgcagcctg   1020
gcgcaagcgt gttcgtgaat gtgacagacc ctagccaggt gtcccacggc accggcttta   1080
catctttcgg actgctgaag ctgtgaacag tgtcaccttg caggctgtgg tggagctgac   1140
gctgggagtc ttcataatac agcacagcgg ttaagcccac cccctgttaa ctgcctattt   1200
ataaccctag gatcctcctt atggagaact atttattata cactccaagg catgtagaac   1260
tgtaataagt gaattacagg tcacatgaaa ccaaaacggg ccctgctcca taagagctta   1320
tatatctgaa gcagcaaccc cactgatgca gacatccaga gagtcctatg aaaagacaag   1380
gccattatgc acaggttgaa ttctgagtaa acagcagata acttgccaag ttcagttttg   1440
tttctttgcg tgcagtgtct ttccatggat aatgcatttg atttatcagt gaagatgcag   1500
aagggaaatg gggagcctca gctcacattc agttatggtt gactctgggt tcctatggcc   1560
ttgttggagg gggccaggct ctagaacgtc taacacagtg gagaaccgaa accccccccc   1620
cccgccaccc tctcggacag ttattcattc tctttcaatc tctctctctc catctctctc   1680
tttcagtctc tctctctcaa cctctttctt ccaatctctc tttctcaatc tctctgtttc   1740
cctttgtcag tctcttccct ccccccagtct ctcttctcaa tccccctttc taacacacac   1800
```

```
acacacacac acacacacac acacacacac acacacacac acacagagtc aggccgttgc    1860
tagtcagttc tcttctttcc accctgtccc tatctctacc actatagatg agggtgagga    1920
gtagggagtg cagccctgag cctgcccact cctcattacg aaatgactgt atttaaagga    1980
aatctattgt atctacctgc agtctccatt gtttccagag tgaacttgta attatcttgt    2040
tatttatttt ttgaataata aagacctctt aacattacgc gcttaacatt atcgttgttg    2100
tttgagtacc taaagctccc agccaggttg gggaaagagg aagcatttgg agggaatttt    2160
cccaaccttt gtgatgtttt cataaacttt gttctcaagc tacttacatt acgcgtacta    2220
gttggctccg gtgcccgtca gtgggcagag cgcacatcgc ccacagtccc cgagaagttg    2280
gggggagggg tcggcaattg aaccggtgcc tagagaaggt ggcgcggggt aaactgggaa    2340
agtgatgtcg tgtactggct ccgccttttt cccgagggtg ggggagaacc gtatataagt    2400
gcagtagtcg ccgtgaacgt tctttttcgc aacgggtttg ccgccagaac acaggtgtcg    2460
tgacgcggat cgtacccggg ttaagggcga attccagcac actggcggcc gttactagtg    2520
gatccaccgg tcgccaccat ggtgagcaag ggcgaggagc tgttcaccgg ggtggtgccc    2580
atcctggtcg agctggacgg cgacgtaaac ggccacaagt tcagcgtgtc cggcgagggc    2640
gagggcgatg ccacctacgg caagctgacc ctgaagttca tctgcaccac cggcaagctg    2700
cccgtgccct ggcccaccct cgtgaccacc ctgacctacg gcgtgcagtg cttcagccgc    2760
taccccgacc acatgaagca gcacgacttc ttcaagtccg ccatgcccga aggctacgtc    2820
caggagcgca ccatcttctt caaggacgac ggcaactaca agacccgcgc cgaggtgaag    2880
ttcgagggcg acaccctggt gaaccgcatc gagctgaagg gcatcgactt caaggaggac    2940
ggcaacatcc tggggcacaa gctggagtac aactacaaca gccacaacgt ctatatcatg    3000
gccgacaagc agaagaacgg catcaaggtg aacttcaaga tccgccacaa catcgaggac    3060
ggcagcgtgc agctcgccga ccactaccag cagaacaccc ccatcggcga cggccccgtg    3120
ctgctgcccg acaaccacta cctgagcacc cagtccgccc tgagcaaaga ccccaacgag    3180
aagcgcgatc acatggtcct gctggagttc gtgaccgccg ccgggatcac tctcggcatg    3240
gacgagctgt acaagtaaag cggccgcgtc gagtctagag ggcccgttta aacccgctga    3300
tcagcctcga ctgtgccttc tagttgccag ccatctgttg tttgcccctc cccgtgcctt    3360
tccttgaccc tggaaggtgc cactcccact gcccttttcct aataaaatga ggaaattgca    3420
tcgcattgtc tgagtaggtg tcattctatt ctggggggtg gggtggggca ggacagcaag    3480
ggggaggatt gggaagacaa tagcaggcat gctggggatg cggtgggctc tatggtacca    3540
gcttcatctg gatgattgca ctttatcagg catcaagagg cacgtgcccc ggagacagca    3600
agtaagctct ttaaacatgc tttgacatac gattttttaat aaaacatgag catttgaata    3660
aaaacgactt cctcatactg taaacatcac gcatgcacat tagacaataa tccagtaacg    3720
aaacggcttc agtcgtaatc gcccatatag ttggctacag aatgttggat agagaactta    3780
agtacgctaa ggcggcgtat tttcttaata tttggactga tatttaccgt actatttaca    3840
tgtgctctta attacagcag aagctgccag ctaactgaat cttgttttga atctaaaaaa    3900
tctactctta aagcaagaaa atggtataaa attagttgat aat                     3943
```

```
<210> SEQ ID NO 43
<211> LENGTH: 4140
<212> TYPE: DNA
<213> ORGANISM: Artificial Sequence
<220> FEATURE:
<223> OTHER INFORMATION: Donor sequence, donor 10 gRNA-D_HA + cDNA +
```

GFP + Stuffer

<400> SEQUENCE: 43

```
agatctttga ttagttttct ggctgttcct aaaattctgg atgcaggaac tgtggctaga      60
aagcatctgg atgattgcac tttatcaggg atacttgagt gtcctctctt aggatctgga     120
cctagaatta atgtcatgag attttttctaa caggataagg tgaggtagtg agggctgaag    180
tcattactct taattcatta catattgtgc ggtcgaattc agggagccga taatgcggtt     240
acaataattc ctatacttaa atatacaaag atttaaaatt tcaaaaaatg gttaccagca     300
tcgttagtgc gtatacatca agaggcacgt gccccggaga cagcaagtaa gctctttaaa     360
catgctttga catacgattt ttaataaaac atgagcattt gaataaaaac gacttcctca     420
tactgtaaac atcacgcatg cacattagac aataatccag taacgaaaga attctgtaca     480
tttaattatt ctaagacatt ggaagcttcc ttaggtttac atgtgctctt aattacagca     540
gaaccggtct gacctcttct cttcctccca cagatcgagg acgagagaaa cctgcacgag     600
gacttcgtgt tcatgaagac catccagcgg tgcaacaccg gcgagagaag tctgagcctg     660
ctgaactgcg aggaaatcaa gagccagttc gagggcttcg tgaaggacat catgctgaac     720
aaagaggaaa cgaagaaaga aaactccttc gagatgcaga agggcgacca gaatcctcag     780
atcgccgctc acgtgatcag cgaggccagc agcaagacaa caagcgtgct gcagtgggcc     840
gagaagggct actacaccat gagcaacaac ctggtcaccc tggaaaacgg caagcagctg     900
acagtgaagc ggcagggcct gtactacatc tacgcccaag tgaccttctg cagcaacaga     960
gaggccagtc tcaggccccc ttttatcgcc agcctgtgcc tgaagtcccc tggcagattc    1020
gagcggattc tgctgagagc cgccaacaca cacagcagcg ccaaaccttg tggccagcag    1080
tctattcacc tcggcggagt gtttgagctg cagcctggcg caagcgtgtt cgtgaatgtg    1140
acagacccta gccaggtgtc ccacggcacc ggctttacat ctttcggact gctgaagctg    1200
tgaacagtgt caccttgcag gctgtggtgg agctgacgct gggagtcttc ataatacagc    1260
acagcggtta agcccacccc ctgttaactg cctatttata accctaggat cctccttatg    1320
gagaactatt tattatacac tccaaggcat gtagaactgt aataagtgaa ttacaggtca    1380
catgaaacca aaacgggccc tgctccataa gagcttatat atctgaagca gcaaccccac    1440
tgatgcagac atccagagag tcctatgaaa agacaaggcc attatgcaca ggttgaattc    1500
tgagtaaaca gcagataact tgccaagttc agttttgttt ctttgcgtgc agtgtctttc    1560
catggataat gcatttgatt tatcagtgaa gatgcagaag ggaaatgggg agcctcagct    1620
cacattcagt tatggttgac tctgggttcc tatggccttg ttggaggggg ccaggctcta    1680
gaacgtctaa cacagtggag aaccgaaacc ccccccccc gccaccctct cggacagtta    1740
ttcattctct ttcaatctct ctctctccat ctctctcttt cagtctctct ctctcaacct    1800
ctttcttcca atctctcttt ctcaatctct ctgtttccct ttgtcagtct cttccctccc    1860
ccagtctctc ttctcaatcc cccttttctaa cacacacaca cacacacaca cacacacaca    1920
cacacacaca cacacacaca cagagtcagg ccgttgctag tcagttctct tctttccacc    1980
ctgtccctat ctctaccact atagatgagg gtgaggagta gggagtgcag ccctgagcct    2040
gcccactcct cattacgaaa tgactgtatt taaaggaaat ctattgtatc tacctgcagt    2100
ctccattgtt tccagagtga acttgtaatt atcttgttat ttatttttg aataataaag    2160
acctcttaac attacgcgct taacattatc gttgttgttt gagtacctaa agctcccagc    2220
caggttgggg aaagaggaag catttggagg gaattttccc aacctttgtg atgttttcat    2280
```

```
aaactttgtt ctcaagctac ttacattacg cgtactagtt ggctccggtg cccgtcagtg   2340
ggcagagcgc acatcgccca cagtccccga gaagttgggg ggaggggtcg gcaattgaac   2400
cggtgcctag agaaggtggc gcggggtaaa ctgggaaagt gatgtcgtgt actggctccg   2460
cctttttccc gagggtgggg gagaaccgta tataagtgca gtagtcgccg tgaacgttct   2520
ttttcgcaac gggtttgccg ccagaacaca ggtgtcgtga cgcggatcgt acccgggtta   2580
agggcgaatt ccagcacact ggcggccgtt actagtggat ccaccggtcg ccaccatggt   2640
gagcaagggc gaggagctgt tcaccggggt ggtgcccatc ctggtcgagc tggacggcga   2700
cgtaaacggc cacaagttca gcgtgtccgg cgagggcgag ggcgatgcca cctacggcaa   2760
gctgaccctg aagttcatct gcaccaccgg caagctgccc gtgcctggc ccaccctcgt   2820 gaccaccctg acctacggcg tgcagtgctt cagccgctac cccgaccaca tgaagcagca   2880
cgacttcttc aagtccgcca tgcccgaagg ctacgtccag gagcgcacca tcttcttcaa   2940
ggacgacggc aactacaaga cccgcgccga ggtgaagttc gagggcgaca ccctggtgaa   3000
ccgcatcgag ctgaagggca tcgacttcaa ggaggacggc aacatcctgg ggcacaagct   3060
ggagtacaac tacaacagcc acaacgtcta tatcatggcc gacaagcaga agaacggcat   3120
caaggtgaac ttcaagatcc gccacaacat cgaggacggc agcgtgcagc tcgccgacca   3180
ctaccagcag aacacccca tcggcgacgg ccccgtgctg ctgcccgaca ccactacct   3240 gagcacccag tccgccctga gcaaagaccc caacgagaag cgcgatcaca tggtcctgct   3300
ggagttcgtg accgccgccg ggatcactct cggcatggac gagctgtaca agtaaagcgg   3360
ccgcgtcgag tctagagggc ccgtttaaac ccgctgatca gcctcgactg tgccttctag   3420
ttgccagcca tctgttgttt gcccctcccc cgtgccttcc ttgaccctgg aaggtgccac   3480
tcccactgcc ctttcctaat aaaatgagga aattgcatcg cattgtctga gtaggtgtca   3540
ttctattctg gggggtgggg tggggcagga cagcaagggg gaggattggg aagacaatag   3600
caggcatgct ggggatgcgg tgggctctat ggtaccagct ttaaatacca atcatagatg   3660
taaaggagaa agcggcttca gtcgtaatcg cccatatagt tggctacaga atgttggata   3720
gagaacttaa gtacgctaag gcggcgtatt ttcttaatat ttaggggtat tgccgcagtc   3780
attacagata accgcctatg cggccatgcc aggattatag ataacttttt aacattagcc   3840
gcagaggtgg ccactgggtt atccaaatat taggtttcac tgctgacaaa agaggggct   3900 tctggtctgg ttggttattt gtgtttggcc tgatgtgctc tgtcaatcaa atgtatggac   3960
ataggcctag cttctaaagg ggcaatagtg acctcagtgg actgatattt accgtactat   4020
ttacatgtgc tcttaattac agcagaagct gccagctaac tgaatcttgt tttgaatcta   4080
aaaaatctac tcttaaagca agaaaatggt ataaaattag ttgataatgc aagtagatct   4140
```

<210> SEQ ID NO 44
<211> LENGTH: 3678
<212> TYPE: DNA
<213> ORGANISM: Artificial Sequence
<220> FEATURE:
<223> OTHER INFORMATION: Donor sequence, donor 11 gRNA-D_HA + cDNA + GFP - Stuffer

<400> SEQUENCE: 44

```
agatctttga ttagttttct ggctgttcct aaaattctgg atgcaggaac tgtggctaga     60
aagcatctgg atgattgcac tttatcaggg atacttgagt gtcctctctt aggatctgga    120
cctagaatta atgtcatgag attttttctaa caggataagg tgaggtagtg agggctgaag    180
```

```
tcatgaattc tgtacattta attattctaa gacattggaa gcttccttag gtttacatgt    240
gctcttaatt acagcagaac cggtctgacc tcttctcttc ctcccacaga tcgaggacga    300
gagaaacctg cacgaggact tcgtgttcat gaagaccatc cagcggtgca acaccggcga    360
gagaagtctg agcctgctga actgcgagga aatcaagagc cagttcgagg gcttcgtgaa    420
ggacatcatg ctgaacaaag aggaaacgaa gaaagaaaac tccttcgaga tgcagaaggg    480
cgaccagaat cctcagatcg ccgctcacgt gatcagcgag gccagcagca agacaacaag    540
cgtgctgcag tgggccgaga agggctacta caccatgagc aacaacctgg tcaccctgga    600
aaacggcaag cagctgacag tgaagcggca gggcctgtac tacatctacg cccaagtgac    660
cttctgcagc aacagagagg ccagctctca ggccccttttt atcgccagcc tgtgcctgaa    720 gtccctggc agattcgagc ggattctgct gagagccgcc aacacacaca gcagcgccaa    780
accttgtggc cagcagtcta ttcacctcgg cggagtgttt gagctgcagc ctggcgcaag    840
cgtgttcgtg aatgtgacag accctagcca ggtgtcccac ggcaccggct ttacatcttt    900
cggactgctg aagctgtgaa cagtgtcacc ttgcaggctg tggtggagct gacgctggga    960
gtcttcataa tacagcacag cggttaagcc caccccctgt taactgccta tttataaccc   1020
taggatcctc cttatggaga actatttatt atacactcca aggcatgtag aactgtaata   1080
agtgaattac aggtcacatg aaaccaaaac gggccctgct ccataagagc ttatatatct   1140
gaagcagcaa ccccactgat gcagacatcc agagagtcct atgaaaagac aaggccatta   1200
tgcacaggtt gaattctgag taaacagcag ataacttgcc aagttcagtt ttgtttcttt   1260
gcgtgcagtg tctttccatg gataatgcat ttgatttatc agtgaagatg cagaagggaa   1320
atggggagcc tcagctcaca ttcagttatg gttgactctg ggttcctatg gccttgttgg   1380 aggggggccag gctctagaac gtctaacaca gtggagaacc gaaacccccc cccccgcca   1440 ccctctcgga cagttattca ttctctttca atctctctct ctccatctct ctctttcagt   1500
ctctctctct caacctcttt cttccaatct ctctttctca atctctctgt ttcccttttgt   1560 cagtctcttc cctccccag tctctcttct caatcccct ttctaacaca cacacacaca   1620
cacacacaca cacacacaca cacacacaca cacacacaga gtcaggccgt tgctagtcag   1680
ttctcttctt tccaccctgt ccctatctct accactatag atgagggtga ggagtaggga   1740
gtgcagccct gagcctgccc actcctcatt acgaaatgac tgtatttaaa ggaaatctat   1800
tgtatctacc tgcagtctcc attgtttcca gagtgaactt gtaattatct tgttatttat   1860 ttttttgaata ataaagacct cttaacatta cgcgcttaac attatcgttg ttgtttgagt   1920
acctaaagct cccagccagg ttggggaaag aggaagcatt tggagggaat tttcccaacc   1980
tttgtgatgt tttcataaac tttgttctca agctacttac attacgcgta ctagttggct   2040
ccggtgcccg tcagtgggca gagcgcacat cgcccacagt ccccgagaag ttgggggggag   2100 gggtcggcaa ttgaaccggt gcctagaaa ggtggcgcgg ggtaaactgg gaaagtgatg   2160
tcgtgtactg gctccgcctt tttcccgagg gtgggggaga accgtatata agtgcagtag   2220
tcgccgtgaa cgttcttttt cgcaacgggt ttgccgccag aacacaggtg tcgtgacgcg   2280
gatcgtaccc gggttaaggg cgaattccag cacactggcg gccgttacta gtggatccac   2340
cggtcgccac catggtgagc aagggcgagg agctgttcac cggggtggtg cccatcctgg   2400
tcgagctgga cggcgacgta aacggccaca agttcagcgt gtccggcgag ggcgagggcg   2460
atgccaccta cggcaagctg accctgaagt tcatctgcac caccggcaag ctgcccgtgc   2520
```

```
cctggcccac cctcgtgacc accctgacct acggcgtgca gtgcttcagc cgctaccccg    2580
accacatgaa gcagcacgac ttcttcaagt ccgccatgcc cgaaggctac gtccaggagc    2640
gcaccatctt cttcaaggac gacggcaact acaagacccg cgccgaggtg aagttcgagg    2700
gcgacaccct ggtgaaccgc atcgagctga agggcatcga cttcaaggag gacggcaaca    2760
tcctggggca caagctggag tacaactaca acagccacaa cgtctatatc atggccgaca    2820
agcagaagaa cggcatcaag gtgaacttca agatccgcca caacatcgag gacggcagcg    2880
tgcagctcgc cgaccactac cagcagaaca ccccccatcgg cgacggcccc gtgctgctgc    2940
ccgacaacca ctacctgagc acccagtccg ccctgagcaa agaccccaac gagaagcgcg    3000
atcacatggt cctgctggag ttcgtgaccg ccgccgggat cactctcggc atggacgagc    3060
tgtacaagta aagcggccgc gtcgagtcta gagggcccgt ttaaacccgc tgatcagcct    3120
cgactgtgcc ttctagttgc cagccatctg ttgtttgccc ctcccccgtg ccttccttga    3180
ccctggaagg tgccactccc actgcccttt cctaataaaa tgaggaaatt gcatcgcatt    3240
gtctgagtag gtgtcattct attctggggg gtggggtggg gcaggacagc aagggggagg    3300
attgggaaga caatagcagg catgctgggg atgcggtggg ctctatggta ccagctttaa    3360
ataccaatca tagatgtaaa ggagaaagcc actgggttat ccaaatatta ggtttcactg    3420
ctgacaaaag aggggcttc tggtctggtt ggttatttgt gtttggcctg atgtgctctg    3480
tcaatcaaat gtatggacat aggcctagct tctaaagggg caatagtgac ctcagtggac    3540
tgatatttac cgtactattt acatgtgctc ttaattacag cagaagctgc cagctaactg    3600
aatcttgttt tgaatctaaa aaatctactc ttaaagcaag aaaatggtat aaaattagtt    3660
gataatgcaa gtagatct                                                 3678

<210> SEQ ID NO 45
<211> LENGTH: 2817
<212> TYPE: DNA
<213> ORGANISM: Artificial Sequence
<220> FEATURE:
<223> OTHER INFORMATION: Donor sequence, donor 12 gRNA-D_HA + cDNA -
      GFP + Stuffer

<400> SEQUENCE: 45
agatctttga ttagttttct ggctgttcct aaaattctgg atgcaggaac tgtggctaga     60
aagcatctgg atgattgcac tttatcaggg atacttgagt gtcctctctt aggatctgga    120
cctagaatta atgtcatgag atttttctaa caggataagg tgaggtagtg agggctgaag    180
tcattactct taattcatta catattgtgc ggtcgaattc agggagccga taatgcggtt    240
acaataattc ctatacttaa atatacaaag atttaaaatt tcaaaaaatg gttaccagca    300
tcgttagtgc gtatacatca agaggcacgt gccccggaga cagcaagtaa gctctttaaa    360
catgctttga catacgattt ttaataaaac atgagcattt gaataaaaac gacttcctca    420
tactgtaaac atcacgcatg cacattagac aataatccag taacgaaaga attctgtaca    480
tttaattatt ctaagacatt ggaagcttcc ttaggtttac atgtgctctt aattacagca    540
gaaccggtct gacctcttct cttcctccca cagatcgagg acgagagaaa cctgcacgag    600
gacttcgtgt tcatgaagac catccagcgg tgcaacaccg cgagagaag tctgagcctg    660 ctgaactgcg aggaaatcaa gagccagttc gagggcttcg tgaaggacat catgctgaac    720
aaagaggaaa cgaagaaaga aaactccttc gagatgcaga agggcgacca gaatcctcag    780
atcgccgctc acgtgatcag cgaggccagc agcaagacaa caagcgtgct gcagtgggcc    840
```

-continued

```
gagaagggct actacaccat gagcaacaac ctggtcaccc tggaaaacgg caagcagctg    900
acagtgaagc ggcagggcct gtactacatc tacgcccaag tgaccttctg cagcaacaga    960
gaggccagct ctcaggcccc ttttatcgcc agcctgtgcc tgaagtcccc tggcagattc   1020
gagcggattc tgctgagagc cgccaacaca cacagcagcg ccaaaccttg tggccagcag   1080
tctattcacc tcggcggagt gtttgagctg cagcctggcg caagcgtgtt cgtgaatgtg   1140
acagaccta gccaggtgtc ccacggcacc ggctttacat ctttcggact gctgaagctg   1200
tgaacagtgt caccttgcag gctgtggtgg agctgacgct gggagtcttc ataatacagc   1260
acagcggtta agcccacccc ctgttaactg cctatttata accctaggat cctccttatg   1320
gagaactatt tattatacac tccaaggcat gtagaactgt aataagtgaa ttacaggtca   1380
catgaaacca aaacgggccc tgctccataa gagcttatat atctgaagca gcaaccccac   1440
tgatgcagac atccagagag tcctatgaaa agacaaggcc attatgcaca ggttgaattc   1500
tgagtaaaca gcagataact tgccaagttc agttttgttt ctttgcgtgc agtgtctttc   1560
catggataat gcatttgatt tatcagtgaa gatgcagaag ggaaatgggg agcctcagct   1620
cacattcagt tatggttgac tctgggttcc tatggccttg ttggagggg ccaggctcta   1680
gaacgtctaa cacagtggag aaccgaaacc cccccccc gccaccctct cggacagtta   1740
ttcattctct ttcaatctct ctctctccat ctctctcttt cagtctctct ctctcaacct   1800
cttcttcca atctctcttt tcaatctct ctgttccct ttgtcagtct cttccctccc    1860
ccagtctctc ttctcaatcc ccctttctaa cacacacaca cacacacaca cacacacaca   1920
cacacacaca cacacacaca cagagtcagg ccgttgctag tcagttctct tctttccacc   1980
ctgtccctat ctctaccact atagatgagg gtgaggagta gggagtgcag ccctgagcct   2040
gcccactcct cattacgaaa tgactgtatt taaaggaaat ctattgtatc tacctgcagt   2100
ctccattgtt tccagagtga acttgtaatt atcttgttat ttattttttg aataataaag   2160
acctcttaac attacgcgct taacattatc gttgttgttt gagtacctaa agctcccagc   2220
caggttgggg aaagaggaag catttggagg gaattttccc aacctttgtg atgttttcat   2280
aaactttgtt ctcaagctac ttacattacg cgtactagta aataccaatc atagatgtaa   2340
aggagaaagc ggcttcagtc gtaatcgccc atatagttgg ctacagaatg ttggatagag   2400
aacttaagta cgctaaggcg gcgtattttc ttaatattta ggggtattgc cgcagtcatt   2460
acagataacc gcctatgcgg ccatgccagg attatagata acttttttaac attagccgca   2520
gaggtggcca ctgggttatc caaatattag gtttcactgc tgacaaaaga gggggcttct   2580
ggtctggttg gttatttgtg tttggcctga tgtgctctgt caatcaaatg tatggacata   2640
ggcctagctt ctaaaggggc aatagtgacc tcagtggact gatatttacc gtactattta   2700
catgtgctct taattacagc agaagctgcc agctaactga atcttgtttt gaatctaaaa   2760
aatctactct taaagcaaga aaatggtata aaattagttg ataatgcaag tagatct     2817
```

<210> SEQ ID NO 46
<211> LENGTH: 2355
<212> TYPE: DNA
<213> ORGANISM: Artificial Sequence
<220> FEATURE:
<223> OTHER INFORMATION: Donor sequence, donor 13 gRNA-D_HA + cDNA -
    GFP - Stuffer

<400> SEQUENCE: 46

```
agatctttga ttagttttct ggctgttcct aaaattctgg atgcaggaac tgtggctaga     60
```

```
aagcatctgg atgattgcac tttatcaggg atacttgagt gtcctctctt aggatctgga    120
cctagaatta atgtcatgag attttttctaa caggataagg tgaggtagtg agggctgaag    180
tcatgaattc tgtacattta attattctaa gacattggaa gcttccttag gtttacatgt    240
gctcttaatt acagcagaac cggtctgacc tcttctcttc ctcccacaga tcgaggacga    300
gagaaacctg cacgaggact tcgtgttcat gaagaccatc cagcggtgca acaccggcga    360
gagaagtctg agcctgctga actgcgagga aatcaagagc cagttcgagg gcttcgtgaa    420
ggacatcatg ctgaacaaag aggaaacgaa gaaagaaaac tccttcgaga tgcagaaggg    480
cgaccagaat cctcagatcg ccgctcacgt gatcagcgag gccagcagca agacaacaag    540
cgtgctgcag tgggccgaga agggctacta caccatgagc aacaacctgg tcaccctgga    600
aaacggcaag cagctgacag tgaagcggca gggcctgtac tacatctacg cccaagtgac    660
cttctgcagc aacagagagg ccagctctca ggcccctttt atcgccagcc tgtgcctgaa    720
gtcccctggc agattcgagc ggattctgct gagagccgcc aacacacaca gcagcgccaa    780
accttgtggc cagcagtcta ttcacctcgg cggagtgttt gagctgcagc ctggcgcaag    840
cgtgttcgtg aatgtgacag accctagcca ggtgtcccac ggcaccggct ttacatcttt    900
cggactgctg aagctgtgaa cagtgtcacc ttgcaggctg tggtggagct gacgctggga    960
gtcttcataa tacagcacag cggttaagcc cacccctgt taactgccta tttataaccc    1020
taggatcctc cttatggaga actatttatt atacactcca aggcatgtag aactgtaata    1080
agtgaattac aggtcacatg aaaccaaaac gggccctgct ccataagagc ttatatatct    1140
gaagcagcaa ccccactgat gcagacatcc agagagtcct atgaaaagac aaggccatta    1200
tgcacaggtt gaattctgag taaacagcag ataacttgcc aagttcagtt ttgtttcttt    1260
gcgtgcagtg tctttccatg gataatgcat ttgatttatc agtgaagatg cagaagggaa    1320
atggggagcc tcagctcaca ttcagttatg gttgactctg ggttcctatg gccttgttgg    1380 aggggggccag gctctagaac gtctaacaca gtggagaacc gaaaccccccc cccccgcca    1440 ccctctcgga cagttattca ttctctttca atctctctct ctccatctct ctctttcagt    1500
ctctctctct caacctcttt cttccaatct ctctttctca atctctctgt ttcccttgt    1560 cagtctcttc cctcccccag tctctcttct caatcccccct ttctaacaca cacacacaca    1620
cacacacaca cacacacaca cacacacaca cacacacaga gtcaggccgt tgctagtcag    1680
ttctcttctt tccaccctgt ccctatctct accactatag atgagggtga ggagtaggga    1740
gtgcagccct gagcctgccc actcctcatt acgaaatgac tgtatttaaa ggaaatctat    1800
tgtatctacc tgcagtctcc attgtttcca gagtgaactt gtaattatct tgttatttat    1860
tttttgaata ataaagacct cttaacatta cgcgcttaac attatcgttg ttgtttgagt    1920
acctaaagct cccagccagg ttggggaaag aggaagcatt tggagggaat tttcccaacc    1980
tttgtgatgt tttcataaac tttgttctca agctacttac attacgcgta ctagtaaata    2040
ccaatcatag atgtaaagga gaaagccact gggttatcca atattaggt ttcactgctg    2100 acaaaagagg gggcttctgg tctggttggt tatttgtgtt tggcctgatg tgctctgtca    2160
atcaaatgta tggacatagg cctagcttct aaagggcaa tagtgacctc agtggactga    2220
tatttaccgt actatttaca tgtgctctta attacagcag aagctgccag ctaactgaat    2280
cttgttttga atctaaaaaa tctactctta aagcaagaaa atggtataaa attagttgat    2340
aatgcaagta gatct                                                    2355
```

<210> SEQ ID NO 47
<211> LENGTH: 12164
<212> TYPE: DNA
<213> ORGANISM: Homo sapiens

<400> SEQUENCE: 47

| | | | | | |
|---|---|---|---|---|---|
| accatttcaa | ctttaacaca | gcatgatcga | aacatacaac | caaacttctc | cccgatctgc | 60 |
| ggccactgga | ctgcccatca | gcatgaaaat | ttttatgtat | ttacttactg | tttttcttat | 120 |
| cacccagatg | attgggtcag | cacttttgc | tgtgtatctt | catagaaggt | tggacaaggt | 180 |
| aagatgaacc | acaagccttt | attaactaaa | tttggggtcc | ttactaattc | ataggttggt | 240 |
| tctacccaaa | tgatggatga | tggtagaaac | caaatagaag | aatggtcttg | tggcataatg | 300 |
| tttgttgcct | agtcaatgaa | gtctcatatt | cttgtctctg | gttaggatct | tgggatctgg | 360 |
| agtcagactg | cctgggttca | aatcttggct | ctgcccatac | catctctgtt | atcctggggc | 420 |
| aagtgcctca | gtttccacat | ctgagaaatg | gggatggtat | tggtgtccat | ttcatagatt | 480 |
| aagtgagttt | agccttgtaa | aaagcttagg | aggggggtctg | atacatagta | agcactatgt | 540 |
| acgcactagc | tataattatt | tgctaaagtt | ctgctttaaa | agtaagctat | ttttttatgg | 600 |
| agacagcttt | tttcttttaa | atttccagct | aggcaagaag | agcgtcaatt | tgatctaaaa | 660 |
| tttcataatg | cttcagatta | acatagacat | ggataagtcc | cagaatttgc | agtcttttag | 720 |
| taaaagtagc | attttctgtg | taattcttca | caagcactga | ttgtagttgc | aggatgctca | 780 |
| gtctccctct | gagatgtttt | acattttaa | atggttagac | ttgcaggaac | aaaagagcag | 840 |
| agtaacttag | taggctgttt | tgcattctta | ggaaaagaaa | accatcagga | cttattttgt | 900 |
| tttcatgtat | tttttcactt | ccactgagga | gtataattgg | ctggtgttga | caaaatacca | 960 |
| atcatagatg | taaaggagaa | agttgattag | ttttctggct | gttcctaaaa | ttctggatgc | 1020 |
| aggaactgtg | gctagaaagc | atctggatga | ttgcacttta | tcagggatac | ttgagtgtcc | 1080 |
| tctcttagga | tctggaccta | gaattaatgt | catgagattt | ttctaacagg | ataaggtgag | 1140 |
| gtagtgaggg | ctgaagtcat | ccactgggtt | atccaaatat | taggtttcac | tgctgacaaa | 1200 |
| agaggggggct | tctggtctgg | ttggttattt | gtgtttggcc | tgatgtgctc | tgtcaatcaa | 1260 |
| atgtatggac | ataggcctag | cttctaaagg | ggcaatagtg | acctcagtgg | actgatattt | 1320 |
| accgtactat | ttacatgtgc | tcttaattac | agcagaagct | gccagctaac | tgaatcttgt | 1380 |
| tttgaatcta | aaaatctac | tcttaaagca | agaaaatggt | ataaaattag | ttgataatgc | 1440 |
| aagtgaattc | tgtacattta | attattctaa | gacattggaa | aataaaatat | cttgttactt | 1500 |
| tgaggataaa | agatgatttc | tttaaaaatg | caaatgtttt | ctacaaatac | taagttaaa | 1560 |
| agggagagag | atgtaattag | aactcgttaa | ctgacacatt | gcaaattaac | ttcttttat | 1620 |
| aaagcactgc | atcacaaaca | ctaaaatgaa | gtgggcaaat | tagctctgca | gaaaactatt | 1680 |
| ttctaggctg | atgtttataa | tgaccaatca | ttactgaagc | aatgagaaat | gtgacaatta | 1740 |
| cagaatattg | ctgctatagt | atgttgaaaa | aatatgcatt | ttgtagtgaa | catttagtag | 1800 |
| aatagctctg | atttctacct | ggagtttctg | ataacatgac | atcttaattg | ctgtctttta | 1860 |
| tagattttta | aactgcaaat | acaaaatagc | aatcagccaa | tataataact | tattattctc | 1920 |
| catttatgcc | tgaaagtcct | cctcttgttg | atgccgtgga | aatgaatgta | gaggcagata | 1980 |
| tcattagctg | tattctcctt | ccgaatgaca | tttatcatat | ccttgttatt | ccaaaataga | 2040 |
| tagaagatga | aaggaatctt | catgaagatt | ttgtattcat | gaaaacgata | cagagatgca | 2100 |
| acacaggaga | aagatcctta | tccttactga | actgtgagga | gattaaaagc | cagtttgaag | 2160 |

```
gctttgtgaa ggtaagcagc ttaattactg gtaaaagtgt cattgaaata ttttactaca    2220
tttgctagat cgggaaactg acaatgccaa tgtttaaaga ttggttatag acacagacac    2280
acagacacac acacacatat atatgcatgc agatatacac acatacatgg gtgtgtgtgt    2340
gggggttaaa aaaaaaaaac acaaagacac tctctgggga aaatacaccc ttaggggcac    2400
agtcacacat atttgtcagc ttacatatgc agctaccact aggcaaaatg atgaagtcca    2460
ccaagcttgg tttttgcatt gctgtgtctc cccatccaaa ccttgatgct ctcgcactgg    2520
ggacccagag tctgatcccc atttcccagg gaagcaatag ccgtcaacag ctgccgtggc    2580
agcaggccac aagtgaaggg acacctgaag actggtaaca gtctctggtg cttctctgat    2640
gatggaattt taggtgtcct gacagtgaga tctttccctt ttactgggga gagaggtgca    2700
gggaataagt aatagacatt ctcagtgtcg ctcaaaccag actccatata atatcacttg    2760
ctcatgaagc ccgcccactc tatggccggt catgaccaga ggcacagagg gttcaaagcc    2820
ttttagccca ccaggctggt agctagcatg aagtcactgc agtgactgtg gcttataaca    2880
gatacctaaa acaagaattt ttagaacctt tacattaatt ccatcatcac agacataggg    2940
tctagggget ctttctcctg aggcagaaca tcaagagttc tttctgccta tgtcccttc    3000
agaacactga gtcaaatacc cttgggcctc ggctcactta ggggtcattt ctaggaggca    3060
gcactccaca ttgaggacag ttctgggcca ggtgggtggg tatctgggta aaccaacagg    3120
aattagttct cacatataga tgatgtgtaa tttaatgcag gcgtaaaagg gttaagatct    3180
tatttctgat cttatttctg ccctcctgta ctgtcaccga ggtgccattt aattcattag    3240
tgaagactct aacagcttat tcctgagtca cctacggaga acagaatgtg gctcaaatcc    3300
gctgcttgct ttcaggttct ttacactaat ctaggcttta gatgaaactc ctaaaccctt    3360
tcttgcaag actggccagc taggaaaatg atttgagttt cttcggttct tcgaggattt    3420
gggccagtat tacagagtat tggaagatgt taccagttta aatgtgaata aaggcacttt    3480
caaaacaatg gctaataatc caaataacag actgaatgtg cttggctatg tgactttggg    3540
taaataactt caccttctg ggcctcagtt ttgtcatcta aacatgaga agacagatta    3600
tctgtaaggg cactatcagc tctgacattc tacaattatg tgataagcct tcagttccct    3660
ccaatggcag tgagagtggc ttgtcagtcc ccctcgtttc ttacggagac ttttacggtt    3720
gaattgtcaa ttcctcacgt cattatttca ggttggctat gtatgtaaag ctcccaaaat    3780
cagctaccga ggataggagt aaagaaaaca gtcagtttgg cctccctgct tatgcttgta    3840
tgaaaaagt gacagctcca aagtttcata ttcttaaaag gcagatcttc tcaggcatgt    3900
cagccagggc cccagggatc tcctccttac atgcaactaa ggaggctcct tgtctctact    3960
gcagcaggtg tggaacccta gtcaacacca cctatatccta ggattacgta caatgagtag    4020
atacaaagtc ctccagctac ccaatcctcc cccaatgacg gatcccctttt ccaatacgct    4080
ttcccccaaa tttctcaccc taaaacaaaa ttcgagactt tgaaaaaact caataggaca    4140
attatagaat agctccagat tagattcata ttttcttagc taatgttagt aggctttctt    4200
tccgggccac agtctggctg cacctaagca acctcaagtt tgaatttgga gtctttgaat    4260
caggtcttga tggggtctta gaagtcatca gatccaattc tcaatccaca acttcagtct    4320
tctctccacc tcctgactaa gtggtcatcc aatctctgtt tgaacatctc tagtgacaag    4380
gaactcatta tctctggagg caggtagcac taatctgtca ttttggggga aagatgggtat    4440
tcagggctca agtgagggta agcagaggta ttattttgaa tagtataatt tcatattaaa    4500
acttacaacc caccacacct ctgctagatg ttcagttcca tgattatttg cccaccaatg    4560
```

-continued

```
cctgcgatgc ctttgagaga gccaaagcat ttctatttca agttaaaggg caacctgtcc    4620 ataccctgcca catggaactc ccactaagag agaaataacc cattctggat tttctgaaag    4680
tccactttaa aaagtatttc agttgaggtg gggagtgaag caagaaaaaa aaaaggctct    4740
ggggagtgtg gttgggcgaa agttcacgga aaggctaggc tgggctcatg aaacacgagc    4800
tttgctgact tcatgttttc atcttggcca ggcctcaaca ccaatgcaac aacttagcct    4860
aaaagtatct caaccttgat caccacactc tactttttga aaagacacta aatagtcatt    4920
tgtttacttg tgatctcaca aacatttttcc tgtcaccaca tcttcatagt gccgcgcttc    4980
agctcaaatg gaaagttgaa gctctggggc ccatgtgagt gttctgaggc tcaggttccc    5040
ctggaggctc tatgaactac gcccttaaat ctggcaactg agctgggcct acagccagca    5100
ctcaacagtg acagcacaaa ttccttctgg aggaggaaat aaaaggaagg gtcctataga    5160
caactgattc caggagtggg aaggagcaca ggactttgat tatcataaga tgtgaaaata    5220
ctactgtctt cttcccttgt gtgcagagga tagacagatg gaattagcta agcccagcct    5280
atgaatgcca tctcacagtt tccactcttg gtttaaacct cagcttcttt gggtgacctc    5340
ataatgacca gttaagccct ccaggccttt tgttcagtct cttaaaatg gcagcaacag    5400 cctttatcat cttccaacct gtgttgatgg aagttcctgt tagcttcttt aaatacctct    5460
agacttcctt cagtttataa gtgaaaagaa accttttaag aagtgtcgca cttgcctttg    5520
aacatcaaca ccattgggag atggcctgtg tttccgaaat gctgattatt ctaagtaaat    5580
acagtgcaac tatcaataag agaatctctt cagcccattg aaagggatag caaaattaaa    5640
aatgtctgag ggtcttttca tagtctggca tttctcccca aggtcaaact tactattatc    5700
ttttcctaca ggatttcaga ccaaatttat tctaatagat acacaccatg ctttatgttt    5760
aataatattc catataccag ttcccagggt agaatcatct ccccattcgg cattatttgt    5820
caatatctgt caaagccaag gaggttgagg tcataggaag ggtcaggatc acagcctctg    5880
gtctggagag agcactggaa tggagataat aaggcctgga ttttacttcc agattctccc    5940
ctgggctttc tgggttgttg gctcatctgt cagatccatg gactcccaat tggcatgatg    6000
gaattaatga caggatctga gtctatatga taatcctcac cagaaacaga caacagagta    6060
atgacagatg caaaacgaat gataatttta aaccccaca gcagagcccc tgtcaaaatg    6120
acctcttgca atgcttctta ttttaggata taatgttaaa caaagaggag acgaagaaag    6180
aaaacagctt tgaaatgcaa aaaggtaggt ttgctatttg ctaatttcta tgaatgccta    6240
aaaactaaaa ggaagcttta ggctgatcat attgaacaac ccagtgttgt tgcatcaggg    6300 aactttttagc cctggaaata aaacaggaac acaattgtca aattgacacc ttctctggtc    6360
cctgtgattt ggaaagactt tgtacatata tatttatgaa aaaaggatgt gttccttttaa    6420 tgccgatgat accaaatctg aagaaatccc attatgttca ataccttaat agaagcaacc    6480
atacagcctg ataccaccta cagtggaata agaagacagg aaagtcatca tttggtaaca    6540
gtggcattca tcactcattg ataacagttt ttcatggggc acagtggccg gtggagcctc    6600
tgggatcaag gagtgacaat gtcacagtgt tctattattt gcccggttct taaagtgaga    6660
gcatcctgaa catctcaggg ttggaagaga acttgagagt tctcaaatcc agcaccatcc    6720
ccacaacaaa aatctccttc acaataacac tgaccgtcca gcctctgatc aaacatgtcg    6780
agggatgagg caccttccac ctcataaggc agcctgatcc gtctttgaat ggctctaata    6840
ataccaagat tactatacta ctccagagaa gtctttcctc ctcaagtcaa actttgttcc    6900
```

```
tataatctcc actcattggt cccagttctg ctctttgagg ccctagtaaa caaagtataa    6960
ttgctctcct acccagcagc tgtccagata tggaagacag caatcatggt ggccaagcct    7020
tgactgagct ttttcttctc caggctaaag atccctgatg tcttccactg tttctcctat    7080
gacccttttcc aggaccttc ttctgccact cacctccttt tcttggacac actaacgttt    7140
tcctgttctt ttagaatgtg gcatcgcaaa ccaatacaat aatgcgtgaa gtgacttcag    7200
cagcagatta tgggaaagac ggggtgttgt tagagagaat tttatatcac aaagttggtg    7260
aacatgatgt tatggcttct gcaaatttaa tacacacaaa aacatacata catacaggga    7320
tagagatact attttctgag gcaaagagag tactcagacc ttgccttaac tgttgttctg    7380
gatactaaat ggtcatccga cttccatgaa ggttttatct tcagaatgac tgcaagatat    7440
gttgagtaat agtaccacgc tgtctgttaa ttacagagaa atctgaggaa acagtttatg    7500
tagatgctgc ctagaagtct tcagggaaat gataatatta ccaaactgg tcatttaggt     7560
catgcaattt aactcaacat ttatagggca cttacaaagt gcccaatatc aggctcataa    7620
ctggacaaaa agaaacttcc acacagtctc tgcccttaga agattgacac atctcattag    7680
ggagcagggc tttaacacaa gaaataatta aagacagata caatagttca gccagttgct    7740
tgaccaattc agaaaccata agaatcttac taagtgtgca gactttggag cccactaaaa    7800
tccccagtgt atggagttgt tcctaaaagc aagattcacg gtatgtttaa tgaagaccag    7860
tgttttagc ctgtgtcaat ctatgcaaaa tggaatcgag tattgatcaa ctgttaggag     7920
aatgagaccg atggaaacag ccaattcaat tactcagata ttagaaacca acttttcctt    7980
cagtgggaga gatgtcagac catttatct ttcctttat ataatctatt tttgcacagt      8040
ctctattaca cagttgtaga actggaccag atagttttgt gggcagtttt tgcattattt    8100
tagcctgaca gttttggtt ccatttcagg tgatcagaat cctcaaattg cggcacatgt     8160
cataagtgag gccagcagta aaacaacatc tggtaagtca cacagcatct gagcggtagc    8220
cacccaaggg gaaaggctgg gatgccgaag tcatgttacc taatggttaa actcctcttt    8280
tccctggga cccaatttac aaacctaccc ctacacttct cctattccct tctttgtctt     8340
caaagtgagt tcaaatgcac agatgggact tagagggaca aaaggaggtg gaatgcaatc    8400
tggatgttct cattatgttc ttgctcaatg gctgattcta aatgatgaat tactgggtgg    8460
agggaccatt gttctgacaa catagaagaa atggcatgta gtgacctcct gactgggagc    8520
atccctcctc ctaacccatc ttcactgtgt ggaaatgggc ctcatggggt atttcctgcc    8580
atctgtcaat ccctgtatga ttaagctcag cctcactgag gccaacctca gggaaagtaa    8640
aggtaaaatc attctgtaaa gatcaatagg tcccaagacg ttacattttc caatgaagta    8700
acaacagacg acatattgtg atcttttcaa ctctgaacga ttttattttcc atatacgttc    8760
tgccaccatt ctagccttta gatatttttt cccaaatgtg catcttgcga taactggtgc    8820
caaagaatat gtcgtatctg ataaatggat ggaaacatgc acgctaacat aaagtctccc    8880
atcaacataa aggcaagagc gtcagaggag tctttgaaaa attctacaga gtgctccgga    8940
atggagttct aagcagtgca tgtgtgtgtg catatgtgta tgtgtgtgac agggagagaa    9000
agagagatgg acagagagag aaaaaagaca ctgcttcatc tctgaagtgg cttgggcttc    9060
tcagtaggcg taacacatgg acagttatca ttatcatgga tcatggtacc aaagtaagag    9120
cactgaatag ggagttttttg aacactggga ttcaaggacc atgaccactg cttgctgggt   9180
gaccttgagc aagacccttt acctatgcag cagtttttcta cttcacctac tttacagggt   9240
ggctttgagc atcaaatcag ctaatgtggc cgaaagtgat gctgtcgagt gctgtacaac    9300
```

-continued

```
cgtaaggtga cactacttag tttacttcac catggcttag atgtcaaaag ggtgacataa    9360
agcccctcac taataccagt tagttacaca atatttaata attttgtcaa gtaccccttc    9420
tctcttctgg atcagatgac aacaacagag aaatctccta gaagaatagc ttcccactgg    9480 tcttttttttg cctgtatcta aaccttgat cttggatata tttcatagag ctcagattct    9540
cccaaaaggc ttgtaatgga tatcagtcct acaatatctt acagtctgca tcacaatagg    9600
tttccagggg atcagatggg aagacagtaa cattccaccc ccaccccagt cccaaacctc    9660
ttcttcctac ctagccatgc tgctaaaatc ttgccctaca tcccacagca agtactaaaa    9720
ttaggtaagg acgtaccaaa gtaaacttac tgaactaaaa gattgagaac ctgcccttt     9780 tttctcaata aaatggttca aaagggcaaa cattctaatg aagcattgtt tctggagtgg    9840
tctggagggc ccggatctgt caggcatttc aggatgcctc cctattagta aagggcgagt    9900
cttaccaggt gggatcttgt gccctgatag acctaagact atcgaatagg aattattttt    9960
taaaaagctc aaggaagcaa acacatcagt actttcactt ttcctcaacc ctcaccccca   10020
tcagtcagtc tagctttctg tgggagctga gatttcaagt cgggtgcaca cactactttg   10080
aacccactca acatctcagc cgagaaaatg gcacactgtt ggtgggtact ctggcttagc   10140
cacaagaata ctggtacttt caagttggtg gcgcccacta caatgggaga tcaaaacata   10200
ccgtgaaatg agcacacagt ttattttcat acttccttgc ctaattttag tccttgctgg   10260
gggaggcaga tcaggtttgc aacagcatga tcaggtagga agaaatgggg tcttttctct   10320
gtgctgaggc tgagctaggt agactgacaa ctctctgact ttgtaaaatt caaggcaagc   10380
aaggtattca tggtaatatt agcaaaaatt tggtccgagt aatttggtat gtataattta   10440
tgatgtcaaa ttttgaaatc atttgtgcct tcttaagttc aaggcaaatt ggctataaga   10500
actctaacga gagaaagaaa ctcactgtga tctcttactt tatttaatct tcacaagtct   10560
ctgaaatatg ctccaatatg agccccgtgt tgcagatgag gaactgaagc tcatggagat   10620
ttagagactt gcccaagctt aaatagagcc tagattggaa catggctctg tctgactctg   10680
aagcccatgg aagggggcctt gagaatccat ccctatacaa agccaatatc caacattaaa   10740
ctatattttt tgtcagaatg tgaaccatgc tctgcttcac ctcaccacaa actttcctt    10800 tctttgtaac agtgttacag tgggctgaaa aaggatacta caccatgagc aacaacttgg   10860
taaccctgga aaatgggaaa cagctgaccg ttaaaagaca aggactctat tatatctatg   10920
cccaagtcac cttctgttcc aatcgggaag cttcgagtca agctccattt atagccagcc   10980
tctgcctaaa gtcccccggt agattcgaga gaatcttact cagagctgca aatacccaca   11040
gttccgccaa accttgcggg caacaatcca ttcacttggg aggagtattt gaattgcaac   11100
caggtgcttc ggtgtttgtc aatgtgactg atccaagcca agtgagccat ggcactggct   11160
tcacgtcctt tggcttactc aaactctgaa cagtgtcacc ttgcaggctg tggtggagct   11220
gacgctggga gtcttcataa tacagcacag cggttaagcc cacccctgt  taactgccta   11280 tttataaccc taggatcctc cttatggaga actatttatt atacactcca aggcatgtag   11340
aactgtaata agtgaattac aggtcacatg aaaccaaaac gggccctgct ccataagagc   11400
ttatatatct gaagcagcaa ccccactgat gcagacatcc agagagtcct atgaaaagac   11460
aaggccatta tgcacaggtt gaattctgag taaacagcag ataacttgcc aagttcagtt   11520
ttgtttcttt gcgtgcagtg tctttccatg gataatgcat ttgatttatc agtgaagatg   11580
cagaagggaa atggggagcc tcagctcaca ttcagttatg gttgactctg ggttcctatg   11640
```

```
gccttgttgg aggggggccag gctctagaac gtctaacaca gtggagaacc gaaaccccc    11700 ccccccccc  gccaccctct cggacagtta ttcattctct ttcaatctct ctctctccat   11760
ctctctcttt cagtctctct ctctcaacct ctttcttcca atctctcttt ctcaatctct   11820
ctgtttccct ttgtcagtct cttccctccc ccagtctctc ttctcaatcc ccctttctaa   11880
cacacacaca cacacacaca cacacacaca cacacacaca cacacacaca cagagtcagg   11940
ccgttgctag tcagttctct tctttccacc ctgtccctat ctctaccact atagatgagg   12000
gtgaggagta gggagtgcag ccctgagcct gcccactcct cattacgaaa tgactgtatt   12060
taaaggaaat ctattgtatc tacctgcagt ctccattgtt tccagagtga acttgtaatt   12120
atcttgttat ttattttttg aataataaag acctcttaac atta                   12164

<210> SEQ ID NO 48
<211> LENGTH: 632
<212> TYPE: DNA
<213> ORGANISM: Artificial Sequence
<220> FEATURE:
<223> OTHER INFORMATION: CD40L codon optimized sequence (exons 2-5)

<400> SEQUENCE: 48
agatcgagga cgagagaaac ctgcacgagg acttcgtgtt catgaagacc atccagcggt    60
gcaacaccgg cgagagaagt ctgagcctgc tgaactgcga ggaaatcaag agccagttcg   120
agggcttcgt gaaggacatc atgctgaaca agaggaaac gaagaaagaa aactccttcg   180
agatgcagaa gggcgaccag aatcctcaga tcgccgctca cgtgatcagc gaggccagca   240
gcaagacaac aagcgtgctg cagtgggccg agaagggcta ctacaccatg agcaacaacc   300
tggtcaccct ggaaaacggc aagcagctga cagtgaagcg gcagggcctg tactacatct   360
acgcccaagt gaccttctgc agcaacagag aggccagctc tcaggcccct tttatcgcca   420
gcctgtgcct gaagtcccct ggcagattcg agcggattct gctgagagcc gccaacacac   480
acagcagcgc caaaccttgt ggccagcagt ctattcacct cggcggagtg tttgagctgc   540
agcctggcgc aagcgtgttc gtgaatgtga cagaccctag ccaggtgtcc cacggcaccg   600
gctttacatc tttcggactg ctgaagctgt ga                                 632
```

SYSTEMS AND METHODS FOR TREATING HYPER-IGM SYNDROME

RELATED APPLICATIONS

This application is a national stage application under 35 U.S.C. § 371 of International Application No. PCT/US2018/057354, filed Oct. 24, 2018, which claims the priority of U.S. Provisional Application No. 62/746,900, filed Oct. 17, 2018; U.S. Provisional Application No. 62/690,284, filed Jun. 26, 2018; U.S. Provisional Application No. 62/673,039, filed May 17, 2018; U.S. Provisional Application No. 62/664,800, filed Apr. 30, 2018; and U.S. Provisional Application No. 62/576,277, filed Oct. 24, 2017, the disclosures of each of which are explicitly incorporated by reference herein in their entirety.

FIELD

The present disclosure relates to CRISPR/Cas-related methods and components for treating Hyper-IgM Syndrome, methods of editing a CD40L target nucleic acid sequence, and modulating expression of a CD40L target nucleic acid sequence, and applications thereof.

BACKGROUND

CRISPRs (Clustered Regularly Interspaced Short Palindromic Repeats) evolved in bacteria and archea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a Cas9 protein to a target sequence in the viral genome. The Cas9 protein, in turn, cleaves and thereby silences the viral target.

Recently, the CRISPR/Cas system has been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR).

Hyper-IgM syndrome (HIGM) is an immunoglobulin deficiency characterized by normal or elevated serum IgM levels, and decreased levels or absence of other serum immunoglobulins, resulting in susceptibility to infections. Most HIGM cases are X-linked and caused by mutations in a gene on the X chromosome that encodes a protein (CD40 ligand, "CD40L") on the surface of activated helper T cells. Mutations in the CD40L gene ("CD40LG") in subjects having hyper IgM syndrome include missense mutations, nonsense mutations, splice site mutations, deletions and insertions and are well known to those of ordinary skill in the art. See, for example, Seyama et al., (1998) *Blood*, 92(7):2421-2434. In the presence of cytokines, normal CD40 ligand interacts with B cells and, thus, signals them to switch from producing IgM to producing IgA, IgG, and/or IgE. In X-linked hyper-IgM syndrome, T cells lack functional CD40 ligand and cannot signal B cells to switch. Thus, B cells of HIGM subjects produce only IgM, and IgM levels may be normal or elevated.

Treatment of HIGM syndrome usually includes immunoglobulin replacement therapy, long-term antibiotic and antifungal prophylaxes, and G-CSF treatment for neutropenia. Hematopoietic stem cell transplantation is also preferred if an HLA-identical sibling donor is available. However, current treatments are not efficient, as about 80% of HIGM patients die before the age of thirty. Accordingly, there remains an ongoing and unmet need for the development of novel therapeutic strategies and products to treat HIGM.

SUMMARY

An adoptive immunotherapy approach based on gene corrected autologous T cells may be sufficient to induce the generation of protective immunity in recipient HIGM1 patients and possibly also the production of some long living memory B cells. However, multiple administrations of edited T-cells may be required to reconstitute a long-lasting and broad T cell repertoire that can mediate efficient T cell help in response to a wide range of pathogens. Moreover, while CD40LG has a critical function on CD4 T cells (Th0, Th1 and Th2), this molecule is also expressed on several other hematopoietic cell types, such as activated B cells, platelets, NK cells, monocytes, basophils and eosinophils. Therefore, the present disclosure surprisingly expands the gene editing strategy from the correction of T-cells to the correction of autologous Hematopoietic stem/progenitor cells (HSPC), which provides a much broader and prolonged therapeutic benefit.

The present disclosure is based, at least in part, on the discovery that CD40 ligand (CD40L)-edited cells surprisingly produce functionally active CD40L protein and can be used to restore the function of B cell class switching for the treatment of hyper-IgM syndrome. In particular, when one or more of exons 2-5 of the CD40L gene, are edited in cells, e.g., T cells or hematopoietic stem cells (HSCs), using a genome editing system, the edited cells demonstrate high levels of CD40L gene editing and high levels of functional exogenous CD40L expression. Specifically, CD40L edited T cells restored the capability of B cell class switching, by increasing the level of IgG produced while decreasing the level of IgM. In addition, mice receiving hematopoietic stem cells comprising at least 10% of CD40L edited cells produced a higher level of IgG upon vaccination, demonstrating the therapeutic benefit of CD40L-edited hematopoietic stem cells for use in the treatment of hyper-IgM syndrome.

The genome editing systems disclosed herein are designed so that exon 1 of the CD40L gene is not edited, avoiding the potential for random integration events or off-target events. Specifically, editing of exon 1 may lead to loss of promoter control of the locus, affecting expression of the CD40L gene, and leading to lymphoproliferaterive disorders, especially in the context of hematopoietic stem cell transplants.

Accordingly, in one aspect, disclosed herein is an isolated oligonucleotide donor template which comprises, from 5' to 3', A1-N-UTR-pA-A2, wherein A1 is a homology arm that is substantially identical to a first homology arm of a target CD40L nucleic acid; N is a cargo comprising one or more of exons 2-5 of a CD40L gene; UTR is a CD40L 3' untranslated region (UTR); pA is a polyA tail; and A2 is a homology arm that is substantially identical to a second homology arm of the target CD40L nucleic acid.

In one aspect, disclosed herein is an isolated oligonucleotide donor template which comprises, from 5' to 3', A1-S1-N-UTR-pA-S2-A2, wherein A1 is a homology arm that is substantially identical to a first homology arm of a target CD40L nucleic acid; S1 is a first stuffer, N is a cargo comprising one or more of exons 2-5 of a CD40L gene; UTR is a CD40L 3' untranslated region (UTR); pA is a polyA tail;

S2 is a second stuffer, and A2 is a homology arm that is substantially identical to a second homology arm of the target CD40L nucleic acid.

In one aspect, disclosed herein is an isolated oligonucleotide donor template which comprises, from 5' to 3', A1-S1-N-UTR-pA-R-S2-A2, wherein A1 is a homology arm that is substantially identical to a first homology arm of a target CD40L nucleic acid; S1 is a first stuffer, N is a cargo comprising one or more of exons 2-5 of a CD40L gene; UTR is a CD40L 3' untranslated region (UTR); pA is a polyA tail; wherein R is a reporter; S2 is a second stuffer, and A2 is a homology arm that is substantially identical to a second homology arm of the target CD40L nucleic acid.

In one aspect, disclosed herein is an isolated oligonucleotide donor template which comprises, from 5' to 3', A1-N-UTR-pA-R-A2, wherein A1 is a homology arm that is substantially identical to a first homology arm of a target CD40L nucleic acid; N is a cargo comprising one or more of exons 2-5 of a CD40L gene; UTR is a CD40L 3' untranslated region (UTR); pA is a polyA tail; R is a reporter; and A2 is a homology arm that is substantially identical to a second homology arm of the target CD40L nucleic acid.

In any aspect described herein, the cargo may comprise exon 2 of the CD40L gene; exon 3 of the CD40L gene; exon 4 of the CD40L gene; exon 5 of the CD40L gene; exons 2-5 of the CD40L gene; exons 2-4 of the CD40L gene; exons 2 and 3 of the CD40L gene; exons 3-5 of the CD40L gene; exons 3 and 4 of the CD40L gene; or exons 4 and 5 of the CD40L gene. In one embodiment, the cargo comprises a codon optimized CD40L sequence. For example, the cargo can comprise a codon optimized version of CD40L exon 2, CD40L exon 3, CD40L exon 4, CD40L exon 5, or a combination thereof, e.g., a codon optimized exon 2-5 sequence, a codon optimized exon 2-4 sequence; a codon optimized exon 2 and 3 sequence; a codon optimized exon 3-5 sequence; a codon optimized exon 3 and 4 sequence; or a codon optimized exon 4 and 5 sequence. An exemplary codon optimized version of CD40L, exons 2-5, is provided as SEQ ID NO:48.

In one embodiment, the CD40L gene is a wild-type CD40L sequence. In one embodiment, the target CD40L nucleic acid comprises a mutation. In one embodiment, the oligonucleotide donor template further comprises a sequence encoding a reporter. In one embodiment, the reporter is a green fluorescence protein (GFP), a yellow fluorescence protein (YFB), DS-Red, or luciferase. In one embodiment, the reporter can be a marker which can be detected in live cells using art-standard methods, e.g., surface antigens detectable by antibodies, peptides that catalyze or otherwise facilitate a chemical reaction that produce an optically detectable product, e.g., luciferase. In one embodiment, the reporter is a selectable marker. In an exemplary embodiment, the selectable marker is low affinity nerve growth factor receptor (NGFR). In other embodiments, the selectable marker can be a drug-resistance protein (such as neomycin or puromycin resistance, mutant version of the MGMT gene), a truncated version of a cell surface protein (e.g. CD19, EGFR), a gene that confers a selective growth and/or engraftment advantage after in vivo transplantation of the edited cells (e.g. CXCR4, CD47, IL2 receptor) or a fluorescent reporter protein (e.g., green fluorescent protein (GFP), blue fluorescent protein (BFP), yellow fluorescent protein (YFP), etc., or a combination thereof. In one embodiment, the isolated oligonucleotide donor template is a single-stranded oligonucleotide donor template. In one embodiment, the isolated oligonucleotide donor template is a double-stranded oligonucleotide donor template.

In one aspect, disclosed herein is a composition comprising an isolated oligonucleotide donor template and, optionally, a pharmaceutically acceptable carrier.

In one aspect, disclosed herein is a vector comprising an isolated oligonucleotide donor template. In one embodiment, the vector is an AAV vector, a lentivirus, a naked DNA vector, or a lipid nanoparticle. In one embodiment, the AAV vector is an AAV6 vector.

In one aspect, disclosed herein is an isolated gRNA molecule comprising any one of SEQ ID NOs: 18-25. In one embodiment, the isolated gRNA molecule comprises SEQ ID NO:18. In one embodiment, the isolated gRNA molecule comprises SEQ ID NO:19. In one embodiment, the isolated gRNA molecule comprises SEQ ID NO:20. In one embodiment, the isolated gRNA molecule comprises SEQ ID NO:21. In one embodiment, the isolated gRNA molecule comprises SEQ ID NO:22. In one embodiment, the isolated gRNA molecule comprises SEQ ID NO:23. In one embodiment, the isolated gRNA molecule comprises SEQ ID NO:24. In one embodiment, the isolated gRNA molecule comprises SEQ ID NO:25.

In one aspect, disclosed herein is a genome editing system comprising an isolated oligonucleotide donor template. In one embodiment, the genome editing system further comprises a RNA-guided nuclease and at least one gRNA molecule. In one embodiment, the genome editing system further comprises an isolated gRNA molecule disclosed herein.

In one aspect, disclosed herein is a method of altering a cell comprising contacting the cell with a genome editing system disclosed herein, thereby altering the cell.

In one aspect, disclosed herein is a kit comprising a genome editing system.

In one aspect, disclosed herein is an isolated oligonucleotide donor template, a composition, a vector, an isolated gRNA molecule, a gene editing system, a method, or a kit, for use in medicine.

In one aspect, disclosed herein is a method of altering a cell, comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, thereby altering the cell.

In one aspect, disclosed herein is a method of altering a cell, comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises the first donor homology arm that is substantially identical to the first homology arm, a first stuffer, the cargo comprising one or more of exons 2-5 of the CD40L gene, the 3' CD40L untranslated region (UTR), the polyA tail, a second stuffer, and the second donor homology arm that is substantially identical to the second homology arm, thereby altering the cell.

In one aspect, disclosed herein is a method of altering a cell, comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises the first donor homology arm that is substantially identical to the first homology arm, the first stuffer, the cargo comprising one or more of exons 2-5 of the CD40L gene, the 3' CD40L untranslated region (UTR), the polyA tail, a reporter, the second stuffer, and the second donor homology arm that is substantially identical to the second homology arm, thereby altering the cell.

In one aspect, disclosed herein is a method of altering a cell, comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises the first donor homology arm that is substantially identical to the first homology arm, the cargo comprising one or more of exons 2-5 of the CD40L gene, the 3' CD40L untranslated region (UTR), the polyA tail, a reporter, and the second donor homology arm that is substantially identical to the second homology arm, thereby altering the cell.

In one embodiment, the cargo comprises all or a portion of: exon 2 of the CD40L gene; exon 3 of the CD40L gene; exon 4 of the CD40L gene; exon 5 of the CD40L gene; exons 2-5 of the CD40L gene; exons 2-4 of the CD40L gene; exons 2 and 3 of the CD40L gene; exons 3-5 of the CD40L gene; exons 3 and 4 of the CD40L gene; or exons 4 and 5 of the CD40L gene.

In one embodiment, the CD40L gene is a wild-type CD40L sequence. In one embodiment, the target CD40L nucleic acid comprises a mutation.

In one embodiment, the reporter is a green fluorescence protein (GFP), a yellow fluorescence protein (YFB), DS-Red, or luciferase. In one embodiment, the reporter can be a marker which can be detected in live cells using art-standard methods, e.g., surface antigens detectable by antibodies, peptides that catalyze or otherwise facilitate a chemical reaction that produce an optically detectable product, e.g., luciferase. In another embodiment, the reporter is a selectable marker. In an exemplary embodiment, the reporter is NGFR.

In one embodiment, the step of forming the at least one single- or double-strand break comprises contacting the cell with an RNA-guided nuclease. In one embodiment, the RNA-guided nuclease is a Class 2 Clustered Regularly Interspersed Repeat (CRISPR)-associated nuclease. In one embodiment, the RNA-guided nuclease is selected from the group consisting of wild-type Cas9, a Cas9 nickase, a wild-type Cpf1, and a Cpf1 nickase.

In one embodiment, contacting the RNA-guided nuclease with the cell comprises introducing into the cell a ribonucleoprotein (RNP) complex comprising the RNA-guided nuclease and a guide RNA (gRNA). In one embodiment, the step of recombining the exogenous oligonucleotide donor template into the target CD40L nucleic acid by homologous recombination comprises introducing the exogenous oligonucleotide donor template into the cell. In one embodiment, the step of introducing comprises electroporation of the cell in the presence of the RNP complex and/or the exogenous oligonucleotide donor template.

In one aspect, disclosed herein is a method of altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby altering the target CD40L nucleic acid in the cell.

In one aspect, disclosed herein is a method of altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises the first donor homology arm that is substantially identical to the first homology arm, a first stuffer, the cargo comprising one or more of exons 2-5 of the CD40L gene, the 3' CD40L untranslated region (UTR), the polyA tail, a second stuffer, and the second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby altering the target CD40L nucleic acid in the cell.

In one aspect, disclosed herein is a method of altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises the first donor homology arm that is substantially identical to the first homology arm, the first stuffer, the cargo comprising one or more of exons 2-5 of the CD40L gene, the 3' CD40L untranslated region (UTR), the polyA tail, a reporter, the second stuffer, and the second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby altering the target CD40L nucleic acid in the cell.

In one aspect, disclosed herein is a method of altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises the first donor homology arm that is substantially identical to the first homology arm, the cargo comprising one or more of exons 2-5 of the CD40L gene, the 3' CD40L untranslated region (UTR), the polyA tail, a reporter, and the second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby altering the target CD40L nucleic acid in the cell.

In one embodiment, the method further comprises contacting the cell with (d) a second gRNA molecule, wherein the second gRNA molecule and the RNA-guided nuclease molecule interact with the target nucleic acid, resulting in a second cleavage event at or near the cleavage site, and wherein the second cleavage event is repaired by the at least one DNA repair pathway.

In one embodiment, the cargo comprises all or a portion of: exon 2 of the CD40L gene; exon 3 of the CD40L gene; exon 4 of the CD40L gene; exon 5 of the CD40L gene; exons 2-5 of the CD40L gene; exons 2-4 of the CD40L gene; exons 2 and 3 of the CD40L gene; exons 3-5 of the CD40L gene; exons 3 and 4 of the CD40L gene; or exons 4 and 5 of the CD40L gene.

In one embodiment, the CD40L gene is a wild-type CD40L sequence. In one embodiment, the target CD40L nucleic acid comprises a mutation.

In one embodiment, the reporter is a green fluorescence protein (GFP), a yellow fluorescence protein (YFB), DS-Red, or luciferase. In one embodiment, the reporter can be a marker which can be detected in live cells using art-standard methods, e.g., surface antigens detectable by antibodies, peptides that catalyze or otherwise facilitate a chemical reaction that produce an optically detectable product, e.g., luciferase. In another embodiment, the reporter is a selectable marker. In an exemplary embodiment, the reporter is NGFR.

In one embodiment, the altered CD40L nucleic acid comprises, from 5' to 3', the first donor homology arm, the cargo, the 3' UTR, the polyA tail, and the second donor homology arm. In one embodiment, the altered CD40L nucleic acid comprises, from 5' to 3', the first donor homology arm, the first stuffer, the cargo, the 3' UTR, the polyA tail, the second stuffer, and the second donor homology arm. In one embodiment, the altered CD40L nucleic acid comprises, from 5' to 3', the first donor homology arm, the first stuffer, the cargo, the 3' UTR, the polyA tail, the reporter, the second stuffer, and the second donor homology arm. In one embodiment, the altered CD40L nucleic acid comprises, from 5' to 3', the first donor homology arm, the cargo, the 3' UTR, the polyA tail, the reporter, and the second donor homology arm.

In one embodiment, the cell is contacted first with the at least one gRNA molecule and the RNA-guided nuclease molecule, followed by contacting the cell with the exogenous oligonucleotide donor template. In one embodiment, the cell is contacted with the at least one gRNA molecule, the RNA-guided nuclease molecule, and the exogenous oligonucleotide donor template at the same time.

In one embodiment, the exogenous oligonucleotide donor template is a single-stranded oligonucleotide donor template. In one embodiment, the exogenous oligonucleotide donor template is a double-stranded oligonucleotide donor template.

In one embodiment, the exogenous oligonucleotide donor template is present in a vector. In one embodiment, the vector is a viral vector. In one embodiment, the viral vector is an AAV vector or a lentiviral vector.

In one embodiment, the DNA repair pathway repairs the target CD40L nucleic acid to result in targeted integration of the exogenous oligonucleotide donor template. In one embodiment, the cleavage event, or both the cleavage event and the second cleavage event, is/are repaired by gene correction.

In one embodiment, the altered CD40L nucleic acid comprises a sequence that is different than a sequence of the target CD40L nucleic acid.

In one embodiment, the gRNA molecule is a gRNA nucleic acid, and wherein the RNA-guided nuclease molecule is a RNA-guided nuclease protein. In one embodiment, the gRNA molecule is a gRNA nucleic acid, and wherein the RNA-guided nuclease molecule is a RNA-guided nuclease nucleic acid. In one embodiment, the cell is contacted with the gRNA molecule and the RNA-guided nuclease molecule as a pre-formed complex. In one embodiment, the RNA-guided nuclease is selected from the group consisting of wild-type Cas9, a Cas9 nickase, a wild-type Cpf1, and a Cpf1 nickase.

In one embodiment, the cell is a eukaryotic cell. In one embodiment, the eukaryotic cell is a human cell. In one embodiment, the cell is a T cell. In one embodiment, the cell is a hematopoietic stem cell (HSC).

In one embodiment, the cell is from a subject suffering from hyper IgM syndrome. In one embodiment, the cell is from a subject having at least one mutation at the cleavage site. In one embodiment, the method further comprises isolating the cell from the subject prior to contacting the forming step or the contacting step. In one embodiment, the method further comprises introducing the cell into a subject after the recombining step or after the cleavage event is repaired by the at least one DNA repair pathway.

In one embodiment, the forming step and the recombining step, or the contacting step, is performed in vitro. In one embodiment, the forming step and the recombining step, or the contacting step, is performed ex vivo. In one embodiment, the forming step and the recombining step, or the contacting step, is performed in vivo.

In one embodiment, the recipient subject is conditioned prior to administration of the edited cells to the subject. Conditioning can involve lymphodepletion of the subject. For example, in one embodiment, the subject is conditioned with chemotherapy causing lymphodepletion, prior to receipt of the edited cells. In one embodiment, T cells from the subject are depleted by conditioning. Agents suitable for conditioning the subject include agents that induce lymphodepletion, for example, depletion of T cells. In one embodiment, the conditioning agent is cyclophosphamide. In some embodiments, the method can optionally comprise a step of administering a conditioning agent to the subject, e.g., a conditioning agent causing lymphodepletion. In one embodiment, the conditioning agent is a chemotherapeutic agent, e.g. cyclophosphamide, fludarabine, busulfan, treosulfan, or a combination thereof. In one embodiment, the conditioning agent is a polyclonal or monoclonal depleting antibody, e.g. anti-thymocyte globulin (ATG), anti-CD3, anti-CD4, anti-CD52, anti-CD2, anti-TCRαβ, anti-IL2Rα, or a combination thereof. In another embodiment, the subject is not conditioned prior to administration of the edited cells to the subject.

In one embodiment, the cells are stimulated prior to administration to the subject. In one embodiment, the cells are stimulated using cytokines, e.g., IL-7, IL-15, IL-2, or a combination thereof.

In one embodiment, class switching is restored in the subject. In one embodiment, levels of IgM are decreased in a subject. In one embodiment, levels of IgG are increased in a subject.

In one embodiment, the cell is a population of cells, and the DNA repair pathway repairs the target CD40L nucleic acid to result in targeted integration of the exogenous oligonucleotide donor template in at least about 10% of the cells in the population of cells. In one embodiment, the cell is a population of cells, and the DNA repair pathway repairs the target CD40L nucleic acid to result in targeted integration of the exogenous oligonucleotide donor template in at least about 15%, 20%, 25%, 30%, 35%, 40%, 45%, 50%, 55%, 60%, 65%, 70%, or 75% of the cells in the population of cells. In one embodiment, the cell is a population of cells, and the DNA repair pathway repairs the target CD40L nucleic acid to result in targeted integration of the exogenous oligonucleotide donor template in at least about 15% of the cells in the population of cells. In one embodiment, the cell is a population of cells, and the DNA repair pathway repairs the target CD40L nucleic acid to result in targeted integration of the exogenous oligonucleotide donor template in at least about 20% of the cells in the population of cells. In one embodiment, the cell is a population of cells, and the DNA repair pathway repairs the target CD40L nucleic acid to result in targeted integration of the exogenous oligonucleotide donor template in at least about 30% of the cells in the population of cells. In one embodiment, the cell is a population of cells, and the DNA repair pathway repairs the target CD40L nucleic acid to result in targeted integration of the exogenous oligonucleotide donor template in at least about 40% of the cells in the population of cells. In one embodiment, the cell is a population of cells, and the DNA repair pathway repairs the target CD40L nucleic acid to result in targeted integration of the exogenous oligonucleotide donor template in at least about 50% of the cells in the population of cells. In one embodiment, the cell is a population of cells, and the DNA repair pathway repairs the target CD40L nucleic acid to result in targeted integration of the exogenous oligonucleotide donor template in at least about 60% of the cells in the population of cells. In one embodiment, the cell is a population of cells, and the DNA repair pathway repairs the target CD40L nucleic acid to result in targeted integration of the exogenous oligonucleotide donor template in at least about 75% of the cells in the population of cells.

In one aspect, disclosed herein is a cell altered by a method disclosed herein. In one aspect, disclosed herein is a population of cells altered by a method disclosed herein.

In one embodiment, the cells are hematopoietic stem cells (HSCs), and wherein at least about 10% of the cells in the population of HSCs comprise an altered CD40L nucleic acid which is a functional CD40L allele. In one embodiment, the cells are T cells.

In one aspect, disclosed herein is a pharmaceutical composition comprising a cell, or population of cells.

In one aspect, disclosed herein is a method of treating a subject having hyper-IgM syndrome by altering a target CD40L in a cell, the method comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, thereby treating the subject having hyper-IgM syndrome.

In one aspect, disclosed herein is a method of treating a subject having hyper IgM syndrome by altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby treating the subject having hyper IgM syndrome.

In one aspect, disclosed herein is a method of restoring B cell class switching in a subject by altering a target CD40L in a cell, the method comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, thereby restoring B cell class switching in the subject.

In one aspect, disclosed herein is a method of restoring B cell class switching in a subject by altering a target CD40L nucleic acid in a cell, wherein the target CD40L nucleic acid comprises a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby restoring B cell class switching in the subject.

In one aspect, disclosed herein is a method of decreasing a level of IgM in a subject by altering a target CD40L in a cell, the method comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, thereby decreasing the level of IgM in the subject.

In one aspect, disclosed herein is a method of decreasing a level of IgM in a subject by altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby decreasing the level of IgM in the subject.

In one aspect, disclosed herein is a method of increasing a level of IgG in a subject by altering a target CD40L in a cell, the method comprising the steps of: forming, in a target CD40L nucleic acid of the cell, at least one single- or double-strand break at a cleavage site, wherein the target CD40L nucleic acid comprises: a first homology arm 5' to the cleavage site and a second homology arm 3' to the cleavage site, and recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, thereby increasing the level of IgG in the subject.

In one aspect, disclosed herein is a method of increasing a level of IgG in a subject by altering a target CD40L nucleic acid in a cell, wherein the target CD40L nucleic acid comprises: a first homology arm 5' to the cleavage site and a second homology arm 3' to the cleavage site, the method comprising: contacting the cell with (a) at least one gRNA molecule, (b) a RNA-guided nuclease molecule, and (c) an exogenous oligonucleotide donor template, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, wherein the gRNA molecule and the RNA-guided nuclease molecule interact with the target CD40L nucleic acid, resulting in a cleavage event at or near the cleavage site, and wherein the cleavage event is repaired by at least one DNA repair pathway to produce an altered CD40L nucleic acid, thereby increasing the level of IgG in the subject.

In one aspect, disclosed herein is a population of cells, characterized in that at least 10% of the cells in the population comprise at least one copy of an engineered CD40L sequence. In one embodiment, at least 15% of the cells in the population comprise at least one copy of an engineered CD40L sequence. In one embodiment, at least 20% of the cells in the population comprise at least one copy of an engineered CD40L sequence. In one embodiment, at least 30% of the cells in the population comprise at least one copy of an engineered CD40L sequence. In one embodiment, at least 40% of the cells in the population comprise at least one copy of an engineered CD40L sequence. In one embodiment, at least 50% of the cells in the population comprise at least one copy of an engineered CD40L sequence. In one embodiment, at least 60% of the cells in the population comprise at least one copy of an engineered CD40L sequence.

In one embodiment, the at least one copy is inserted into an intron of an endogenous CD40L gene. In one embodiment, the population of cells, or progeny of the population of cells, are capable of restoring class switching in a subject suffering from Hyper IgM syndrome.

In one aspect, disclosed herein is an isolated population of cells, wherein at least about 5% to about 100% of cells in the population of cells express a functional CD40L allele, wherein the population of cells have been isolated from a subject, and wherein the subject has previously been diagnosed as having hyper IgM syndrome. In one embodiment, at least about 6% of cells in the population of cells express a functional CD40L allele. In one embodiment, at least about 7% of cells in the population of cells express a functional CD40L allele. In one embodiment, at least about 8% of cells in the population of cells express a functional CD40L allele. In one embodiment, at least about 9% of cells in the population of cells express a functional CD40L allele. In one embodiment, at least about 10% of cells in the population of cells express a functional CD40L allele. In one embodiment, at least about 15% of cells in the population of cells express a functional CD40L allele. In one embodiment, at least about 20% of cells in the population of cells express a functional CD40L allele. In one embodiment, at least about 25% of cells in the population of cells express a functional CD40L allele.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 1A depicts a construct comprising homology arms, CD40L cDNA, GFP, and Stuffer sequences. FIG. 1B depicts a construct comprising homology arms, CD40L cDNA, and GFP, without Stuffer sequences. FIG. 1C depicts a construct comprising homology arms, CD40L cDNA, and Stuffer sequences, without GFP. FIG. 1D depicts a construct comprising homology arms and CD40L cDNA, without GFP and without Stuffer sequences.

FIGS. 2A-2J depict that the genome editing systems described herein resulted in high levels of CD40LG gene editing. Specifically, FIG. 2A is a schematic of exemplary constructs for CD40L gene editing. FIG. 2B depicts the position in CD40LG intron 1 targeted by 8 S. Pyogenes and 30 S. aureus gRNAs screened for efficacy of cutting CD40LG in primary human T cells. FIG. 2C depicts the editing percentages including the insertion/deletion rates for exemplary gRNAs from FIG. 2B delivered with nuclease as an RNP complex to primary human T cells. FIG. 2D depicts the experimental procedure of CD40L gene editing in T lymphocytes. FIG. 2E depicts the percentage of GFP positive cells in T cell populations upon gene editing. T stem memory cells (TSCM) are defined as CD62L+CD45RA+, T central memory (TCM) as CD62L+CD45RA−, T effector memory (TEM) as CD62L− CD45RA− and terminal effectors (TEMRA) asCD62L−CD45RA+. FIG. 2F depicts representative plots of T cells 7 days (left panel) and 20 days (right panel) after treatment that express CD45RA and CD62 by FACS analysis. FIG. 2G depicts the T cell culture composition 7 and 19 days (left panel) and 20 days (right panel) after treatment, measured by FACS analysis. FIG. 2H is a schematic protocol for gene editing in T cells using a donor template provided by AAV6 or IDLV. FIG. 2I depicts the HDR outcome (assessed as the percentage of GFP+ cells) in various T cell subpopulations. FIG. 2J depicts the levels of gene editing in HD and patient cells.

FIGS. 3A-3E depict targeted integration and CD40L expression after editing with three exemplary gRNAs (gRNAs A, D, and G). FIG. 3A depicts the location of exemplary gRNAs within CD40LG intron 1. FIG. 3B depicts the experimental procedures and timeline for the experiments presented in FIG. 3D-3E. FIG. 3C provides the rate of targeted integration (% of GFP+ cells) following treatment with the indicated RNP complexes and the AAV6 donor template. FIG. 3D depicts CD40L expression in the GFP-positive cell population, determined by FACS analysis. FIG. 3E depicts the CD40L+ cell fraction at various time points following re-stimulation.

FIGS. 4A-4F depict that edited CD40L preserves physiologic regulation. Specifically, FIGS. 4A and 4B depict the constructs and experimental procedure used for CD40L gene editing and expression in T lymphocytes. FIGS. 4C and 4E depict the kinetics of CD40L expression in edited T cells after the induction of CD40L surface expression by a polyclonal stimulation (PMA/Ionomycin). FIG. 4D depicts a representative plot showing expression of CD40L in activated CD4+ and CD8+ cells. FIG. 4F depicts a representative plot showing expression of CD40L in stimulated CD4+ cells.

FIGS. 5A and 5B depict the constructs and experimental procedure used for CD40L gene editing and expression in T lymphocytes. FIG. 5C depicts expression of CD40L and CD8 in wild type and edited T cells. FIG. 5D depicts the kinetics of CD40L expression in edited T cells. FIG. 5E depicts the effect of AAV6 on gene editing efficiency.

FIGS. 6A and 6B demonstrate that gene editing produces high levels of CD40L gene editing (FIG. 6A) and high levels of exogenous CD40L expression, using different transgene configurations (wild type cDNA (non recoded) or codon optimized (recoded) sequence; endogenous polyadenylation signal or viral SV40 polyadenylation signal (FIG. 6B).

FIGS. 7A-7F depict the results of experiments that evaluate the specificity of exemplary gRNAs targeting CD40LG. FIG. 7A presents Guide-Seq analysis of gRNA A and gRNA D. FIGS. 7B and 7E validate the on-target and off-target editing observed with gRNA A using Amplicon-Seq analysis. FIG. 7C-7D present the results of Digenome analysis to identify potential off-target sites for gRNA A and gRNA D. FIG. 7F depicts an overview of the results of the Amplicon-Seq analysis for the identified off-target cut sites for gRNA A and D.

In FIG. 12A are shown the percentages of CD8 and CD4 cells measured within the circulating wild type T cell population. In FIG. 12B are shown the percentages of effectors (CD44+CD62L−), central memory (TCM, CD44+CD62L+), naive (CD44−CD62L+) and early effector (CD44−CD62L−) T cells, measured within the CD8 and CD4 fractions of circulating wild type T cells.

FIG. 14A shows the amount of antigen specific IgG response before or after 2 boosts of immunization with the TNP-KLH antigen in the serum of the HIGM1 mice transplanted with or without different doses of conditioning. FIG. 14B shows the correlation graph between the serum levels of TNP/KLH specific IgG and the amounts of circulating wild type CD4 T cells (percentages on the top and absolute numbers on the bottom).

FIGS. 14C and 14E depict the percentages of recipient and donor T cells during time in the mice treated or not with the pre-conditioning regimen. The levels of specific IgG response to the vaccination correlates with the dose of conditioning administered (FIG. 14D).

FIG. 15A-15B depict immunohistochemistry analysis of GC B Cells in Spleen sections of adoptively transplanted mice from FIG. 14 after TNP-KLH-immunization. FIG. 15A depicts immunohistochemistry staining analysis of GC B Cells in Spleen sections with Peanut agglutinin in brown and hematoxylin counterstaining in blue. FIG. 15B depicts a histogram, quantifying the immunohistochemistry analysis depicted in FIG. 15A.

FIGS. 16A-16C depicts hematopoietic stem cell therapy in murine hyper-IgM syndrome models. As shown in FIG. 16A, different doses of CD40LG wild type hematopoietic stem cells, harvested from wild type C57BL/6 mice, were transplanted at different ratios together with CD40LG negative HSPC, harvested from HIGM1 mice, in recipient HIGM1 mice prior to immunization with a thymus-dependent antigen (TNP-KLH). The dot plot depicts the amount of TNP-KLH specific IgG in the serum of the transplanted animals before or after 14 and 28 days from immunization of the transplanted mice with the TNP-KLH antigen. FIG. 16B depicts a second experiment in which CD40L mice transplanted with different percentages of wild type HSPC and CD40LG negative HSPC as described for FIG. 16A. The mice were immunized with TNP-KLH, and were subsequently immunized with ovalbumin. The dot plot depicts the amount of TNP-specific IgG (left panel) and the amount of OVA-specific IgG (right panel) before and after immunization. FIG. 16C depict the donor T cell engraftment in peripheral blood, measured at different time points after transplant.

FIG. 17A shows the percentage of GFP+ edited cells measured in different T cell subpopulations 17 days after treatment.

FIG. 17B shows the culture composition measured by cytofluorimetric analysis (GFP marking). FIG. 17C compares gene editing efficiency measured by ddPCR molecular analysis (left bars) and by cytofluorimetric analysis (GFP by FACS, right bars). FIG. 17D shows TCR diversity in untreated patient cells (gray/right panels) and in edited patient cells (black/left panels), assessed by 5 different multiplex PCR reactions that discriminate 21 families of TCR-B.

FIG. 18A shows representative flow cytometry dot plots depicting CD40L and GFP expression 8 hours upon PMA/Ionomycin (P/I) stimulation in HD and patient cells from FIG. 17. FIG. 18B shows the time course of CD40L surface expression, as Relative Fluorescence Intensity (RFI, calculated with the ratio on T0) and as percentage, measured at 0, 3, 8, 24, and 48 hours following P/I activation.

FIG. 19A shows a schematic representation of the protocol of T and B cell co-culture assays. FIG. 19B and FIG. 19C depict flow cytometry plots and histograms, respectively, showing the percentage of proliferating B-cells in co-culture with resting, bead-activated (1:1 ratio) or PMA/Ionomycin stimulated T cells (untreated (UT) or edited (GFP+)). Negative control: B cells alone; positive control: B cell+soluble CD40L.

FIG. 20A and FIG. 20B depict Elispot images and histograms, respectively, showing the percentage of IgG switched B-cells in co-culture with resting, bead-activated (1:1 ratio) or PMA/Ionomycin stimulated T cells (untreated (UT) or edited (GFP+)). Negative control: B cells alone; positive control: B cell+soluble CD40L.

FIG. 21A is a schematic of the donor construct used to edit CD34+ cells. FIG. 21B, FIG. 21C and FIG. 21E show the percentage of targeted integration in bulk treated CD34 cells and in the indicated sorted subpopulations, respectively, measured by digital droplet PCR analysis performed on the 5' vector to genome junction. FIG. 21D depicts the culture composition of the treated and untreated (UT) cells. FIG. 21F depicts the percentage of hCD45+ cells (left panel) and the percentage of HDR cells (right panel) within the graft, measured at different time point after transplant.

FIG. 22A depicts the donor DNA construct carrying the corrective CD40LG gene, an Internal ribosome entry site (IRES) sequence and a selector gene (e.g. delta LNGFR). FIG. 22B is a schematic depiction of the targeted integration protocol that indicates the different time points at which the expression of the selector gene was assessed by cytofluorimetric analyses. FIG. 22C depicts the expression of the reporter gene at the indicated time points (6 days, 13 days, and 20 days) in both CD4 and CD8 T cells treated as described in FIG. 22B. FIG. 22D depicts the kinetics of CD40L expression after re-stimulation of the T cells treated for gene editing. FIG. 22E depicts the expression level (mean fluorescent intensity, MFI) of the CD40L gene (left) and the percentage of the CD40L+ cells in the untreated, NGFR+ and NGFR− T cell population. FIG. 22F depicts the ability of CD40L edited T cells to restore B cell class switching in a co-culture assay, showing the percentage of IgG switched B-cells in co-culture with resting, bead-activated (1:1 ratio) or PMA/Ionomycin stimulated T cells (untreated (UT) or edited (NGFR+)). Negative control: B cells alone; positive control: B cell+soluble CD40L.

FIG. 23A depicts the percentage of NGFR+ cells obtained after gene editing, measured within different T cell subpopulations (from left to right: terminal effectors (TEMRA), CD45RA+CD62L−; effector memory (TEM), CD62L− CD45RA−; central memory (TCM), CD45RA−CD62L+; and T stem memory cells (TSCM), CD45RA+CD62L+). FIG. 23B depicts the fraction of T cell subpopulations measured pre- or post-NGFR selection. FIG. 23C depicts the percentage of CD40LG gene editing measured by molecular analysis (ddPCR) or by NGFR expression, pre- or post-NGFR selection.

FIG. 24A depicts the percentage of human cells (hCD45+ cells; top left and bottom left and right panels) and the percentage of NGFR+ cells (top right panel) within the human graft, measured at different time point after transplant. FIG. 24B depicts the fraction of T cell subpopulations (terminal effectors (TEMRA), CD45RA+CD62L−; effector memory (TEM), CD62L− CD45RA−−; central memory (TCM), CD45RA−CD62L+; and T stem memory cells (TSCM), CD45RA+CD62L+) of the engrafted T cells measured at 4, 8 and 16 weeks after transplant. FIG. 24C depicts the levels of CD40LG expression and the percentage of CD40LG+ cells recovered from the NSG mice.

FIGS. 25A-25D depict experiments demonstrating that HSPC editing is portable to the CRISPR/Cas platform. FIG. 25A presents a protocol for editing CD34+ cells obtained from cord blood. FIG. 25B depicts the targeted integration efficiency (expressed as the percentage of GFP+cells) in various cell populations obtained through gene editing using ZFN or RNP. FIG. 25C depicts the culture composition after gene editing using ZFN or RNP, compared to untreated cells (UT). FIG. 25D depicts the fold induction of interferon (IFN) responsive genes RIG1, IRF7, and OAS1, following treatment with RNP, ZFN, Cas9 alone, or RNP-mod, compared to untreated cells (UT).

FIG. 26A presents a protocol for editing CD34+ cells from cord blood (CB), bone marrow (BM), or mobilized peripheral blood (MPB). FIG. 26B depicts the targeted integration efficiency (expressed as the percentage of GFP+ cells) in various cell populations obtained using the indicated editing procedures. FIG. 25C depicts the culture composition after editing. FIG. 26D depicts the expression of IFN responsive genes RIG1, IRF7, and OAS1 in edited cells.

FIG. 27A depicts the percentage of edited (GFP+) cell subpopulations using ZFN or RNP in conjunction with IDLV or AAV6 donor templates. FIG. 27B depicts the percentage of edited (GFP+) cell subpopulations using CD34+ cells derived from cord blood, bone marrow, and mobilized peripheral blood (mPB).

DETAILED DESCRIPTION

Definitions and Abbreviations

Figure 1:
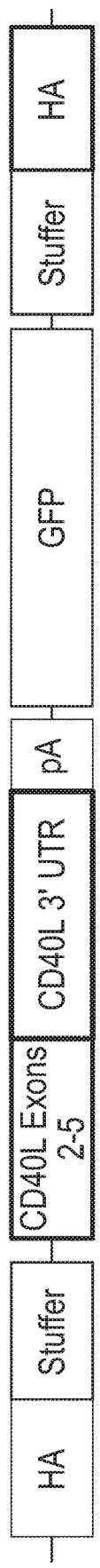
FIGS. 1A-D depict the configuration of exemplary CD40L donor templates for gene editing.
Figure 1:
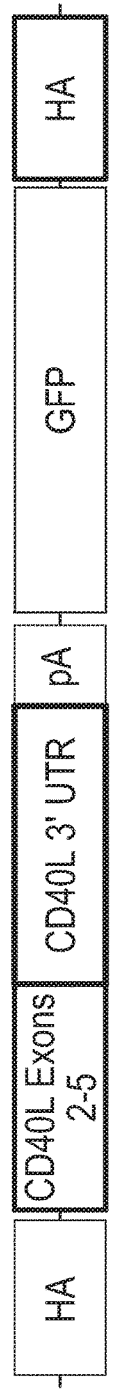
Figure 1:
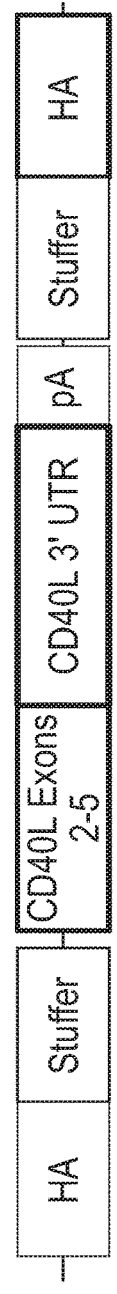
Figure 1:

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

As used herein, the term "cleavage event" refers to a break in a nucleic acid molecule. A cleavage event may be a single-strand cleavage event, or a double-strand cleavage event. A single-strand cleavage event may result in a 5' overhang or a 3' overhang. A double-stranded cleavage event may result in blunt ends, two 5' overhangs, or two 3' overhangs.

The term "cleavage site," as used herein in reference to a site on a target nucleic acid sequence, e.g., a target CD40L nucleic acid sequence, refers to a target position between two nucleotide residues of the target nucleic acid where a double-stranded break occurs, or alternatively, to a target position within a span of several nucleotide residues of the target nucleic acid wherein two single stranded breaks occur, as mediated by a RNA-guided nuclease-dependent process. A cleavage site may be the target position for, e.g., a blunt double stranded break. Alternatively, a cleavage site may be a target site within a span of several nucleotide residues of the target nucleic acid for, e.g., two single strand breaks or nicks which form a double strand break and which are separated by, e.g., about 10 base pairs. The double strand break(s) or the closer of the two single strand nicks in a pair will ideally be within 0-500 bp of a target position (e.g., no more than 450, 400, 350, 300, 250, 200, 150, 100, 50, or 25 bp from the target position). When dual nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20, or 10 bp).

The phrase "consisting essentially of" means that the species recited are the predominant species, but that other species may be present in trace amounts or amounts that do not affect structure, function or behavior of the subject composition. For instance, a composition that consists essentially of a particular species will generally comprise 90%, 95%, 96%, or more of that species.

"Domain" is used to describe a segment of a protein or nucleic acid. Unless otherwise indicated, a domain is not required to have any specific functional property.

As used herein, the term "endogenous" gene, "endogenous" nucleic acid, or "endogenous" homologous region refers to a native gene, nucleic acid, or region of a gene, which is in its natural location in the genome, e.g., chromosome or plasmid, of a cell. In contrast, the term "exogenous" gene or "exogenous" nucleic acid refers to a gene, nucleic acid, or region of a gene which is not native within a cell, but which is introduced into the cell during the methods of the invention. An exogenous gene or exogenous nucleic acid may be homologous to, or identical to, an endogenous gene or an endogenous nucleic acid.

The term "exon" refers to a coding region of a gene that contains the information required to encode a protein. In eukaryotes, genes are made up of coding exons interspersed with non-coding introns. In RNA splicing, introns are removed and exons are covalently linked to one another to make a functioning mature messenger RNA (mRNA) that can be translated into a protein. The term exon refers to both the DNA sequence within a gene and to the corresponding sequence in RNA transcripts.

"Gene conversion" refers to the alteration of a DNA sequence by incorporation of an endogenous homologous sequence (e.g., a homologous sequence within a gene array). "Gene correction" refers to the alteration of a DNA sequence by incorporation of an exogenous homologous sequence, such as an exogenous single- or double stranded donor template DNA. Gene conversion and gene correction are products of the repair of DNA double-strand breaks by HDR pathways such as those described below.

The terms "homology" or "identity," as used interchangeably herein, refer to sequence identity between two amino acid sequences or two nucleic acid sequences, with identity being a more strict comparison. The phrases "percent identity or homology" and "% identity or homology" refer to the percentage of sequence identity found in a comparison of two or more amino acid sequences or nucleic acid sequences. Two or more sequences can be anywhere from 0-100% identical, or any value there between. Identity can be determined by comparing a position in each sequence that can be aligned for purposes of comparison to a reference sequence. When a position in the compared sequence is occupied by the same nucleotide base or amino acid, then the molecules are identical at that position. A degree of identity of amino acid sequences is a function of the number of identical amino acids at positions shared by the amino acid sequences. A degree of identity between nucleic acid sequences is a function of the number of identical or matching nucleotides at positions shared by the nucleic acid sequences. A degree of homology of amino acid sequences is a function of the number of amino acids at positions shared by the polypeptide sequences.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

The term "homology arm", as used herein, refers to one or more regions that are homologous to regions of DNA, e.g., a target nucleic acid, within or near (e.g., flanking or adjoining) a target sequence to be cleaved, e.g., a cleavage site.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai et al. (Nat. Biotechnol. 34(5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

The term "intron" refers to a long stretch of noncoding DNA found between exons (or coding regions) in a gene. Intron usually begins and ends with a specific series of nucleotides and are spliced out before the RNA molecule is translated into a protein. These sequences act as the boundary between introns and exons and are known as splice sites. The recognition of the boundary between coding and non-coding DNA is crucial for the creation of functioning genes.

The term "isolated gene" or "isolated nucleic acid" is a gene or nucleic acid that by virtue of its origin or source of derivation is not associated with naturally associated components that accompany it in its native state; is substantially free of other proteins from the same species; is expressed by a cell from a different species; or does not occur in nature. Thus, a nucleic acid that is chemically synthesized or synthesized in a cellular system different from the cell from which it naturally originates will be "isolated" from its naturally associated components. A nucleic acid may also be rendered substantially free of naturally associated components by isolation, using protein purification techniques well known in the art.

Conventional IUPAC notation is used in nucleotide sequences presented herein, as shown in Table 1, below (see also Cornish-Bowden A, Nucleic Acids Res. 1985 May 10; 13(9):3021-30, incorporated by reference herein). It should be noted, however, that "T" denotes "Thymine or Uracil" in those instances where a sequence may be encoded by either DNA or RNA, for example in gRNA targeting domains.

TABLE 1

IUPAC nucleic acid notation

| Character | Base |
| --- | --- |
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

A "kit" refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g., suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

The terms "poly(A)", "poly(A) tail", and "polyadenylation" refer to the addition of a poly(A) tail on a messenger RNA. The poly-A tail is a long chain of adenine nucleotides that is added to a messenger RNA (mRNA) molecule during RNA processing to increase the stability of the molecule. Immediately after a gene in a eukaryotic cell is transcribed, the new RNA molecule undergoes several modifications known as RNA processing. These modifications alter both ends of the primary RNA transcript to produce a mature mRNA molecule. The processing of the 3' end adds a poly-A tail to the RNA molecule.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides, nucleotide sequences, nucleic acids etc. can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases. A "CD40L" nucleic acid, as used herein, refers to a series of nucleotide bases which encode a CD40L protein.

"Prevent," "preventing," and "prevention" refer to the prevention of a disease in a mammal, e.g., in a human, including (a) avoiding or precluding the disease; (b) affecting the predisposition toward the disease; or (c) preventing or delaying the onset of at least one symptom of the disease.

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

"Replacement" or "replaced," when used with reference to a modification of a molecule (e.g., a nucleic acid or protein), does not require a process limitation but merely indicates that the replacement entity is present.

The term "stuffer sequence", as used herein, refers to a heterologous or random nucleic acid sequence that has been selected to facilitate the targeted integration of a donor template into a target site and the subsequent amplification of an amplicon comprising the stuffer sequence. The presence of stuffer sequence also prevents driving integration of the donor template into another site. Stuffer sequences are described in more detail herein.

"Subject" means a human or non-human animal A human subject can be any age (e.g., an infant, child, young adult, or adult), and may suffer from a disease, or may be in need of alteration of a gene. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "substantially identical" as used herein in reference to two nucleic acid sequences refers, in some embodiments, to a sequence identity of at least 95% between across an at least 20 nucleotide contiguous stretch of each of the two nucleic acid sequences. For example, a first nucleic acid sequence is substantially identical to a second nucleic acid sequence when the first nucleic acid sequence has at least 95%, at least 96%, at least 97%, at least 98%, at least 99%, or 100% identity across an at least 20 nucleotide contiguous stretch of the second nucleic acid sequence. In some embodiments, a first nucleic acid sequence is substantially identical to a second nucleic acid sequence when the first nucleic acid sequence has at least 95% identity across the entire length of the second nucleic acid sequence. In some embodiments, the term "substantially identical" is used in the context of priming sites, and refers to the ability of the priming sites to support priming with the same PCR primer during an amplification reaction. In some embodiments, the term "substantially identical" is used to describe the relationship between the homology arm of a donor template and the homology arm of a target nucleic acid, and refers to a nucleic acid identity between the homology arms that allows for the efficient recombination of the donor template at the target nucleic acid with tolerance for some degree of polymorphism, e.g., to eliminate PAM or protospacer sequences in the recombined locus.

"Target CD40L nucleic acid" as used herein, refers to a CD40L nucleic acid present in, e.g., the chromosome, that is targeted for modification by a RNA-guided nuclease-dependent process using the genome editing systems disclosed herein. A target CD40L nucleic acid may comprise, for example, a mutation. In some embodiments, the mutation leads to loss of B cell class switching due to defective CD40 signaling.

"Target position" as used herein, refers to a site on a target nucleic acid (e.g., the chromosome) that is modified by a RNA-guided nuclease-dependent process. In an embodiment, a target position can be a site between two nucleotides, e.g., adjacent nucleotides, on the target nucleic acid. The target position may comprise one or more nucleotides that are altered, e.g., corrected, by a template nucleic acid. In an embodiment, the target position is within a "target sequence" (e.g., the sequence to which the gRNA binds). In an embodiment, a target position is upstream or downstream of a target sequence (e.g., the sequence to which the gRNA binds).

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

The term "untranslated region" or "UTR" refers to either one of the two nonprotein coding sections of the mRNA. The 5' untranslated region (5' UTR), also known as a leader sequence or leader RNA, is the region of an mRNA that is directly upstream from the initiation codon. The 3' untranslated region (3' UTR) refers to the section of mRNA that immediately follows the translation termination codon.

The term "variant" refers to an entity such as a polypeptide, polynucleotide or small molecule that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity.

Overview

Provided herein are genome editing systems, donor templates, gRNA molecules, and related methods which allow for treatment of Hyper IgM Syndrome, a group of disorders characterized by defective CD40 signaling. The compositions and methods described herein rely on the use of donor templates comprising one or more of exons 2-5 of CD40L to functionally restore proper CD40 signaling and class switch recombination.

Genome Editing Systems

The term "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

Naturally occurring CRISPR systems are organized evolutionarily into two classes and five types (Makarova et al. Nat Rev Microbiol. 2011 June; 9(6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e., target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g., administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes two gRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant", incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932, Mar. 11, 2014 (Davis) (describing Alt-HDR); Frit et al. DNA Repair 17(2014) 81-97 (Frit) (describing Alt-NHEJ); and Iyama and Wilson III, DNA Repair (Amst.) 2013 August; 12(8): 620-636 (Iyama) (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence, such as a CD40L sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 (Briner), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science August 17; 337(6096): 816-821 ("Jinek"), all of which are incorporated by reference herein.)

Guide RNAs, whether unimolecular or modular, include a "targeting domain" that is fully or partially complementary to a target domain within a target sequence, such as a CD40L sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 (Nishimasu 2014) and Nishimasu et al., Cell 162, 1113-1126, Aug. 27, 2015 (Nishimasu 2015), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "*nexus*" (Briner). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate that, although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA Design

Methods for selection and validation of target sequences as well as off-target analyses have been described previously, e.g., in Mali; Hsu; Fu et al., 2014 Nat Biotechnol. 32(3): 279-84, Heigwer et al., 2014 Nat methods 11(2):122-3; Bae et al. (2014) Bioinformatics 30(10): 1473-5; and Xiao A et al. (2014) Bioinformatics 30(8): 1180-1182. Each of these references is incorporated by reference herein. As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

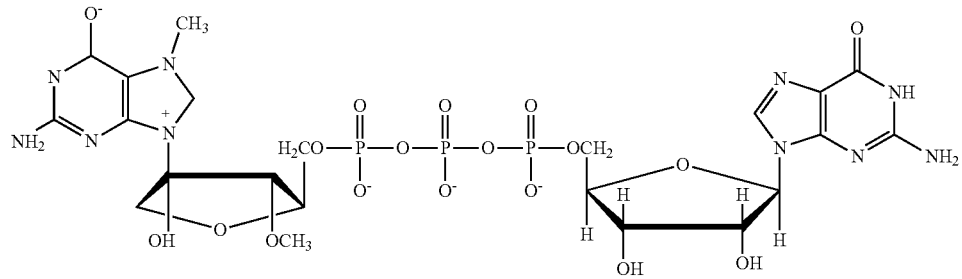

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., E. coli Poly(A)Polymerase), or in vivo by means of a polyadenylation sequence, as described in Maeder.

It should be noted that the modifications described herein can be combined in any suitable manner, e.g., a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

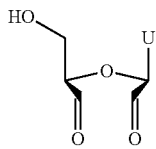

wherein "U" can be an unmodified or modified uridine.

The 3' terminal U ribose can be modified with a 2'3' cyclic phosphate as shown below:

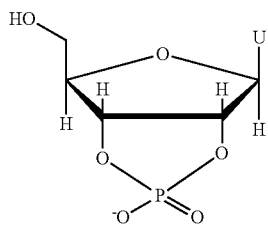

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH$_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., NH$_2$; alkylamino, dialkylamino, heterocyclyl, arylamino, diarylamino, heteroarylamino, or diheteroarylamino, ethylenediamine, or polyamino) and aminoalkoxy or O(CH$_2$)$_n$-amino (wherein amino can be, e.g., NH$_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deazaadenosine, can be incorporated into the gRNA. In certain embodiments, 0- and N-alkylated nucleotides, e.g., N6-methyl adenosine, can be incorporated into the gRNA. In certain embodiments, one or more or all of the nucleotides in a gRNA are deoxynucleotides.

CD40L Donor Templates

Donor templates, e.g., oligonucleotide donor templates, according to this disclosure may be implemented in any suitable way, including without limitation single stranded or double stranded DNA, linear or circular, naked or comprised within a vector, and/or associated, covalently or non-covalently (e.g., by direct hybridization or splint hybridization) with a guide RNA. Some preferred donor template designs are schematically depicted in FIG. 1.

In some embodiments, the donor template is a ssODN. Where a linear ssODN is used, it can be configured to (i) anneal to a nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, or no more than 150-200 nucleotides (e.g., 150, 160, 170, 180, 190, or 200 nucleotides). In other embodiments, the ssODN has a length of about 100-3000 nucleotides, for example, about 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 nucleotides. In other embodiments, the ssODN has a length of at least 100-3000 nucleotides, for example, at least 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 nucleotides. In other embodiments, the ssODN has a length of no more than 100-3000 nucleotides, for example, no more than 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 nucleotides.

In other embodiments, the donor template is a dsODN. In one embodiment, the donor template comprises a first strand. In another embodiment, a donor template comprises a first strand and a second strand. A dsODN may have any suitable length, e.g., about, or no more than 150-200 base pairs (e.g., 150, 160, 170, 180, 190, or 200 base pairs). In other embodiments, the dsODN has a length of about 100-3000 base pairs, for example, about 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 base pairs. In other embodiments, the dsODN has a length of at least 100-3000 base pairs, for example, at least 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 base pairs. In other embodiments, the dsODN has a length of no more than 100-3000 base pairs, for example, no more than 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 base pairs.

In some embodiments, a donor template is an exogenous oligonucleotide, e.g., an oligonucleotide that is not naturally present in a cell.

It should be noted that a donor template can also be comprised within a nucleic acid vector, such as a viral genome or circular double-stranded DNA, e.g., a plasmid. In some embodiments, the donor template can be a doggy-bone shaped DNA (see, e.g., U.S. Pat. No. 9,499,847). Nucleic acid vectors comprising donor templates can include other coding or non-coding elements. For example, a donor template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino. In one embodiment, the donor template is present in an AAV6 vector. In another embodiment, the donor template is present in an IDLV vector.

A. Homology Arms

Whether single-stranded or double-stranded, donor templates generally include one or more regions that are homologous to regions of DNA, e.g., a target nucleic acid, CD40L sequence, within or near (e.g., flanking or adjoining) a target sequence to be cleaved, e.g., the cleavage site. These homologous regions are referred to here as "homology arms," and are illustrated schematically in FIG. 1.

The homology arms of the donor templates described herein may be of any suitable length, provided such length is sufficient to allow efficient resolution of a cleavage site on a targeted nucleic acid by a DNA repair process requiring a donor template. In some embodiments, where amplification by, e.g., PCR, of the homology arm is desired, the homology arm is of a length such that the amplification may be performed. In some embodiments, where sequencing of the homology arm is desired, the homology arm is of a length such that the sequencing may be performed. In some embodiments, where quantitative assessment of amplicons is desired, the homology arms are of such a length such that a similar number of amplifications of each amplicon is achieved, e.g., by having similar G/C content, amplification temperatures, etc. In some embodiments, the homology arm is double-stranded. In some embodiments, the double stranded homology arm is single stranded.

In some embodiments, the 5' homology arm is between 150 to 250 nucleotides in length. In some embodiments, the 5' homology arm is 700 nucleotides or less in length. In some embodiments, the 5' homology arm is 650 nucleotides or less in length. In some embodiments, the 5' homology arm is 600 nucleotides or less in length. In some embodiments, the 5' homology arm is 550 nucleotides or less in length. In some embodiments, the 5' homology arm is 500 nucleotides or less in length. In some embodiments, the 5' homology arm is 400 nucleotides or less in length. In some embodiments, the 5' homology arm is 300 nucleotides or less in length. In some embodiments, the 5' homology arm is 250 nucleotides or less in length. In some embodiments, the 5' homology arm is 200 nucleotides or less in length. In some embodiments, the 5' homology arm is 150 nucleotides or less in length. In some embodiments, the 5' homology arm is less than 100 nucleotides in length. In some embodiments, the 5' homology arm is 50 nucleotides in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 5' homology arm is 40 nucleotides in length. In some embodiments, the 3' homology arm is 250 nucleotides in length or less. In other embodiments, the 5' homology arm is at least 50 nucleotides in length. In some embodiments, the 5' homology arm is at least 100 nucleotides in length. In some embodiments, the 5' homology arm is at least 150 nucleotides in length. In some embodiments, the 5' homology arm is at least 200 nucleotides in length. In some embodiments, the 5' homology arm is at least 250 nucleotides in length. In some embodiments, the 5' homology arm is at least 300 nucleotides in length. In some embodiments, the 5' homology arm is at least 350 nucleotides in length. In some embodiments, the 5' homology arm is at least 400 nucleotides in length. In some embodiments, the 5' homology arm is at least 450 nucleotides in length. In some embodiments, the 5' homology arm is at least 500 nucleotides in length. In some embodiments, the 5' homology arm is at least 550 nucleotides in length. In some embodiments, the 5' homology arm is at least 600 nucleotides in length. In some embodiments, the 5' homology arm is at least 650 nucleotides in length. In some embodiments, the 5' homology arm is at least 700 nucleotides in length. In one embodiment, the 5' homology arm is between 200-700 nucleotides in length. In one embodiment, the 5' homology arm is between 200-300 nucleotides in length. In one embodiment, the 5' homology arm is between 200-400 nucleotides in length. In one embodiment, the 5' homology arm is between 200-500 nucleotides in length. In one embodiment, the 5' homology arm is between 400-700 nucleotides in length. In one embodiment, the 5' homology arm is between 500-700 nucleotides in length. In one embodiment, the 5' homology arm is about 500 nucleotides in length.

In some embodiments, the 3' homology arm is between 150 to 250 nucleotides in length. In some embodiments, the 3' homology arm is 700 nucleotides or less in length. In some embodiments, the 3' homology arm is 650 nucleotides or less in length. In some embodiments, the 3' homology arm is 600 nucleotides or less in length. In some embodiments, the 3' homology arm is 550 nucleotides or less in length. In some embodiments, the 3' homology arm is 500 nucleotides or less in length. In some embodiments, the 3' homology arm is 400 nucleotides or less in length. In some embodiments, the 3' homology arm is 300 nucleotides or less in length. In some embodiments, the 3' homology arm is 200 nucleotides in length or less. In some embodiments, the 3' homology arm is 150 nucleotides in length or less. In some embodiments, the 3' homology arm is 100 nucleotides in length or less. In some embodiments, the 3' homology arm is 50 nucleotides in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 3' homology arm is 40 nucleotides in length. In other embodiments, the 3' homology arm is at least 50 nucleotides in length. In some embodiments, the 3' homology arm is at least 100 nucleotides in length. In some embodiments, the 3' homology arm is at least 150 nucleotides in length. In some embodiments, the 3' homology arm is at least 200 nucleotides in length. In some embodiments, the 3' homology arm is at least 250 nucleotides in length. In some embodiments, the 3' homology arm is at least 300 nucleotides in length. In some embodiments, the 3' homology arm is at least 350 nucleotides in length. In some embodiments, the 3' homology arm is at least 400 nucleotides in length. In some embodiments, the 3' homology arm is at least 450 nucleotides in length. In some embodiments, the 3' homology arm is at least 500 nucleotides in length. In some embodiments, the 3' homology arm is at least 550 nucleotides in length. In some embodiments, the 3' homology arm is at least 600 nucleotides in length. In some embodiments, the 3' homology arm is at least 650 nucleotides in length. In some embodiments, the 3' homology arm is at least 700 nucleotides in length. In one embodiment, the 3' homology arm is between 200-700 nucleotides in length. In one embodiment, the 3' homology arm is between 200-300 nucleotides in length. In one embodiment, the 3' homology arm is between 200-400 nucleotides in length. In one embodiment, the 3' homology arm is between 200-500 nucleotides in length. In one embodiment, the 3' homology arm is between 400-700 nucleotides in length. In one embodiment, the 3' homology arm is between 500-700 nucleotides in length. In one embodiment, the 3' homology arm is about 500 nucleotides in length.

In some embodiments, the 5' homology arm is between 150 basepairs to 250 basepairs in length. In some embodiments, the 5' homology arm is 700 basepairs or less in length. In some embodiments, the 5' homology arm is 650 basepairs or less in length. In some embodiments, the 5' homology arm is 600 basepairs or less in length. In some embodiments, the 5' homology arm is 550 basepairs or less in length. In some embodiments, the 5' homology arm is 500 basepairs or less in length. In some embodiments, the 5' homology arm is 400 basepairs or less in length. In some embodiments, the 5' homology arm is 300 basepairs or less in length. In some embodiments, the 5' homology arm is 250 basepairs or less in length. In some embodiments, the 5' homology arm is 200 basepairs or less in length. In some embodiments, the 5' homology arm is 150 basepairs or less in length. In some embodiments, the 5' homology arm is less than 100 basepairs in length. In some embodiments, the 5' homology arm is 50 basepairs in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 basepairs in length. In some embodiments, the 5' homology arm is 40 basepairs in length. In other embodiments, the 5' homology arm is at least 50 basepairs in length. In some embodiments, the 5' homology arm is at least 100 basepairs in length. In some embodiments, the 5' homology arm is at least 150 basepairs in length. In some embodiments, the 5' homology arm is at least 200 basepairs in length. In some embodiments, the 5' homology arm is at least 250 basepairs in length. In some embodiments, the 5' homology arm is at least 300 basepairs in length. In some embodiments, the 5' homology arm is at least 350 basepairs in length. In some embodiments, the 5' homology arm is at least 400 basepairs in length. In some embodiments, the 5' homology arm is at least 450 basepairs in length. In some embodiments, the 5' homology arm is at least 500 basepairs in length. In some embodiments, the 5' homology arm is at least 550 basepairs in length. In some embodiments, the 5' homology arm is at least 600 basepairs in length. In some embodiments, the 5' homology arm is at least 650 basepairs in length. In some embodiments, the 5' homology arm is at least 700 basepairs in length. In one embodiment, the 5' homology arm is between 200-700 basepairs in length. In one embodiment, the 5' homology arm is between 200-300 basepairs in length. In one embodiment, the 5' homology arm is between 200-400 basepairs in length. In one embodiment, the 5' homology arm is between 200-500 basepairs in length. In one embodiment, the 5' homology arm is between 400-700 basepairs in length. In one embodiment, the 5' homology arm is between 500-700 basepairs in length. In one embodiment, the 5' homology arm is about 500 basepairs in length.

In some embodiments, the 3' homology arm is between 150 basepairs to 250 basepairs in length. In some embodiments, the 3' homology arm is 700 basepairs or less in length. In some embodiments, the 3' homology arm is 650 basepairs or less in length. In some embodiments, the 3' homology arm is 600 basepairs or less in length. In some embodiments, the 3' homology arm is 550 basepairs or less in length. In some embodiments, the 3' homology arm is 500 basepairs or less in length. In some embodiments, the 3' homology arm is 400 basepairs or less in length. In some embodiments, the 3' homology arm is 300 basepairs or less in length. In some embodiments, the 3' homology arm is 250 basepairs in length or less. In some embodiments, the 3' homology arm is 200 basepairs in length or less. In some embodiments, the 3' homology arm is 150 basepairs in length or less. In some embodiments, the 3' homology arm is 100 basepairs in length or less. In some embodiments, the 3' homology arm is 50 basepairs in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 basepairs in length. In some embodiments, the 3' homology arm is 40 basepairs in length. In other embodiments, the 3' homology arm is at least 50 basepairs in length. In some embodiments, the 3' homology arm is at least 100 basepairs in length. In some embodiments, the 3' homology arm is at least 150 basepairs in length. In some embodiments, the 3' homology arm is at least 200 basepairs in length. In some embodiments, the 3' homology arm is at least 250 basepairs in length. In some embodiments, the 3' homology arm is at least 300 basepairs in length. In some embodiments, the 3' homology arm is at least 350 basepairs in length. In some embodiments, the 3' homology arm is at least 400 basepairs in length. In some embodiments, the 3' homology arm is at least 450 basepairs in length. In some embodiments, the 3' homology arm is at least 500 basepairs in length. In some embodiments, the 3' homology arm is at least 550 basepairs in length. In some embodiments, the 3' homology arm is at least 600 basepairs in length. In some embodiments, the 3' homology arm is at least 650 basepairs in length. In some embodiments, the 3' homology arm is at least 700 basepairs in length. In one embodiment, the 3' homology arm is between 200-700 basepairs in length. In one embodiment, the 3' homology arm is between 200-300 basepairs in length. In one embodiment, the 3' homology arm is between 200-400 basepairs in length. In one embodiment, the 3' homology arm is between 200-500 basepairs in length. In one embodiment, the 3' homology arm is between 400-700 basepairs in length. In one embodiment, the 3' homology arm is between 500-700 basepairs in length. In one embodiment, the 3' homology arm is about 500 basepairs in length.

The 5' and 3' homology arms can be of the same length or can differ in length. In some embodiments, the 5' and 3' homology arms are amplified to allow for the quantitative assessment of gene editing events, such as targeted integration, at a target nucleic acid, e.g., CD40L. In some embodiments, the quantitative assessment of the gene editing events may rely on the amplification of both the 5' junction and 3' junction at the site of targeted integration by amplifying the whole or a part of the homology arm using a single pair of PCR primers in a single amplification reaction. Accordingly, although the length of the 5' and 3' homology arms may differ, the length of each homology arm should be capable of amplification (e.g., using PCR), as desired. Moreover, when amplification of both the 5' and the difference in lengths of the 5' and 3' homology arms in a single PCR reaction is desired, the length difference between the 5' and 3' homology arms should allow for PCR amplification using a single pair of PCR primers.

In some embodiments, the length of the 5' and 3' homology arms does not differ by more than 75 nucleotides. Thus, in some embodiments, when the 5' and 3' homology arms differ in length, the length difference between the homology arms is less than 70, 60, 50, 40, 30, 20, 10, 9, 8, 7, 6, 5, 4, 3, 2, 1 nucleotides or base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In some embodiments, the length difference between the 5' and 3' homology arms is less than 70, 60, 50, 40, 30, 20, 10, 9, 8, 7, 6, 5, 4, 3, 2, 1 base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 base pairs.

Whatever format is used, a donor template can be designed to avoid undesirable sequences. In certain embodiments, one or both homology arms can be shortened to avoid overlap with certain sequence repeat elements, e.g., Alu repeats, LINE elements, etc.

B. Cargo—CD40L Exons

The donor template of the gene editing systems described herein comprises a cargo (e.g., CD40L gene correction cargo). The cargo disclosed herein may comprise one or more of exons 2-5 of a CD40L nucleic acid. The cargo may be of any length necessary in order to achieve the desired outcome. For example, a cargo sequence may be less than 2500 base pairs or less than 2500 nucleotides in length. Those of skill in the art will readily ascertain that when the donor template is delivered using a delivery vehicle (e.g., a viral delivery vehicle such as an adeno-associated virus (AAV) or herpes simplex virus (HSV) delivery vehicle) with size limitations, the size of the donor template, including cargo, should not exceed the size limitation of the delivery system.

In some embodiments, the cargo comprises a replacement sequence. In one embodiment, the replacement sequence is a wild-type CD40L sequence. In one embodiment, the replacement sequence is a codon optimized CD40L sequence, which would increase translation of the CD40L protein. In one embodiment, the wild-type CD40L sequence does not comprise a mutation which would render CD40L non-functional or affect its expression and/or splicing.

In some embodiments, the cargo comprises all or a portion of an exon of a gene sequence, CD40L, e.g., all or a portion of one or more of exons 2, 3, 4 and 5 of CD40L. In some embodiments, the cargo comprises all or a portion of exon 2 of CD40L. In some embodiments, the cargo comprises all or a portion of exon 3 of CD40L. In some embodiments, the cargo comprises all or a portion of exon 4 of CD40L. In some embodiments, the cargo comprises all or a portion of exon 5 of CD40L. In some embodiments, the cargo comprises all or a portion of exons 2-5 of CD40L. In some embodiments, the cargo comprises all or a portion of exons 2 and 3 of CD40L. In some embodiments, the cargo comprises all or a portion of exons 2-4 of CD40L. In some embodiments, the cargo comprises all or a portion of exons 3 and 4 of CD40L. In some embodiments, the cargo comprises all or a portion of exons 3-5 of CD40L. In some embodiments, the cargo comprises all or a portion of exons 3 and 5 of CD40L. In some embodiments, the cargo comprises all or a portion of exons 4 and 5 of CD40L. In some embodiments, the cargo does not comprise exon 1 of CD40L. In a preferred embodiments, the cargo comprise a splice acceptor (SA) signal before the CD40L.

The sequence of the CD40L gene, as well as the exon and intron boundaries, are well known to one of ordinary skill in the art. In one embodiment, the CD40L mRNA sequence is described at least at NM_000074, the entire contents of which are expressly incorporated herein by reference. In one embodiment, the CD40L RefSeq Gene sequence from chromosome X is described at least at NG_007280.1, the entire contents of which are expressly incorporated herein by reference. A codon optimized version of one or more exons of CD40L can be used in the donor template, in some embodiments, as described herein. An exemplary codon optimized version of CD40L, exons 2-5, is provided as SEQ ID NO:48.

| | |
|---|---|
| CD40L mRNA (NM_000074) (SEQ ID NO: 1) | ACTTTGACAGTCTTCTCATGCTGCCTCTGCCACCTTCTCTGCCAGAAGATACCATTTCAACTTTAA<br>CACAGCATGATCGAAACATACAACCAAACTTCTCCCCGATCTGCGGCCACTGGACTGCCCATCAGC<br>ATGAAAATTTTTATGTATTTACTTACTGTTTTTCTTATCACCCAGATGATTGGGTCAGCACTTTTT<br>GCTGTGTATCTTCATAGAAGGTTGGACAAGATAGAAGATGAAAGGAATCTTCATGAAGATTTTGTA<br>TTCATGAAAACGATACAGAGATGCAACACAGGAGAAAGATCCTTATCCTTACTGAACTGTGAGGAG<br>ATTAAAAGCCAGTTTGAAGGCTTTGTGAAGGATATAATGTTAAACAAAGAGGAGACGAAGAAAGAA<br>AACAGCTTTGAAATGCAAAAAGGTGATCAGAATCCTCAAATTGCGGCACATGTCATAAGTGAGGCC<br>AGCAGTAAAACAACATCTGTGTTACAGTGGGCTGAAAAAGGATACTACACCATGAGCAACAACTTG<br>GTAACCCTGGAAAATGGGAAACAGCTGACCGTTAAAAGACAAGGACTCTATTATATCTATGCCCAA<br>GTCACCTTCTGTTCCAATCGGGAAGCTTCGAGTCAAGCTCCATTTATAGCCAGCCTCTGCCTAAAG<br>TCCCCCGGTAGATTCGAGAGAATCTTACTCAGAGCTGCAAATACCCACAGTTCCGCCAAACCTTGC<br>GGGCAACAATCCATTCACTTGGGAGGAGTATTTGAATTGCAACCAGGTGCTTCGGTGTTTGTCAAT<br>GTGACTGATCCAAGCCAAGTGAGCCATGGCACTGGCTTCACGTCCTTTGGCTTACTCAAACTCTGA<br>ACAGTGTCACCTTGCAGGCTGTGGTGGAGCTGACGCTGGGAGTCTTCATAATACAGCACAGCGGTT<br>AAGCCCACCCCCTGTTAACTGCCTATTTATAACCCTAGGATCCTCCTTATGGAGAACTATTTATTA<br>TACACTCCAAGGCATGTAGAACTGTAATAAGTGAATTACAGGTCACATGAAACCAAACGGGCCCT<br>GCTCCATAAGAGCTTATATATCTGAAGCAGCAACCCCACTGATGCAGACATCCAGAGAGTCCTATG<br>AAAAGACAAGGCCATTATGCACAGGTTGAATTCTGAGTAAACAGCAGATAACTTGCCAAGTTCAGT<br>TTTGTTTCTTTGCGTGCAGTGTCTTTCCATGGATAATGCATTTGATTTATCAGTGAAGATGCAGAA<br>GGGAAATGGGGAGCCTCAGCTCACATTCAGTTATGGTTGACTCTGGGTTCCTATGGCCTTGTTGGA<br>GGGGGCCAGGCTCTAGAACGTCTAACACAGTGGAGAACCGAAACCCCCCCCCCCCCCCGCCACCC<br>TCTCGGACAGTTATTCATTCTCTTTCAATCTCTCTCTCCATCTCTCTCTTTCAGTCTCTCTCTC<br>TCAACCTCTTTCTTCCAATCTCTCTTTCTCAATCTCTCTGTTTCCCTTTGTCAGTCTCTTCCCTCC<br>CCCAGTCTCTCTTCTCAATCCCCCTTTCTAACACACACACACACACACACACACACACACACAC<br>ACACACACACACACAGAGTCAGGCCGTTGCTAGTCAGTTCTCTTCTTTCCACCCTGTCCCTATC<br>TCTACCACTATAGATGAGGGTGAGGAGTAGGGAGTGCAGCCCTGAGCCTGCCCACTCCTCATTACG<br>AAATGACTGTATTTAAAGGAAATCTATTGTATCTACCTGCAGTCTCCATTGTTTCCAGAGTGAACT<br>TGTAATTATCTTGTTATTTATTTTTGAATAATAAAGACCTCTTAACATTAA |
| CD40L RefSeqGene on chromosome X (NG_007280) (SEQ ID NO: 47) | ACCATTTCAACTTTAACACAGCATGATCGAAACATACAACCAAACTTCTCCCCGATCTGCGGCCAC<br>TGGACTGCCCATCAGCATGAAAATTTTTATGTATTTACTTACTGTTTTTCTTATCACCCAGATGAT<br>TGGGTCAGCACTTTTTGCTGTGTATCTTCATAGAAGGTTGGACAAGGTAAGATGAACCACAAGCCT<br>TTATTAACTAAATTTGGGGTCCTTACTAATTCATAGGTTGGTTCTACCCAAATGATGGATGATGGT<br>AGAAACCAAATAGAAGAATGGTCTTGTGGCATAATGTTTGTTGCCTAGTCAATGAAGTCTCATATT<br>CTTGTCTCTGGTTAGGATCTTGGGATCTGGAGTCAGACTGCCTGGGTTCAAATCTTGGCTCTGCCC<br>ATACCATCTCTGTTATCCTGGGGCAAGTGCCTCAGTTTCCACATCTGAGAAATGGGGATGGTATTG<br>GTGTCCATTTCATAGATTAAGTGAGTTTAGCCTTGTAAAAAGCTTAGGAGGGGGTCTGATACATAG<br>TAAGCACTATGTACGCACTAGCTATAATTATTTGCTAAAGTTCTGCTTTAAAAGTAAGCTATTTTT<br>TTATGGAGACAGCTTTTTTCTTTTAAATTTCCAGCTAGGCAAGAAGAGCGTCAATTTGATCTAAAA<br>TTTCATAATGCTTCAGATTAACATAGACATGGATAAGTCCCAGAATTTGCAGTCTTTTAGTAAAAG<br>TAGCATTTTCTGTGTAATTCTTCACAAGCACTGATTGTAGTTGCAGGATGCTCAGTCTCCCTCTGA<br>GATGTTTTACATTTTTAAATGGTTAGACTTGCAGGAACAAAAGAGCAGAGTAACTTAGTAGGCTGT<br>TTTGCATTCTTAGGAAAAGAAAACCATCAGGACTTATTTTGTTTTCATGTATTTTTCACTTCCAC<br>TGAGGAGTATAATTGGCTGGTGTTGACAAAATACCAATCATAGATGTAAAGGAGAAAGTTGATTAG<br>TTTTCTGGCTGTTCCTAAAATTCTGGATGCAGGAACTGTGGCTAGAAAGCATCTGGATGATTGCAC<br>TTTATCAGGGATACTTGAGTGTCCTCTCTTAGGATCTGGACCTAGAATTAATGTCATGAGATTTTT<br>CTAACAGGATAAGGTGAGGTAGTGAGGGCTGAAGTCATCCACTGGGTTATCCAAATATTAGGTTTC<br>ACTGCTGACAAAAGAGGGGGCTTCTGGTCTGGTTGGTTATTTGTGTTTGGCCTGATGTGCTCTGTC<br>AATCAAATGTATGGACATAGGCCTAGCTTCTAAAGGGGCAATAGTGACCTCAGTGGACTGATATTT<br>ACCGTACTATTTACATGTGCTCTTAATTACAGCAGAAGCTGCCAGCTAACTGAATCTTGTTTTGAA<br>TCTAAAAAATCTACTCTTAAAGCAAGAAAATGGTATAAAATTAGTTGATAATGCAAGTGAATTCTG<br>TACATTTAATTATTCTAAGACATTGGAAAATAAAATATCTTGTTACTTTGAGGATAAAAGATGATT<br>TCTTTAAAAATGCAAATGTTTTCTACAAATACTAAAGTTAAAAGGGAGAGAGATGTAATTAGAACT<br>CGTTAACTGACACATTGCAAATTAACTTCTTTTTATAAAGCACTGCATCACAAACACTAAAATGAA |

```
GTGGGCAAATTAGCTCTGCAGAAAACTATTTTCTAGGCTGATGTTTATAATGACCAATCATTACTG
AAGCAATGAGAAATGTGACAATTACAGAATATTGCTGCTATAGTATGTTGAAAAAATATGCATTTT
GTAGTGAACATTTAGTAGAATAGCTCTGATTTCTACCTGGAGTTTCTGATAACATGACATCTTAAT
TGCTGTCTTTTATAGATTTTTAAACTGCAAATACAAAATAGCAATCAGCCAATATAATAACTTATT
ATTCTCCATTTATGCCTGAAAGTCCTCCTCTTGTTGATGCCGTGGAAATGAATGTAGAGGCAGATA
TCATTAGCTGTATTCTCCTTCCGAATGACATTTATCATATCCTTGTTATTCCAAAATAGATAGAAG
ATGAAAGGAATCTTCATGAAGATTTTGTATTCATGAAACGATACAGAGATGCAACACAGGAGAAA
GATCCTTATCCTTACTGAACTGTGAGGAGATTAAAAGCCAGTTTGAAGGCTTTGTGAAGGTAAGCA
GCTTAATTACTGGTAAAAGTGTCATTGAAATATTTTACTACATTTGCTAGATCGGGAAACTGACAA
TGCCAATGTTTAAAGATTGGTTATAGACACAGACACACAGACACACACACACATATATATGCATGC
AGATATACACACATACATGGGTGTGTGTGGGGGTTAAAAAAAAAAAACACAAAGACACTCTCTG
GGGAAAATACACCCTTAGGGGCACAGTCACACATATTTGTCAGCTTACATATGCAGCTACCACTAG
GCAAAATGATGAAGTCCACCAAGCTTGGTTTTTGCATTGCTGTGTCTCCCCATCCAAACCTTGATG
CTCTCGCACTGGGGACCCAGAGTCTGATCCCCATTTCCCAGGGAAGCAATAGCCGTCAACAGCTGC
CGTGGCAGCAGGCCACAAGTGAAGGGACACCTGAAGACTGGTAACAGTCTCTGGTGCTTCTCTGAT
GATGGAATTTTAGGTGTCCTGACAGTGAGATCTTTCCCTTTTACTGGGGAGAGAGGTGCAGGGAAT
AAGTAAATAGACATTCTCAGTGTCGCTCAAACCAGACTCCATATAATATCCACTTGCTCATGAAGCCC
GCCCACTCTATGGCCGGTCATGACCAGAGGCACAGAGGGTTCAAAGCCTTTTAGCCCACCAGGCTG
GTAGCTAGCATGAAGTCACTGCAGTGACTGTGGCTTATAACAGATACCTAAAACAAGAATTTTTAG
AACCTTTACATTAATTCCATCATCACAGACATAGGGTCTAGGGGCTCTTTCTCCTGAGGCAGAACA
TCAAGAGTTCTTTCTGCCTATGTCCCTTTCAGAACACTGAGTCAAATACCCTTGGGCCTCGGCTCA
CTTAGGGGTCATTTCTAGGAGGCAGCACTCCACATTGAGGACAGTTCTGGGCCAGGTGGGTGGGTA
TCTGGGTAAACCAACAGGAATTAGTTCTCACATATAGATGATGTGTAATTTAATGCAGGCGTAAAA
GGGTTAAGATCTTATTTCTGATCTTATTTCTGCCCTCCTGTACTGTCACCGAGGTGCCATTTAATT
CATTAGTGAAGACTCTAACAGCTTATTCCTGAGTCACCTACGGAGAACAGAATGTGGCTCAAATCC
GCTGCTTGCTTTCAGGTTCTTTACACTAATCTAGGCTTTAGATGAAACTCCTAAACCCTTTCTTTG
CAAGACTGGCCAGCTAGGAAAATGATTTGAGTTTCTTCGGTTCTTCGAGGATTTGGGCCAGTATTA
CAGAGTATTGGAAGATGTTACCAGTTTAAATGTGAATAAAGGCACTTTCAAAACAATGGCTAATAA
TCCAAATAACAGACTGAATGTGCTTGGCTATGTGACTTTGGGTAAATAACTTCACCTTTCTGGGCC
TCAGTTTTGTCATCTATAACATGAGAAGACAGATTATCTGTAAGGGCACTATCAGCTCTGACATTC
TACAATTATGTGATAAGCCTTCAGTTCCCTCCAATGGCAGTGAGAGTGGCTTGTCAGTCCCCCTCG
TTTCTTACGGAGACTTTTACGGTTGAATTGTCAATTCCTCACGTCATTATTTCAGGTTGGCTATGT
ATGTAAAGCTCCCAAAATCAGCTACCGAGGATAGGAGTAAAGAAAACAGTCAGTTTGGCCTCCCTG
CTTATGCTTGTATGAAAAAAGTGACAGCTCCAAAGTTTCATATTCTTAAAAGGCAGATCTTCTCAG
GCATGTCAGCCAGGGCCCCAGGGATCTCCTCCTTACATGCAACTAAGGAGGCTCCTTGTCTCTACT
GCAGCAGGTGTGGAACCCTAGTCAACACCACCTATACCTAGGATTACGTACAATGAGTAGATACAA
AGTCCTCCAGCTACCCAATCCTCCCCAATGACGGATCCCCTTTCCAATACGCTTTCCCCCAAATT
TCTCACCCTAAAACAAAATTCGAGACTTTGAAAAACTCAATAGGACAATTATAGAATAGCTCCAG
ATTAGATTCATATTTCTTAGCTAATGTTAGTAGGCTTTCTTTCCGGGCCACAGTCTGGCTGCACC
TAAGCAACCTCAAGTTTGAATTTGGAGTCTTTGAATCAGGTCTTGATGGGGTCTTAGAAGTCATCA
GATCCAATTCTCAATCCACAACTTCAGTCTTCTCTCCACCTCCTGACTAAGTGGTCATCCAATCTC
TGTTTGAACATCTCTAGTGACAAGGAACTCATTATCTCTGGAGGCAGGTAGCACTAATCTGTCATT
TTGGGGGAAAGATGGTATTCAGGGCTCAAGTGAGGGTAAGCAGAGGTATTATTTTGAATAGTATAA
TTTCATATTAAAACTTACAACCCACCACACCTCTGCTAGATGTTCAGTTCCATGATTATTTGCCCA
CCAATGCCTGCGATGCCTTTGAGAGAGCCAAAGCATTTCTATTTCAAGTTAAAGGGCAACCTGTCC
ATACCTGCCACATGGAACTCCCACTAAGAGAGAAATAACCCATTCTGGATTTTCTGAAAGTCCACT
TTAAAAAGTATTTCAGTTGAGGTGGGGAGTGAAGCAAGAAAAAAAAAAAGGCTCTGGGGAGTGTGGT
TGGGCGAAAGTTCACGGAAAGGCTAGGCTGGGCTCATGAAACACGAGCTTTGCTGACTTCATGTTT
TCATCTTGGCCAGGCCTCAACACCAATGCAACAACTTAGCCTAAAAGTATCTCAACCTTGATCACC
ACACTCTACTTTTTGAAAAGACACTAAATAGTCATTTGTTTACTTGTGATCTCACAAACATTTTCC
TGTCACCACATCTTCATAGTGCCGCGCTTCAGCTCAAATGGAAAGTTGAAGCTCTGGGGCCCATGT
GAGTGTTCTGAGGCTCAGGTTCCCCTGGAGGCTCTATGAACTACGCCCTTAAATCTGGCAACTGAG
CTGGGCCTACAGCCAGCACTCAACAGTGACAGCACAAATTCCTTCTGGAGGAGGAAATAAAAGGAA
GGGTCCTATAGACAACTGATTCCAGGAGTGGGAAGGAGCACAGGACTTTGATTATCATAAGATGTG
AAAATACTACTGTCTTCTTCCCTTGTGTGCAGAGGATAGACAGATGGAATTAGCTAAGCCCAGCCT
ATGAATGCCATCTCACAGTTTCCACTCTTGGTTTAAACCTCAGCTTCTTTGGGTGACCTCATAATG
ACCAGTTAAGCCCTCCAGGCCTTTTGTTCAGTCTCTTTAAAATGGCAGCAACAGCCTTTATCATCT
TCCAACCTGTGTTGATGGAAGTTCCTGTTAGCTTCTTTAAATACCTCTAGACTTCCTTCAGTTTAT
AAGTGAAAAGAAACCTTTTAAGAAGTGTCGCACTTGCCTTTGAACATCAACACCATTGGGAGATGG
CCTGTGTTTCCGAAATGCTGATTATTCTAAGTAAATACAGTGCAACTATCAATAAGAGAATCTCTT
CAGCCCATTGAAAGGGATAGCAAAATTAAAAATGTCTGAGGGTCTTTTCATAGTCTGGCATTTCTC
CCCAAGGTCAAACTTACTATTATCTTTTCCTACAGGATTTCAGACCAAATTTATTCTAATAGATAC
ACACCATGCTTTATGTTTAATAATATTCCATATACCAGTTCCCAGGGTAGATCATCTCCCCATTC
GGCATTATTTGTCAATATCTGTCAAAGCCAAGGAGGTTGAGGTCATAGGAAGGGTCAGGATCACAG
CCTCTGGTCTGGAGAGAGCACTGGAATGGAGATAATAAGGCCTGGATTTTACTTCCAGATTCTCCC
CTGGGCTTTCTGGGTTGTTGGCTCATCTGTCAGATCCATGGACTCCCAATTGGCATGATGGAATTA
ATGACAGGATCTGAGTCTATATGATAATCCTCACCAGAAACAGACAACAGAGTAATGACAGATGCA
AAACGAATGATAATTTAAAACCCCACAGCAGAGCCCCTGTCAAAATGACCTCTTGCAATGCTTCT
TATTTTAGGATATAATGTTAAACAAAGAGGAGCGAAGAAAGAAAACAGCTTTGAAATGCAAAAG
GTAGGTTTGCTATTTGCTAATTTCTATGAATGCCTAAAAACTAAAAGGAAGCTTTAGGCTGATCAT
ATTGAACAACCCAGTGTTGTTGCATCAGGGAACTTTTAGCCCTGGAAATAAAACAGGAACACAATT
GTCAAATTGACACCTTCTCTGGTCCCTGTGATTTGGAAAGACTTTGTACATATATATTTATGAAAA
AAGGATGTGTTCCTTTAATGCCGATGATACCAAATCTGAAGAAATCCCATTATGTTCAATACCTTA
ATAGAAGCAACCATACAGCCTGATACCACCTACAGTGGAATAAGAAGACAGGAAAGTCATCATTTG
GTAACAGTGGCATTCATCACTCATTGATAACAGTTTTTCATGGGCACAGTGGCCGGTGGAGCCTC
TGGGATCAAGGAGTGACAATGTCACAGTGTTCTATTATTTGCCCGGTTCTTAAAGTGAGAGCATCC
TGAACATCTCAGGGTTGGAAGAGAACTTGAGAGTTCTCAAATCCAGCACCATCCCCACAACAAAAA
TCTCCTTCACAATAACACTGACCGTCCAGCCTCTGATCAAACATGTCGAGGGATGAGGCACCTTCC
ACCTCATAAGGCAGCCTGATCCGTCTTTGAATGGCTCTAATAATACCAAGATTACTATACTACTCC
```

-continued

```
AGAGAAGTCTTTCCTCCTCAAGTCAAACTTTGTTCCTATAATCTCCACTCATTGGTCCCAGTTCTG
CTCTTTGAGGCCCTAGTAAACAAAGTATAATTGCTCTCCTACCCAGCAGCTGTCCAGATATGGAAG
ACAGCAATCATGGTGGCCAAGCCTTGACTGAGCTTTTTCTTCTCCAGGCTAAAGATCCCTGATGTC
TTCCACTGTTTCTCCTATGACCCTTTCCAGGACCTTTCTTCTGCCACTCACCTCCTTTTCTTGGAC
ACACTAACGTTTTCCTGTTCTTTTAGAATGTGGCATCGCAAACCAATACAATAATGCGTGAAGTGA
CTTCAGCAGCAGATTATGGGAAAGACGGGGTGTTGTTAGAGAGAATTTTATATCACAAAGTTGGTG
AACATGATGTTATGGCTTCTGCAAATTTAATACACACAAAAACATACATACATACAGGGATAGAGA
TACTATTTTCTGAGGCAAAGAGAGTACTCAGACCTTGCCTTAACTGTTGTTCTGGATACTAAATGG
TCATCCGACTTCCATGAAGGTTTTATCTTCAGAATGACTGCAAGATATGTTGAGTAATAGTACCAC
GCTGTCTGTTAATTACAGAGAAATCTGAGGAAACAGTTTATGTAGATGCTGCCTAGAAGTCTTCAG
GGAAATGATAATATTAACCAAACTGGTCATTTAGGTCATGCAATTTAACTCAACATTTATAGGGCA
CTTACAAAGTGCCCAATATCAGGCTCATAACTGGACAAAAAGAAACTTCCACACAGTCTCTGCCCT
TAGAAGATTGACACATCTCATTAGGGAGCAGGGCTTTAACACAAGAAATAATTAAAGACAGATACA
ATAGTTCAGCCAGTTGCTTGACCAATTCAGAAACCATAAGAATCTTACTAAGTGTGCAGACTTTGG
AGCCCACTAAAATCCCCAGTGTATGGAGTTGTTCCTAAAAGCAAGATTCACGGTATGTTTAATGAA
GACCAGTGTTTTAGCCTGTGTCAATCTATGCAAATGGAATCGAGTATTGATCAACTGTTAGGAG
AATGACCGATGGAAACAGCCAATTCAATTACTCAGATATTAGAAACCAACTTTTCCTTCAGTGG
GAGAGATGTCAGACCATTTTATCTTTCCTTTTATATAATCTATTTTTGCACAGTCTCTATTACACA
GTTGTAGAACTGGACCAGATAGTTTTGTGGGCAGTTTTTGCATTATTTTAGCCTGACAGTTTTTGG
TTCCATTTCAGGTGATCAGAATCCTCAAATTGCGGCACATGTCATAAGTGAGGCCAGCAGTAAAAC
AACATCTGGTAAGTCACACAGCATCTGAGCGGTAGCCACCCAAGGGGAAAGGCTGGGATGCCGAAG
TCATGTTACCTAATGGTTAAACTCCTCTTTTCCCCTGGGACCCAATTTACAAACCTACCCCTACAC
TTCTCCTATTCCCTTCTTTGTCTTCAAAGTGAGTTCAAATGCACAGATGGGACTTAGAGGGACAAA
AGGAGGTGGAATGCAATCTGGATGTTCTCATTATGTTCTTGCTCAATGGCTGATTCTAAATGATGA
ATTACTGGGTGGAGGGACCATTGTTCTGACAACATAGAAGAAATGGCATGTAGTGACCTCCTGACT
GGGAGCATCCCTCCTCCTAACCCATCTTCACTGTGTGGAAATGGGCCTCATGGGGTATTTCCTGCC
ATCTGTCAATCCCTGTATGATTAAGCTCAGCCTCACTGAGGCCAACCTCAGGGAAAGTAAAGGTAA
AATCATTCTGTAAAGATCAATAGGTCCCAAGACGTTACATTTTCCAATGAAGTAACAACAGACGAC
ATATTGTGATCTTTTCAACTCTGAACGATTTTATTTCCATATACGTTCTGCCACCATTCTAGCCTT
TAGATATTTTTTCCCAAATGTGCATCTTGCGATAACTGGTGCCAAAGAATATGTCGTATCTGATAA
ATGGATGGAAACATGCACGCTAACATAAAGTCTCCCATCAACATAAAGGCAAGAGCGTCAGAGGAG
TCTTTGAAAAATTCTACAGAGTGCTCCGGAATGGAGTTCAAGCAGTGCATGTGTGTGCATATG
TGTATGTGTGTGACAGGGAGAGAAAGAGAGATGGACAGAGAGAGAAAAAGACACTGCTTCATCTC
TGAAGTGGCTTGGGCTTCTCAGTAGGCGTAACACATGGACAGTTATCATTATCATGGATCATGGTA
CCAAAGTAAGAGCACTGAATAGGGAGTTTTTGAACACTGGGATTCAAGGACCATGACCACTGCTTG
CTGGGTGACCTTGAGCAAGACCCTTTACCTATGCAGCAGTTTTCTACTTCACCTACTTTACAGGGT
GGCTTTGAGCATCAAATCAGCTAATGTGGCCGAAAGTGATGCTGTCGAGTGCTGTACAACCGTAAG
GTGACACTACTTAGTTTACTTCACCATGGCTTAGATGTCAAAAGGGTGACATAAAGCCCCTCACTA
ATACCAGTTAGTTACACAATATTTAATAATTTTGTCAAGTACCCCTTCTCTCTTCTGGATCAGATG
ACAACAACAGAGAAATCTCCTAGAAGAATAGCTTCCCACTGGTCTTTTTTGCCTGTATCTAAACC
CTTGATCTTGGATATATTTCATAGAGCTCAGATTCTCCCAAAAGGCTTGTAATGGATATCAGTCCT
ACAATATCTTACAGTCTGCATCACAATAGGTTTCCAGGGGATCAGATGGGAAGACAGTAACATTCC
ACCCCCACCCCAGTCCCAAACCTCTTCTTCCTACCTAGCCATGCTGCTAAAATCTTGCCCTACATC
CCACAGCAAGTACTAAAATTAGGTAAGGACGTACCAAAGTAAACTTACTGAACTAAAAGATTGAGA
ACCTGCCCTTTTTTTCTCAATAAAATGGTTCAAAAGGGCAAACATTCTAATGAAGCATTGTTTCTG
GAGTGGTCTGGAGGGCCCGGATCTGTCAGGCATTTCAGGATGCCTCCCTATTAGTAAAGGGCGAGT
CTTACCAGGTGGGATCTTGTGCCCTGATAGACCTAAGACTATCGAATAGGAATTATTTTTTAAAAA
GCTCAAGGAAGCAAACACATCAGTACTTTCACTTTTCCTCAACCCTCACCCCCATCAGTCAGTCTA
GCTTTCTGTGGGAGCTGAGATTTCAAGTCGGGTGCACACACTACTTTGAACCCACTCAACATCTCA
GCCGAGAAAATGGCACACTGTTGGTGGGTACTCTGGCTTAGCCACAAGAATACTGGTACTTTCAAG
TTGGTGGCGCCCACTACAATGGGAGATCAAAACATACCGTGAAATGAGCACACAGTTTATTTTCAT
ACTTCCTTGCCTAATTTTAGTCCTTGCTGGGGAGGCAGATCAGGTTTGCAACAGCATGATCAGGT
AGGAAGAAATGGGGTCTTTTCTCTGTGCTGAGGCTGAGCTAGGTAGACTGACAACTCTCTGACTTT
GTAAAATTCAAGGCAAGCAAGGTATTCATGGTAATATTAGCAAAAATTTGGTCCGAGTAATTTGGT
ATGTATAATTTATGATGTCAAATTTTGAAATCATTTGTGCCTTCTTAAGTTCAAGGCAAATTGGCT
ATAAGAACTCTAACGAGAGAAAGAAACTCACTGTGATCTCTTACTTTATTTAATCTTCACAAGTCT
CTGAAATATGCTCCAATATGAGCCCCGTGTTGCAGATGAGGAACTGAAGCTCATGGAGATTAGAG
ACTTGCCCAAGCTTAAATAGAGCCTAGATTGGAACATGGCTCTGTCTGACTCTGAAGCCCATGGAA
GGGGCCTTGAGAATCCATCCCTATACAAAGCCAATATCCAACATTAAACTATATTTTTTGTCAGAA
TGTGAACCATGCTCTGCTTCACCTCACCACAAACTTTCCCTTTCTTTGTAACAGTGTTACAGTGGG
CTGAAAAAGGATACTACACCATGAGCAACAACTTGGTAACCCTGGAAAATGGGAAACAGCTGACCG
TTAAAAGACAAGGACTCTATTATATCTATGCCCAAGTCACCTTCTGTTCCAATCGGGAAGCTTCGA
GTCAAGCTCCATTTATAGCCAGCCTCTGCCTAAAGTCCCCGGTAGATTCGAGAGAATCTTACTCA
GAGCTGCAAATACCCACAGTTCCGCCAAACCTTGCGGGCAACAATCCATTCACTTGGGAGGAGTAT
TTGAATTGCAACCAGGTGCTTCGGTGTTTGTCAATGTGACTGATCCAAGCCAAGTGAGCCATGGCA
CTGGCTTCACGTCCTTTGGCTTACTCAAACTCTGAACAGTGTCACCTTGCAGGCTGTGGTGGAGCT
GACGCTGGGAGTCTTCATAATACAGCACAGCGGTTAAGCCCACCCCCTGTTAACTGCCTATTTATA
ACCCTAGGATCCTCCTTATGGAGAACTATTTATTATACACTCCAAGGCATGTAGAACTGTAATAAG
TGAATTACAGGTCACATGAAACCAAAACGGGCCCTGCTCCATAAGAGCTTATATATCTGAAGCAGC
AACCCCACTGATGCAGACATCCAGAGAGTCCTATGAAAAGACAAGGCCATTATGCACAGGTTGAAT
TCTGAGTAAACAGCAGATAACTTGCCAAGTTCAGTTTTGTTTCTTTGCGTGCAGTGTCTTTCCATG
GATAATGCATTTGATTTATCAGTGAAGATGCAGAAGGGAAATGGGGAGCCTCAGCTCACATTCAGT
TATGGTTGACTCTGGGTTCCTATGGCCTTGTTGGAGGGGGCCAGGCTCTAGAACGTCTAACACAGT
GGAGAACCGAAACCCCCCCCCCCCCCCCGCCACCCTCTCGGACAGTTATTCATTCTCTTTCAATCT
CTCTCTCTCCATCTCTCTCTTTCAGTCTCTCTCTCTCAACCTCTTTCTTCCAATCTCTCTTTCTCA
ATCTCTCTGTTTCCCTTTGTCAGTCTCTTCCCTCCCCAGTCTCTCTTCTCAATCCCCTTTCTAA
CACACACACACACACACACACACACACACACACACACACACACAGAGTCAGGCCGTTG
CTAGTCAGTTCTCTTCTTTCCACCCTGTCCCTATCTCTACCACTATAGATGAGGGTGAGGAGTAGG
GAGTGCAGCCCTGAGCCTGCCCACTCCTCATTACGAAATGACTGTATTTAAAGGAAATCTATTGTA
```

| | |
|---|---|
| | TCTACCTGCAGTCTCCATTGTTTCCAGAGTGAACTTGTAATTATCTTGTTATTTATTTTTTGAATA<br>ATAAAGACCTCTTAACATTA |
| CD40L Codon<br>Optimized<br>Sequence<br>(Exons 2-5)<br>(SEQ ID<br>NO: 48) | AGATCGAGGACGAGAGAAACCTGCACGAGGACTTCGTGTTCATGAAGACCATCCAGCGGTGCAACA<br>CCGGCGAGAGAAGTCTGAGCCTGCTGAACTGCGAGGAAATCAAGAGCCAGTTCGAGGGCTTCGTGA<br>AGGACATCATGCTGAACAAAGAGGAAACGAAGAAAGAAAACTCCTTCGAGATGCAGAAGGGCGACC<br>AGAATCCTCAGATCGCCGCTCACGTGATCAGCGAGGCCAGCAGCAAGACAACAAGCGTGCTGCAGT<br>GGGCCGAGAAGGGCTACTACACCATGAGCAACAACCTGGTCACCCTGGAAAACGGCAAGCAGCTGA<br>CAGTGAAGCGGCAGGGCCTGTACTACATCTACGCCCAAGTGACCTTCTGCAGCAACAGAGAGGCCA<br>GCTCTCAGGCCCCTTTTATCGCCAGCCTGTGCCTGAAGTCCCCTGGCAGATTCGAGCGGATTCTGC<br>TGAGAGCCGCCAACACACACAGCAGCGCCAAACCTTGTGGCCAGCAGTCTATTCACCTCGGCGGAG<br>TGTTTGAGCTGCAGCCTGGCGCAAGCGTGTTCGTGAATGTGACAGACCCTAGCCAGGTGTCCCACG<br>GCACCGGCTTTACATCTTTCGGACTGCTGAAGCTGTGA |

In some embodiments, the cargo comprises an intron of a gene sequence. In some embodiments, the cargo comprises a cDNA sequence. In some embodiments, the cargo comprises a transcriptional regulatory element. In some embodiments, the cargo comprises a reverse complement of a replacement sequence, an exon of a gene sequence, an intron of a gene sequence, a cDNA sequence or a transcriptional regulatory element. In some embodiments, the cargo comprises a portion of a replacement sequence, an exon of a gene sequence, an intron of a gene sequence, a cDNA sequence or a transcriptional regulatory element.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

In some embodiments, the oligonucleotide donor template can further comprise a sequence encoding a reporter. In one embodiment, the reporter is a green fluorescence protein (GFP), a yellow fluorescence protein (YFB), DS-Red, or luciferase. In one embodiment, the reporter can be a marker which can be detected in live cells using art-standard methods, e.g., surface antigens detectable by antibodies, peptides that catalyze or otherwise facilitate a chemical reaction that produce an optically detectable product, e.g., luciferase. In one embodiment, the reporter is a selectable marker. In an exemplary embodiment, the selectable marker is low affinity nerve growth factor receptor (NGFR). In other embodiments, the selectable marker can be a drug-resistance protein (such as neomycin or puromycin resistance, mutant version of the MGMT gene), a truncated version of a cell surface protein (e.g. CD19, EGFR), a gene that confers a selective growth and/or engraftment advantage after in vivo transplantation of the edited cells (e.g. CXCR4, CD47, IL2 receptor) or a fluorescent reporter protein (e.g., green fluorescent protein (GFP), blue fluorescent protein (BFP), yellow fluorescent protein (YFP), etc., or a combination thereof.

C. Stuffers

In some embodiments, the donor template may optionally comprise one or more stuffer sequences. Generally, a stuffer sequence is a heterologous or random nucleic acid sequence that has been selected to (a) facilitate (or to not inhibit) the targeted integration of a donor template of the present disclosure into a target site and the subsequent amplification of an amplicon comprising the stuffer sequence according to certain methods of this disclosure, but (b) to avoid driving integration of the donor template into another site. The stuffer sequence may be positioned, for instance, between a homology arm and a CD40L exon sequence to adjust the size of the amplicon that will be generated when the donor template sequence is integrated into the target site. Such size adjustments may be employed, as one example, to balance the size of the amplicons produced by integrated and non-integrated target sites and, consequently to balance the efficiencies with which each amplicon is produced in a single PCR reaction; this in turn may facilitate the quantitative assessment of the rate of targeted integration based on the relative abundance of the two amplicons in a reaction mixture.

To facilitate targeted integration and amplification, the stuffer sequence may be selected to minimize the formation of secondary structures which may interfere with the resolution of the cleavage site by the DNA repair machinery (e.g., via homologous recombination) or which may interfere with amplification.

In one embodiment, the first stuffer has a sequence comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 275, at least 300, at least 325, at least 350, at least 375, at least 400, at least 425, at least 450, at least 475, or at least 500 nucleotides. In another embodiment, the second stuffer has a sequence comprising at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 275, at least 300, at least 325, at least 350, at least 375, at least 400, at least 425, at least 450, at least 475, or at least 500 nucleotides.

It is preferable that the stuffer sequence not interfere with the resolution of the cleavage site at the target nucleic acid. Thus, the stuffer sequence should have minimal sequence identity to the nucleic acid sequence at the cleavage site of the target nucleic acid. In some embodiments, the stuffer sequence is less than 80%, 70%, 60%, 55%, 50%, 45%, 40%, 35%, 30%, 25%, 20%, or 10% identical to any nucleic acid sequence within 500, 450, 400, 350, 300, 250, 200, 150, 100, 50 nucleotides from the cleavage site of the target nucleic acid. In some embodiments, the stuffer sequence is less than 80%, 70%, 60%, 55%, 50%, 45%, 40%, 35%, 30%, 25%, 20%, or 10% identical to any nucleic acid sequence within 500, 450, 400, 350, 300, 250, 200, 150, 100, 50 base pairs from the cleavage site of the target nucleic acid.

In order to avoid off-target molecular recombination events, it is preferable that the stuffer sequence have minimal homology to a nucleic acid sequence in the genome of the target cell. In some embodiments, the stuffer sequence has minimal sequence identity to a nucleic acid in the genome of the target cell. In some embodiments, the stuffer sequence is less than 80%, 70%, 60%, 55%, 50%, 45%, 40%, 35%, 30%, 25%, 20%, or 10% identical to any nucleic acid sequence of the same length (as measured in base pairs or nucleotides) in the genome of the target cell. In some embodiments, a 20 base pair stretch of the stuffer sequence is less than 80%, 70%, 60%, 55%, 50%, 45%, 40%, 35%, 30%, 25%, 20%, or 10% identical to any at least 20 base pair stretch of nucleic acid of the target cell genome. In some embodiments, a 20 nucleotide stretch of the stuffer sequence is less than 60%, 55%, 50%, 45%, 40%, 35%, 30%, 25%, 20%, or 10% identical to any at least 20 nucleotide stretch of nucleic acid of the target cell genome.

In some embodiments, the stuffer sequence has minimal sequence identity to a nucleic acid sequence in the donor template (e.g., the nucleic acid sequence of the cargo, or the nucleic acid sequence of a priming site present in the donor template). In some embodiments, the stuffer sequence is less than 80%, 70%, 60%, 55%, 50%, 45%, 40%, 35%, 30%, 25%, 20%, or 10% identical to any nucleic acid sequence of the same length (as measured in base pairs or nucleotides) in the donor template. In some embodiments, a 20 base pair stretch of the stuffer sequence is less than 80%, 70%, 60%, 55%, 50%, 45%, 40%, 35%, 30%, 25%, 20%, or 10% identical to any 20 base pair stretch of nucleic acid of the donor template. In some embodiments, a 20 nucleotide stretch of the stuffer sequence is less than 80%, 70%, 60%, 55%, 50%, 45%, 40%, 35%, 30%, 25%, 20%, or 10% identical to any 20 nucleotide stretch of nucleic acid of the donor template.

Stuffer sequences are described in more detail in, U.S. Provisional Application No. 62/532,509, filed on Jul. 14, 2017, the entire contents of which are expressly incorporated herein by reference in their entirety.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized on the bottom or non-complementary strand:

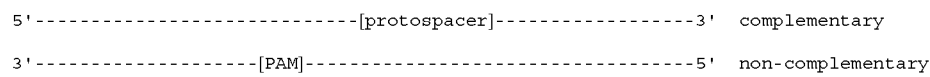

Cpf1, on the other hand, generally recognizes PAM sequences that are 5' of the protospacer as visualized on the bottom or non-complementary strand:

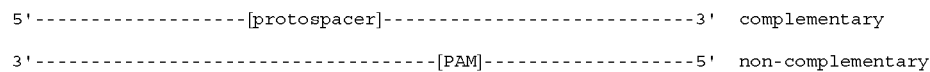

In addition to recognizing specific sequential orientations of PAMs and protospacers, RNA-guided nucleases can also recognize specific PAM sequences. *S. aureus* Cas9, for instance, recognizes a PAM sequence of NNGRRT or NNGRRV, wherein the N residues are immediately 3' of the region recognized by the gRNA targeting domain. *S. pyogenes* Cas9 recognizes NGG PAM sequences. And *F. novicida* Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 (Ran), incorporated by reference herein), or that that do not cut at all.

Cas9

Crystal structures have been determined for S. pyogenes Cas9 (Jinek 2014), and for S. aureus Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in S. pyogenes and S. aureus). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of *Acidaminococcus* sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a psuedoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand. On the other hand, inactivation of a Cas9 HNH domain results in a nickase that cleaves the bottom or non-complementary strand.

Modifications of PAM specificity relative to naturally occurring Cas9 reference molecules has been described by Kleinstiver et al. for both S. pyogenes (Kleinstiver et al., Nature. 2015 Jul. 23; 523(7561):481-5 (Kleinstiver I) and S. aureus (Kleinstiver et al., Nat Biotechnol. 2015 December; 33(12): 1293-1298 (Klienstiver II)). Kleinstiver et al. have also described modifications that improve the targeting fidelity of Cas9 (Nature, 2016 January 28; 529, 490-495 (Kleinstiver III)). Each of these references is incorporated by reference herein.

RNA-guided nucleases have been split into two or more parts, as described by Zetsche et al. (Nat Biotechnol. 2015 February; 33(2):139-42 (Zetsche II), incorporated by reference), and by Fine et al. (Sci. Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g., Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g., different stoichiometric ratios of gRNA: RNA-guided nuclease protein, different buffer solutions, etc.) to identify optimal conditions for RNP formation; and (b) testing modifications (e.g., chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g., 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g., 2 µM) of Cas9 in water+10× SYPRO Orange® (Life Technologies cat # S-6650) is dispensed into a 384 well plate. An equimolar amount of gRNA diluted in solutions with varied pH and salt is then added. After incubating at room temperature for 10 minutes and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g., 2 µM) Cas9 in optimal buffer from assay 1 above and incubating (e.g., at RT for 10') in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e., to alter) targeted regions of DNA within or obtained from a cell. Various strategies are described herein to generate particular edits, and these strategies are generally described in terms of the desired repair outcome, the number and positioning of individual edits (e.g., SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double stranded, as described in greater detail below. Single or double stranded templates can be exogenous, in which case they will promote gene correction, or they can be endogenous (e.g., a homologous sequence within the cellular genome), to promote gene conversion. Exogenous templates can have asymmetric overhangs (i.e., the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g., a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g., ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of multiple DSBs, or SSBs, are described in, for instance, Cotta-Ramusino.

Donor Template Design

Donor template design is described in detail in the literature, for instance in Cotta-Ramusino. DNA oligomer donor templates (oligodeoxynucleotides or ODNs), which can be single stranded (ssODNs) or double-stranded (dsODNs), can be used to facilitate HDR-based repair of DSBs, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g., flanking or adjoining) a target sequence to be cleaved. These homologous regions are referred to here as "homology arms," and are illustrated schematically below:

[5' homology arm]-[replacement sequence]-[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson et al. Nature Biotechnology 34, 339-344 (2016) (Richardson), which is incorporated by reference, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

Figure 22:
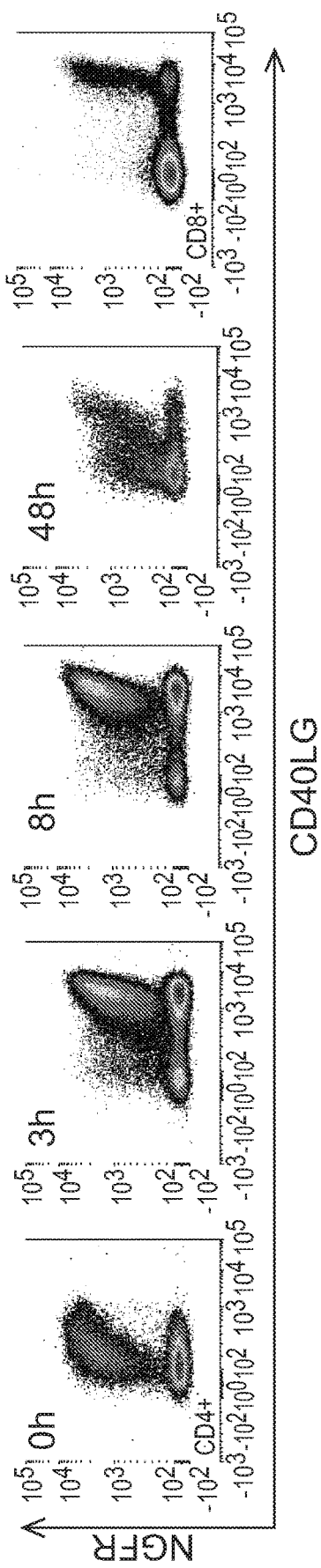
FIGS. 22A-22F depict a selection strategy developed to enrich CD40LG edited T cells.
Figure 22:
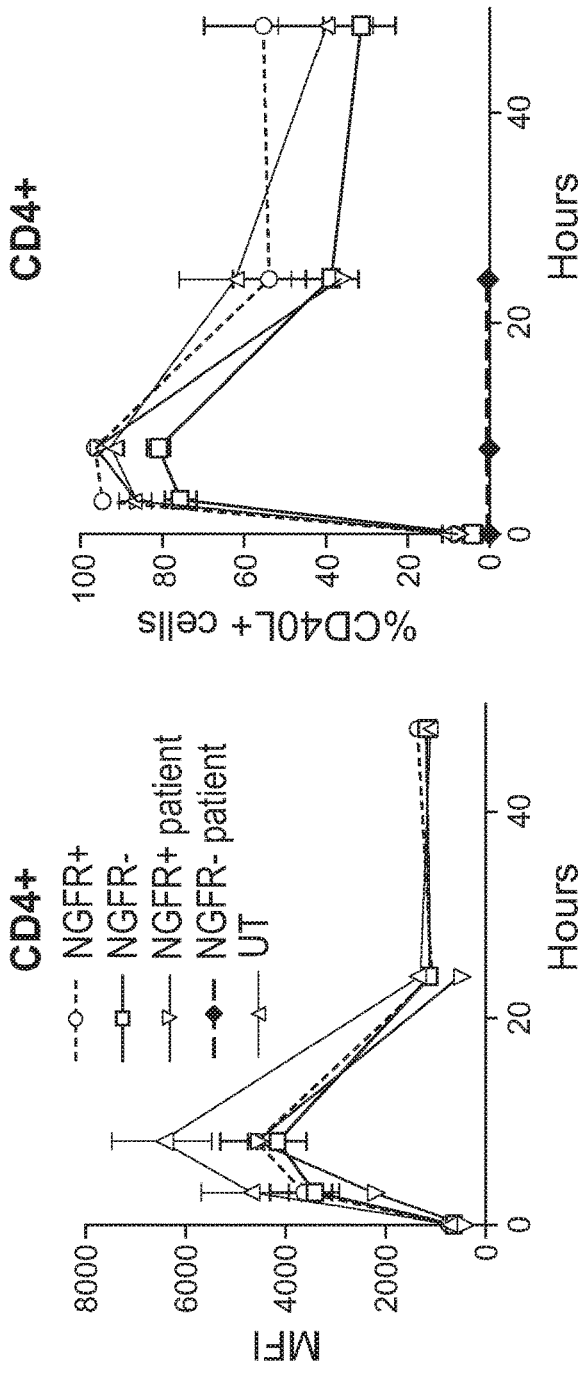

In addition to homology arms, donor templates may comprise additional elements such as stuffer sequences and/or reporter sequences, e.g., a GFP reporter (see FIG. 1), or a NGFR sequence (see FIG. 22). In some embodiments, a donor template comprises a first homology arm, a first stuffer sequence, a cargo sequence, e.g., one or more of exons 2-5 of CD40L, a 3' UTR sequence, a polyA sequence, a reporter sequence, e.g., a GFP reporter sequence or a NGFR sequence, a second stuffer sequence, and a second homology arm. In another embodiment, a donor template comprises a first homology arm, a cargo sequence, e.g., one or more of exons 2-5 of CD40L, a 3' UTR sequence, a polyA sequence, a reporter sequence, e.g., a GFP reporter sequence or a NGFR sequence, and a second homology arm. In another embodiment, a donor template comprises a first homology arm, a first stuffer sequence, a cargo sequence, e.g., one or more of exons 2-5 of CD40L, a 3' UTR sequence, a polyA sequence, a second stuffer sequence, and a second homology arm. In another embodiment, a donor template comprises a first homology arm, a cargo sequence, e.g., one or more of exons 2-5 of CD40L, a 3' UTR sequence, a polyA sequence, and a second homology arm.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

For treatment of Hyper IgM Syndrome, a target cell may be a hematopoietic stem cell (HSC) or a population of HSCs. Alternatively, a target cell may be a T cell, or a population of T cells.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g., administered to a subject) immediately, or they can be maintained or stored for later use. Those of skill in the art will appreciate that cells can be maintained in culture or stored (e.g., frozen in liquid nitrogen) using any suitable method known in the art.

Method of Treatment

Genome editing systems according to this disclosure can be used to treat Hyper-IgM syndrome (HIGM) and associated disorders. HIGM is an immunoglobulin deficiency characterized by normal or elevated serum IgM levels and decreased levels or absence of other serum immunoglobulins, resulting in susceptibility to bacterial infections. Patients with HIGM syndrome have an inability to switch from the production of antibodies of the IgM type to antibodies of the IgG, IgA and/or IgE types. As a result, subjects with this disease have decreased levels of IgG and IgA but normal or elevated levels of IgM in their blood. These different types of antibodies perform different functions and are all important in fighting infections. Normally, B-lymphocytes can produce IgM antibodies on their own, but they require interactive help from T-lymphocytes in order to switch from IgM to IgG, IgA or IgE. HIGM results from a variety of genetic defects that affect this interaction between T-lymphocytes and B-lymphocytes.

The most common form of HIGM syndrome results from a defect or deficiency of a protein that is found on the surface of activated T-lymphocytes. The affected protein is called CD40 ligand (CD40L) because it binds, or ligates, to a protein on B-lymphocytes called CD40. CD40 ligand is made by a gene on the X-chromosome. Therefore, this primary immunodeficiency disease is inherited as an X-linked recessive trait.

As a consequence of the deficiency in CD40 ligand, the T-lymphocytes in patients with X-linked Hyper IgM (XHIGM) are unable to instruct B-lymphocytes to switch their production of immunoglobulins from IgM to IgG, IgA and/or IgE. CD40 ligand is also important for other functions carried out by T-lymphocytes, so patients with X-linked hyper IgM syndrome (XHIM) have defective cellular immunity and are also susceptible to many kinds of infections, particularly opportunistic infections, and to some types of cancer. Patients with this form may also have severe neutropenia and often present during infancy with *Pneumocystis jirovecii* pneumonia. Lymphoid tissue is very small because deficient CD40 ligand signaling does not activate B cells.

Diagnosis of hyper-IgM syndrome is suspected based on clinical criteria. Serum Ig levels are measured; normal or elevated serum IgM levels and low levels or absence of other immunoglobulins support the diagnosis. Flow cytometry testing of CD40 ligand expression on T-cell surfaces should be done. When possible, the diagnosis is confirmed by genetic testing. Prenatal genetic testing can be offered to women considering pregnancy if they have a family history of CD40 ligand deficiency. Genetic testing of other relatives is not routinely done. Other laboratory findings include a reduced number of memory B cells (CD27) and absence of class-switched memory B cells (IgD-CD27).

Treatments that have been shown to help prevent the recurrent infections associated with Hyper-IgM Syndrome include the prophylactic administration of antibiotic medication and/or infusions with antibodies (immunoglobulins) obtained from plasma. In addition, although steroid therapy is often effective in the treatment of neutropenia, autoimmune disorders in children with Hyper-IgM Syndrome may present a difficult treatment dilemma since the use of steroid medications often suppresses an already weak immune system. In some cases, non-steroidal anti-inflammatory drugs may be helpful in controlling the autoimmune-like symptoms while avoiding the use of corticosteroids.

The data presented herein provide evidence that, when T cells and hematopoietic stem cells are edited to correct the expression and function of CD40L using the genome-editing systems, as described herein, edited T cells restored the capability of B cell class switching. Similarly, mice receiving hematopoietic stem cells comprising 10% CD40L edited cells had a much higher level of IgG, suggesting that hematopoietic stem cells with at least 10% of CD40L editing demonstrate a great therapeutic potential for treating hyper-IgM syndrome. Accordingly, the genome editing systems, as described herein, provide an important new treatment for subjects with hyper-IgM syndrome.

In one embodiment, at least 5% of edited cells in a population of cells are sufficient to functionally restore class cell switching. In another embodiment, at least 6% of edited cells in a population of cells are sufficient to functionally restore class cell switching. In another embodiment, at least 7% of edited cells in a population of cells are sufficient to functionally restore class cell switching. In another embodiment, at least 8% of edited cells in a population of cells are sufficient to functionally restore class cell switching. In another embodiment, at least 9% of edited cells in a population of cells are sufficient to functionally restore class cell switching. In another embodiment, at least 10% of edited cells in a population of cells are sufficient to functionally restore class cell switching. In another embodiment, at least 15% of edited cells in a population of cells are sufficient to functionally restore class cell switching. In another embodiment, at least 20% of edited cells in a population of cells are sufficient to functionally restore class cell switching.

In some embodiments, it can be desirable for subjects with hyper-IgM syndrome to be lymphodepleted prior to administration of the edited cells. Accordingly, in one embodiment, the subject is conditioned prior to administration of the edited cells. Conditioning can involve lymphodepletion of the subject. For example, in one embodiment, the subject is conditioned with chemotherapy causing lymphodepletion, prior to receipt of the edited cells. In one embodiment, T cells from the subject are depleted by conditioning. Agents suitable for conditioning the subject include agents that induce lymphodepletion, for example, depletion of T cells. Agents, i.e., conditioning agents, that induce lymphodepletion are known in the art. In one embodiment, the conditioning agent is a chemotherapeutic agent. In one embodiment, the conditioning agent is cyclophosphamide. In some embodiments, the method can optionally comprise a step of administering a conditioning agent to the subject, e.g., a conditioning agent causing lymphodepletion. In one embodiment, the conditioning agent is a chemotherapeutic agent. In one embodiment, the conditioning agent is cyclophosphamide.

In another embodiment, edited cells are administered to the subject without lymphodepletion. In this embodiment, the subject is not conditioned prior to administration of the edited cells.

In one embodiment, the cells are stimulated prior to administration to the subject. In one embodiment, the cells are stimulated using cytokines, e.g., stimulatory cytokines. For example, the cells can be stimulated with IL-7, IL-15, IL-2, or a combination thereof.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 5 and 6 set forth several, non-limiting examples of genome editing system implementations. Those of skill in the art will appreciate, however, that these listings are not comprehensive, and that other implementations are possible. With reference to Table 5 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 5

Genome Editing System Components

| RNA-guided Nuclease | gRNA | Donor Template | Comments |
|---|---|---|---|
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |

TABLE 5-continued

Genome Editing System Components

| RNA-guided Nuclease | gRNA | Donor Template | Comments |
|---|---|---|---|
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | | DNA | A first DNA or DNA vector encoding an RNA-guided nuclease and second DNA or DNA vector encoding a gRNA and a donor template. |
| | DNA | DNA | A first DNA or DNA vector encoding an RNA-guided nuclease and a donor template, and a second DNA or DNA vector encoding a gRNA |
| | DNA | | A DNA or DNA vector encoding an RNA-guided nuclease and a donor template, and a gRNA |
| | RNA | | |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 6 summarizes various delivery methods for the components of genome editing systems, as described herein. Again, the listing is intended to be exemplary rather than limiting.

TABLE 6

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 6, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 6, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g., lipid and/or polymer) nanoparticles can be suitable for use as delivery vehicles in certain embodiments of this disclosure. Exemplary lipids for use in nanoparticle formulations, and/or gene transfer are shown in Table 7, and Table 8 lists exemplary polymers for use in gene transfer and/or nanoparticle formulations.

TABLE 7

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethyl-ammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamide | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propyl-amino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 8

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e g, minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

The present invention is further illustrated by the following examples, which are not intended to be limiting in any way. The entire contents of all references, patents and published patent applications cited throughout this application, as well as the Figures, are hereby incorporated by reference.

EXAMPLES

The following Examples are merely illustrative and are not intended to limit the scope or content of the invention in any way.

Example 1: Gene Editing of CD40L on T Lymphocytes

Figure 2A:
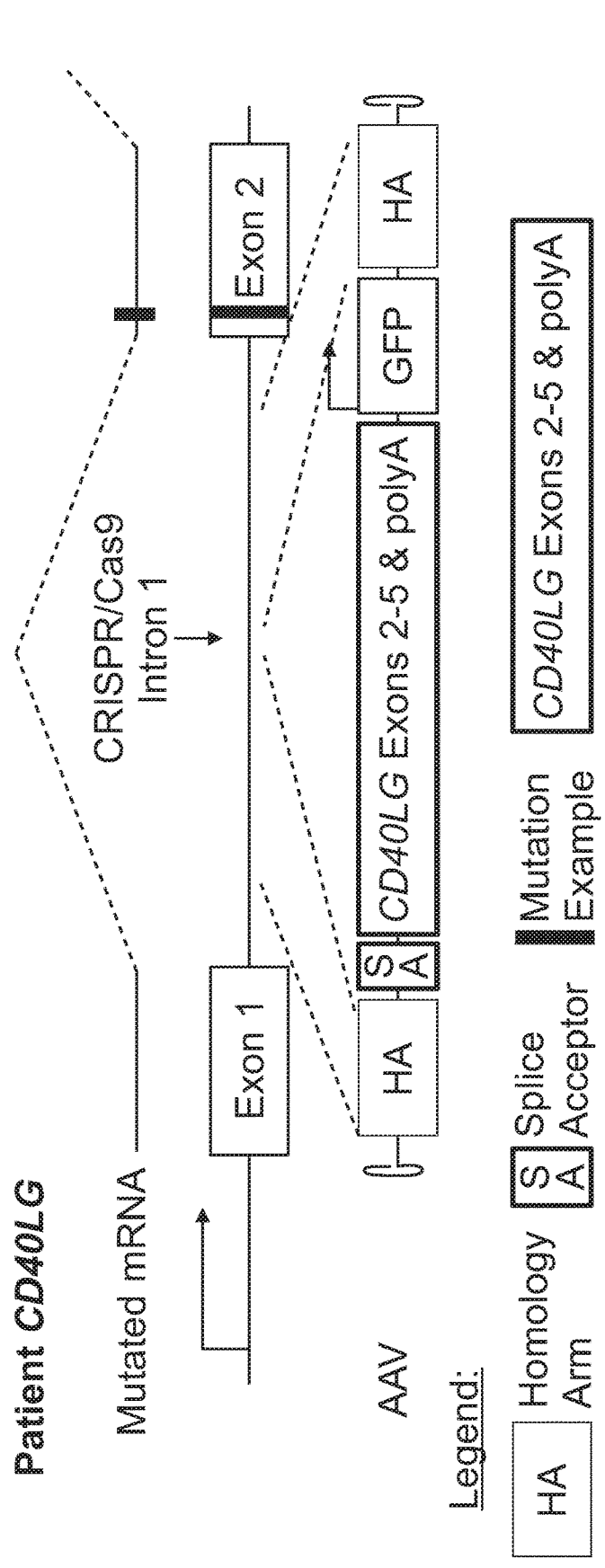
Figure 2A:
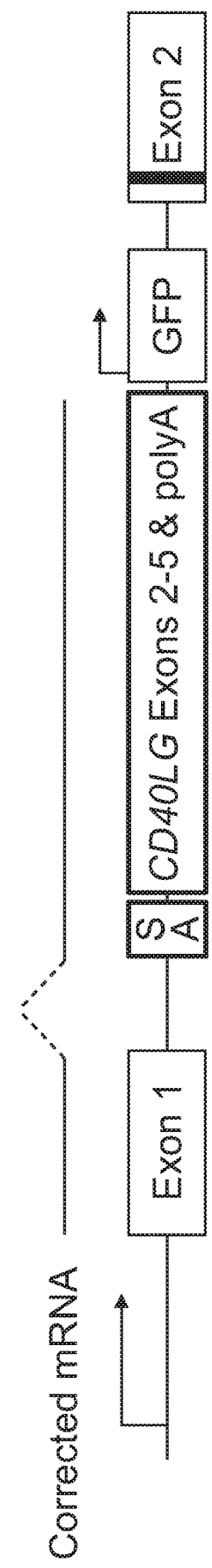
Figure 2B:
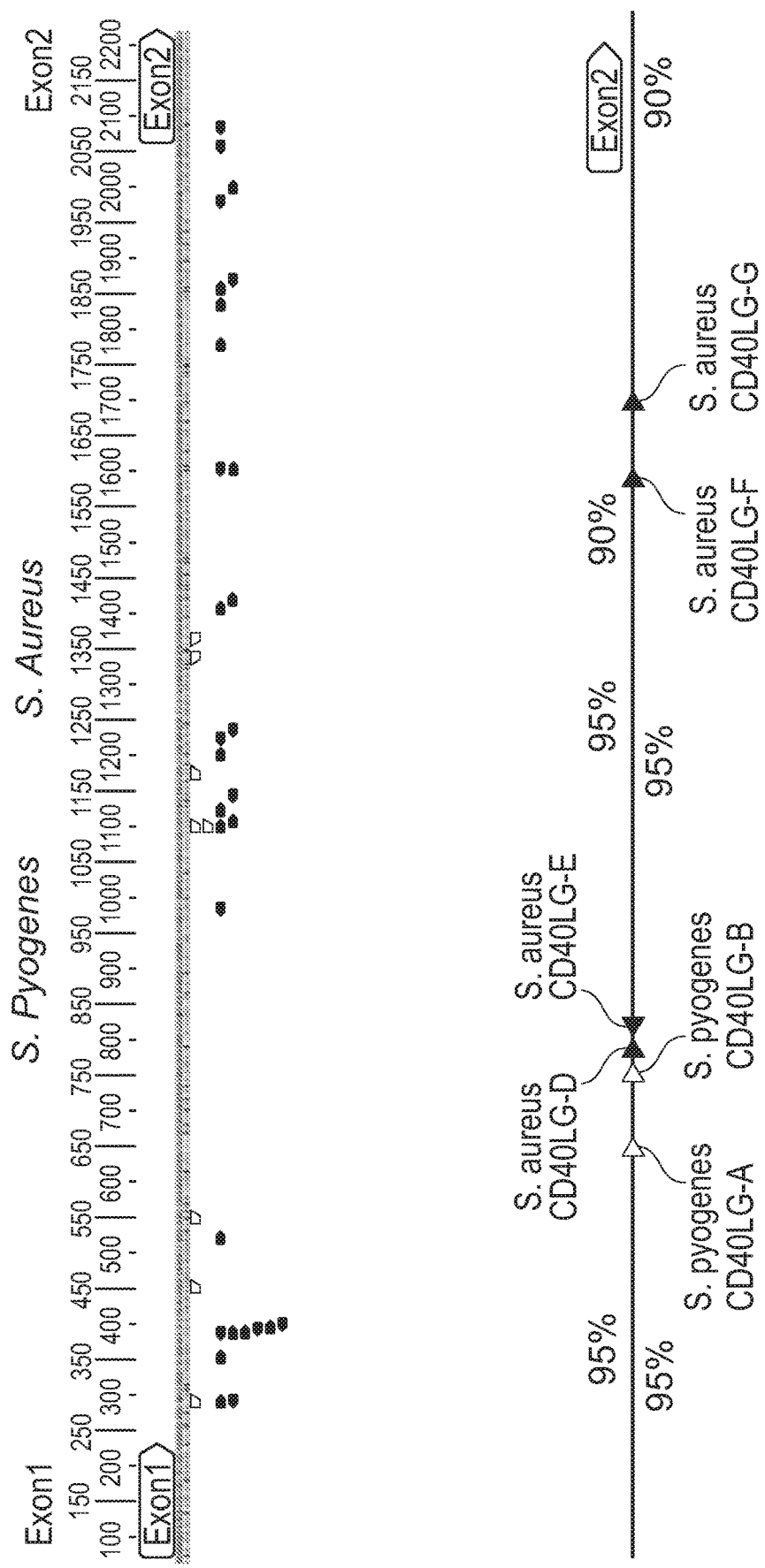
Figure 2E:
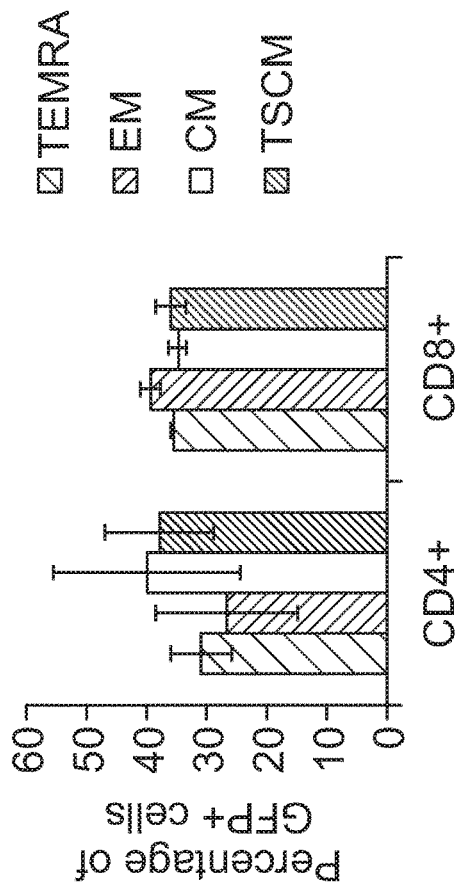
Figure 2F:
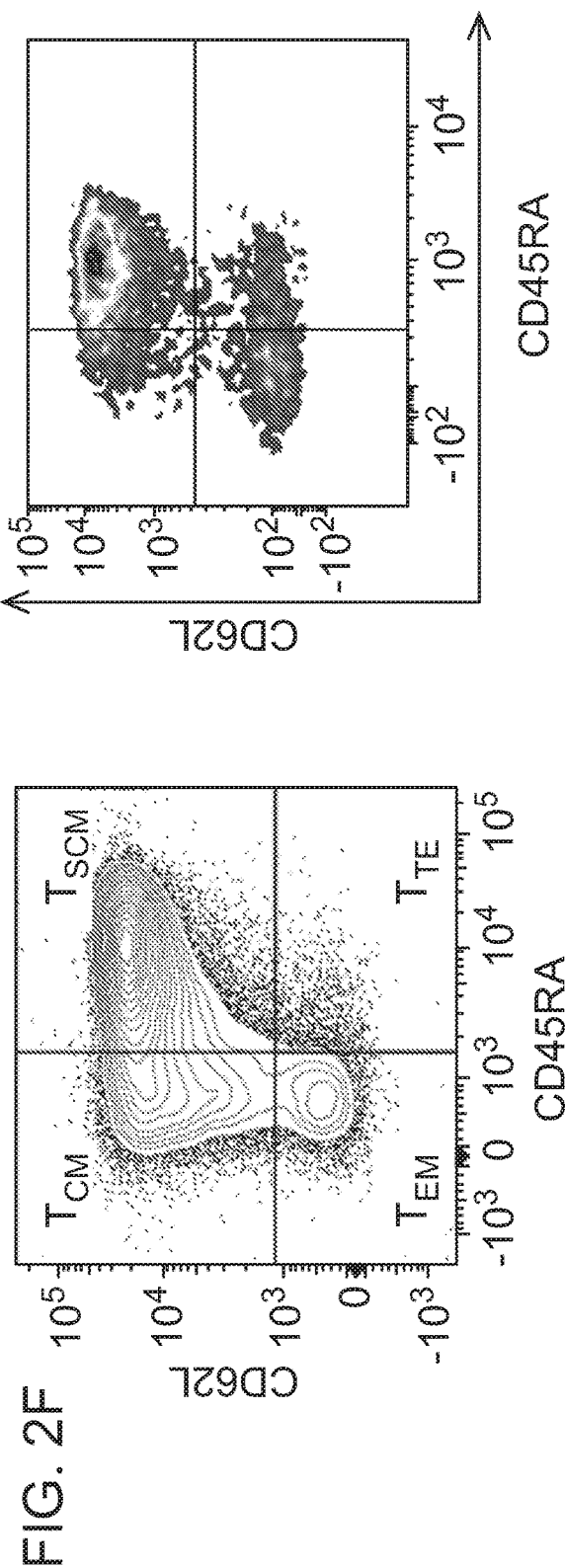
Figure 2G:
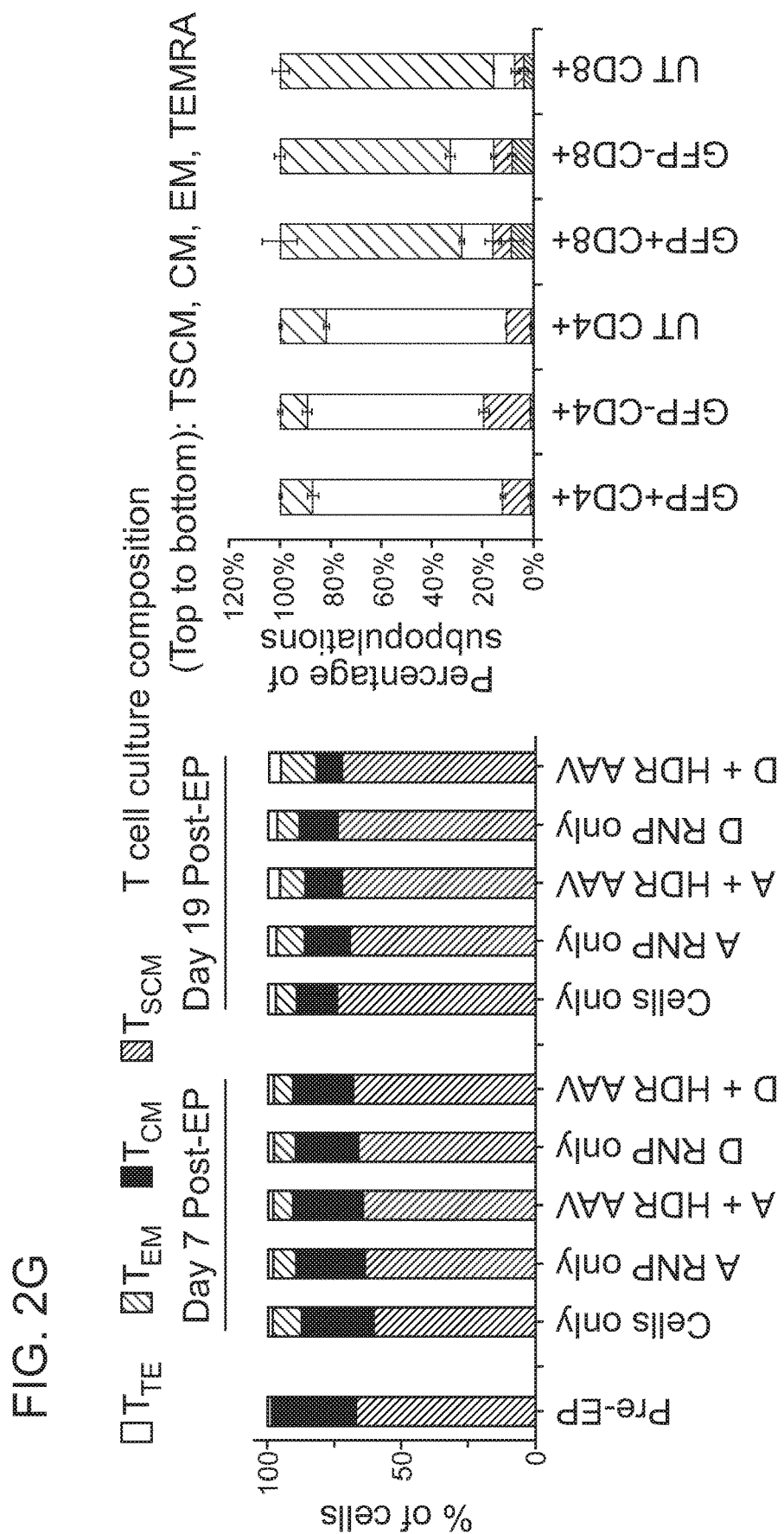
Figure 2H:
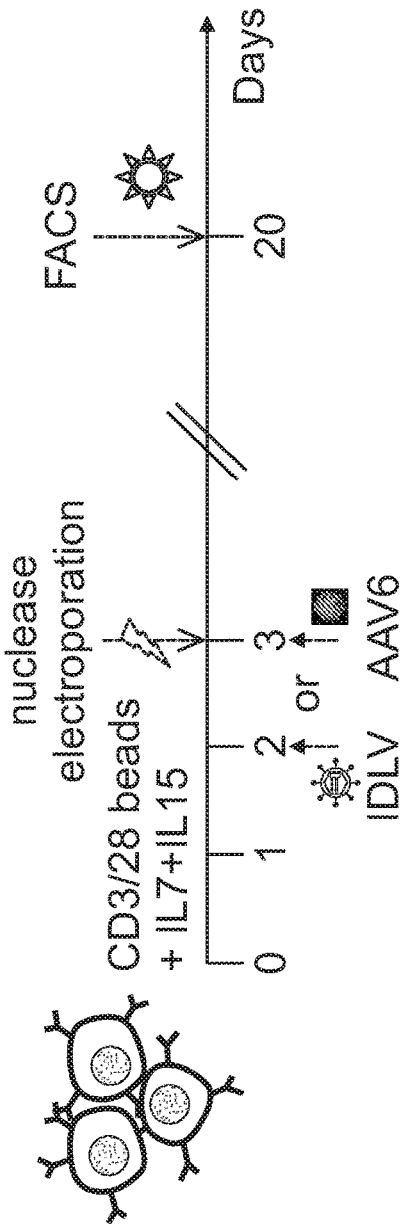
Figure 2I:
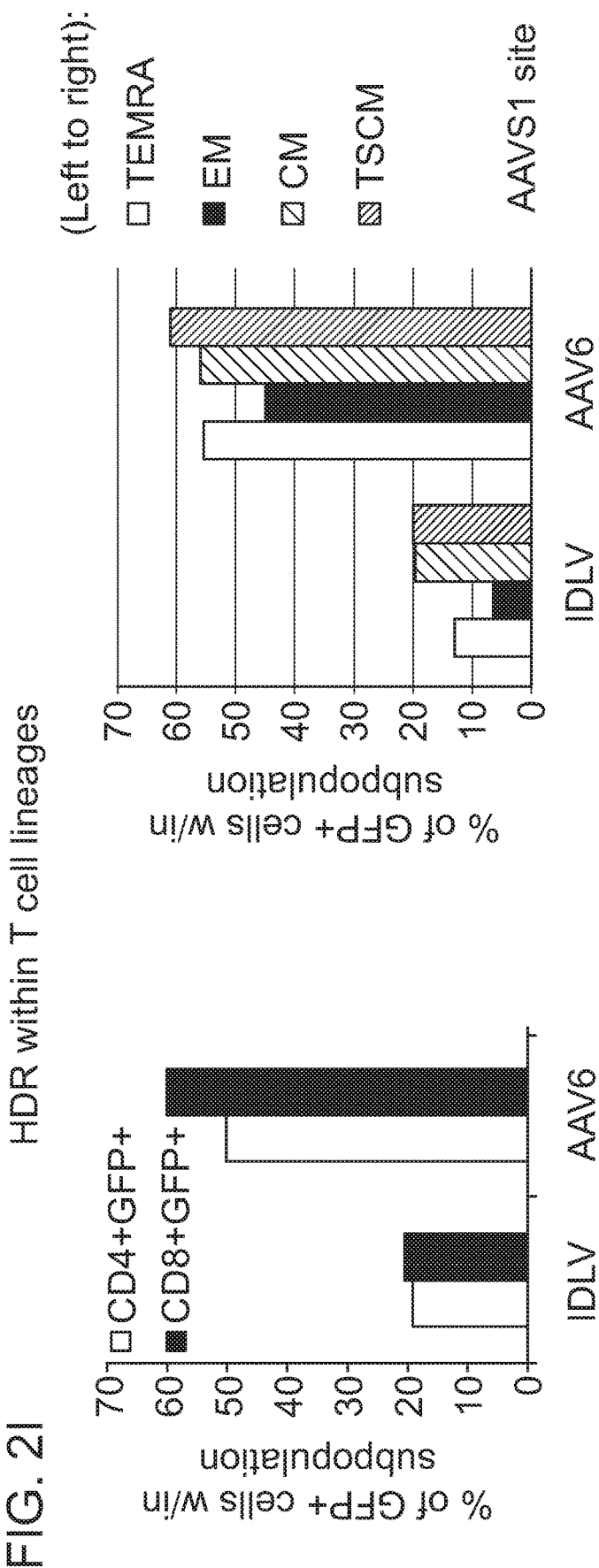
Figure 2J:
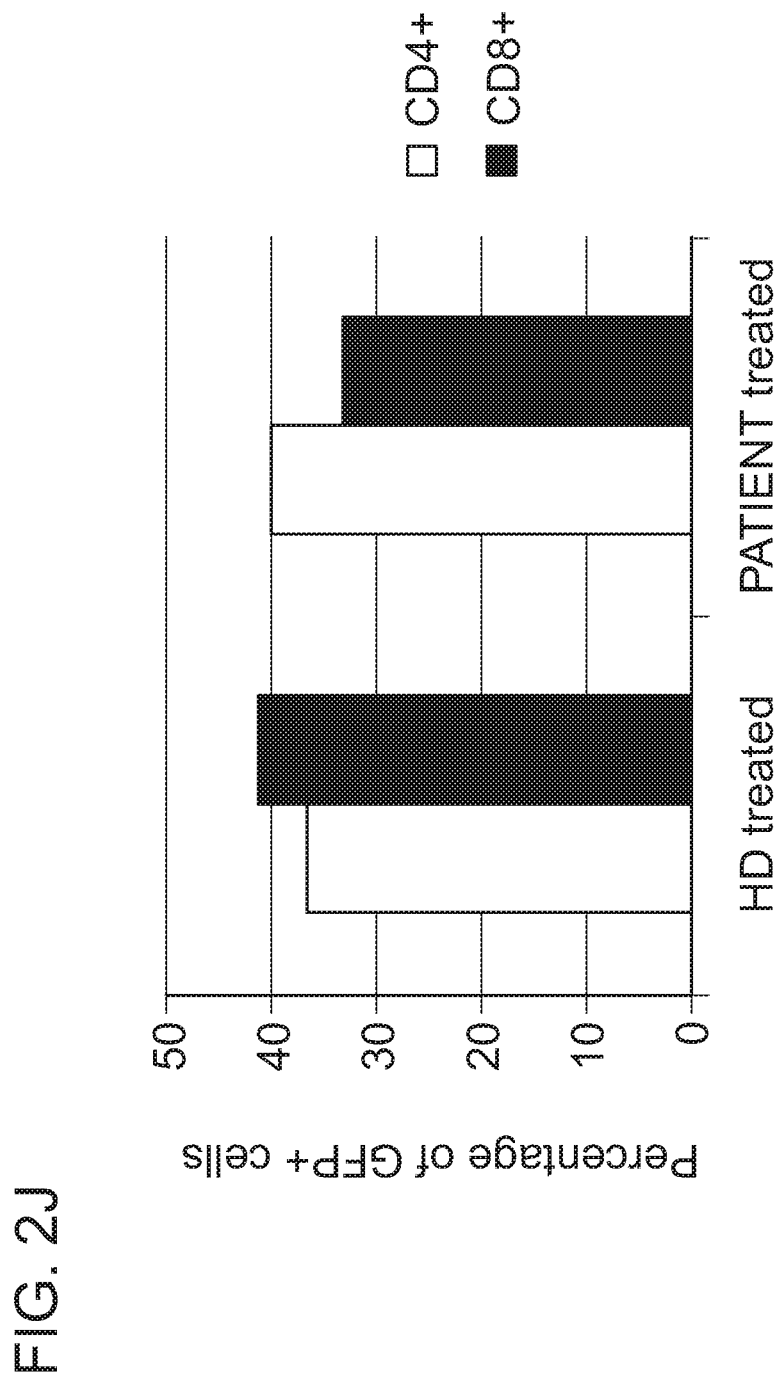

Targeted integration experiments were conducted in T cells with wild-type *S. pyogenes* Cas9 ribonucleoprotein (RNP) targeted to the CD40L locus. gRNA sequences are shown in Table 9. CD40L donor sequences are shown in Table 10. FIG. 2A shows a schematic representation of the CD40L locus after targeted integration. 8 *S. pyogenes* and 30 *S. aureus* gRNAs targeting CD40LG Exon 1 were screened in primary human T cells for editing efficiency in conjunction with *S. pyogenes* or *S. aureus* wild-type Cas9. The position of the gRNAs in CD40LG Exon 1 is depicted in FIG. 2B. Approximately 90%-95% of the CD40LG mutations were corrected to restore both the expression and function of the gene, in *S. pyogenes* and *S. aureus*. FIG. 2C shows the insertion/deletion rates for each gRNA measured in T-cells. To determine the level of editing and the types of edits at multiple gRNA sites identified in CD40LG intron 1, ribonucleoprotein (RNP) was introduced into primary human male CD4+ T cells. T cells were thawed and activated for 2 days with anti-CD3/CD28 magnetic beads, after which the beads were removed and the cells were allowed to expand for 2 days in X-Vivo 15 media before nucleofections were performed. Media during all steps contained human cytokines (IL-2, IL-7, and IL-15). T cells were nucleofected with 2.27 µM RNP at a 2:1 gRNA:Cas9 ratio using the Lonza nucleofection system. Cells were then allowed to expand for 4 days in T cell media before genomic DNA was isolated. The genomic DNA (gDNA) was then PCR amplified using primers that surround the cut site of interest, sequenced, and analyzed for insertions and deletions at the cut site. Over 70% overall editing was achieved for each gRNA presented in FIG. 2C, although the ratio of insertions to deletions varied. The results depicted in FIG. 2C represent at least 2 independent samples. The percentage of editing achieved with each RNP is also presented in Table 9.

gRNAs exhibiting high editing efficiency were used in targeted integration experiments in conjunction with an AAV6 vector containing the CD40LG donor template depicted in FIG. 2A. AAV6 was added after electroporation of RNP on Day 3 and GFP fluorescence was measured by FACS 20 days after the experiment, as shown in FIG. 2D. The percentage of GFP positive cells in T cell populations following gene editing is shown in FIG. 2E. T stem memory cells (TSCM) are defined as CD62L+CD45RA+, T central memory (TCM) as CD62L+ CD45RA−, T effector memory (TEM) as CD62L− CD45RA− and terminal effectors (TEMRA) as CD62L−CD45RA+. The CRISPR/Cas9 and AAV6 combination allowed high levels of CD40L gene editing in multiple T cell populations. Representative plots of T cells expressing CD45RA and CD62L 7 days (left panel) and 20 days (right panel) after treatment are presented in FIG. 2F. The T cell culture composition 7 and 19 days (left panel) and 20 days (right panel) after treatment is shown in FIG. 2G. This data indicates that there is no skewing of T cell subpopulations following gene editing at the CD40L locus, relative to the unedited ("cells only") control. Targeted integration experiments were also performed in conjunction with an IDLV vector containing the CD40LG donor template, as shown in FIG. 2H. The level of HDR (assessed by determining the percentage of GFP+ cells) within various T cell lineages is shown in FIG. 2I. FIG. 2J depicts that similar and high levels of gene editing are observed in both HD and patient cells.

TABLE 9

| Guide RNA, Protospacer and PAM Sequences | | |
|---|---|---|
| gRNA Name | Protospacer Sequence (5' to 3') | PAM |
| A | TGGATGATTGCACTTTATCA (SEQ ID NO: 2) | GGG (SEQ ID NO: 10) |
| B | TTTTCTAACAGGATAAGGTG (SEQ ID NO: 3) | AGG (SEQ ID NO: 11) |
| C | CGGTAAATATCAGTCCACTG (SEQ ID NO: 4) | AGG (SEQ ID NO: 12) |
| D | AGTGAGGGCTGAAGTCATCCA (SEQ ID NO: 5) | CTGGGT (SEQ ID NO: 13) |

TABLE 9 -continued

Guide RNA, Protospacer and PAM Sequences

| | | | |
|---|---|---|---|
| E | ACCTAATATTTGGATAACCCA (SEQ ID NO: 6) | GTGGAT (SEQ ID NO: 14) | |
| F | CAATGAGAAATGTGACAATTA (SEQ ID NO: 7) | CAGAAT (SEQ ID NO: 15) | |
| G | AGAATAGCTCTGATTTCTACC (SEQ ID NO: 8) | TGGAGT (SEQ ID NO: 16) | |
| H | GAGGACTTTCAGGCATAAATG (SEQ ID NO: 9) | GAGAAT (SEQ ID NO: 17) | |

| gRNA Name | Cas9 | gRNA Sequence | PAM | % Editing (sequencing) |
|---|---|---|---|---|
| A | S. pyogenes | UGGAUGAUUGCACUUUAUCA (SEQ ID NO: 18) | GGG (SEQ ID NO: 26) | 90% |
| B | S. pyogenes | UUUUCUAACAGGAUAAGGUG (SEQ ID NO: 19) | AGG (SEQ ID NO: 27) | 70% |
| C | S. pyogenes | CGGUAAAUAUCAGUCCACUG (SEQ ID NO: 20) | AGG (SEQ ID NO: 28) | 85% |
| D | S. aureus | AGUGAGGGCUGAAGUCAUCCA (SEQ ID NO: 21) | CTGGGT (SEQ ID NO: 29) | 90% |
| E | S. aureus | ACCUAAUAUUUGGAUAACCCA (SEQ ID NO: 22) | GTGGAT (SEQ ID NO: 30) | 90% |
| F | S. aureus | CAAUGAGAAAUGUGACAAUUA (SEQ ID NO: 23) | CAGAAT (SEQ ID NO: 31) | 80% |
| G | S. aureus | AGAAUAGCUCUGAUUUCUACC (SEQ ID NO: 24) | TGGAGT (SEQ ID NO: 32) | 80% |
| H | S. aureus | GAGGACUUUCAGGCAUAAAUG (SEQ ID NO: 25) | GAGAAT (SEQ ID NO: 33) | 15-20% |

TABLE 10

CD40L Donor Sequences

| Donor Name | Donor Description | Donor Sequence |
|---|---|---|
| 1 | gRNA-A_HA + cDNA + GFP + Stuffer | (SEQ ID NO: 34) TGTTTTGCATTCTTAGGAAAAGAAAACCATCAGGACTTATTTTGTTTTCATGTA TTTTTTCACTTCCACTGAGGAGTATAATTGGCTGGTGTTGACAAAATACCAATC ATAGATGTAAAGGAGAAAGTTGATTAGTTTTCTGGCTGTTCCTAAAATTCTGG ATGCAGGAACTGTGGCTAGAAAGCATCTGGATGATTGCACTTTATACTCTTAA TTCATTACATATTGTGCGGTCGAATTCAGGGAGCCGATAATGCGGTTACAATA ATTCCTATACTTAAATATACAAAGATTTAAAATTTCAAAAAATGGTTACCAGCA TCGTTAGTGCGTATACATCAAGAGGCACGTGCCCCGGAGACAGCAAGTAAGC TCTTTAAACACCTGATGTGCTCTGTCAATCAAATGTAAAGCTTCCTTAGGTTTA CATGTGCTCTTAATTACAGCAGAACCGGTCTGACCTCTTCTCTTCCTCCCACAG ATCGAGGACGAGAGAAACCTGCACGAGGACTTCGTGTTCATGAAGACCATCC AGCGGTGCAACACCGGCGAGAGAAGTCTGAGCCTGCTGAACTGCGAGGAAA TCAAGAGCCAGTTCGAGGGCTTCGTGAAGGACATCATGCTGAACAAAGAGGA AACGAAGAAAGAAAACTCCTTCGAGATGCAGAAGGGCGACCAGAATCCTCAG ATCGCCGCTCACGTGATCAGCGAGGCCAGCAGCAAGACAACAAGCGTGCTGC AGTGGGCCGAGAAGGGCTACTACACCATGAGCAACAACCTGGTCACCCTGGA AAACGGCAAGCAGCTGACAGTGAAGCGGCAGGGCCTGTACTACATCTACGCC CAAGTGACCTTCTGCAGCAACAGAGAGGCCAGCTCTCAGGCCCCTTTTATCGC CAGCCTGTGCCTGAAGTCCCCTGGCAGATTCGAGCGGATTCTGCTGAGAGCC GCCAACACACACAGCAGCGCCAAACCTTGTGGCCAGCAGTCTATTCACCTCGG CGGAGTGTTTGAGCTGCAGCCTGGCGCAAGCGTGTTCGTGAATGTGACAGAC CCTAGCCAGGTGTCCCACGGCACCGGCTTTACATCTTTCGGACTGCTGAAGCT GTGAACAGTGTCACCTTGCAGGCTGTGGTGGAGCTGACGCTGGGAGTCTTCA TAATACAGCACAGCGGTTAAGCCCACCCCCTGTTAACTGCTATTTATAACCCT AGGATCCTCCTTATGGAGAACTATTTATTATACACTCCAAGGCATGTAGAACT GTAATAAGTGAATTACAGGTCACATGAAACCAAACGGGCCCTGCTCCATAA GAGCTTATATATCTGAAGCAGCAACCCCACTGATGCAGACATCCAGAGAGTCC TATGAAAAGACAAGGCCATTATGCACAGGTTGAATTCTGAGTAAACAGCAGA TAACTTGCCAAGTTCAGTTTTGTTTCTTTGCGTGCAGTGTCTTTCCATGGATAA |

TABLE 10 -continued

CD40L Donor Sequences

| Donor Name | Donor Description | Donor Sequence |
|---|---|---|
|  |  | TGCATTTGATTTATCAGTGAAGATGCAGAAGGGAAATGGGGAGCCTCAGCTC<br>ACATTCAGTTATGGTTGACTCTGGGTTCCTATGGCCTTGTTGGAGGGGCCAG<br>GCTCTAGAACGTCTAACACAGTGGAGAACCGAAACCCCCCCCCCGCCACCC<br>TCTCGGACAGTTATTCATTCTCTTTCAATCTCTCTCTCCATCTCTCTCTTTCAG<br>TCTCTCTCTCTCAACCTCTTTCTTCCAATCTCTCTTTCTCAATCTCTCTGTTTCCCT<br>TTGTCAGTCTCTTCCCTCCCCCAGTCTCTCTTCTCAATCCCCCTTTCTAACACACA<br>CACACACACACACACACACACACACACACACACACACACACACACAGAGTCAG<br>GCCGTTGCTAGTCAGTTCTCTTCTTTCCACCCTGTCCCTATCTCTACCACTATAG<br>ATGAGGGTGAGGAGTAGGGAGTGCAGCCCTGAGCCTGCCCACTCCTCATTAC<br>GAAATGACTGTATTTAAAGGAAATCTATTGTATCTACCTGCAGTCTCCATTGTT<br>TCCAGAGTGAACTTGTAATTATCTTGTTATTTATTTTTTGAATAATAAAGACCTC<br>TTAACATTACGCGCTTAACATTATCGTTGTTGTTTGAGTACCTAAAGCTCCCAG<br>CCAGGTTGGGGAAAGAGGAAGCATTTGGAGGGAATTTTCCCAACCTTTGTGA<br>TGTTTTCATAAACTTTGTTCTCAAGCTACTTACATTACGCGTACTAGTTGGCTCC<br>GGTGCCCGTCAGTGGGCAGAGCGCACATCGCCCACAGTCCCCGAGAAGTTGG<br>GGGGAGGGGTCGGCAATTGAACCGGTGCCTAGAGAAGGTGGCGCGGGGTA<br>AACTGGGAAAGTGATGTCGTGTACTGGCTCCGCCTTTTTCCCGAGGGTGGGG<br>GAGAACCGTATATAAGTGCAGTAGTCGCCGTGAACGTTCTTTTTCGCAACGGG<br>TTTGCCGCCAGAACACAGGTGTCGTGACGCGGATCGTACCCGGGTTAAGGGC<br>GAATTCCAGCACACTGGCGGCCGTTACTAGTGGATCCACCGGTCGCCACCATG<br>GTGAGCAAGGGCGAGGAGCTGTTCACCGGGGTGGTGCCCATCCTGGTCGAG<br>CTGGACGGCGACGTAAACGGCCACAAGTTCAGCGTGTCCGGCGAGGGCGAG<br>GGCGATGCCACCTACGGCAAGCTGACCCTGAAGTTCATCTGCACCACCGGCA<br>AGCTGCCCGTGCCCTGGCCCACCCTCGTGACCACCCTGACCTACGGCGTGCAG<br>TGCTTCAGCCGCTACCCCGACCACATGAAGCAGCACGACTTCTTCAAGTCCGC<br>CATGCCCGAAGGCTACGTCCAGGAGCGCACCATCTTCTTCAAGGACGACGGC<br>AACTACAAGACCCGCGCCGAGGTGAAGTTCGAGGGCGACACCCTGGTGAACC<br>GCATCGAGCTGAAGGGCATCGACTTCAAGGAGGACGGCAACATCCTGGGGC<br>ACAAGCTGGAGTACAACTACAACAGCCACAACGTCTATATCATGGCCGACAA<br>GCAGAAGAACGGCATCAAGGTGAACTTCAAGATCCGCCACAACATCGAGGAC<br>GGCAGCGTGCAGCTCGCCGACCACTACCAGCAGAACACCCCCATCGGCGACG<br>GCCCCGTGCTGCTGCCCGACAACCACTACCTGAGCACCCAGTCCGCCCTGAGC<br>AAAGACCCCAACGAGAAGCGCGATCACATGGTCCTGCTGGAGTTCGTGACCG<br>CCGCCGGGATCACTCTCGGCATGGACGAGCTGTACAAGTAAAGCGGCCGCGT<br>CGAGTCTAGAGGGCCCGTTTAAACCCGCTGATCAGCCTCGACTGTGCCTTCTA<br>GTTGCCAGCCATCTGTTGTTTGCCCCTCCCCCGTGCCTTCCTTGACCCTGGAAG<br>GTGCCACTCCCACTGCCCTTTCCTAATAAAATGAGGAAATTGCATCGCATTGTC<br>TGAGTAGGTGTCATTCTATTCTGGGGGGTGGGGTGGGGCAGGACAGCAAGG<br>GGGAGGATTGGGAAGACAATAGCAGGCATGCTGGGGATGCGGTGGGCTCTA<br>TGGTACCAGCTTAAAGAGCAGAGTAACTTAGTAGGCTGCTTTGACATACGATT<br>TTTAATAAAACATGAGCATTTGAATAAAAACGACTTCCTCATACTGTAAACATC<br>ACGCATGCACATTAGACAATAATCCAGTAACGAAACGGCTTCAGTCGTAATCG<br>CCCATATAGTTGGCTACAGAATGTTGGATAGAGAACTTAAGTACGCTAAGGC<br>GGCGTATTTTCTTAATATTTAGGGGTATTTCAGGGATACTTGAGTGTCCTCTCT<br>TAGGATCTGGACCTAGAATTAATGTCATGAGATTTTTCTAACAGGATAAGGTG<br>AGGTAGTGAGGGCTGAAGTCATCCACTGGGTTATCCAAATATTAGGTTTCACT<br>GCTGACAAAAGAGGGGGCTTCTGGTCTGGTTGGTTATTTGTGTTTGG |
| 2 | gRNA-A_HA +<br>cDNA +<br>GFP -<br>Stuffer | (SEQ ID NO: 35)<br>TGTTTTGCATTCTTAGGAAAAGAAAACCATCAGGACTTATTTTGTTTTCATGTA<br>TTTTTTCACTTCCACTGAGGAGTATAATTGGCTGGTGTTGACAAAATACCAATC<br>ATAGATGTAAAGGAGAAAGTTGATTAGTTTTCTGGCTGTTCCTAAAATTCTGG<br>ATGCAGGAACTGTGGCTAGAAAGCATCTGGATGATTGCACTTTACCTGATGTG<br>CTCTGTCAATCAAATGTAAAGCTTCCTTAGGTTTACATGTGCTCTTAATTACAG<br>CAGAACCGGTCTGACCTCTTCTCTTCCTCCCACAGATCGAGGACGAGAGAAAC<u><br>CTGCACGAGGACTTCGTGTTCATGAAGACCATCCAGCGGTGCAACACCGGCG<br>AGAGAAGTCTGAGCCTGCTGAACTGCGAGGAAATCAAGAGCCAGTTCGAGG<br>GCTTCGTGAAGGACATCATGCTGAACAAAGAGGAAACGAAGAAAGAAAACT<br>CCTTCGAGATGCAGAAGGGCGACCAGAATCCTCAGATCGCCGCTCACGTGAT<br>CAGCGAGGCCAGCAGCAAGACAACAAGCGTGCTGCAGTGGGCCGAGAAGGG<br>CTACTACACCATGAGCAACAACCTGGTCACCCTGGAAAACGGCAAGCAGCTG<br>ACAGTGAAGCGGCAGGGCCTGTACTACATCTACGCCCAAGTGACCTTCTGCA<br>GCAACAGAGAGGCCAGCTCTCAGGCCCCTTTTATCGCCAGCCTGTGCCTGAAG<br>TCCCCTGGCAGATTCGAGCGGATTCTGCTGAGAGCCGCCAACACACACAGCA<br>GCGCCAAACCTTGTGGCCAGCAGTCTATTCACCTCGGCGGAGTGTTTGAGCTG<br>CAGCCTGGCGCAAGCGTGTTCGTGAATGTGACAGACCCTAGCCAGGTGTCCC<br>ACGGCACCGGCTTTACATCTTTCGGACTGCTGAAGCTGTGAACAGTGTCACCT<br>TGCAGGCTGTGGTGGAGCTGACGCTGGGAGTCTTCATAATACAGCACAGCGG</u><br>TTAAGCCCACCCCCTGTTAACTGCCTATTTATAACCCTAGGATCCTCCTTATGG<br>AGAACTATTTATTATACACTCCAAGGCATGTAGAACTGTAATAAGTGAATTAC<br>AGGTCACATGAAACCAAAACGGGCCCTGCTCCATAAGAGCTTATATATCTGAA<br>GCAGCAACCCCACTGATGCAGACATCCAGAGAGTCCTATGAAAAGACAAGGC<br>CATTATGCACAGGTTGAATTCTGAGTAAACAGCAGATAACTTGCCAAGTTCAG<br>TTTTGTTTCTTTGCGTGCAGTGTCTTTCCATGGATAATGCATTTGATTTATCAGT<br>GAAGATGCAGAAGGGAAATGGGGAGCCTCAGCTCACATTCAGTTATGGTTGA |

TABLE 10 -continued

CD40L Donor Sequences

| Donor Name | Donor Description | Donor Sequence |
|---|---|---|
| | | CTCTGGGTTCCTATGGCCTTGTTGGAGGGGGCCAGGCTCTAGAACGTCTAACA<br>CAGTGGAGAACCGAAACCCCCCCCCCCGCCACCCTCTCGGACAGTTATTCAT<br>TCTCTTTCAATCTCTCTCTCCATCTCTCTCTTTCAGTCTCTCTCTCTCAACCTCT<br>TTCTTCCAATCTCTCTTTCTCAATCTCTCTGTTTCCCTTTGTCAGTCTCTTCCCTCC<br>CCCAGTCTCTCTTCTCAATCCCCCTTTCTAACACACACACACACACACACACA<br>CACACACACACACACACACACACACAGAGTCAGGCCGTTGCTAGTCAGTTC<br>TCTTCTTTCCACCCTGTCCCTATCTCTACCACTATAGATGAGGGTGAGGAGTAG<br>GGAGTGCAGCCCTGAGCCTGCCCACTCCTCATTACGAAATGACTGTATTTAAA<br>GGAAATCTATTGTATCTACCTGCAGTCTCCATTGTTTCCAGAGTGAACTTGTAA<br>TTATCTTGTTATTTATTTTTTGAATAATAAAGACCTCTTAACATTACGCGCTTAA<br>CATTATCGTTGTTGTTTGAGTACCTAAAGCTCCCAGCCAGGTTGGGGAAAGAG<br>GAAGCATTTGGAGGGAATTTTCCCAACCTTTGTGATGTTTTCATAAACTTTGTT<br>CTCAAGCTACTTACATTACGCGTACTAGTTGGCTCCGGTGCCCGTCAGTGGGC<br>AGAGCGCACATCGCCCACAGTCCCCGAGAAGTTGGGGGGAGGGGTCGGCAA<br>TTGAACCGGTGCCTAGAGAAGGTGGCGCGGGGTAAACTGGGAAAGTGATGT<br>CGTGTACTGGCTCCGCCTTTTTCCCGAGGGTGGGGGAGAACCGTATATAAGT<br>GCAGTAGTCGCCGTGAACGTTCTTTTTCGCAACGGGTTTGCCGCCAGAACACA<br>GGTGTCGTGACGCGGATCGTACCCGGGTTAAGGGCGAATTCCAGCACACTGG<br>CGGCCGTTACTAGTGGATCCACCGGTCGCCACCATGGTGAGCAAGGGCGAGG<br>AGCTGTTCACCGGGGTGGTGCCCATCCTGGTCGAGCTGGACGGCGACGTAAA<br>CGGCCACAAGTTCAGCGTGTCCGGCGAGGGCGAGGGCGATGCCACCTACGG<br>CAAGCTGACCCTGAAGTTCATCTGCACCACCGGCAAGCTGCCCGTGCCCTGGC<br>CCACCCTCGTGACCACCCTGACCTACGGCGTGCAGTGCTTCAGCCGCTACCCC<br>GACCACATGAAGCAGCACGACTTCTTCAAGTCCGCCATGCCCGAAGGCTACGT<br>CCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGC<br>ATCGACTTCAAGGAGGACGGCAACATCCTGGGGCACAAGCTGGAGTACAACT<br>ACAACAGCCACAACGTCTATATCATGGCCGACAAGCAGAAGAACGGCATCAA<br>GGTGAACTTCAAGATCCGCCACAACATCGAGGACGGCAGCGTGCAGCTCGCC<br>GACCACTACCAGCAGAACACCCCCATCGGCGACGGCCCCGTGCTGCTGCCCG<br>ACAACCACTACCTGAGCACCCAGTCCGCCCTGAGCAAAGACCCCAACGAGAA<br>GCGCGATCACATGGTCCTGCTGGAGTTCGTGACCGCCGCGGGATCACTCTC<br>GGCATGGACGAGCTGTACAAGTAAAGCGGCCGCGTCGAGTCTAGAGGGCCC<br>GTTTAAACCCGCTGATCAGCCTCGACTGTGCCTTCTAGTTGCCAGCCATCTGTT<br>GTTTGCCCCTCCCCCGTGCCTTCCTTGACCCTGGAAGGTGCCACTCCCACTGCC<br>CTTTCCTAATAAAATGAGGAAATTGCATCGCATTGTCTGAGTAGGTGTCATTCT<br>ATTCTGGGGGGTGGGGTGGGGCAGGACAGCAAGGGGGAGGATTGGGAAGA<br>CAATAGCAGGCATGCTGGGGATGCGGTGGGCTCTATGGTACCAGCTTAAAGA<br>GCAGAGTAACTTAGTAGGCTCAGGGATACTTGAGTGTCCTCTCTTAGGATCTG<br>GACCTAGAATTAATGTCATGAGATTTTTCTAACAGGATAAGGTGAGGTAGTG<br>AGGGCTGAAGTCATCCACTGGGTTATCCAAATATTAGGTTTCACTGCTGACAA<br>AAGAGGGGGCTTCTGGTCTGGTTGGTTATTTGTGTTTGG |
| 3 | gRNA-A_HA +<br>cDNA -<br>GFP +<br>stuffer | (SEQ ID NO: 36)<br>TGTTTTGCATTCTTAGGAAAAGAAAACCATCAGGACTTATTTTGTTTTCATGTA<br>TTTTTTCACTTCCACTGAGGAGTATAATTGGCTGGTGTTGACAAAATACCAATC<br>ATAGATGTAAAGGAGAAAGTTGATTAGTTTTCTGGCTGTTCCTAAAATTCTGG<br>ATGCAGGAACTGTGGCTAGAAAGCATCTGGATGATTGCACTTTATACTCTTAA<br>TTCATTACATATTGTGCGGTCGAATTCAGGGAGCCGATAATGCGGTTACAATA<br>ATTCCTATACTTAAATATACAAAGATTTAAAATTTCAAAAAATGGTTACCAGCA<br>TCGTTAGTGCGTATACATCAAGAGGCACGTGCCCCGGAGACAGCAAGTAAGC<br>TCTTTAAACACCTGATGTGCTCTGTCAATCAAATGTAAAGCTTCCTTAGGTTTA<br>CATGTGCTCTTAATTACAGCAGAACCGGTCTGACCTCTTCTCTTCCTCCCACAG<br><u>ATCGAGGACGAGAGAAACCTGCACGAGGACTTCGTGTTCATGAAGACCATCC</u><br><u>AGCGGTGCAACACCGGCGAGAGAAGTCTGAGCCTGCTGAACTGCGAGGAAA</u><br><u>TCAAGAGCCAGTTCGAGGGCTTCGTGAAGGACATCATGCTGAACAAAGAGGA</u><br><u>AACGAAGAAAGAAAACTCCTTCGAGATGCAGAAGGGCGACCAGAATCCTCAG</u><br><u>ATCGCCGCTCACGTGATCAGCGAGGCCAGCAGCAAGACAACAAGCGTGCTGC</u><br><u>AGTGGGCCGAGAAGGGCTACTACACCATGAGCAACAACCTGGTCACCCTGGA</u><br><u>AAACGGCAAGCAGCTGACAGTGAAGCGGCAGGGCCTGTACTACATCTACGCC</u><br><u>CAAGTGACCTTCTGCAGCAACAGAGAGGCCAGCTCTCAGGCCCCTTTTATCGC</u><br><u>CAGCCTGTGCCTGAAGTCCCCTGGCAGATTCGAGCGGATTCTGCTGAGAGCC</u><br><u>GCCAACACACACAGCAGCGCCAAACCTTGTGGCCAGCAGTCTATTCACCTCGG</u><br><u>CGGAGTGTTTGAGCTGCAGCCTGGCGCAAGCGTGTTCGTGAATGTGACAGAC</u><br><u>CCTAGCCAGGTGTCCCACGGCACCGGCTTTACATCTTTCGGACTGCTGAAGCT</u><br><u>GTGAACAGTGTCACCTTGCAGGCTGTGGTGGAGCTGACGCTGGGAGTCTTCA</u><br>TAATACAGCACAGCGGTTAAGCCCACCCCCTGTTAACTGCCTATTTATAACCCT<br>AGGATCCTCCTTATGGAGAACTATTTATTATACACTCCAAGGCATGTAGAACT<br>GTAATAAGTGAATTACAGGTCACATGAAACCAAAACGGGCCCTGCTCCATAA<br>GAGCTTATATATCTGAAGCAGCAACCCCACTGATGCAGACATCCAGAGAGTCC<br>TATGAAAAGACAAGGCCATTATGCACAGGTTGAATTCTGAGTAAACAGAGA<br>TAACTTGCCAAGTTCAGTTTTGTTTCTTTGCGTGCAGTGTCTTTCCATGGATAA<br>TGCATTTGATTTATCAGTGAAGATGCAGAAGGGAAATGGGGAGCCTCAGCTC<br>ACATTCAGTTATGGTTGACTCTGGGTTCCTATGGCCTTGTTGGAGGGGGCCAG<br>GCTCTAGAACGTCTAACACAGTGGAGAACCGAAACCCCCCCCCCCGCCACCC |

TABLE 10 -continued

CD40L Donor Sequences

| Donor Name | Donor Description | Donor Sequence |
|---|---|---|
| | | TCTCGGACAGTTATTCATTCTCTTTCAATCTCTCTCTCCATCTCTCTCTTTCAG<br>TCTCTCTCTCTCAACCTCTTTCTTCCAATCTCTCTTTCTCAATCTCTCTGTTTCCCT<br>TTGTCAGTCTCTTCCCTCCCCCAGTCTCTCTTCTCAATCCCCCTTTCTAACACACA<br>CACACACACACACACACACACACACACACACACACACACACACAGAGTCAG<br>GCCGTTGCTAGTCAGTTCTCTTCTTTCCACCCTGTCCCTATCTCTACCACTATAG<br>ATGAGGGTGAGGAGTAGGGAGTGCAGCCCTGAGCCTGCCCACTCCTCATTAC<br>GAAATGACTGTATTTAAAGGAAATCTATTGTATCTACCTGCAGTCTCCATTGTT<br>TCCAGAGTGAACTTGTAATTATCTTGTTATTTATTTTTTGAATAATAAAGACCTC<br>TTAACATTACGCGCTTAACATTATCGTTGTTGTTTGAGTACCTAAAGCTCCCAG<br>CCAGGTTGGGGAAAGAGGAAGCATTTGGAGGGAATTTTCCCAACCTTTGTGA<br>TGTTTTCATAAACTTTGTTCTCAAGCTACTTACATTACGCGTACTAGTTACCAGC<br>TTAAAGAGCAGAGTAACTTAGTAGGCTGCTTTGACATACGATTTTTAATAAAA<br>CATGAGCATTTGAATAAAAACGACTTCCTCATACTGTAAACATCACGCATGCA<br>CATTAGACAATAATCCAGTAACGAAACGGCTTCAGTCGTAATCGCCCATATAG<br>TTGGCTACAGAATGTTGGATAGAGAACTTAAGTACGCTAAGGCGGCGTATTTT<br>CTTAATATTTAGGGGTATTTCAGGGATACTTGAGTGTCCTCTCTTAGGATCTGG<br>ACCTAGAATTAATGTCATGAGATTTTTCTAACAGGATAAGGTGAGGTAGTGA<br>GGGCTGAAGTCATCCACTGGGTTATCCAAATATTAGGTTTCACTGCTGACAAA<br>AGAGGGGGCTTCTGGTCTGGTTGGTTATTTGTGTTTGG |
| 4 | gRNA-A_HA +<br>cDNA -<br>GFP -<br>stuffer | (SEQ ID NO: 37)<br>TGTTTTGCATTCTTAGGAAAAGAAAACCATCAGGACTTATTTTGTTTTCATGTA<br>TTTTTTCACTTCCACTGAGGAGTATAATTGGCTGGTGTTGACAAAATACCAATC<br>ATAGATGTAAAGGAGAAAGTTGATTAGTTTTCTGGCTGTTCCTAAAATTCTGG<br>ATGCAGGAACTGTGGCTAGAAAGCATCTGGATGATTGCACTTTACCTGATGTG<br>CTCTGTCAATCAAATGTAAAGCTTCCTTAGGTTTACATGTGCTCTTAATTACAG<br>CAGAACCGGTCTGACCTCTTCTCTTCCTCCCACAGATCGAGGACGAGAGAAAC<br>CTGCACGAGGACTTCGTGTTCATGAAGACCATCCAGCGGTGCAACACCGGCG<br>AGAGAAGTCTGAGCCTGCTGAACTGCGAGGAAATCAAGAGCCAGTTCGAGG<br>GCTTCGTGAAGGACATCATGCTGAACAAAGAGGAAACGAAGAAAGAAAACT<br>CCTTCGAGATGCAGAAGGGCGACCAGAATCCTCAGATCGCCGCTCACGTGAT<br>CAGCGAGGCCAGCAGCAAGACAACAAGCGTGCTGCAGTGGGCCGAGAAGGG<br>CTACTACACCATGAGCAACAACCTGGTCACCCTGGAAAACGGCAAGCAGCTG<br>ACAGTGAAGCGGCAGGGCCTGTACTACATCTACGCCCAAGTGACCTTCTGCA<br>GCAACAGAGAGGCCAGCTCTCAGGCCCCTTTTATCGCCAGCCTGTGCCTGAAG<br>TCCCCTGGCAGATTCGAGCGGATTCTGCTGAGAGCCGCCAACACACACAGCA<br>GCGCCAAACCTTGTGGCCAGCAGTCTATTCACCTCGGCGGAGTGTTTGAGCTG<br>CAGCCTGGCGCAAGCGTGTTCGTGAATGTGACAGACCCTAGCCAGGTGTCCC<br>ACGGCACCGGCTTTACATCTTTCGGACTGCTGAAGCTGTGAACAGTGTCACCT<br>TGCAGGCTGTGGTGGAGCTGACGCTGGGAGTCTTCATAATACAGCACAGCGG<br>TTAAGCCCACCCCCTGTTAACTGCCTATTTTATAACCCTAGGATCCTCCTTATGG<br>AGAACTATTTATTATACACTCCAAGGCATGTAGAACTGTAATAAGTGAATTAC<br>AGGTCACATGAAACCAAAACGGGCCCTGCTCCATAAGAGCTTATATATCTGAA<br>GCAGCAACCCCACTGATGCAGACATCCAGAGAGTCCTATGAAAAGACAAGGC<br>CATTATGCACAGGTTGAATTCGAGTAAACAGCAGATAACTTGCCAAGTTCAG<br>TTTTGTTTCTTTGCGTGCAGTGTCTTTCCATGGATAATGCATTTGATTTATCAGT<br>GAAGATGCAGAAGGGAAATGGGGAGCCTCAGCTCACATTCAGTTATGGTTGA<br>CTCTGGGTTCCTATGGCCTTGTTGGAGGGGGCCAGGCTCTAGAACGTCTAACA<br>CAGTGGGAGAACCGAAACCCCCCCCCCCGCCACCCTCTCGGACAGTTATTCAT<br>TCTCTTTCAATCTCTCTCTCTCCATCTCTCTCTTTCAGTCTCTCTCTCTCAACCTCT<br>TTCTTCCAATCTCTCTTTCTCAATCTCTCTGTTTCCCTTTGTCAGTCTCTTCCCTCC<br>CCCAGTCTCTCTTCTCAATCCCCCTTTCTAACACACACACACACACACACACACA<br>CACACACACACACACACACACACACACACACAGAGTCAGGCCGTTGCTAGTTC<br>TCTTCTTTCCACCCTGTCCCTATCTCTACCACTATAGATGAGGGTGAGGAGTAG<br>GGAGTGCAGCCCTGAGCCTGCCCACTCCTCATTACGAAATGACTGTATTTAAA<br>GGAAATCTATTGTATCTACCTGCAGTCTCCATTGTTTCCAGAGTGAACTTGTAA<br>TTATCTTGTTATTTATTTTTTGAATAATAAAGACCTCTTAACATTACGCGCTTAA<br>CATTATCGTTGTTGTTTGAGTACCTAAAGCTCCCAGCCAGGTTGGGGAAAGAG<br>GAAGCATTTGGAGGGAATTTTCCCAACCTTTGTGATGTTTTCATAAACTTTGTT<br>CTCAAGCTACTTACATTACGCGTACTAGTTACCAGCTTAAAGAGCAGAGTAAC<br>TTAGTAGGCTCAGGGATACTTGAGTGTCCTCTCTTAGGATCTGGACCTAGAAT<br>TAATGTCATGAGATTTTTCTAACAGGATAAGGTGAGGTAGTGAGGGCTGAAG<br>TCATCCACTGGGTTATCCAAATATTAGGTTTCACTGCTGACAAAAGAGGGGGC<br>TTCTGGTCTGGTTGGTTATTTGTGTTTGG |
| 5 | gRNA-G_HA +<br>cDNA +<br>GFP +<br>Stuffer | (SEQ ID NO: 38)<br>TTCTTTTTATAAAGCACTGCATCACAAACACTAAAATGAAGTGGGCAAATTAG<br>CTCTGCAGAAAACTATTTTCTAGGCTGATGTTTATAATGACCAATCATTACTGA<br>AGCAATGAGAAATGTGACAATTACAGAATATTGCTGCTATAGTATGTTGAAAA<br>AATATGCATTTTGTAGTGAACATTTAGTAGAATAGCTCTGATTTCTTACTCTTA<br>ATTCATTACATATTGTGCGGTCGAATTCAGGGAGCCGATAATGCGGTTACAAT<br>AATTCCTATACTTAAATATACAAAGATTTAAAATTTCAAAAAATGGTTACCAGC<br>ATCGTTAGTGCGTATACATCAAGAGGCACGTGCCCCGGAGACAGCAAGTAAG<br>CTCTTTAAACATGCTTTGACATACGATTTTTAATAAAACATGAGCATTTGAATA<br>AAAACGACTTCCTCATACTGTAAACATCACGCATGCACATTAGACAATAGATA |

TABLE 10 -continued

CD40L Donor Sequences

| Donor Name | Donor Description | Donor Sequence |
|---|---|---|
| | | CAGAGATGCAACACAGGAGAAGCTTCCTTAGGTTTACATGTGCTCTTAATTAC<br>AGCAGAACCGGTCTGACCTCTTCTCTTCCTCCCACAGATCGAGGACGAGAGAA<br>ACCTGCACGAGGACTTCGTGTTCATGAAGACCATCCAGCGGTGCAACACCGG<br>CGAGAGAAGTCTGAGCCTGCTGAACTGCGAGGAAATCAAGAGCCAGTTCGA<br>GGGCTTCGTGAAGGACATCATGCTGAACAAAGAGGAAACGAAGAAAGAAAA<br>CTCCTTCGAGATGCAGAAGGGCGACCAGAATCCTCAGATCGCCGCTCACGTG<br>ATCAGCGAGGCCAGCAGCAAGACAACAAGCGTGCTGCAGTGGGCCGAGAAG<br>GGCTACTACACCATGAGCAACAACCTGGTCACCCTGGAAAACGGCAAGCAGC<br>TGACAGTGAAGCGGCAGGGCCTGTACTACATCTACGCCCAAGTGACCTTCTGC<br>AGCAACAGAGAGGCCAGCTCTCAGGCCCCTTTTATCGCCAGCCTGTGCCTGAA<br>GTCCCCTGGCAGATTCGAGCGGATTCTGCTGAGAGCCGCCAACACACACAGC<br>AGCGCCAAACCTTGTGGCCAGCAGTCTATTCACCTCGGCGGAGTGTTTGAGCT<br>GCAGCCTGGCGCAAGCGTGTTCGTGAATGTGACAGACCCTAGCCAGGTGTCC<br>CACGGCACCGGCTTTACATCTTTCGGACTGCTGAAGCTGTGAACAGTGTCACC<br>TTGCAGGCTGTGGTGGAGCTGACGCTGGGAGTCTTCATAATACAGCACAGCG<br>GTTAAGCCCACCCCCTGTTAACTGCCTATTTATAACCCTAGGATCCTCCTTATG<br>GAGAACTATTTATTATACACTCCAAGGCATGTAGAACTGTAATAAGTGAATTA<br>CAGGTCACATGAAACCAAACGGGCCCTGCTCCATAAGAGCTTATATATCTGA<br>AGCAGCAACCCCACTGATGCAGACATCCAGAGAGTCCTATGAAAAGACAAGG<br>CCATTATGCACAGGTTGAATTCTGAGTAAACAGCAGATAACTTGCCAAGTTCA<br>GTTTTGTTTCTTTGCGTGCAGTGTCTTTCCATGGATAATGCATTTGATTTATCA<br>GTGAAGATGCAGAAGGGAAATGGGGAGCCTCAGCTCACATTCAGTTATGGTT<br>GACTCTGGGTTCCTATGGCCTTGTTGGAGGGGGCCAGGCTCTAGAACGTCTA<br>ACACAGTGGAGAACCGAAACCCCCCCCCCCGCCACCCTCTCGGACAGTTATT<br>CATTCTCTTTCAATCTCTCTCTCCATCTCTCTCTTTCAGTCTCTCTCTCTCAACC<br>TCTTTCTTCCAATCTCTCTTTCTCAATCTCTCTGTTTCCCTTTGTCAGTCTCTTCCC<br>TCCCCCAGTCTCTCTTCTCAATCCCCCTTTCTAACACACACACACACACACACAC<br>ACACACACACACACACACACACACACACACAGAGTCAGGCCGTTGCTAGTCA<br>GTTCTCTTCTTTCCACCCTGTCCCTATCTCTACCACTATAGATGAGGGTGAGGA<br>GTAGGGAGTGCAGCCCTGAGCCTGCCCACTCCTCATTACGAAATGACTGTATT<br>TAAAGGAAATCTATTGTATCTACCTGCAGTCTCCATTGTTTCCAGAGTGAACTT<br>GTAATTATCTTGTTATTTATTTTTGAATAATAAAGACCTCTTAACATTACGCGC<br>TTAACATTATCGTTGTTGTTTGAGTACCTAAAGCTCCCAGCCAGGTTGGGGAA<br>AGAGGAAGCATTTGGAGGGAATTTTCCCAACCTTTGTGATGTTTTCATAAACT<br>TTGTTCTCAAGCTACTTACATTACGCGTACTAGTTGGCTCCGGTGCCCGTCAGT<br>GGGCAGAGCGCACATCGCCCACAGTCCCCGAGAAGTTGGGGGGAGGGGTCG<br>GCAATTGAACCGGTGCCTAGAGAAGGTGGCGCGGGGTAAACTGGGAAAGTG<br>ATGTCGTGTACTGGCTCCGCCTTTTTCCCGAGGGTGGGGGAGAACCGTATATA<br>AGTGCAGTAGTCGCCGTGAACGTTCTTTTTCGCAACGGGTTTGCCGCCAGAAC<br>ACAGGTGTCGTGACGCGGATCGTACCCGGGTTAAGGGCGAATTCCAGCACAC<br>TGGCGGCCGTTACTAGTGGATCCACCGGTCGCCACCATGGTGAGCAAGGGCG<br>AGGAGCTGTTCACCGGGGTGGTGCCCATCCTGGTCGAGCTGGACGGCGACGT<br>AAACGGCCACAAGTTCAGCGTGTCCGGCGAGGGCGAGGGCGATGCCACCTA<br>CGGCAAGCTGACCCTGAAGTTCATCTGCACCACCGGCAAGCTGCCCGTGCCCT<br>GGCCCACCCTCGTGACCACCCTGACCTACGGCGTGCAGTGCTTCAGCCGCTAC<br>CCCGACCACATGAAGCAGCACGACTTCTTCAAGTCCGCCATGCCCGAAGGCTA<br>CGTCCAGGAGCGCACCATCTTCTTCAAGGACGACGGCAACTACAAGACCCGC<br>GCCGAGGTGAAGTTCGAGGGCGACACCCTGGTGAACCGCATCGAGCTGAAG<br>GGCATCGACTTCAAGGAGGACGGCAACATCCTGGGGCACAAGCTGGAGTAC<br>AACTACAACAGCCACAACGTCTATATCATGGCCGACAAGCAGAAGAACGGCA<br>TCAAGGTGAACTTCAAGATCCGCCACAACATCGAGGACGGCAGCGTGCAGCT<br>CGCCGACCACTACCAGCAGAACACCCCCATCGGCGACGGCCCCGTGCTGCTG<br>CCCGACAACCACTACCTGAGCACCCAGTCCGCCCTGAGCAAAGACCCCAACGA<br>GAAGCGCGATCACATGGTCCTGCTGGAGTTCGTGACCGCCGCCGGGATCACT<br>CTCGGCATGGACGAGCTGTACAAGTAAAGCGGCCGCGTCGAGTCTAGAGGG<br>CCCGTTTAAACCCGCTGATCAGCCTCGACTGTGCCTTCTAGTTGCCAGCCATCT<br>GTTGTTTGCCCCTCCCCCGTGCCTTCCTTGACCCTGGAAGGTGCCACTCCCACT<br>GCCCTTTCCTAATAAAATGAGGAAATTGCATCGCATTGTCTGAGTAGGTGTCA<br>TTCTATTCTGGGGGGTGGGGTGGGGCAGGACAGCAAGGGGGAGGATTGGG<br>AAGACAATAGCAGGCATGCTGGGGATGCGGTGGGCTCTATGGTACCAGCTTA<br>ACTCGTTAACTGACACATTGCAAATTAACATCCAGTAACGAAACGGCTTCAGT<br>CGTAATCGCCCATATAGTTGGCTACAGAATGTTGGATAGAGAACTTAAGTACG<br>CTAAGGCGGCGTATTTTCTTAATATTTAGGGGTATTGCCGCAGTCATTACAGA<br>TAACCGCCTATGCGGCCATGCCAGGATTATAGATAACTTTTTAACATTAGCCG<br>CAGAGGTGGGACTAGCACGTAATACCTGGAGTTTCTGATAACATGACATCTTA<br>ATTGCTGTCTTTTATAGATTTTTAAACTGCAAATACAAAATAGCAATCAGCCAA<br>TATAATAACTTATTATTCTCCATTTATGCCTGAAAGTCCTCCTCTTGTTGATGCC<br>GTGGAAATGAATGTAGAGGCAGATATCATTAGCTGTATTCTCCTTCCGAATGA<br>CATTTATCATATCCTTGTTATTCCAAAATAGATAGAAGATGAAAGGAATCTTCA<br>TGAAGATTTTGTATTCATGAAAAC |
| 6 | gRNA-G_HA +<br>cDNA +<br>GFP −<br>Stuffer | (SEQ ID NO: 39)<br>TTCTTTTTATAAAGCACTGCATCACAAACACTAAAATGAAGTGGGCAAATTAG<br>CTCTGCAGAAAACTATTTTCTAGGCTGATGTTTATAATGACCAATCATTACTGA<br>AGCAATGAGAAATGTGACAATTACAGAATATTGCTGCTATAGTATGTTGAAAA |

TABLE 10 -continued

CD40L Donor Sequences

| Donor Name | Donor Description | Donor Sequence |
|---|---|---|
| | | AATATGCATTTTGTAGTGAACATTTAGTAGAATAGCTCTGATTTCTGATACAGA<br>GATGCAACACAGGAGAAGCTTCCTTAGGTTTACATGTGCTCTTAATTACAGCA<br>GAACCGGTCTGACCTCTTCTCTTCCTCCCACAGATCGAGGACGAGAGAAACCT<br><u>GCACGAGGACTTCGTGTTCATGAAGACCATCCAGCGGTGCAACACCGGCGAG</u><br><u>AGAAGTCTGAGCCTGCTGAACTGCGAGGAAATCAAGAGCCAGTTCGAGGGCT</u><br><u>TCGTGAAGGACATCATGCTGAACAAAGAGGAAACGAAGAAAGAAAACTCCTT</u><br><u>CGAGATGCAGAAGGGCGACCAGAATCCTCAGATCGCCGCTCACGTGATCAGC</u><br><u>GAGGCCAGCAGCAAGACAACAAGCGTGCTGCAGTGGGCCGAGAAGGGCTAC</u><br><u>TACACCATGAGCAACAACCTGGTCACCCTGGAAAACGGCAAGCAGCTGACAG</u><br><u>TGAAGCGGCAGGGCCTGTACTACATCTACGCCCAAGTGACCTTCTGCAGCAAC</u><br><u>AGAGAGGCCAGCTCTCAGGCCCCTTTTATCGCCAGCCTGTGCCTGAAGTCCCC</u><br><u>TGGCAGATTCGAGCGGATTCTGCTGAGAGCCGCCAACACACACAGCAGCGCC</u><br><u>AAACCTTGTGGCCAGCAGTCTATTCACCTCGGCGGAGTGTTTGAGCTGCAGCC</u><br><u>TGGCCGCAAGCGTGTTCGTGAATGTGACAGACCCTAGCCAGGTGTCCCACGGC</u><br><u>ACCGGCTTTACATCTTTCGGACTGCTGAAGCTGTGAACAGTGTCACCTTGCAG</u><br>GCTGTGGTGGAGCTGACGCTGGGAGTCTTCATAATACAGCACAGCGGTTAAG<br>CCCACCCCCTGTTAACTGCCTATTTATAACCCTAGGATCCTCCTTATGGAGAAC<br>TATTTATTATACACTCCAAGGCATGTAGAACTGTAATAAGTGAATTACAGGTC<br>ACATGAAACCAAAACGGGCCCTGCTCCATAAGAGCTTATATATCTGAAGCAGC<br>AACCCCACTGATGCAGACATCCAGAGAGTCCTATGAAAAGACAAGGCCATTA<br>TGCACAGGTTGAATTCTGAGTAAACAGCAGATAACTTGCCAAGTTCAGTTTTG<br>TTTCTTTGCGTGCAGTGTCTTTCCATGGATAATGCATTTGATTTATCAGTGAAG<br>ATGCAGAAGGGAAATGGGGAGCCTCAGCTCACATTCAGTTATGGTTGACTCT<br>GGGTTCCTATGGCTTGTTGGAGGGGGCCAGGCTCTAGAACGTCTAACACAG<br>TGGAGAACCGAAACCCCCCCCCCCGCCACCCTCTCGGACAGTTATTCATTCTC<br>TTTCAATCTCTCTCTCCATCTCTCTCTTTCAGTCTCTCTCTCAACCTCTTTCT<br>TCCAATCTCTCTTTCTCAATCTCTCTGTTTCCCTTTGTCAGTCTCTTCCCTCCCCC<br>AGTCTCTCTTCTCAATCCCCCTTTCTAACACACACACACACACACACACACACACA<br>CACACACACACACACACACACACACAGAGTCAGGCCGTTGCTAGTCAGTTCTC<br>TTCTTTCCACCCTGTCCCTATCTCTACCACTATAGATGAGGGTGAGGAGTAGG<br>GAGTGCAGCCCTGAGCCTGCCCACTCCTCATTACGAAATGACTGTATTTAAAG<br>GAAATCTATTGTATCTACCTGCAGTCTCCATTGTTTCCAGAGTGAACTTGTAAT<br>TATCTTGTTATTTATTTTTGAATAATAAAGACCTCTTAACATTACGCGCTTAAC<br>ATTATCGTTGTTGTTTGAGTACCTAAAGCTCCCAGCCAGGTTGGGGAAAGAG<br>GAAGCATTTGGAGGGAATTTTCCCAACCTTTGTGATGTTTTCATAAACTTTGTT<br>CTCAAGCTACTTACATTACGCGTACTAGTTGGCTCCGGTGCCCGTCAGTGGGC<br>AGAGCGCACATCGCCCACAGTCCCCGAGAAGTTGGGGGGAGGGGTCGGCAA<br>TTGAACCGGTGCCTAGAGAAGGTGGCGCGGGGTAAACTGGGAAAGTGATGT<br>CGTGTACTGGCTCCGCCTTTTTCCCGAGGGTGGGGGAGAACCGTATATAAGT<br>GCAGTAGTCGCCGTGAACGTTCTTTTTCGCAACGGGTTTGCCGCCAGAACACA<br>GGTGTCGTGACGCGGATCGTACCCGGGTTAAGGGCGAATTCCAGCACACTGG<br>CGGCCGTTACTAGTGGATCCACCGGTCGCCACCATGGTGAGCAAGGGCGAGG<br>AGCTGTTCACCGGGGTGGTGCCCATCCTGGTCGAGCTGGACGGCGACGTAAA<br>CGGCCACAAGTTCAGCGTGTCCGGCGAGGGCGAGGGCGATGCCACCTACGG<br>CAAGCTGACCCTGAAGTTCATCTGCACCACCGGCAAGCTGCCCGTGCCCTGGC<br>CCACCCTCGTGACCACCCTGACCTACGGCGTGCAGTGCTTCAGCCGCTACCCC<br>GACCACATGAAGCAGCACGACTTCTTCAAGTCCGCCATGCCCGAAGGCTACGT<br>CCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGC<br>ATCGACTTCAAGGAGGACGGCAACATCCTGGGGCACAAGCTGGAGTACAACT<br>ACAACAGCCACAACGTCTATATCATGGCCGACAAGCAGAAGAACGGCATCAA<br>GGTGAACTTCAAGATCCGCCACAACATCGAGGACGGCAGCGTGCAGCTCGCC<br>GACCACTACCAGCAGAACACCCCATCGGCGACGGCCCCGTGCTGCTGCCCG<br>ACAACCACTACCTGAGCACCCAGTCCGCCCTGAGCAAAGACCCCAACGAGAA<br>GCGCGATCACATGGTCCTGCTGGAGTTCGTGACCGCCGCCGGGATCACTCTC<br>GGCATGGACGAGCTGTACAAGTAAAGCGGCCGCGTCGAGTCTAGAGGGCCC<br>GTTTAAACCCGCTGATCAGCCTCGACTGTGCCTTCTAGTTGCCAGCCATCTGTT<br>GTTTGCCCCTCCCCCGTGCCTTCCTTGACCCTGGAAGGTGCCACTCCCACTGCC<br>CTTTCCTAATAAAATGAGGAAATTGCATCGCATTGTCTGAGTAGGTGTCATTCT<br>ATTCTGGGGGGTGGGGTGGGGCAGGACAGCAAGGGGGAGGATTGGGAAGA<br>CAATAGCAGGCATGCTGGGGATGCGGTGGGCTCTATGGTACCAGCTTAACTC<br>GTTAACTGACACATTGCAAATTAACACCTGGAGTTTCTGATAACATGACATCTT<br>AATTGCTGTCTTTTATAGATTTTTAAACTGCAAATACAAAATAGCAATCAGCCA<br>ATATAATAACTTATTATTCTCCATTTATGCCTGAAAGTCCTCCTCTTGTTGATGC<br>CGTGGAAATGAATGTAGAGGCAGATATCATTAGCTGTATTCTCCTTCCGAATG<br>ACATTTATCATATCCTTGTTATTCCAAAATAGATAGAAGATGAAAGGAATCTTC<br>ATGAAGATTTTGTATTCATGAAAAC |
| 7 | gRNA-G_HA + cDNA - GFP + Stuffer | (SEQ ID NO: 40)<br>TTCTTTTTATAAAGCACTGCATCACAAACACTAAAATGAAGTGGGCAAATTAG<br>CTCTGCAGAAAACTATTTTCTAGGCTGATGTTTATAATGACCAATCATTACTGA<br>AGCAATGAGAAATGTGACAATTACAGAATATTGCTGCTATAGTATGTTGAAAA<br>AATATGCATTTGTAGTGAACATTTAGTAGAATAGCTCTGATTTCTTACTCTTA<br>ATTCATTACATATTGTGCGGTCGAATTCAGGGAGCCGATAATGCGGTTACAAT<br>AATTCCTATACTTAAATATACAAAGATTTAAAATTTCAAAAAATGGTTACCAGC |

TABLE 10 -continued

CD40L Donor Sequences

| Donor Name | Donor Description | Donor Sequence |
|---|---|---|
| | | ATCGTTAGTGCGTATACATCAAGAGGCACGTGCCCCGGAGACAGCAAGTAAG |
| | | CTCTTTAAACATGCTTTGACATACGATTTTTAATAAAACATGAGCATTTGAATA |
| | | AAAACGACTTCCTCATACTGTAAACATCACGCATGCACATTAGACAATAGATA |
| | | CAGAGATGCAACACAGGAGAAGCTTCCTTAGGTTTACATGTGCTCTTAATTAC |
| | | AGCAGAACCGGTCTGACCTCTTCTCTTCCTCCCACAGATCGAGGACGAGAGAA |
| | | ACCTGCACGAGGACTTCGTGTTCATGAAGACCATCCAGCGGTGCAACACCGG |
| | | CGAGAGAAGTCTGAGCCTGCTGAACTGCGAGGAAATCAAGAGCCAGTTCGA |
| | | GGGCTTCGTGAAGGACATCATGCTGAACAAAGAGGAAACGAAGAAAGAAAA |
| | | CTCCTTCGAGATGCAGAAGGGCGACCAGAATCCTCAGATCGCCGCTCACGTG |
| | | ATCAGCGAGGCCAGCAGCAAGACAACAAGCGTGCTGCAGTGGGCCGAGAAG |
| | | GGCTACTACACCATGAGCAACAACCTGGTCACCCTGGAAAACGGCAAGCAGC |
| | | TGACAGTGAAGCGGCAGGGCCTGTACTACATCTACGCCCAAGTGACCTTCTGC |
| | | AGCAACAGAGAGGCCAGCTCTCAGGCCCCTTTTATCGCCAGCCTGTGCCTGAA |
| | | GTCCCCTGGCAGATTCGAGCGGATTCTGCTGAGAGCCGCCAACACACACAGC |
| | | AGCGCCAAACCTTGTGGCCAGCAGTCTATTCACCTCGGCGGAGTGTTTGAGCT |
| | | GCAGCCTGGCGCAAGCGTGTTCGTGAATGTGACAGACCCTAGCCAGGTGTCC |
| | | CACGGCACCGGCTTTACATCTTTCGGACTGCTGAAGCTGTGAACAGTGTCACC |
| | | TTGCAGGCTGTGGTGGAGCTGACGCTGGGAGTCTTCATAATACAGCACAGCG |
| | | GTTAAGCCCACCCCCTGTTAACTGCCTATTTATAACCCTAGGATCCTCCTTATG |
| | | GAGAACTATTTATTATACACTCCAAGGCATGTAGAACTGTAATAAGTGAATTA |
| | | CAGGTCACATGAAACCAAAACGGGCCCTGCTCCATAAGAGCTTATATATCTGA |
| | | AGCAGCAACCCCACTGATGCAGACATCCAGAGAGTCCTATGAAAAGACAAGG |
| | | CCATTATGCACAGGTTGAATTCTGAGTAAACAGCAGATAACTTGCCAAGTTCA |
| | | GTTTTGTTTCTTTGCGTGCAGTGTCTTTCCATGGATAATGCATTTGATTTATCA |
| | | GTGAAGATGCAGAAGGGAAATGGGGAGCCTCAGCTCACATTCAGTTATGGTT |
| | | GACTCTGGGTTCCTATGGCCTTGTTGGAGGGGGCCAGGCTCTAGAACGTCTA |
| | | ACACAGTGGAGAACCGAAACCCCCCCCCCCGCCACCCTCTCGGACAGTTATT |
| | | CATTCTCTTTCAATCTCTCTCTCCATCTCTCTCTTTCAGTCTCTCTCTCTCAACC |
| | | TCTTTCTTCCAATCTCTCTTTCTCAATCTCTCTGTTTCCCTTTGTCAGTCTCTTCCC |
| | | TCCCCCAGTCTCTCTTCTCAATCCCCCTTTCTAACACACACACACACACACACAC |
| | | ACACACACACACACACACACACACACACAGAGTCAGGCCGTTGCTAGTCA |
| | | GTTCTCTTCTTTCCACCCTGTCCCTATCTCTACCACTATAGATGAGGGTGAGGA |
| | | GTAGGGAGTGCAGCCCTGAGCCTGCCCACTCCTCATTACGAAATGACTGTATT |
| | | TAAAGGAAATCTATTGTATCTACCTGCAGTCTCCATTGTTTCCAGAGTGAACTT |
| | | GTAATTATCTTGTTATTTATTTTTTGAATAATAAAGACCTCTTAACATTACGCGC |
| | | TTAACATTATCGTTGTTGTTTGAGTACCTAAAGCTCCCAGCCAGGTTGGGGAA |
| | | AGAGGAAGCATTTGGAGGGAATTTTCCCAACCTTTGTGATGTTTTCATAAACT |
| | | TTGTTCTCAAGCTACTTACATTACGCGTACTAGTTACCAGCTTAACTCGTTAAC |
| | | TGACACATTGCAAATTAACATCCAGTAACGAAACGGCTTCAGTCGTAATCGCC |
| | | CATATAGTTGGCTACAGAATGTTGGATAGAGAACTTAAGTACGCTAAGGCGG |
| | | CGTATTTTCTTAATATTTAGGGGTATTGCCGCAGTCATTACAGATAACCGCCTA |
| | | TGCGGCCATGCCAGGATTATAGATAACTTTTTAACATTAGCCGCAGAGGTGG |
| | | GACTAGCACGTAATACCTGGAGTTTCTGATAACATGACATCTTAATTGCTGTCT |
| | | TTTATAGATTTTTAAACTGCAAATACAAAATAGCAATCAGCCAATATAATAACT |
| | | TATTATTCTCCATTTATGCCTGAAAGTCCTCCTCTTGTTGATGCCGTGGAAATG |
| | | AATGTAGAGGCAGATATCATTAGCTGTATTCTCCTTCCGAATGACATTTATCAT |
| | | ATCCTTGTTATTCCAAAATAGATAGAAGATGAAAGGAATCTTCATGAAGATTT |
| | | TGTATTCATGAAAAC |
| 8 | gRNA-G_HA + cDNA - GFP - Stuffer | (SEQ ID NO: 41) TTCTTTTTATAAAGCACTGCATCACAAACACTAAAATGAAGTGGGCAAATTAG CTCTGCAGAAAACTATTTCTAGGCTGATGTTTATAATGACCAATCATTACTGA AGCAATGAGAAATGTGACAATTACAGAATATTGCTGCTATAGTATGTTGAAAA AATATGCATTTTGTAGTGAACATTTAGTAGAATAGCTCTGATTTCTGATACAGA GATGCAACACAGGAGAAGCTTCCTTAGGTTTACATGTGCTCTTAATTACAGCA GAACCGGTCTGACCTCTTCTCTTCCTCCCACAGATCGAGGACGAGAGAAACCT GCACGAGGACTTCGTGTTCATGAAGACCATCCAGCGGTGCAACACCGGCGAG AGAAGTCTGAGCCTGCTGAACTGCGAGGAAATCAAGAGCCAGTTCGAGGGCT TCGTGAAGGACATCATGCTGAACAAAGAGGAAACGAAGAAAGAAAACTCCTT CGAGATGCAGAAGGGCGACCAGAATCCTCAGATCGCCGCTCACGTGATCAGC GAGGCCAGCAGCAAGACAACAAGCGTGCTGCAGTGGGCCGAGAAGGGCTAC TACACCATGAGCAACAACCTGGTCACCCTGGAAAACGGCAAGCAGCTGACAG TGAAGCGGCAGGGCCTGTACTACATCTACGCCCAAGTGACCTTCTGCAGCAAC AGAGAGGCCAGCTCTCAGGCCCCTTTTATCGCCAGCCTGTGCCTGAAGTCCCC TGGCAGATTCGAGCGGATTCTGCTGAGAGCCGCCAACACACACAGCAGCGCC AAACCTTGTGGCCAGCAGTCTATTCACCTCGGCGGAGTGTTTGAGCTGCAGCC TGGCGCAAGCGTGTTCGTGAATGTGACAGACCCTAGCCAGGTGTCCCACGGC ACCGGCTTTACATCTTTCGGACTGCTGAAGCTGTGAACAGTGTCACCTTGCAG GCTGTGGTGGAGCTGACGCTGGGAGTCTTCATAATACAGCACAGCGGTTAAG CCCACCCCCTGTTAACTGCCTATTTATAACCCTAGGATCCTCCTTATGGAGAAC TATTTATTATACACTCCAAGGCATGTAGAACTGTAATAAGTGAATTACAGGTC ACATGAAACCAAAACGGGCCCTGCTCCATAAGAGCTTATATATCTGAAGCAGC AACCCCACTGATGCAGACATCCAGAGAGTCCTATGAAAAGACAAGGCCATTA TGCACAGGTTGAATTCTGAGTAAACAGCAGATAACTTGCCAAGTTCAGTTTTG TTTCTTTGCGTGCAGTGTCTTTCCATGGATAATGCATTTGATTTATCAGTGAAG |

TABLE 10 -continued

CD40L Donor Sequences

| Donor Name | Donor Description | Donor Sequence |
|---|---|---|
| | | ATGCAGAAGGGAAATGGGGAGCCTCAGCTCACATTCAGTTATGGTTGACTCT<br>GGGTTCCTATGGCCTTGTTGGAGGGGGCCAGGCTCTAGAACGTCTAACACAG<br>TGGAGAACCGAAACCCCCCCCCCCGCCACCCTCTCGGACAGTTATTCATTCTC<br>TTTCAATCTCTCTCTCCATCTCTCTCTTTCAGTCTCTCTCTCAACCTCTTTCT<br>TCCAATCTCTCTTTCTCAATCTCTCTGTTTCCCTTTGTCAGTCTCTTCCCTCCCCC<br>AGTCTCTCTTCTCAATCCCCCTTTCTAACACACACACACACACACACACACA<br>CACACACACACACACACACACACACAGAGTCAGGCCGTTGCTAGTCAGTTCTC<br>TTCTTTCCACCCTGTCCCTATCTCTACCACTATAGATGAGGGTGAGGAGTAGG<br>GAGTGCAGCCCTGAGCCTGCCCACTCCTCATTACGAAATGACTGTATTTAAAG<br>GAAATCTATTGTATCTACCTGCAGTCTCCATTGTTTCCAGAGTGAACTTGTAAT<br>TATCTTGTTATTTATTTTTTGAATAATAAAGACCTCTTAACATTACGCGCTTAAC<br>ATTATCGTTGTTGTTTGAGTACCTAAAGCTCCCAGCCAGGTTGGGGAAAGAG<br>GAAGCATTTGGAGGGAATTTTCCCAACCTTTGTGATGTTTTCATAAACTTTGTT<br>CTCAAGCTACTTACATTACGCGTACTAGTTACCAGCTTAACTCGTTAACTGACA<br>CATTGCAAATTAACACCTGGAGTTTCTGATAACATGACATCTTAATTGCTGTCT<br>TTTATAGATTTTTAAACTGCAAATACAAAATAGCAATCAGCCAATATAATAACT<br>TATTATTCTCCATTTATGCCTGAAAGTCCTCCTCTTGTTGATGCCGTGGAAATG<br>AATGTAGAGGCAGATATCATTAGCTGTATTCTCCTTCCGAATGACATTTATCAT<br>ATCCTTGTTATTCCAAAATAGATAGAAGATGAAAGGAATCTTCATGAAGATTT<br>TGTATTCATGAAAAC |
| 9 | gRNA-C_HA +<br>cDNA +<br>GFP +<br>Stuffer | (SEQ ID NO: 42)<br>GATACTTGAGTGTCCTCTCTTAGGATCTGGACCTAGAATTAATGTCATGAGAT<br>TTTTCTAACAGGATAAGGTGAGGTAGTGAGGGCTGAAGTCATCCACTGGGTT<br>ATCCAAATATTAGGTTTCACTGCTGACAAAAGAGGGGGCTTCTGGTCTGGTTG<br>GTTATTTGTGTTTGGCCTGATGTGCTCTGTCAATCAAATGTATGGACATAGGC<br>CTAGCTTCTAAAGGGGCAATAGTGACCTCAGTACTCTTAATTCATTACATATTG<br>TGCGGTCGAATTCAGGGAGCCGATAATGCGGTTACAATAATTCCTATACTTAA<br>ATATACAAAGATTTAAAATTTCAAAAAATGGTTACCAGCATCGTTAGTGCGTA<br>TAGCAAGTGAATTCTGTACATTTAATTATTCTAAAAGCTTCCTTAGGTTTACAT<br>GTGCTCTTAATTACAGCAGAACCGGTCTGACCTCTTCTCTTCCTCCCA<u>CAGATC</u><br><u>GAGGACGAGAGAAACCTGCACGAGGACTTCGTGTTCATGAAGACCATCCAGC</u><br><u>GGTGCAACACCGGCGAGAGAAGTCTGAGCCTGCTGAACTGCGAGGAAATCA</u><br><u>AGAGCCAGTTCGAGGGCTTCGTGAAGGACATCATGCTGAACAAAGAGGAAA</u><br><u>CGAAGAAAGAAAACTCCTTCGAGATGCAGAAGGGCGACCAGAATCCTCAGAT</u><br><u>CGCCGCTCACGTGATCAGCGAGGCCAGCAGCAAGACAACAAGCGTGCTGCAG</u><br><u>TGGGCCGAGAAGGGCTACTACACCATGAGCAACAACCTGGTCACCCTGGAAA</u><br><u>ACGGCAAGCAGCTGACAGTGAAGCGGCAGGGCCTGTACTACATCTACGCCCA</u><br><u>AGTGACCTTCTGCAGCAACAGAGAGGCCAGCTCTCAGGCCCCTTTTATCGCCA</u><br><u>GCCTGTGCCTGAAGTCCCCTGGCAGATTCGAGCGGATTCTGCTGAGAGCCGC</u><br><u>CAACACACACAGCAGCGCCAAACCTTGTGGCCAGCAGTCTATTCACCTCGGCG</u><br><u>GAGTGTTTGAGCTGCAGCCTGGCGCAAGCGTGTTCGTGAATGTGACAGACCC</u><br><u>TAGCCAGGTGTCCCACGGCACCGGCTTTACATCTTTCGGACTGCTGAAGCTGT</u><br><u>GAACAGTGTCACCTTGCAGGCTGTGGTGGAGCTGACGCTGGGAGTCTTCATA</u><br><u>AT</u>ACAGCACAGCGGTTAAGCCTCACCCCCTGTTAACTGCCTATTTATAACCCTAG<br>GATCCTCCTTATGGAGAACTATTTATTATACACTCCAAGGCATGTAGAACTGTA<br>ATAAGTGAATTACAGGTCACATGAAACCAAAACGGGCCCTGCTCCATAAGAG<br>CTTATATATCTGAAGCAGCAACCCCACTGATGCAGACATCCAGAGAGTCCTAT<br>GAAAAGACAAGGCCATTATGCACAGGTTGAATTCTGAGTAAACAGCAGATAA<br>CTTGCCAAGTTCAGTTTTGTTTCTTTGCGTGCAGTGTCTTTCCATGGATAATGC<br>ATTTGATTTATCAGTGAAGATGCAGAAGGGAAATGGGGAGCCTCAGCTCACA<br>TTCAGTTATGGTTGACTCTGGGTTCCTATGGCCTTGTTGGAGGGGGCCAGGCT<br>CTAGAACGTCTAACACAGTGGAGAACCGAAACCCCCCCCCCCGCCACCCTCT<br>CGGACAGTTATTCATTCTCTTTCAATCTCTCTCTCCATCTCTCTCTTTCAGTCT<br>CTCTCTCAACCTCTTTCTTCCAATCTCTCTTTCTCAATCTCTCTGTTTCCCTTTG<br>TCAGTCTCTTCCCTCCCCAGTCTCTCTTCTCAATCCCCCTTTCTAACACACACA<br>CACACACACACACACACACACACACACACACACACACACAGAGTCAGGC<br>CGTTGCTAGTCAGTTCTCTTCTTTCCACCCTGTCCCTATCTCTACCACTATAGAT<br>GAGGGTGAGGAGTAGGGAGTGCAGCCCTGAGCCTGCCCACTCCTCATTACGA<br>AATGACTGTATTTAAAGGAAATCTATTGTATCTACCTGCAGTCTCCATTGTTTC<br>CAGAGTGAACTTGTAATTATCTTGTTATTTATTTTTTGAATAATAAAGACCTCTT<br>AACATTACGCGCTTAACATTATCGTTGTTGTTTGAGTACCTAAAGCTCCCAGCC<br>AGGTTGGGGAAAGAGGAAGCATTTGGAGGGAATTTTCCCAACCTTTGTGATG<br>TTTTCATAAACTTTGTTCTCAAGCTACTTACATTACGCGTACTAGTTGGCTCCG<br>GTGCCCGTCAGTGGGCAGAGCGCACATCGCCCACAGTCCCCGAGAAGTTGGG<br>GGGAGGGGTCGGCAATTGAACCGGTGCCTAGAGAAGGTGGCGCGGGGTAA<br>ACTGGGAAAGTGATGTCGTGTACTGGCTCCGCCTTTTTCCCGAGGGTGGGGG<br>AGAACCGTATATAAGTGCAGTAGTCGCCGTGAACGTTCTTTTTCGCAACGGGT<br>TTGCCGCCAGAACACAGGTGTCGTGACGCGGATCGTACCCGGGTTAAGGGCG<br>AATTCCAGCACACTGGCGGCCGTTACTAGTGGATCCGGCTTACTAAAAGCCAGATCTG<br>TGAGCAAGGGCGAGGAGCTGTTCACCGGGGTGGTGCCCATCCTGGTCGAGCT<br>GGACGGCGACGTAAACGGCCACAAGTTCAGCGTGTCCGGCGAGGGCGAGGG<br>CGATGCCACCTACGGCAAGCTGACCCTGAAGTTCATCTGCACCACCGGCAAGC<br>TGCCCGTGCCCTGGCCCACCCTCGTGACCACCCTGACCTACGGCGTGCAGTGC<br>TTCAGCCGCTACCCCGACCACATGAAGCAGCACGACTTCTTCAAGTCCGCCAT |

TABLE 10 -continued

CD40L Donor Sequences

| Donor Name | Donor Description | Donor Sequence |
|---|---|---|
| | | GCCCGAAGGCTACGTCCAGGAGCGCACCATCTTCTTCAAGGACGACGGCAAC<br>TACAAGACCCGCGCCGAGGTGAAGTTCGAGGGCGACACCCTGGTGAACCGC<br>ATCGAGCTGAAGGGCATCGACTTCAAGGAGGACGGCAACATCCTGGGGCAC<br>AAGCTGGAGTACAACTACAACAGCCACAACGTCTATATCATGGCCGACAAGC<br>AGAAGAACGGCATCAAGGTGAACTTCAAGATCCGCCACAACATCGAGGACGG<br>CAGCGTGCAGCTCGCCGACCACTACCAGCAGAACACCCCCATCGGCGACGGC<br>CCCGTGCTGCTGCCCGACAACCACTACCTGAGCACCCAGTCCGCCCTGAGCAA<br>AGACCCCAACGAGAAGCGCGATCACATGGTCCTGCTGGAGTTCGTGACCGCC<br>GCCGGGATCACTCTCGGCATGGACGAGCTGTACAAGTAAAGCGGCCGCGTCG<br>AGTCTAGAGGGCCCGTTTAAACCCGCTGATCAGCCTCGACTGTGCCTTCTAGT<br>TGCCAGCCATCTGTTGTTTGCCCCTCCCCCGTGCCTTCCTTGACCCTGGAAGGT<br>GCCACTCCCACTGCCCTTTCCTAATAAAATGAGGAAATTGCATCGCATTGTCTG<br>AGTAGGTGTCATTCTATTCTGGGGGGTGGGGTGGGGCAGGACAGCAAGGGG<br>GAGGATTGGGAAGACAATAGCAGGCATGCTGGGGATGCGGTGGGCTCTATG<br>GTACCAGCTTCATCTGGATGATTGCACTTTATCAGGCATCAAGAGGCACGTGC<br>CCCGGAGACAGCAAGTAAGCTCTTTTAAACATGCTTTGACATACGATTTTTAAT<br>AAAACATGAGCATTTGAATAAAAACGACTTCCTCATACTGTAAACATCACGCA<br>TGCACATTAGACAATAATCCAGTAACGAAACGGCTTCAGTCGTAATCGCCCAT<br>ATAGTTGGCTACAGAATGTTGGATAGAGAACTTAAGTACGCTAAGGCGGCGT<br>ATTTTCTTAATATTTGGACTGATATTTACCGTACTATTTACATGTGCTCTTAATT<br>ACAGCAGAAGCTGCCAGCTAACTGAATCTTGTTTTGAATCTAAAAAATCTACT<br>CTTAAAGCAAGAAAATGGTATAAAATTAGTTGATAAT |
| 10 | gRNA-D_HA +<br>cDNA +<br>GFP +<br>Stuffer | (SEQ ID NO: 43)<br>AGATCTTTGATTAGTTTTCTGGCTGTTCCTAAAATTCTGGATGCAGGAACTGTG<br>GCTAGAAAGCATCTGGATGATTGCACTTTATCAGGGATACTTGAGTGTCCTCT<br>CTTAGGATCTGGACCTAGAATTAATGTCATGAGATTTTTCTAACAGGATAAGG<br>TGAGGTAGTGAGGGCTGAAGTCATTACTCTTAATTCATTACATATTGTGCGGT<br>CGAATTCAGGGAGCCGATAATGCGGTTACAATAATTCCTATACTTAAATATAC<br>AAAGATTTAAAATTTCAAAAAATGGTTACCAGCATCGTTAGTGCGTATACATC<br>AAGAGGCACGTGCCCCGGAGACAGCAAGTAAGCTCTTTAAACATGCTTTGAC<br>ATACGATTTTTAATAAAACATGAGCATTTGAATAAAAACGACTTCCTCATACTG<br>TAAACATCACGCATGCACATTAGACAATAATCCAGTAACGAAAGAATTCTGTA<br>CATTTAATTATTCTAAGACATTGGAAGCTTCCTTAGGTTTACATGTGCTCTTAA<br>TTACAGCAGAACCGGTCTGACCTCTTCTCTTCCTCCCACAGATCGAGGACGAG<br><u>AGAAACCTGCACGAGGACTTCGTGTTCATGAAGACCATCCAGCGGTGCAACA</u><br><u>CCGGCGAGAGAAGTCTGAGCCTGCTGAACTGCGAGGAAATCAAGAGCCAGT</u><br><u>TCGAGGGCTTCGTGAAGGACATCATGCTGAACAAAGAGGAAACGAAGAAAG</u><br><u>AAAACTCCTTCGAGATGCAGAAGGGCGACCAGAATCCTCAGATCGCCGCTCA</u><br><u>CGTGATCAGCGAGGCCAGCAGCAAGACAACAAGCGTGCTGCAGTGGGCCGA</u><br><u>GAAGGGCTACTACACCATGAGCAACAACCTGGTCACCCTGGAAAACGGCAAG</u><br><u>CAGCTGACAGTGAAGCGGCAGGGCCTGTACTACATCTACGCCCAAGTGACCT</u><br><u>TCTGCAGCAACAGAGAGGCCAGCTCTCAGGCCCCTTTTATCGCCAGCCTGTGC</u><br><u>CTGAAGTCCCCTGGCAGATTCGAGCGGATTCTGCTGAGAGCCGCCAACACAC</u><br><u>ACAGCAGCGCCAAACCTTGTGGCCAGCAGTCTATTCACCTCGGCGGAGTGTTT</u><br><u>GAGCTGCAGCCTGGCGCAAGCGTGTTCGTGAATGTGACAGACCCTAGCCAGG</u><br>TGTCCCACGGCACCGGCTTTACATCTTTCGGACTGCTGAAGCTGTGAACAGTG<br>TCACCTTGCAGGCTGTGGTGGAGCTGACGCTGGGAGTCTTCATAATACAGCA<br>CAGCGGTTAAGCCCACCCCCTGTTAACTGCCTATTTATAACCCTAGGATCCTCC<br>TTATGGAGAACTATTTATTATACACTCCAAGGCATGTAGAACTGTAATAAGTG<br>AATTACAGGTCACATGAAACCAAAACGGGCCCTGCTCCATAAGAGCTTATATA<br>TCTGAAGCAGCAACCCCACTGATGCAGACATCCAGAGAGTCCTATGAAAAGA<br>CAAGGCCATTATGCACAGGTTGAATTCTGAGTAAACAGCAGATAACTTGCCAA<br>GTTCAGTTTTGTTTCTTTGCGTGCAGTGTCTTTCCATGGATAATGCATTTGATTT<br>ATCAGTGAAGATGCAGAAGGGAAATGGGGAGCCTCAGCTCACATTCAGTTAT<br>GGTTGACTCTGGGTTCCTATGGCCTTGTTGGAGGGGGCCAGGCTCTAGAACG<br>TCTAACACAGTGGAGAACCGAAACCCCCCCCCCCCGCCACCCTCTCGGACAGT<br>TATTCATTCTCTTTCAATCTCTCTCTCCATCTCTCTCTTTCAGTCTCTCTCTC<br>AACCTCTTTCTTCCAATCTCTCTTTCTCAATCTCTCTGTTTCCCTTTGTCAGTCTC<br>TTCCCTCCCCAGTCTCTCTTCTCAATCCCCCTTTCTAACACACACACACACACA<br>CACACACACACACACACACACACACACACACACAGAGTCAGGCCGTTGCTA<br>GTCAGTTCTCTTCTTTCCACCCTGTCCCTATCTCTACCACTATAGATGAGGGTG<br>AGGAGTAGGGAGTGCAGCCCTGAGCCTGCCCACTCCTCATTACGAAATGACT<br>GTATTTAAAGGAAATCTATTGTATCTACCTGCAGTCTCCATTGTTTCCAGAGTG<br>AACTTGTAATTATCTTGTTATTTATTTTTTGAATAATAAAGACCTCTTAACATTA<br>CGCGCTTAACATTATCGTTGTTGTTTGAGTACCTAAAGCTCCCAGCCAGGTTG<br>GGGAAAGAGGAAGCATTTGGAGGGAATTTTCCCAACCTTTGTGATGTTTTCAT<br>AAACTTTGTTCTCAAGCTACTTACATTACGCGTACTAGTTGGCTCCGGTGCCCG<br>TCAGTGGGCAGAGCGCACATCGCCCACAGTCCCCGAGAAGTTGGGGGGAGG<br>GGTCGGCAATTGAACCGGTGCCTAGAGAAGGTGGCGCGGGGTAAACTGGGA<br>AAGTGATGTCGTGTACTGGCTCCGCCTTTTTCCCGAGGGTGGGGGAGAACCG<br>TATATAAGTGCAGTAGTCGCCGTGAACGTTCTTTTTCGCAACGGGTTTGCCGC<br>CAGAACACAGGTGTCGTGACGCGGATCGTACCCGGGTTAAGGGCGAATTCCA<br>GCACACTGGCGGCCGTTACTAGTGGATCCACCGGTCGCCACCATGGTGAGCA<br>AGGGCGAGGAGCTGTTCACCGGGGTGGTGCCCATCCTGGTCGAGCTGGACG |

TABLE 10 -continued

CD40L Donor Sequences

| Donor Name | Donor Description | Donor Sequence |
|---|---|---|
|  |  | GCGACGTAAACGGCCACAAGTTCAGCGTGTCCGGCGAGGGCGAGGGCGATG<br>CCACCTACGGCAAGCTGACCCTGAAGTTCATCTGCACCACCGGCAAGCTGCCC<br>GTGCCCTGGCCCACCCTCGTGACCACCCTGACCTACGGCGTGCAGTGCTTCAG<br>CCGCTACCCCGACCACATGAAGCAGCACGACTTCTTCAAGTCCGCCATGCCCG<br>AAGGCTACGTCCAGGAGCGCACCATCTTCTTCAAGGACGACGGCAACTACAA<br>GACCCGCGCCGAGGTGAAGTTCGAGGGCGACACCCTGGTGAACCGCATCGA<br>GCTGAAGGGCATCGACTTCAAGGAGGACGGCAACATCCTGGGGCACAAGCT<br>GGAGTACAACTACAACAGCCACAACGTCTATATCATGGCCGACAAGCAGAAG<br>AACGGCATCAAGGTGAACTTCAAGATCCGCCACAACATCGAGGACGGCAGCG<br>TGCAGCTCGCCGACCACTACCAGCAGAACACCCCCATCGGCGACGGCCCCGT<br>GCTGCTGCCCGACAACCACTACCTGAGCACCCAGTCCGCCCTGAGCAAAGACC<br>CCAACGAGAAGCGCGATCACATGGTCCTGCTGGAGTTCGTGACCGCCGCCGG<br>GATCACTCTCGGCATGGACGAGCTGTACAAGTAAAGCGGCCGCGTCGAGTCT<br>AGAGGGCCCGTTTAAACCCGCTGATCAGCCTCGACTGTGCCTTCTAGTTGCCA<br>GCCATCTGTTGTTTGCCCCTCCCCCGTGCCTTCCTTGACCCTGGAAGGTGCCAC<br>TCCCACTGCCCTTTCCTAATAAAATGAGGAAATTGCATCGCATTGTCTGAGTA<br>GGTGTCATTCTATTCTGGGGGGTGGGGTGGGGCAGGACAGCAAGGGGGAG<br>GATTGGGAAGACAATAGCAGGCATGCTGGGGATGCGGTGGGCTCTATGGTA<br>CCAGCTTTAAATACCAATCATAGATGTAAAGGAGAAAGCGGCTTCAGTCGTAA<br>TCGCCCATATAGTTGGCTACAGAATGTTGGATAGAGAACTTAAGTACGCTAAG<br>GCGGCGTATTTTCTTAATATTTAGGGGTATTGCCGCAGTCATTACAGATAACC<br>GCCTATGCGGCCATGCCAGGATTATAGATAACTTTTTAACATTAGCCGCAGAG<br>GTGGCCACTGGGTTATCCAAATATTAGGTTTCACTGCTGACAAAAGAGGGGG<br>CTTCTGGTCTGGTTGGTTATTTGTGTTTGGCCTGATGTGCTCTGTCAATCAAAT<br>GTATGGACATAGGCCTAGCTTCTAAAGGGGCAATAGTGACCTCAGTGGACTG<br>ATATTTACCGTACTATTTACATGTGCTCTTAATTACAGCAGAAGCTGCCAGCTA<br>ACTGAATCTTGTTTTGAATCTAAAAAATCTACTCTTAAAGCAAGAAAATGGTAT<br>AAAATTAGTTGATAATGCAAGTAGATCT |
| 11 | gRNA-D_HA +<br>cDNA +<br>GFP −<br>Stuffer | (SEQ ID NO: 44)<br>AGATCTTTGATTAGTTTTCTGGCTGTTCCTAAAATTCTGGATGCAGGAACTGTG<br>GCTAGAAAGCATCTGGATGATTGCACTTTATCAGGGATACTTGAGTGTCCTCT<br>CTTAGGATCTGGACCTAGAATTAATGTCATGAGATTTTTCTAACAGGATAAGG<br>TGAGGTAGTGAGGGCTGAAGTCATGAATTCTGTACATTTAATTATTCTAAGAC<br>ATTGGAAGCTTCCTTAGGTTTACATGTGCTCTTAATTACAGCAGAACCGGTCT<br>GACCTCTTCTCTTCCTCCCACAGATCGAGGACGAGAGAAACCTGCACGAGGAC<br>TTCGTGTTCATGAAGACCATCCAGCGGTGCAACACCGGCGAGAGAAGTCTGA<br>GCCTGCTGAACTGCGAGGAAATCAAGAGCCAGTTCGAGGGCTTCGTGAAGG<br>ACATCATGCTGAACAAAGAGGAAACGAAGAAAGAAAACTCCTTCGAGATGCA<br>GAAGGGCGACCAGAATCCTCAGATCGCCGCTCACGTGATCAGCGAGGCCAGC<br>AGCAAGACAACAAGCGTGCTGCAGTGGGCCGAGAAGGGCTACTACACCATG<br>AGCAACAACCTGGTCACCCTGGAAAACGGCAAGCAGCTGACAGTGAAGCGG<br>CAGGGCCTGTACTACATCTACGCCCAAGTGACCTTCTGCAGCAACAGAGAGG<br>CCAGCTCTCAGGCCCCTTTTATCGCCAGCCTGTGCCTGAAGTCCCCTGGCAGA<br>TTCGAGCGGATTCTGCTGAGAGCCGCCAACACACAGCAGCGCCAAACCTT<br>GTGGCCAGCAGTCTATTCACCTCGGCGGAGTGTTTGAGCTGCAGCCTGGCGC<br>AAGCGTGTTCGTGAATGTGACAGACCCTAGCCAGGTGTCCCACGGCACCGGC<br>TTTACATCTTTCGGACTGCTGAAGCTGTGAACAGTGTCACCTTGCAGGCTGTG<br>GTGGAGCTGACGCTGGGAGTCTTCATAATACAGCACAGCGGTTAAGCCCACC<br>CCCTGTTAACTGCCTATTTATAACCCTAGGATCCTCCTTATGGAGAACTATTTA<br>TTATACACTCCAAGGCATGTAGAACTGTAATAAGTGAATTACAGGTCACATGA<br>AACCAAAACGGGCCCTGCTCCATAAGAGCTTATATATCTGAAGCAGCAACCCC<br>ACTGATGCAGACATCCAGAGAGTCCTATGAAAAGACAAGGCCATTATGCACA<br>GGTTGAATTCTGAGTAAACAGCAGATAACTTGCCAAGTTCAGTTTTGTTTCTTT<br>GCGTGCAGTGTCTTTCCATGGATAATGCATTTGATTTATCAGTGAAGATGCAG<br>AAGGGAAATGGGGAGCCTCAGCTCACATTCAGTTATGGTTGACTCTGGGTTC<br>CTATGGCCTTGTTGGAGGGGGCCAGGCTCTAGAACGTCTAACACAGTGGAGA<br>ACCGAAACCCCCCCCCCCGCCACCCTCTCGGACAGTTATTCATTCTCTTTCAA<br>TCTCTCTCTCTCCATCTCTCTCTTTCAGTCTCTCTCTCAACCTCTTTCTTCCAAT<br>CTCTCTTTCTCAATCTCTCTGTTTCCCTTTGTCAGTCTCTTCCCTCCCCAGTCTC<br>TCTTCTCAATCCCCCTTTCTAACACACACACACACACACACACACACACACACA<br>CACACACACACACACACAGAGTCAGGCCGTTGCTAGTCAGTTCTCTTCTTTC<br>CACCCTGTCCCTATCTCTACCACTATAGATGAGGGTGAGGAGTAGGGAGTGC<br>AGCCCTGAGCCTGCCCACTCCTCATTACGAAATGACTGTATTTAAAGGAAATC<br>TATTGTATCTACCTGCAGTCTCCATTGTTTCCAGAGTGAACTTGTAATTATCTTG<br>TTATTTATTTTTTGAATAATAAAGACCTCTTAACATTACGCGCTTAACATTATCG<br>TTGTTGTTTGAGTACCTAAAGCTCCCAGCCAGGTTGGGGAAAGAGGAAGCAT<br>TTGGAGGGAATTTTCCCAACCTTTGTGATGTTTTCATAAACTTTGTTCTCAAGC<br>TACTTACATTACGCGTACTAGTTGGCTCCGGTGCCCGTCAGTGGGCAGAGCGC<br>ACATCGCCCACAGTCCCCGAGAAGTTGGGGGGAGGGGTCGGCAATTGAACC<br>GGTGCCTAGAGAAGGTGGCGCGGGGTAAACTGGGAAAGTGATGTCGTGTAC<br>TGGCTCCGCCTTTTTCCCGAGGGTGGGGGAGAACCGTATATAAGTGCAGTAG<br>TCGCCGTGAACGTTCTTTTTCGCAACGGGTTTGCCGCCAGAACACAGGTGTCG<br>TGACGCGGATCGTACCCGGGTTAAGGGCGAATTCCAGCACACTGGCGGCCGT<br>TACTAGTGGATCCACCGGTCGCCACCATGGTGAGCAAGGGCGAGGAGCTGTT |

TABLE 10 -continued

CD40L Donor Sequences

| Donor Name | Donor Description | Donor Sequence |
|---|---|---|
| | | CACCGGGGTGGTGCCCATCCTGGTCGAGCTGGACGGCGACGTAAACGGCCAC<br>AAGTTCAGCGTGTCCGGCGAGGGCGAGGGCGATGCCACCTACGGCAAGCTG<br>ACCCTGAAGTTCATCTGCACCACCGGCAAGCTGCCCGTGCCCTGGCCCACCCT<br>CGTGACCACCCTGACCTACGGCGTGCAGTGCTTCAGCCGCTACCCCGACCACA<br>TGAAGCAGCACGACTTCTTCAAGTCCGCCATGCCCGAAGGCTACGTCCAGGA<br>GCGCACCATCTTCTTCAAGGACGACGGCAACTACAAGACCCGCGCCGAGGTG<br>AAGTTCGAGGGCGACACCCTGGTGAACCGCATCGAGCTGAAGGGCATCGACT<br>TCAAGGAGGACGGCAACATCCTGGGGCACAAGCTGGAGTACAACTACAACA<br>GCCACAACGTCTATATCATGGCCGACAAGCAGAAGAACGGCATCAAGGTGAA<br>CTTCAAGATCCGCCACAACATCGAGGACGGCAGCGTGCAGCTCGCCGACCAC<br>TACCAGCAGAACACCCCCATCGGCGACGGCCCCGTGCTGCTGCCCGACAACC<br>ACTACCTGAGCACCCAGTCCGCCCTGAGCAAAGACCCCAACGAGAAGCGCGA<br>TCACATGGTCCTGCTGGAGTTCGTGACCGCCGCCGGGATCACTCTCGGCATGG<br>ACGAGCTGTACAAGTAAAGCGGCCGCGTCGAGTCTAGAGGGCCCGTTTAAAC<br>CCGCTGATCAGCCTCGACTGTGCCTTCTAGTTGCCAGCCATCTGTTGTTTGCCC<br>CTCCCCCGTGCCTTCCTTGACCCTGGAAGGTGCCACTCCCACTGCCCTTTCCTA<br>ATAAAATGAGGAAATTGCATCGCATTGTCTGAGTAGGTGTCATTCTATTCTGG<br>GGGGTGGGGTGGGGCAGGACAGCAAGGGGGAGGATTGGGAAGACAATAGC<br>AGGCATGCTGGGGATGCGGTGGGCTCTATGGTACCAGCTTTAAATACCAATC<br>ATAGATGTAAAGGAGAAAGCCACTGGGTTATCCAAATATTAGGTTTCACTGCT<br>GACAAAAGAGGGGGCTTCTGGTCTGGTTGGTTATTTGTGTTTGGCCTGATGT<br>GCTCTGTCAATCAAATGTATGGACATAGGCCTAGCTTCTAAAGGGGCAATAGT<br>GACCTCAGTGGACTGATATTTACCGTACTATTTACATGTGCTCTTAATTACAGC<br>AGAAGCTGCCAGCTAACTGAATCTTGTTTTGAATCTAAAAAATCTACTCTTAAA<br>GCAAGAAAATGGTATAAAATTAGTTGATAATGCAAGTAGATCT |
| 12 | gRNA-D_HA + cDNA - GFP + Stuffer | (SEQ ID NO: 45)<br>AGATCTTTGATTAGTTTTCTGGCTGTTCCTAAAATTCTGGATGCAGGAACTGTG<br>GCTAGAAAGCATCTGGATGATTGCACTTTATCAGGGATACTTGAGTGTCCTCT<br>CTTAGGATCTGGACCTAGAATTAATGTCATGAGATTTTTCTAACAGGATAAGG<br>TGAGGTAGTGAGGGCTGAAGTCATTACTCTTAATTCATTACATATTGTGCGGT<br>CGAATTCAGGGAGCCGATAATGCGGTTACAATAATTCCTATACTTAAATATAC<br>AAAGATTTAAAATTTCAAAAAATGGTTACCAGCATCGTTAGTGCGTATACATC<br>AAGAGGCACGTGCCCCGGAGACAGCAAGTAAGCTCTTTAAACATGCTTTGAC<br>ATACGATTTTTAATAAAACATGAGCATTTGAATAAAAACGACTTCCTCATACTG<br>TAAACATCACGCATGCACATTAGACAATAATCCAGTAACGAAAGAATTCTGTA<br>CATTTAATTATTCTAAGACATTGGAAGCTTCCTTAGGTTTACATGTGCTCTTAA<br>TTACAGCAGAACCGGTCTGACCTCTTCTCTTCCTCCCA<u>CAGATCGAGGACGAG</u><br><u>AGAAACCTGCACGAGGACTTCGTGTTCATGAAGACCATCCAGCGGTGCAACA</u><br><u>CCGGCGAGAGAAGTCTGAGCCTGCTGAACTGCGAGGAAATCAAGAGCCAGT</u><br><u>TCGAGGGCTTCGTGAAGGACATCATGCTGAACAAAGAGGAAACGAAGAAAG</u><br><u>AAAAACTCCTTCGAGATGCAGAAGGGCGACCAGAATCCTCAGATCGCCGCTCA</u><br><u>CGTGATCAGCGAGGCCAGCAGCAAGACAACAAGCGTGCTGCAGTGGGCCGA</u><br><u>GAAGGGCTACTACACCATGAGCAACAACCTGGTCACCCTGGAAAACGGCAAG</u><br><u>CAGCTGACAGTGAAGCGGCAGGGCCTGTACTACATCTACGCCCAAGTGACCT</u><br><u>TCTGCAGCAACAGAGAGGCCAGCTCTCAGGCCCCTTTTATCGCCAGCCTGTGC</u><br><u>CTGAAGTCCCCTGGCAGATTCGAGCGGATTCTGCTGAGAGCCGCCAACACAC</u><br><u>ACAGCAGCGCCAAACCTTGTGGCCAGCAGTCTATTCACCTCGGCGGAGTGTTT</u><br><u>GAGCTGCAGCCTGGCGCAAGCGTGTTCGTGAATGTGACAGACCCTAGCCAGG</u><br><u>TGTCCCACGGCACCGGCTTTACATCTTTCGGACTGCTGAAGCTGTGAACAGTG</u><br>TCACCTTGCAGGCTGTGGTGGAGCTGACGCTGGGAGTCTTCATAATACAGCA<br>CAGCGGTTAAGCCCACCCCCTGTTAACTGCCTATTTATAACCCTAGGATCCTCC<br>TTATGGAGAACTATTTATTATACACTCCAAGGCATGTAGAACTGTAATAAGTG<br>AATTACAGGTCACATGAAACCAAAACGGGCCCTGCTCCATAAGAGCTTATATA<br>TCTGAAGCAGCAACCCCACTGATGCAGACATCCAGAGAGTCCTATGAAAAGA<br>CAAGGCCATTATGCACAGGTTGAATTCTGAGTAAACAGCAGATAACTTGCCAA<br>GTTCAGTTTTGTTTCTTTGCGTGCAGTGTCTTTCCATGGATAATGCATTTGATTT<br>ATCAGTGAAGATGCAGAAGGGAAATGGGGAGCCTCAGCTCACATTCAGTTAT<br>GGTTGACTCTGGGTTCCTATGGCCTTGTTGGAGGGGGCCAGGCTCTAGAACG<br>TCTAACACAGTGGAGAACCGAAACCCCCCCCCCCCGCCACCCTCTCGGACAGT<br>TATTCATTCTCTTTCAATCTCTCTCTCCATCTCTCTCTTTCAGTCTCTCTCTCTC<br>AACCTCTTTCTTCCAATCTCTCTTTCTCAATCTCTGTTTCCCTTTGTCAGTCTC<br>TTCCCTCCCCCAGTCTCTCTTCTCAATCCCCTTTCTAACACACACACACACACA<br>CACACACACACACACACACACACACACACAGAGTCAGGCCGTTGCTA<br>GTCAGTTCTCTTCTTTCCACCCTGTCCCTATCTCTACCACTATAGATGAGGGTG<br>AGGAGTAGGGAGTGCAGCCCTGAGCCTGCCCACTCCTCATTACGAAATGACT<br>GTATTTAAAGGAAATCTATTGTATCTACCTGCAGTCTCCATTGTTTCCAGAGTG<br>AACTTGTAATTATCTTGTTATTTATTTTTTGAATAATAAAGACCTCTTAACATTA<br>CGCGCTTAACATTATCGTTGTTGTTTGAGTACCTAAAGCTCCCAGCCAGGTTG<br>GGGAAAGAGGAAGCATTTGGAGGGAATTTTCCCAACCTTTGTGATGTTTTCAT<br>AAACTTTGTTCTCAAGCTACTTACATTACGCGTACTAGTAAATACCAATCATAG<br>ATGTAAAGGAGAAAGCGGCTTCAGTCGTAATCGCCCATATAGTTGGCTACAG<br>AATGTTGGATAGAGAACTTAAGTACGCTAAGGCGGCGTATTTTCTTAATATTT<br>AGGGGTATTGCCGCAGTCATTACAGATAACCGCCTATGCGGCCATGCCAGGA<br>TTATAGATAACTTTTTAACATTAGCCGCAGAGGTGGCCACTGGGTTATCCAAA |

TABLE 10 -continued

CD40L Donor Sequences

| Donor Name | Donor Description | Donor Sequence |
|---|---|---|
| | | TATTAGGTTTCACTGCTGACAAAAGAGGGGGCTTCTGGTCTGGTTGGTTATTT<br>GTGTTTGGCCTGATGTGCTCTGTCAATCAAATGTATGGACATAGGCCTAGCTT<br>CTAAAGGGGCAATAGTGACCTCAGTGGACTGATATTTACCGTACTATTTACAT<br>GTGCTCTTAATTACAGCAGAAGCTGCCAGCTAACTGAATCTTGTTTTGAATCTA<br>AAAAATCTACTCTTAAAGCAAGAAAATGGTATAAAATTAGTTGATAATGCAAG<br>TAGATCT |
| 13 | gRNA-D_HA +<br>cDNA −<br>GFP −<br>Stuffer | (SEQ ID NO: 46)<br>AGATCTTTGATTAGTTTTCTGGCTGTTCCTAAAATTCTGGATGCAGGAACTGTG<br>GCTAGAAAGCATCTGGATGATTGCACTTTATCAGGGATACTTGAGTGTCCTCT<br>CTTAGGATCTGGACCTAGAATTAATGTCATGAGATTTTTCTAACAGGATAAGG<br>TGAGGTAGTGAGGGCTGAAGTCATGAATTCTGTACATTTAATTATTCTAAGAC<br>ATTGGAAGCTTCCTTAGGTTTACATGTGCTCTTAATTACAGCAGAACCGGTCT<br>GACCTCTTCTCTTCCTCCCACAGATCGAGGACGAGAGAAACCTGCACGAGGAC<br>TTCGTGTTCATGAAGACCATCCAGCGGTGCAACACCGGCGAGAGAAGTCTGA<br>GCCTGCTGAACTGCGAGGAAATCAAGAGCCAGTTCGAGGGCTTCGTGAAGG<br>ACATCATGCTGAACAAAGAGGAAACGAAGAAAGAAAACTCCTTCGAGATGCA<br>GAAGGGCGACCAGAATCCTCAGATCGCCGCTCACGTGATCAGCGAGGCCAGC<br>AGCAAGACAACAAGCGTGCTGCAGTGGGCCGAGAAGGGCTACTACACCATG<br>AGCAACAACCTGGTCACCCTGGAAAACGGCAAGCAGCTGACAGTGAAGCGG<br>CAGGGCCTGTACTACATCTACGCCCAAGTGACCTTCTGCAGCAACAGAGAGG<br>CCAGCTCTCAGGCCCTTTTATCGCCAGCCTGTGCCTGAAGTCCCCTGGCAGA<br>TTCGAGCGGATTCTGCTGAGAGCCGCCAACACACACAGCAGCGCCAAACCTT<br>GTGGCCAGCAGTCTATTCACCTCGGCGGAGTGTTTGAGCTGCAGCCTGGCGC<br>AAGCGTGTTCGTGAATGTGACAGACCCTAGCCAGGTGTCCCACGGCACCGGC<br>TTTACATCTTTCGGACTGCTGAAGCTGTGAACAGTGTCACCTTGCAGGCTGTG<br>GTGGAGCTGACGCTGGGAGTCTTCATAATACAGCACAGCGGTTAAGCCCACC<br>CCCTGTTAACTGCCTATTTATAACCCTAGGATCCTCCTTATGGAGAACTATTTA<br>TTATACACTCCAAGGCATGTAGAACTGTAATAAGTGAATTACAGGTCACATGA<br>AACCAAAACGGGCCCTGCTCCATAAGAGCTTATATATCTGAAGCAGCAACCCC<br>ACTGATGCAGACATCCAGAGAGTCCTATGAAAAGACAAGGCCATTATGCACA<br>GGTTGAATTCTGAGTAAACAGCAGATAACTTGCCAAGTTCAGTTTTGTTTCTTT<br>GCGTGCAGTGTCTTTCCATGGATAATGCATTTGATTTATCAGTGAAGATGCAG<br>AAGGGAAATGGGGAGCCTCAGCTCACATTCAGTTATGGTTGACTCTGGGTTC<br>CTATGGCCTTGTTGGAGGGGGCCAGGCTCTAGAACGTCTAACACAGTGGAGA<br>ACCGAAACCCCCCCCCCCGCCACCCTCTCGGACAGTTATTCATTCTCTTTCAA<br>TCTCTCTCTCTCCATCTCTCTTTCAGTCTCTCTCTCTCAACCTCTTTCTTCCAAT<br>CTCTCTTTCTCAATCTCTCTGTTTCCCTTTGTCAGTCTCTTCCCTCCCCCAGTCTC<br>TCTTCTCAATCCCCCTTTCTAACACACACACACACACACACACACACACACACA<br>CACACACACACACACACAGAGTCAGGCCGTTGCTAGTCAGTTCTCTTCTTTC<br>CACCCTGTCCCTATCTCTACCACTATAGATGAGGGTGAGGAGTAGGGAGTGC<br>AGCCCTGAGCCTGCCCACTCCTCATTACGAAATGACTGTATTTAAAGGAAATC<br>TATTGTATCTACCTGCAGTCTCCATTGTTTCCAGAGTGAACTTGTAATTATCTTG<br>TTATTTATTTTTTGAATAATAAAGACCTCTTAACATTACGCGCTTAACATTATCG<br>TTGTTGTTTGAGTACCTAAAGCTCCCAGCCAGGTTGGGGAAAGAGGAAGCAT<br>TTGGAGGGAATTTTCCCAACCTTTGTGATGTTTTCATAAACTTTGTTCTCAAGC<br>TACTTACATTACGCGTACTAGTAAATACCAATCATAGATGTAAAGGAGAAAGC<br>CACTGGGTTATCCAAATATTAGGTTTCACTGCTGACAAAAGAGGGGGCTTCTG<br>GTCTGGTTGGTTATTTGTGTTTGGCCTGATGTGCTCTGTCAATCAAATGTATGG<br>ACATAGGCCTAGCTTCTAAAGGGGCAATAGTGACCTCAGTGGACTGATATTTA<br>CCGTACTATTTACATGTGCTCTTAATTACAGCAGAAGCTGCCAGCTAACTGAAT<br>CTTGTTTTGAATCTAAAAAATCTACTCTTAAAGCAAGAAAATGGTATAAAATTA<br>GTTGATAATGCAAGTAGATCT |

Figure 3D:
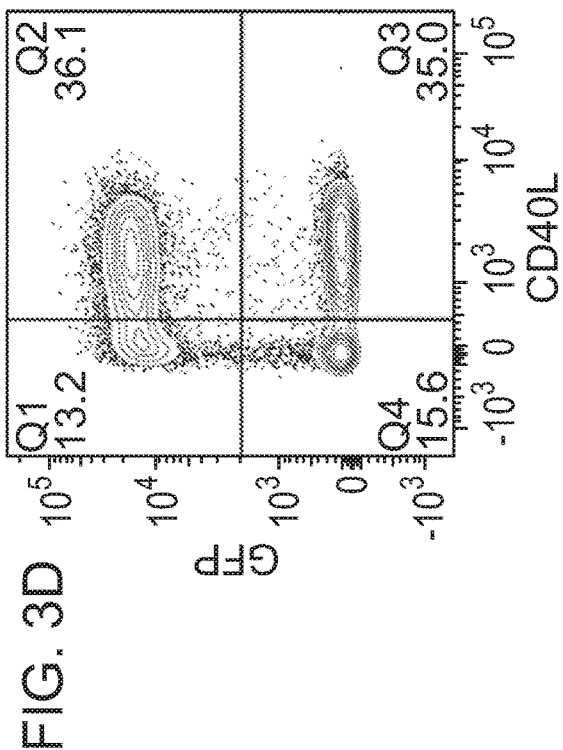
Figure 3E:
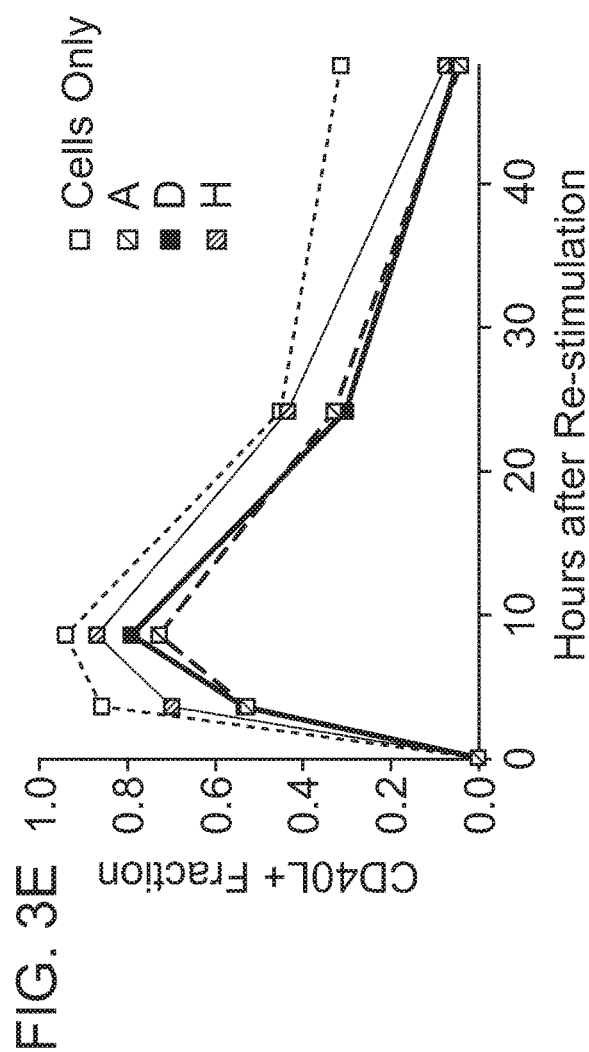
Figure 4D:
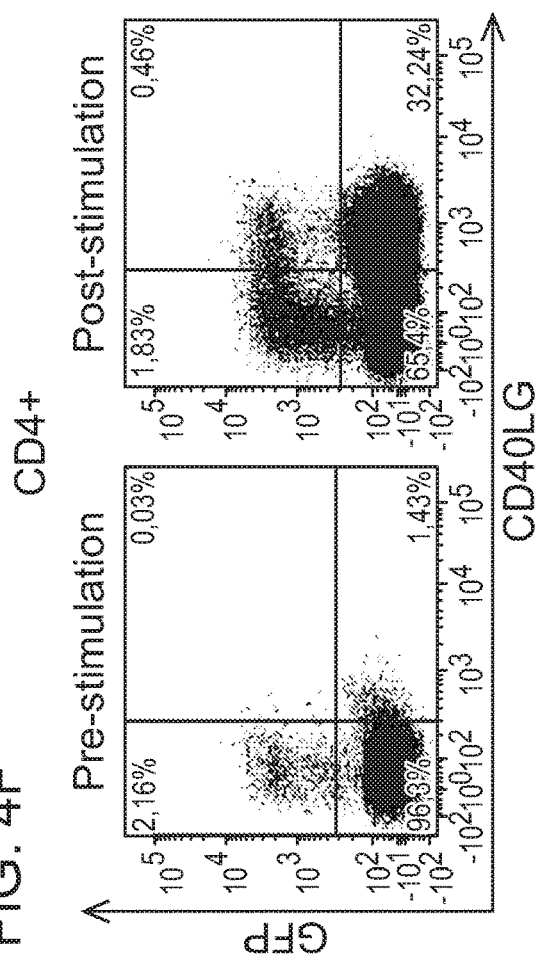
Figure 4F:
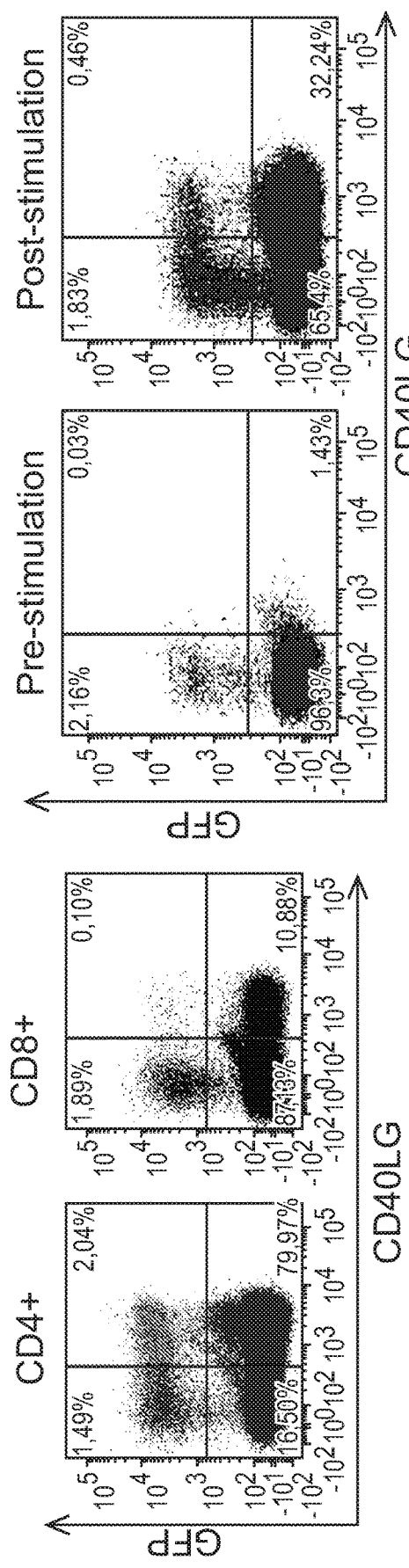
Figure 4E:
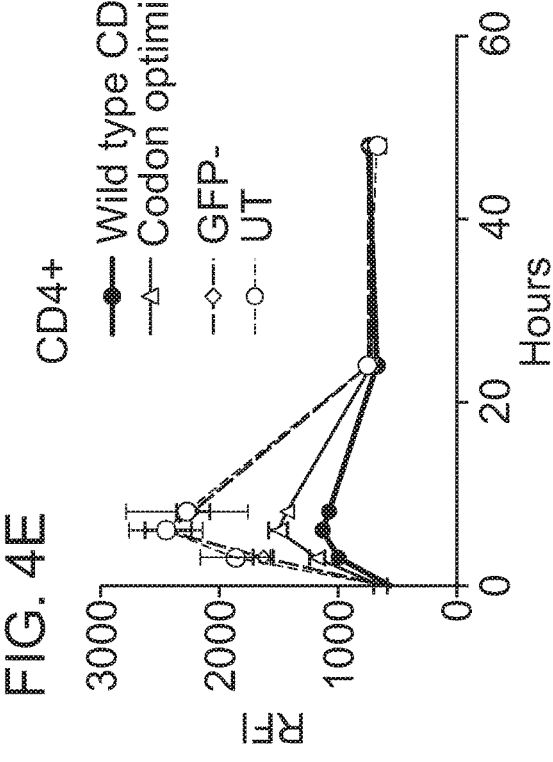

Targeted integration and CD40L expression after editing with three RNP complexes containing exemplary gRNAs (gRNAs A, D, and G) was determined. The location of CD40LG, intron 1, that is targeted by these gRNAs is depicted in FIG. 3A. The experimental procedure is outlined in FIG. 3B. The rate of targeted integration (presented as the percentage of GFP+ cells) following treatment with RNP complexes and the AAV6 donor template is provided in FIG. 3C. The level of targeted integration obtained with gRNA A was comparable to the level of targeted integration obtained with gRNA D, and was higher than that obtained with gRNA G. FIG. 3D depicts CD40L expression in the GFP-positive cell population, determined by FACS analysis. FIG. 3E depicts the CD40L+ cell fraction at various time points following re-stimulation. Integration of the corrective repair template in the 3' end of intron 1 using gRNA G did not change CD40L expression, relative to integration of the corrective repair template in the middle of intron 1 using gRNA A or gRNA D To test whether gene editing of CD40L preserves physiologic regulation, the kinetics of CD40L expression were determined. As shown in FIG. 4B, following RNP electroporation and donor DNA addition, the kinetics of CD40L expression were monitored over a timeline of 48 hours starting on Day 15, after induction of CD40L expression with PMA/Ionomycin. FIGS. 4C and 4E depict the kinetics of CD40L expression in edited CD4+ T cells following PMA/Ionomycin treatment. CD40L expression in activated CD4+ and CD8+ cells is shown in FIGS. 4D and 4F. This data indicates that normal CD40L expression was restored upon gene editing.

Figure 5A:
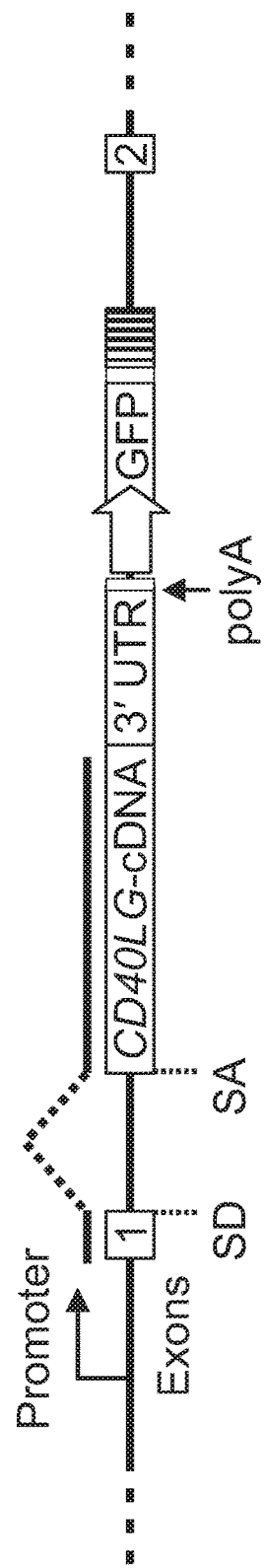
FIGS. 5A-5E depict that edited CD40L preserves physiologic regulation. Specifically.
Figure 5B:
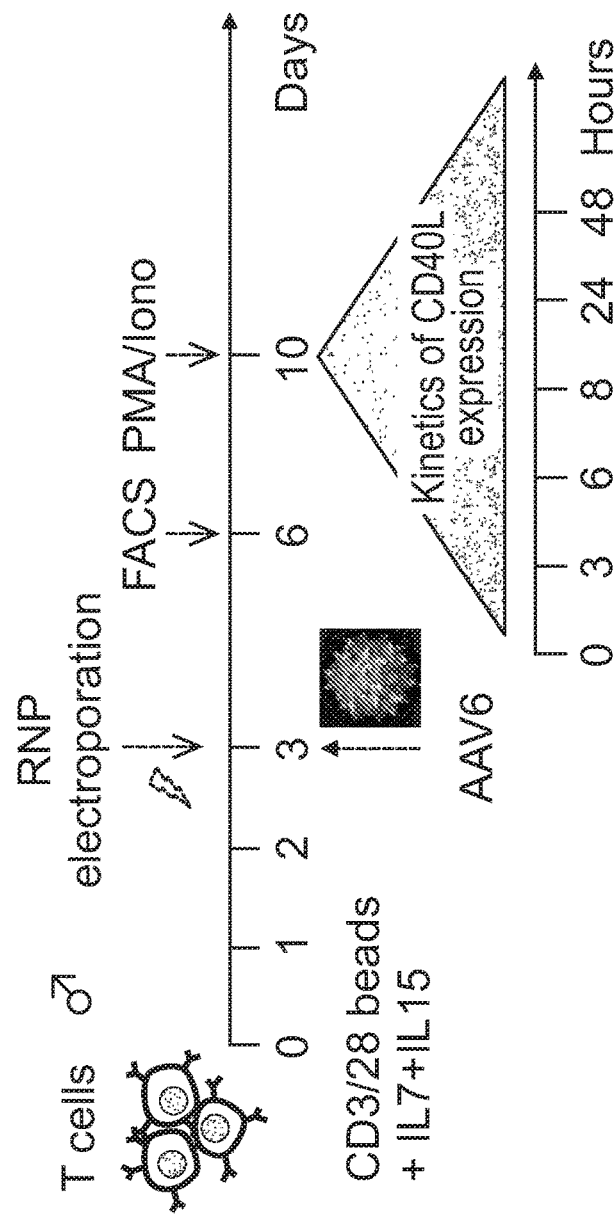
Figure 5C:
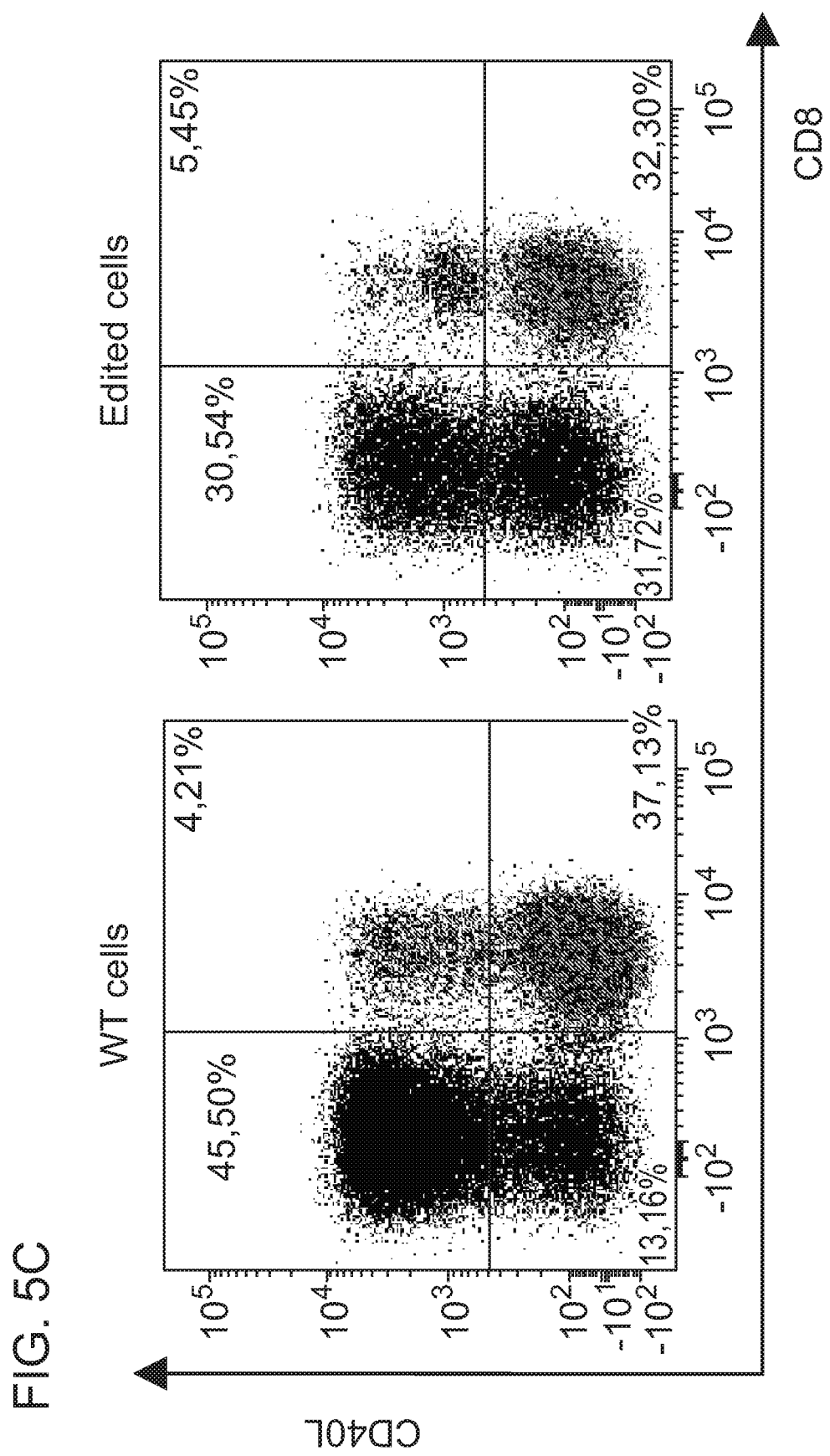
Figure 5E:
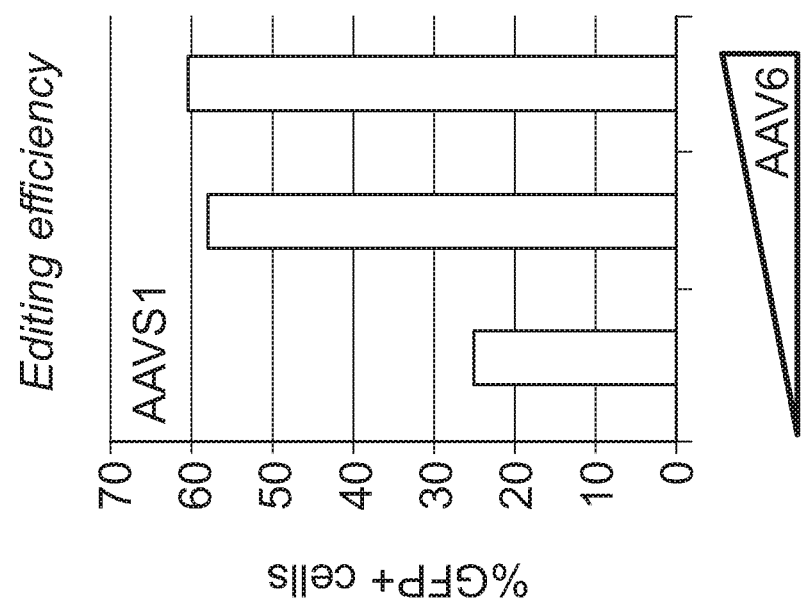
Figure 5D:
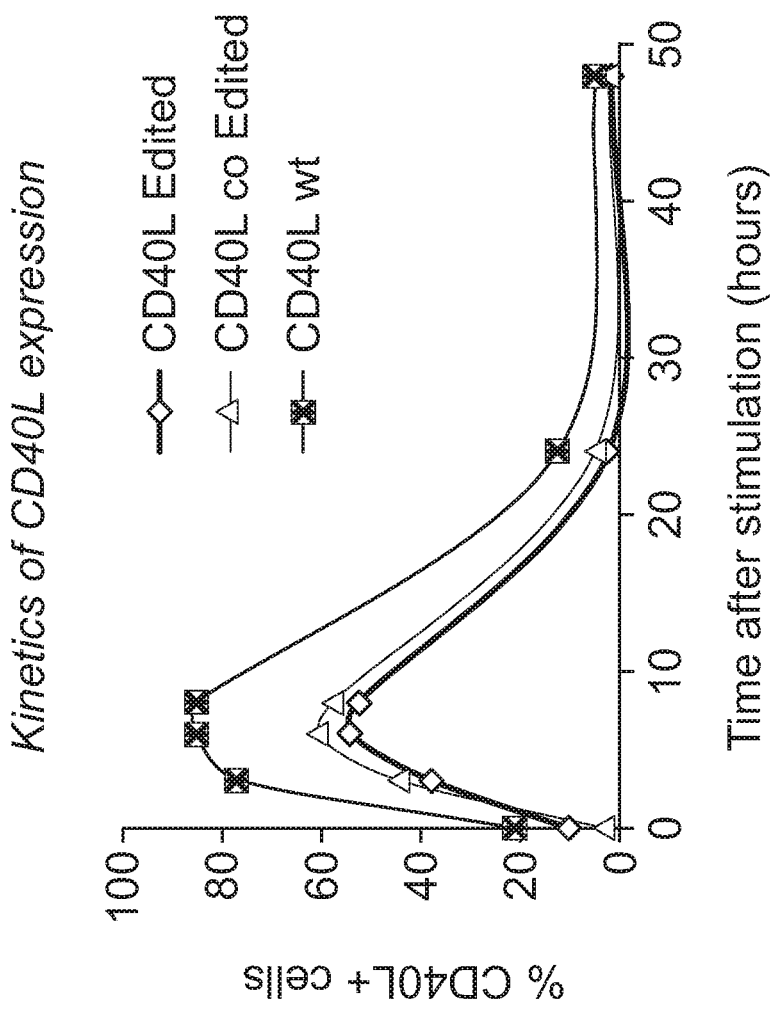
Figure 6B:
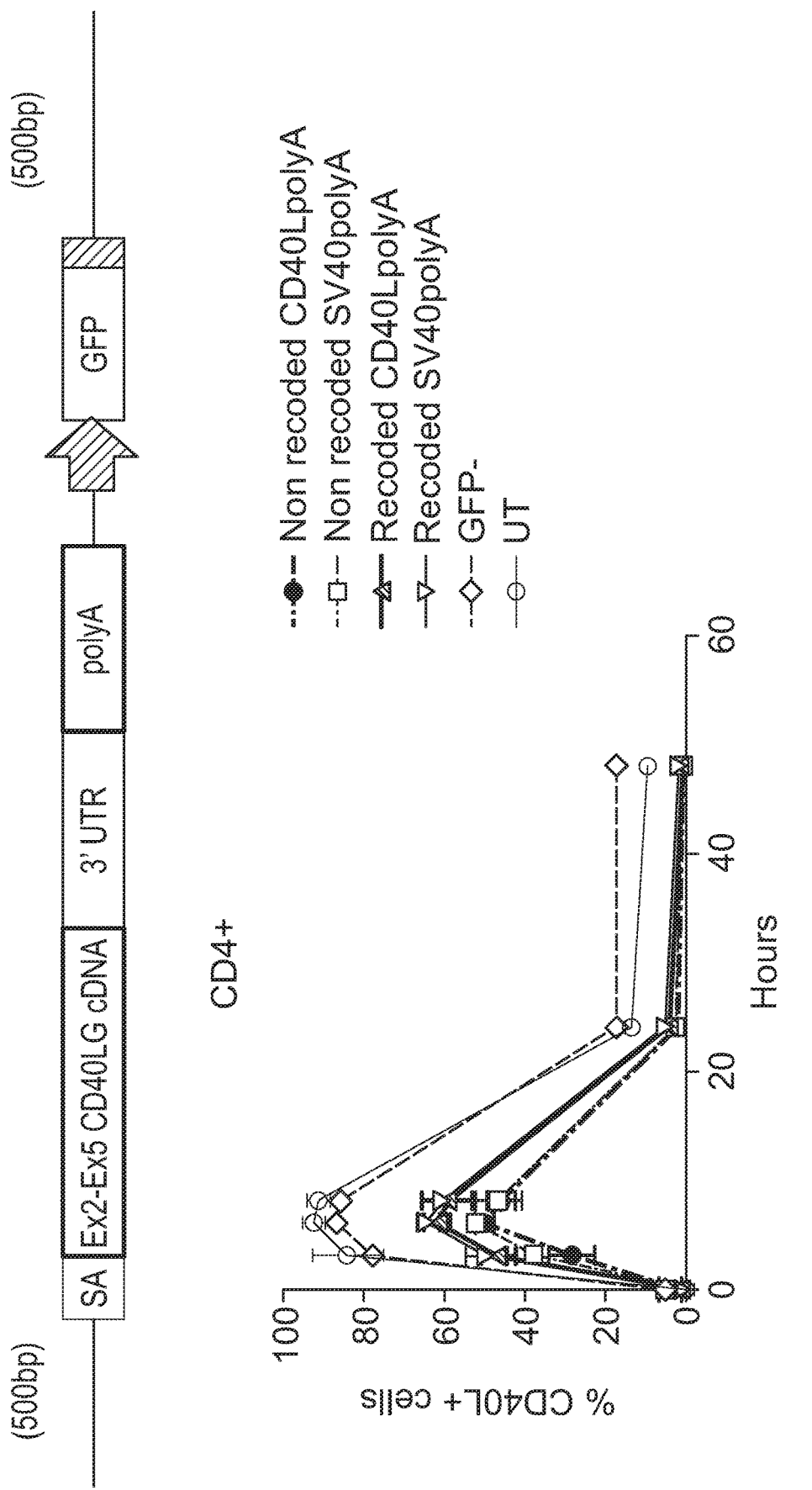

To confirm these results, another experiment was conducted. Human T cells were electroporated with RNP and, 15 minutes later, transduced with an AAV6 vector carrying the corrective donor. FACS analysis was performed 6 days after RNP electroporation, and the kinetics of CD40L expression were determined on Day 15 (FIG. 5B). Editing of CD40LG allows for normal expression of the CD40L protein and preserves the physiologic regulation of CD40L, as shown in FIGS. 5C and 5D. FIGS. 5C and 5D depict the kinetics of CD40L expression in the CD4+ T cells, edited with a wild type or a codon optimized ("co") CD40LG donor following PMA/Ionomycin treatment. CD40L expression in activated CD4+ and CD8+ cells is shown in FIG. 5C. The data show that the codon optimized CD40LG cDNA allows better restoration of CD40L expression. In addition, gene editing efficiency was improved when higher concentrations of AAV6 donor were added to the cells (FIG. 5E). While corrective CD40L expression peaks at lower levels than endogenous CD40L, they both exhibit a sharp decline in expression after approximately 6 hours (data not shown) Similarly, gene editing efficiency was improved by optimizing the doses of RNP and AAV6. FIGS. 6A and 6B demonstrate that the methods described herein produce high levels of CD40L gene editing (FIG. 6A) and high levels of exogenous CD40L expression (FIG. 6B). AAV was observed to inhibit T cell expansion post-electroporation depending on its MOI (data not shown).

The specificity of gRNA A and gRNA D was evaluated using Guide-Seq and Amplicon-Seq (Amp-Seq) analysis. Guide-Seq analysis was performed to assess the number of on-target and off-targeting editing events that occurred following editing with RNPs containing gRNA A or gRNA D, and the results are shown in FIG. 7A. Guide-Seq was performed in male T cells after activation and expansion of the cells. The cells were nucleofected with RNPs containing gRNA A or D and a short double-stranded oligo (Nat. Biotech. 2015, 33: 187-197). gDNA was isolated, sheared, and adapters for PCR amplification were added before PCR amplification. Sequences adjacent to the Guide-Seq oligo were aligned to the genome to find the location of the double-strand oligo insertion. Results of the Guide-Seq analysis are summarized in Table 11.

TABLE 11

Guide-Seq Analysis

| gRNA | Cas9 | Average On-Target Editing | Average On-Target Guide-Seq Reads | # Off-Targets Detected | Average Off-Target Editing | Average Off-Target Guide-Seq Reads |
|---|---|---|---|---|---|---|
| gRNA A | S.p. | 90% | 9173 | 1 | 0.3% | 116 |
| gRNA D | S.a. | 90% | 9287 | 0 | Not detected | N/A |

Figure 7C:
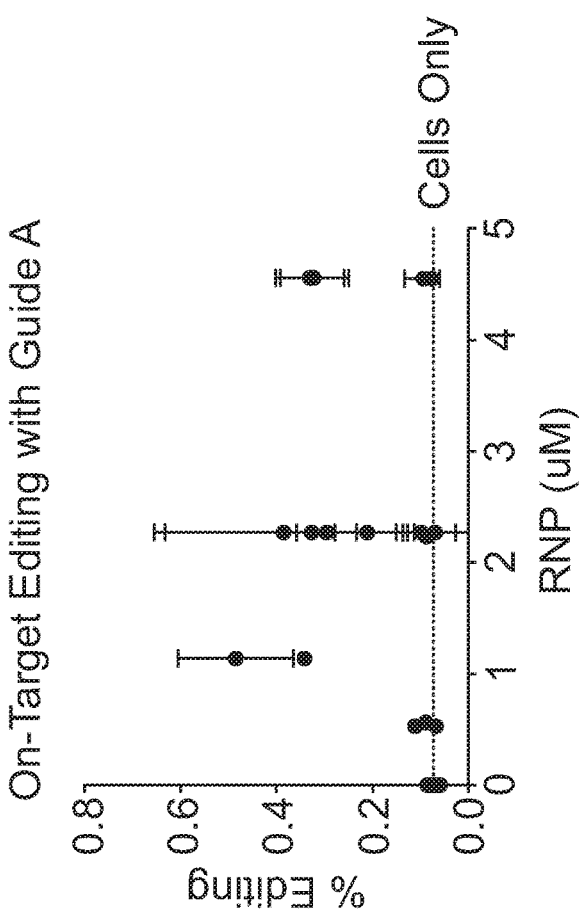
Figure 7D:
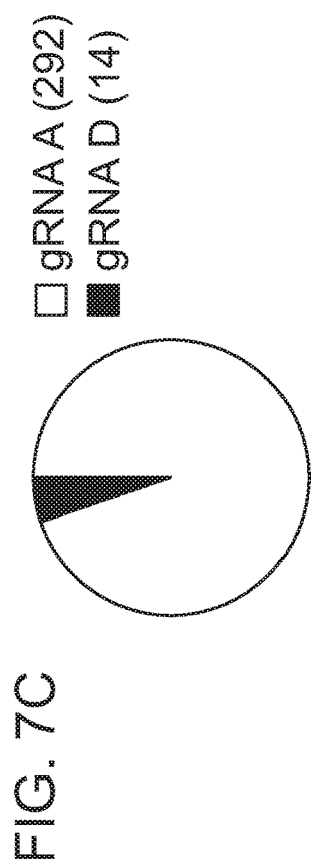
Figure 7E:
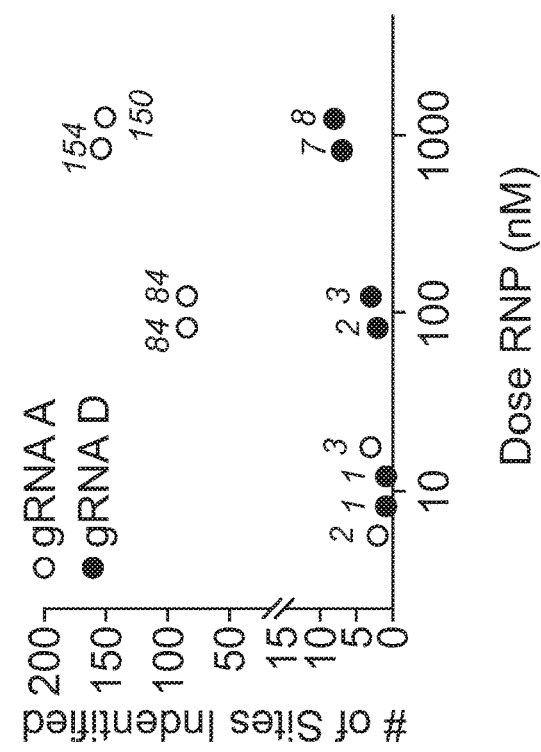
Figure 7F:
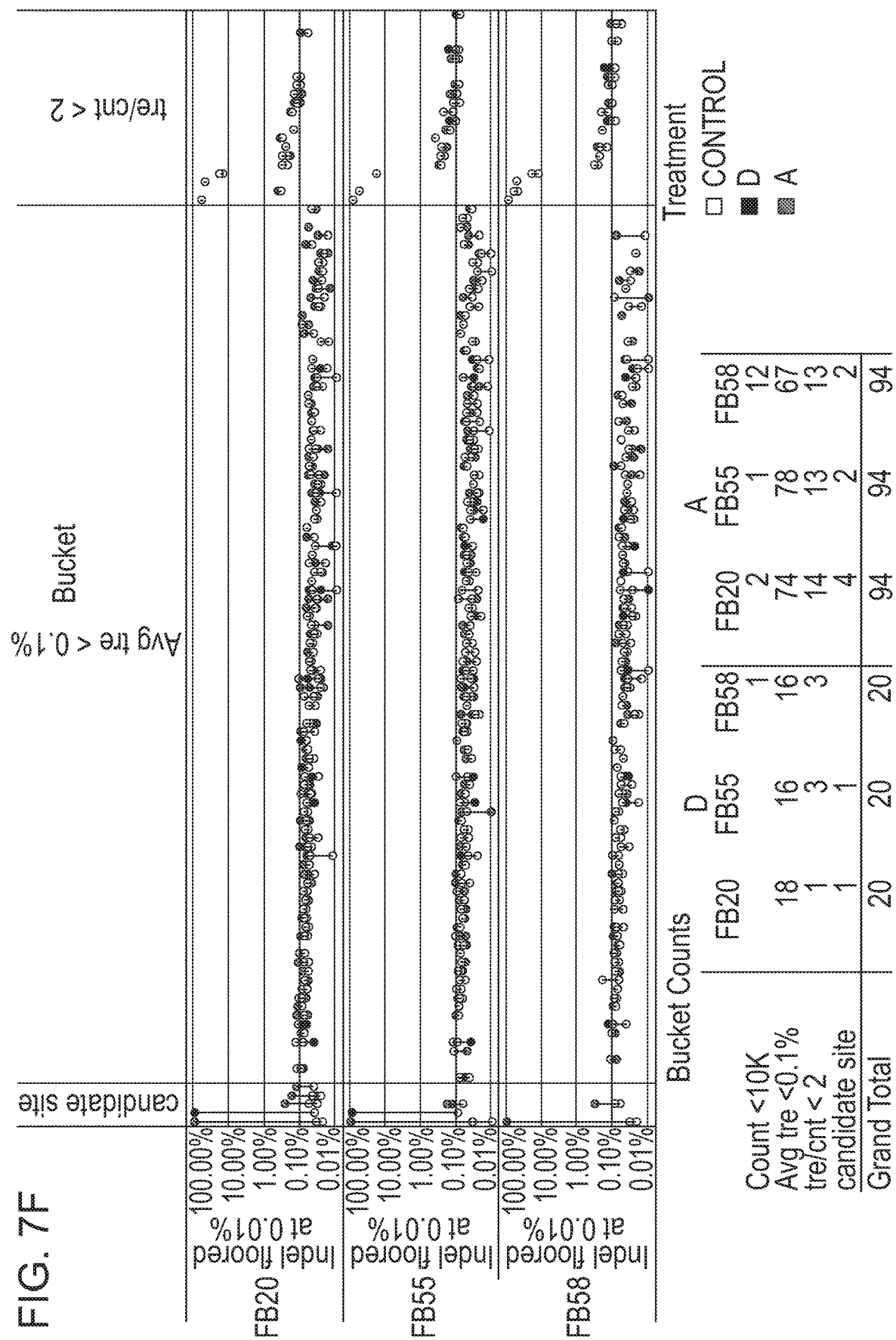

Amp-Seq analysis was performed to validate the off-targeting editing event observed with gRNA A, as shown in FIG. 7B. Amp-Seq was performed by PCR amplifying around the off-target cut site found from Guide-Seq analysis and then using high-throughput sequencing and computational alignment to determine whether there were editing events at the cut site. One off-target cut site was identified for gRNA A by Guide-Seq. This cut site was on chromosome 8, and ~300 kb from another gene. Off-target cutting was reduced to background levels using a higher fidelity Cas9 (eCas9), as shown in FIG. 7B. The on-target editing events for gRNA A are depicted in FIGS. 7B and 7E. No detectable off-target cut sites were observed for gRNA D. Digenome analysis revealed a significantly higher number of potential in vitro cut sites for gRNA A (205), compared to gRNA D (10) (FIG. 7C-7D). gRNA A and gRNA D displayed highly efficient rates of editing and targeted integration, as shown above, in combination with a high level of specificity. CD40L expression from the integrated cargo was comparable to endogenous levels of CD40L. FIG. 7F depicts an overview of the results of the Amplicon-Seq analysis for the identified off-target cut sites for gRNA A and D.

Figure 8:
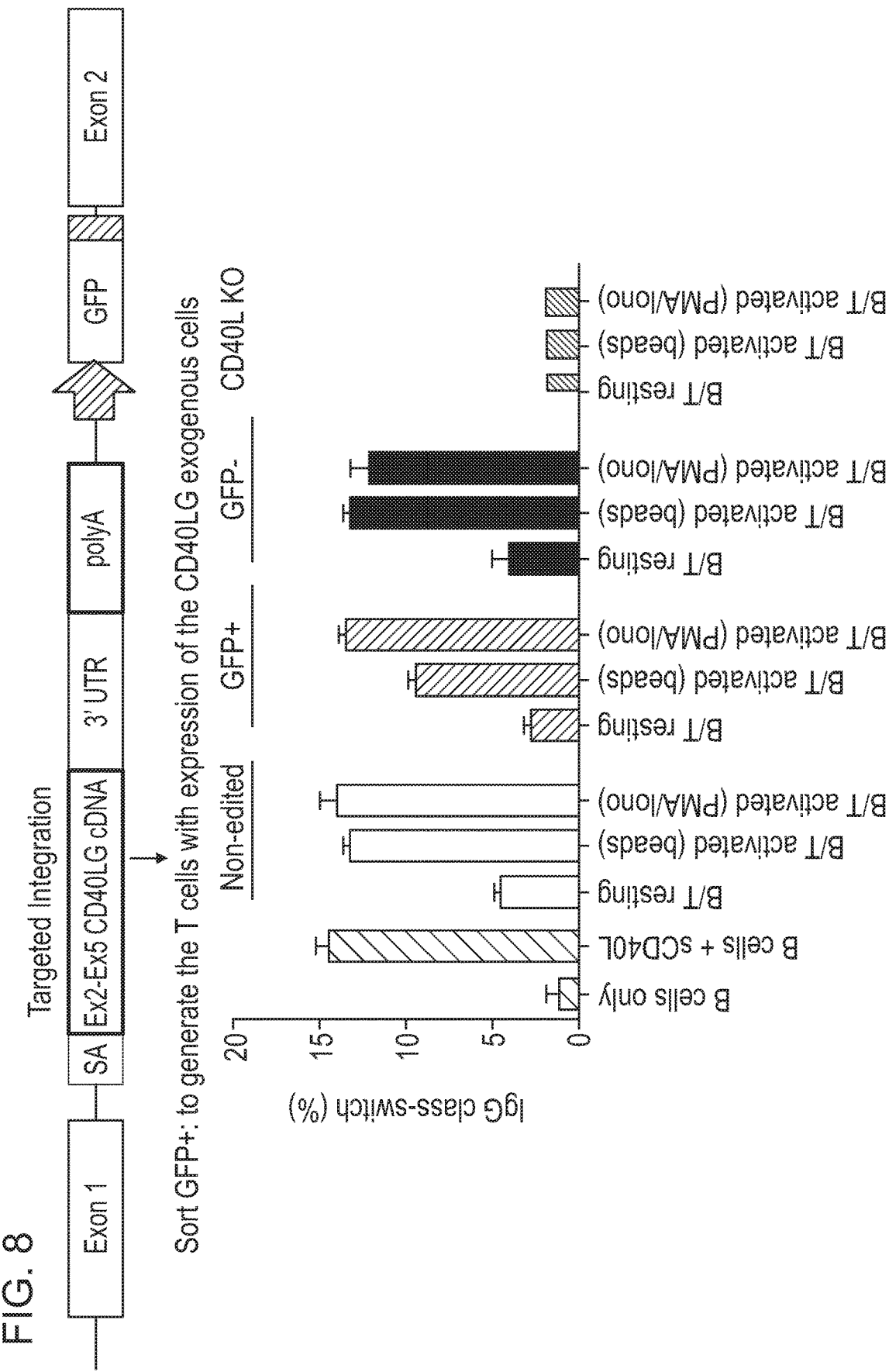
FIG. 8 depicts that CD40L edited T cells restored the capability of B cell class switching in an in vitro co-culture assay. The histogram shows the percentage of B cells that expressed IgG on their surface after 5 days of co-culture with wild type T cells (Non-edited), T cells with edited CD40L gene (GFP+), T cells treated for gene editing but negative for the integration of the corrective transgene (GFP−) or T cells in which the endogenous CD40L gene was knocked out by the integration of a reporter cassette. Cultures with only B cells and with B cells plus the addition of soluble CD40L protein were used as negative and positive controls, respectively. All the T cells were tested without any stimulation (resting) or upon stimulation with antiCD3-CD28 beads (beads) or PMA/Ionomycine.
Figure 9:
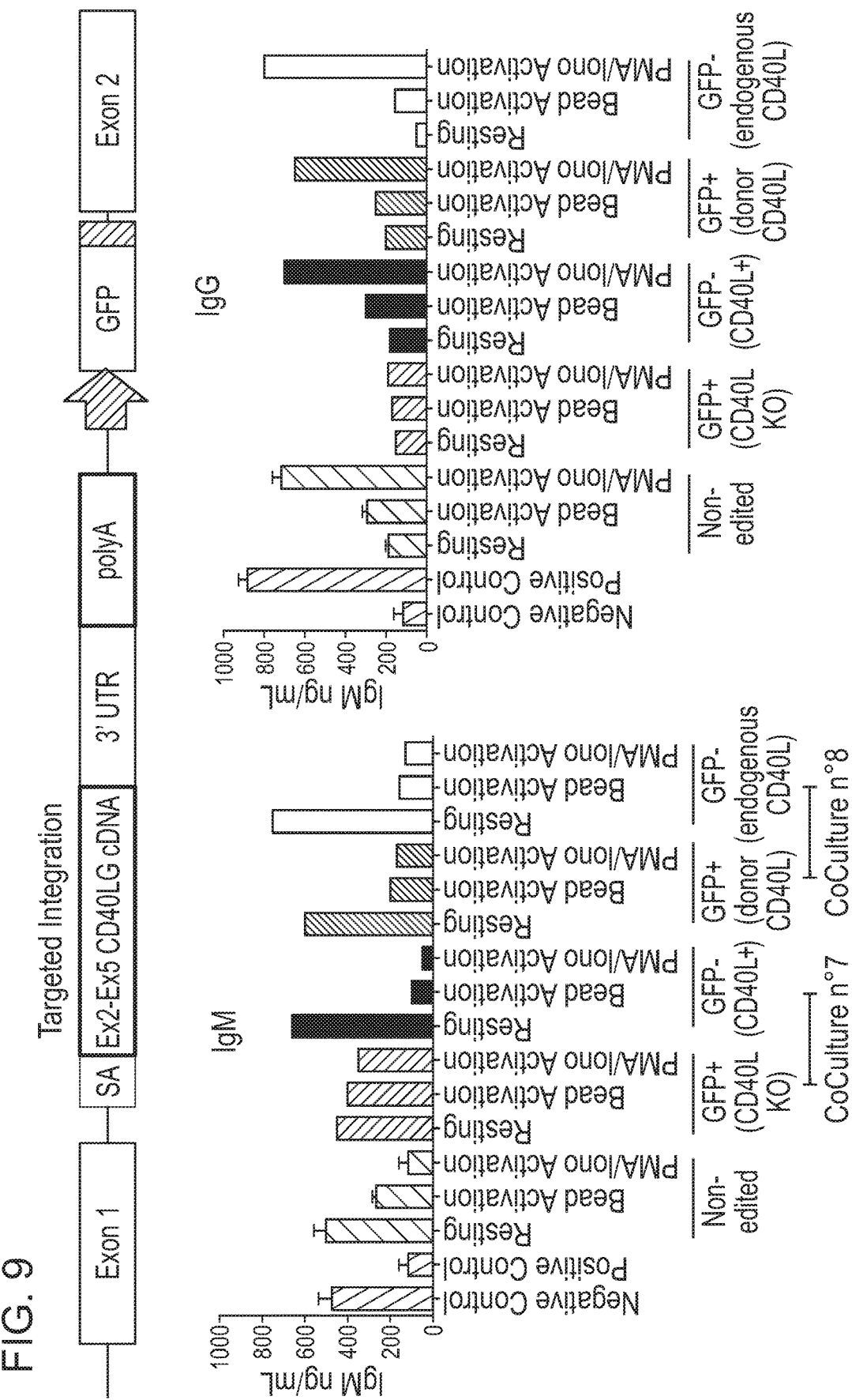
FIG. 9 depicts a decreased level of IgM and an increased level of IgG in the medium of B cells co-cultured with T cells having an edited CD40L locus.

Example 2: Edited CD40L Cells are Functionally Active and Restore B-Cell Class Switch Recombination To determine whether function is restored in CD40L-edited cells, B cells and edited T cells were co-cultured, and surface expression of IgG on the B cells was determined. Gene editing of CD40L in T cells was performed as described above. B cells were co-cultured with wild-type T cells (non-edited), T cells edited and selected for targeted integration of the corrective CD40L gene (GFP+), T cells treated for gene editing but negative for integration of the corrective CD40L gene (GFP−), and T cells in which the endogenous CD40L gene was knocked out by integration of a reporter cassette (CD40L KO). Cultures containing (i) B cells alone, and (ii) B cells and soluble CD40L protein (sCD40L), were used as negative and positive controls, respectively. T cells were tested without stimulation (resting), after stimulation with anti-CD3/CD28 beads (beads), or after stimulation with PMA/Ionomycine (PMA/Iono). After 5 days of co-culture, FACS analysis was performed. As shown in FIG. 8, edited T cells were able to induce B cells class-switching in the coculture assay. Moreover, the IgM levels were significantly reduced and the IgG levels were significantly increased in the medium of B cells co-cultured with T cells after gene editing (FIG. 9). Altogether, the data reported in FIG. 8 and FIG. 9 demonstrate that edited T cells expressed a functional CD40L, which is capable of providing contact-dependent signals to B cells that induced class switching in vitro.

Example 3: Targeted Integration at the CD40L Locus

The baseline level of targeted integration at four gRNA cut sites from Example 1 was determined: gRNA A (*S. pyogenes*), gRNA C (*S. pyogenes*), gRNA D (*S. aureus*) and gRNA G (*S. aureus*). AAV6 donor templates were designed following the depiction in FIG. 1A, so that all donors contained the same cargo (stuffer sequences, CD40LG cDNA/3' UTR/polyA and GFP expression cassette) within short homology arms designed to flank the predicted cut sites. The length of the homology arms in each construct are provided in Table 12.

TABLE 12

| | Homology Arm Length | |
|---|---|---|
| | 5' HA | 3' HA |
| gRNA-A | 205 bp | 178 bp |
| gRNA-C | 242 bp | 131 bp |
| gRNA-D | 178 bp | 284 bp |
| gRNA-G | 206 bp | 270 bp |

Figure 10:
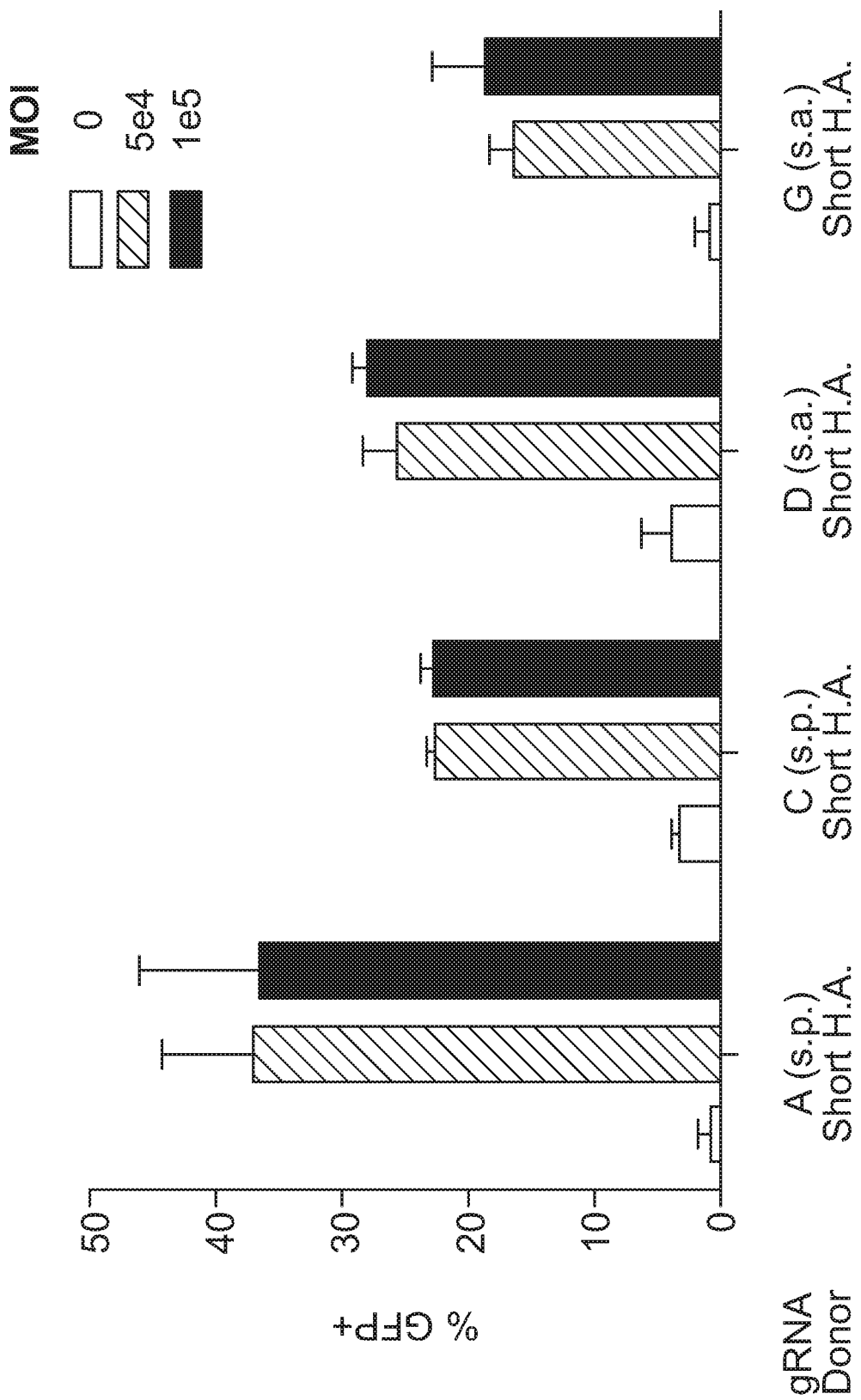
FIG. 10 depicts the baseline level of targeted integration at four gRNA cut sites using an AAV6 donor template comprising the following cargo: stuffer sequences, CD40LG cDNA/3' UTR/polyA, and a GFP expression cassette. Short homology arms flanked the predicted cut sites. Differences in baseline levels of targeted integration between gRNAs were detected, based on GFP expression.

Primary human male CD4+ T cells were grown and nucleofected with the indicated gRNA as described above. Cells were moved to new culture media, and AAV6 particles were added to the culture 15 minutes later at a multiplicity of infection (MOI) of either 5e4 or 1e5. Cells were expanded for 7 days and then assessed for targeted integration based on GFP expression using flow cytometric analysis. At this time point after nucleofection, very little expression of GFP is detectable from the unintegrated AAV donor (data not shown), indicating that cells with high levels of GFP expression underwent targeted integration. Differences were found in baseline levels of targeted integration between gRNAs, based on GFP expression, as shown in FIG. 10 (gRNA A ~35%, gRNA C ~15%, gRNA D ~28%, and gRNA G ~17%). A dose dependent reduction in targeted integration was not observed upon reducing the amount of AAV6 donor given to the cells. Results represent at least 2 independent samples.

Figure 11:
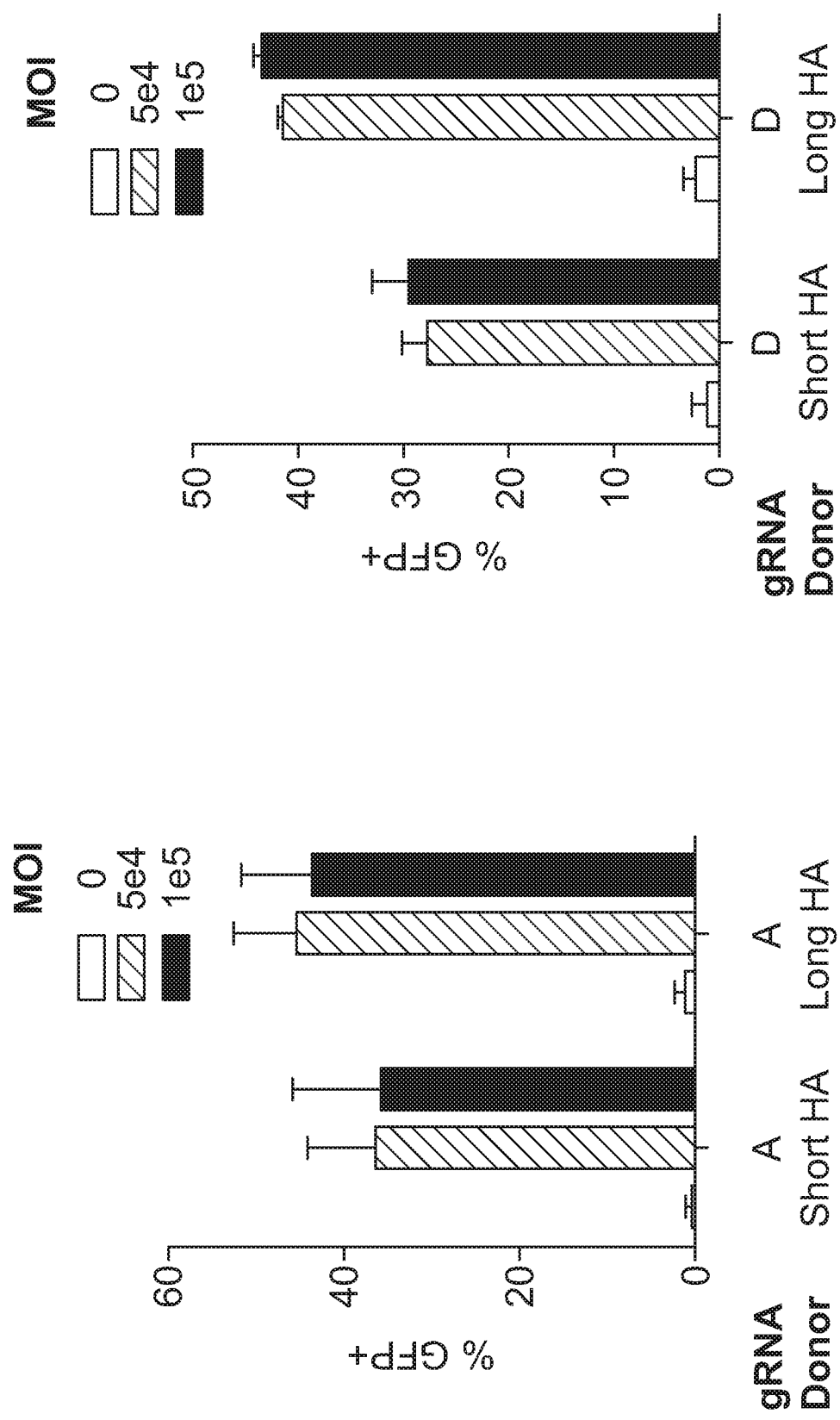
FIG. 11 compares the level of targeted integration obtained using donor templates having varied homology arm length. AAV6 donor templates were prepared as in FIG. 10, lengthening the homology arms to 500 base pairs on each side of the cargo sequence. Increasing the length of the homology arms increased the level of targeted integration for both gRNA cut sites tested.

To increase the baseline level of targeted integration, the effect of lengthening the homology arms was examined. AAV6 donor templates having long homology arms (500 bp on each side of the cargo) were designed for the top gRNA sites based on targeted integration as determined in FIG. 10 (gRNA A and gRNA D). Targeted integration experiments were conducted on primary human male CD4+ T cells as described above. Cells were given an AAV6 donor template with either short HA (the same AAV6 donors used for FIG. 10), or long HA. GFP expression was determined 7 days post-nucleofection by flow cytometry, and is plotted in FIG. 11. Long HA improved the levels of targeted integration for both gRNA cut sites. Targeted integration at the gRNA A site increased from ~35% to ~44%, and targeted integration at the gRNA D site increased from ~28% to ~42%.

Example 4: Adoptive T Cell Therapy in Murine Models

Figure 12:
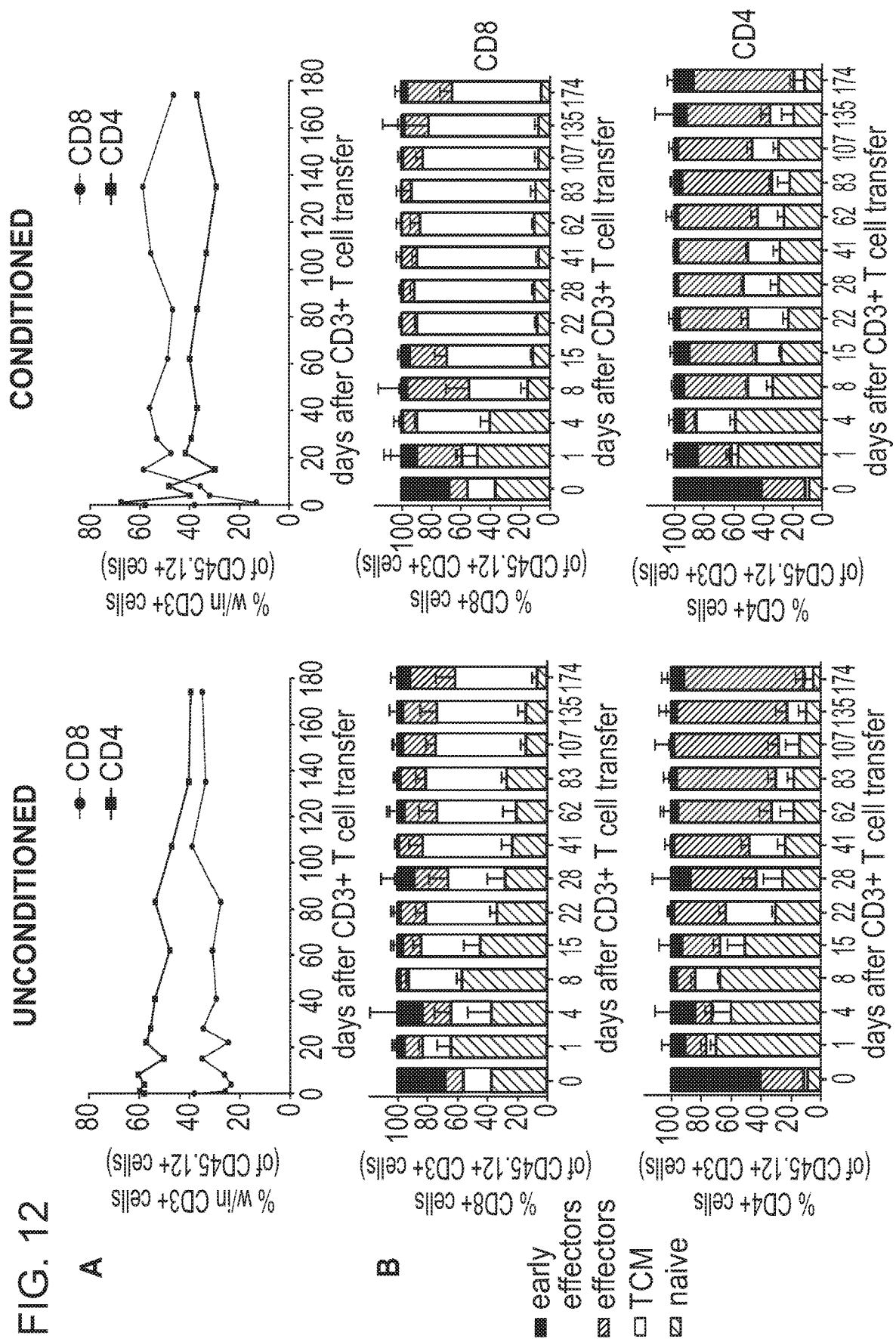
FIGS. 12A and 12B depict the phenotype of the transplanted T cells at different time points after injection.
Figure 13:
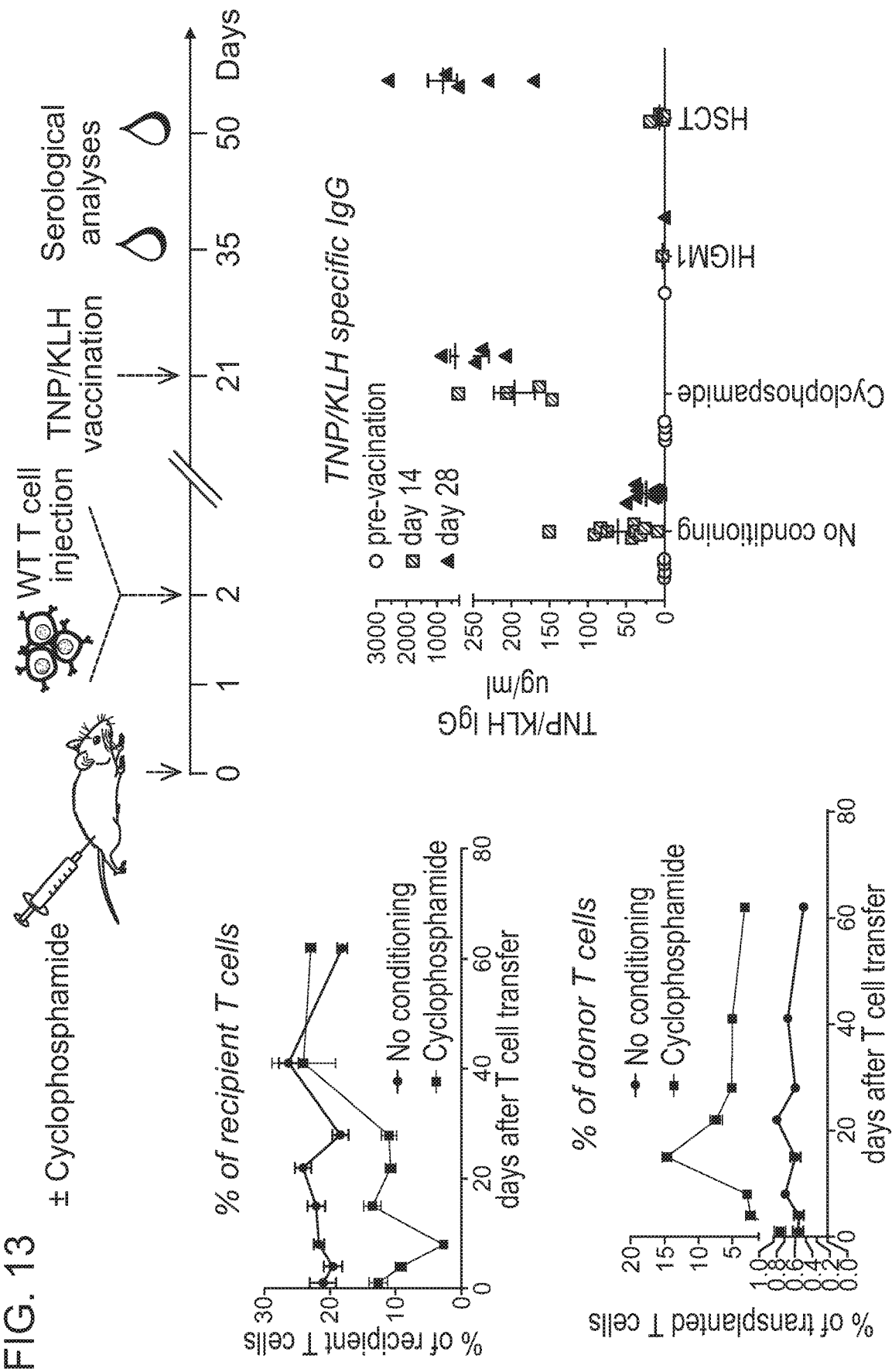
FIG. 13 depicts adoptive T cell therapy in CD40L KO mice using wild type T cells, transplanted with and without a cyclophosphamide pre-conditioning regimen. The graphs on the left, depict the percentages of recipient and donor T cells during time in the mice treated or not with the pre-conditioning regimen. The dot plot on the right depicts the amount of antigen specific IgG in the serum of the transplanted animals before or after 14 and 28 days from an immunization of the transplanted mice with the Trinitrophenyl hapten conjugated to Keyhole Limpet Hemocyanin (TNP-KLH) antigen. HIGM1 mice were used as negative control. Mice transplanted with a full dose of wild type hematopoietic stem cells (HSCT) were used as positive control.
Figure 14:
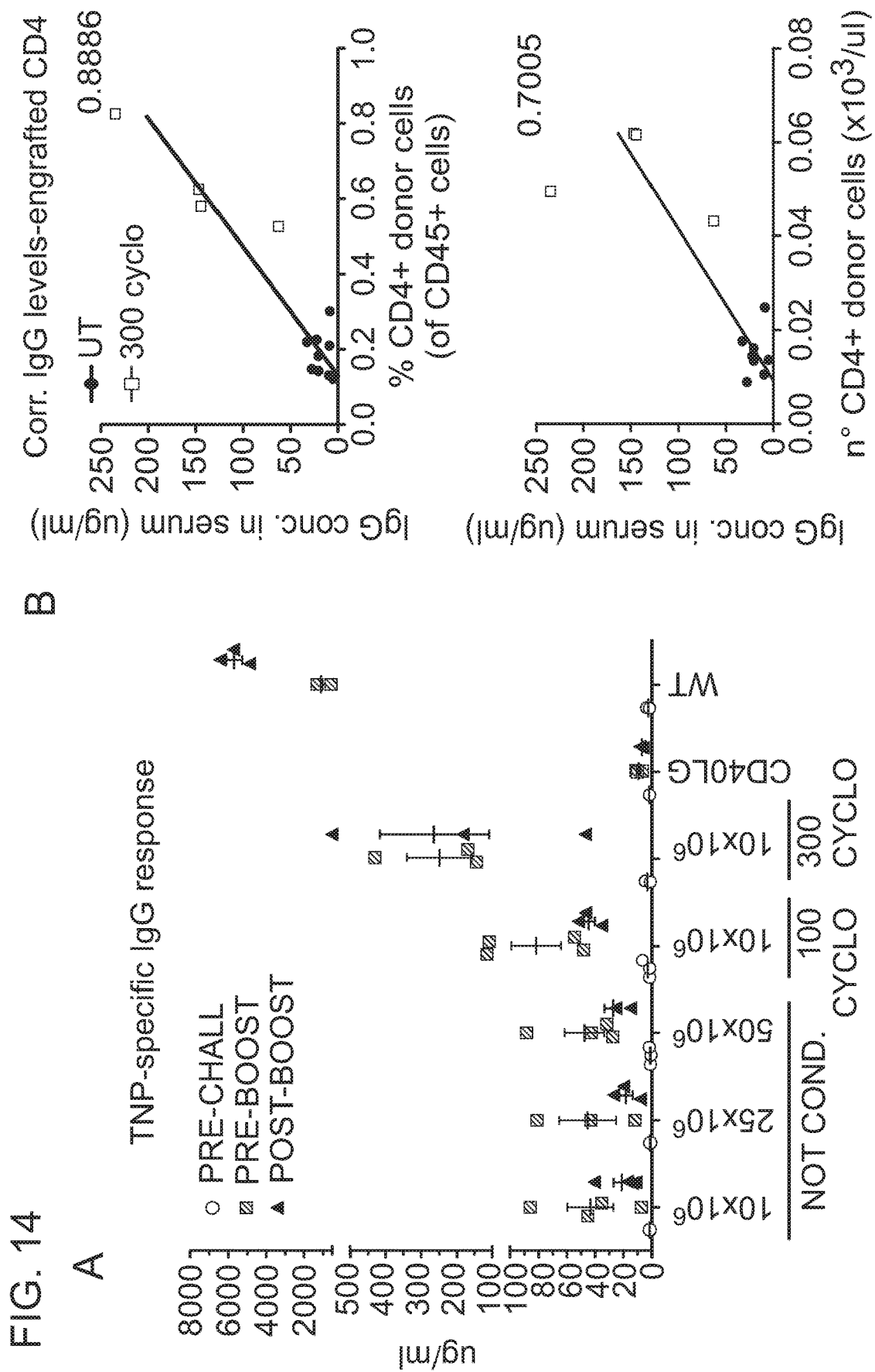
FIGS. 14A and 14B depict the response to vaccination of HIGM1 mice transplanted with wild type T cells.
FIG. 14C-14E depict adoptive T cell therapy in CD40L KO mice using wild type T cells, transplanted with and without anti-leukocytes (ALS) or anti-CD4 antibodies pre-conditioning regimen.
Figure 14:
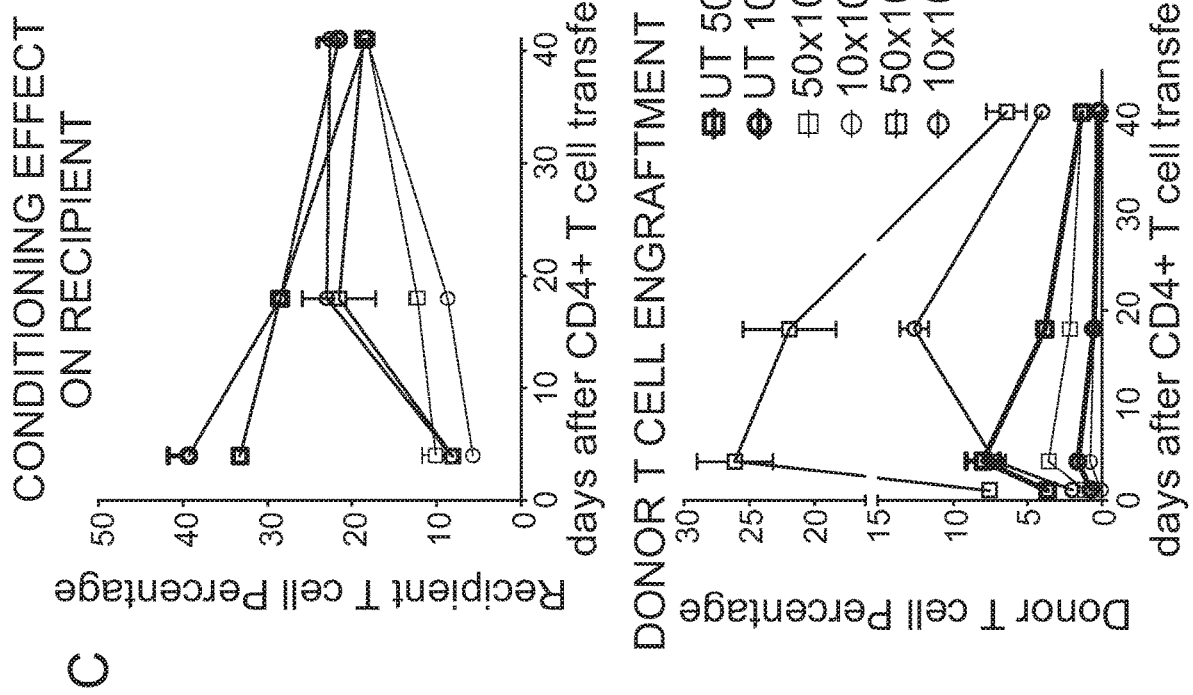
Figure 14:
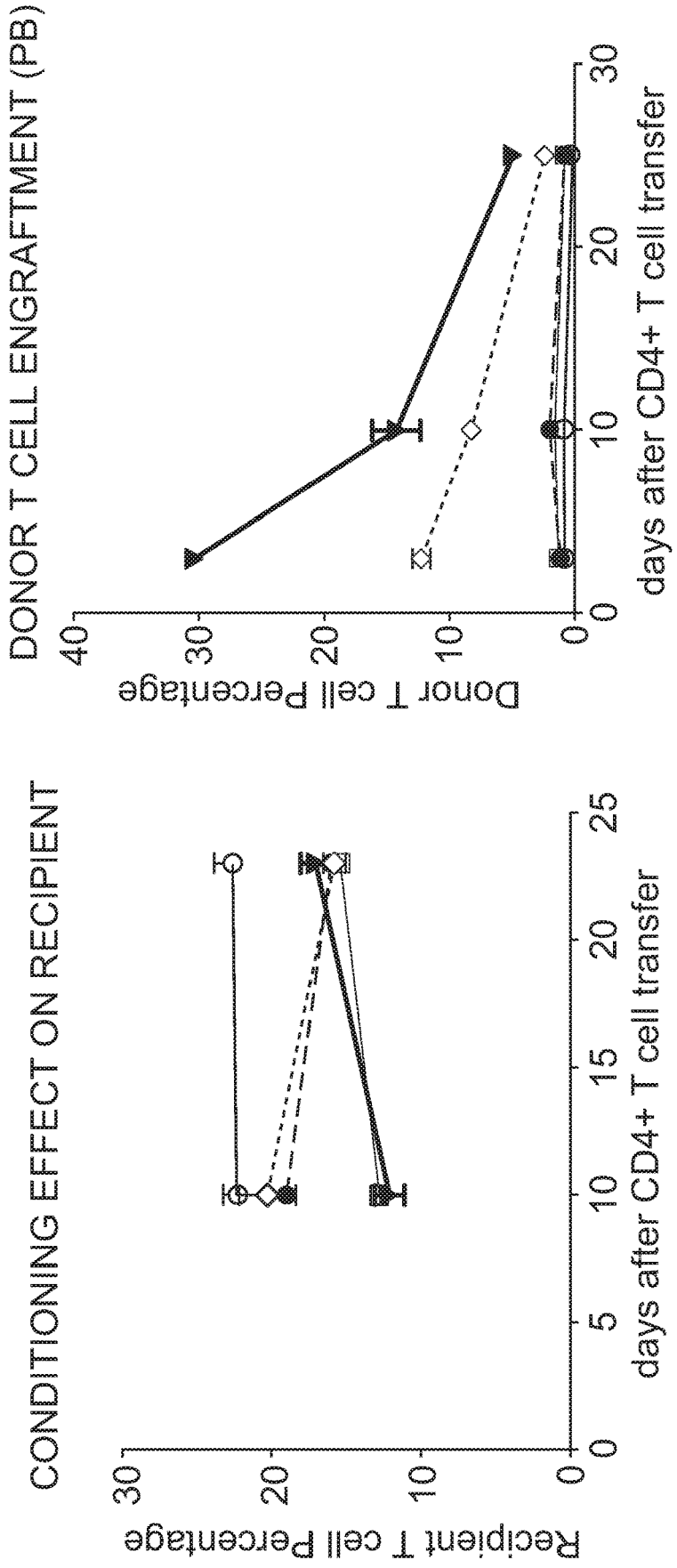
Figure 15B:
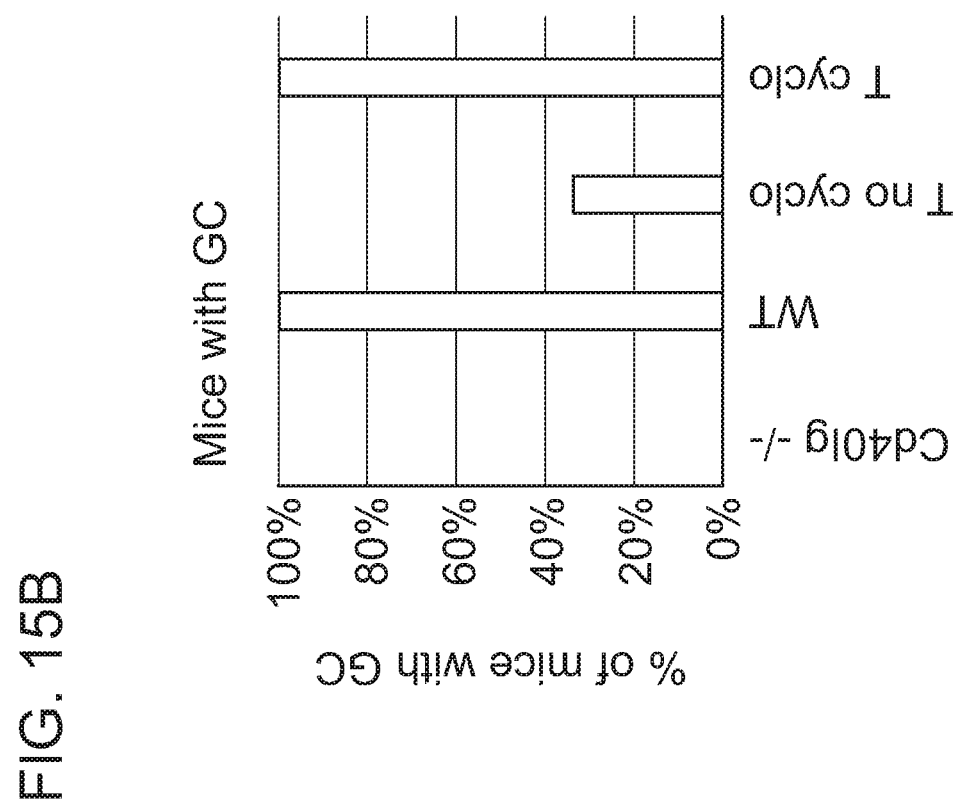

Mice were pre-treated or conditioned with cyclophosphamide on Day 0 in order to deplete recipient cells and create space in the lymphocyte niche, allowing better engraftment of the transplanted cells. Wild type T cells were injected on Day 2, and their engraftment was longitudinally measured over time. The CD8/CD4 ratio remained stable in the unconditioned group, while it significantly increased in the conditioned mice (see FIG. 12A). During that time, the vast majority of the circulating donor CD8 and CD4 T cells displayed a T central memory and an effector memory phenotype, respectively (FIG. 12B). TNP/KLH vaccination was introduced on Day 21, followed by serological assays on Days 35 and 50. As shown in FIG. 13, conditioning with cyclophosphamide resulted in a higher level of TNP/KLH specific IgG in mice. The levels of specific IgG response to the vaccination correlates with the dose of conditioning administered (FIG. 14A) and with the amount of circulating wild type CD4 T cells (percentages and absolute numbers, FIG. 14B). However, the conditioning step is not absolutely required, as mice without conditioning also showed an increased levels of IgG upon vaccination (FIG. 13 and FIG. 14A). In a second experiment, mice were pre-treated or conditioned with anti-leukocytes (ALS) or anti-CD4 antibodies on Day 0. FIGS. 14C and 14E depict the percentages of recipient and donor T cells during time in the mice treated or not with the pre-conditioning regimen. The levels of specific IgG response to the vaccination correlates with the dose of conditioning administered (FIG. 14D). This data provides evidence that lymphodepleting conditioning could be performed also by immune-biologic strategies. Adoptive T cell transplantation restored also the presence of germinal centers in the spleen of the transplanted mice (FIG. 15A and FIG. 15B).

Example 5: Hematopoietic Stem Cell Therapy in Murine Models

CD40L-negative mice were treated with CD40L wild type HSPC, harvested from 6-8 week old wild type C57B/6 mice, mixed at different percentage (100%, 10%, 1%, and 0%) with CD40LG negative cells, harvested from HIGM1 mice. Recipient mice were then immunized with TNP-KLH and the levels of TNP-KLH specific IgG were measured. As shown in FIG. 16A, mice receiving hematopoietic stem cells comprising 10% and 100% of CD40L wild type cells had a much higher level of IgG, suggesting that hematopoietic stem cells with at least 10% of CD40L edited cells demonstrate a therapeutic effect for treating diseases, such as hyper-IgM syndrome.

Figure 16B:
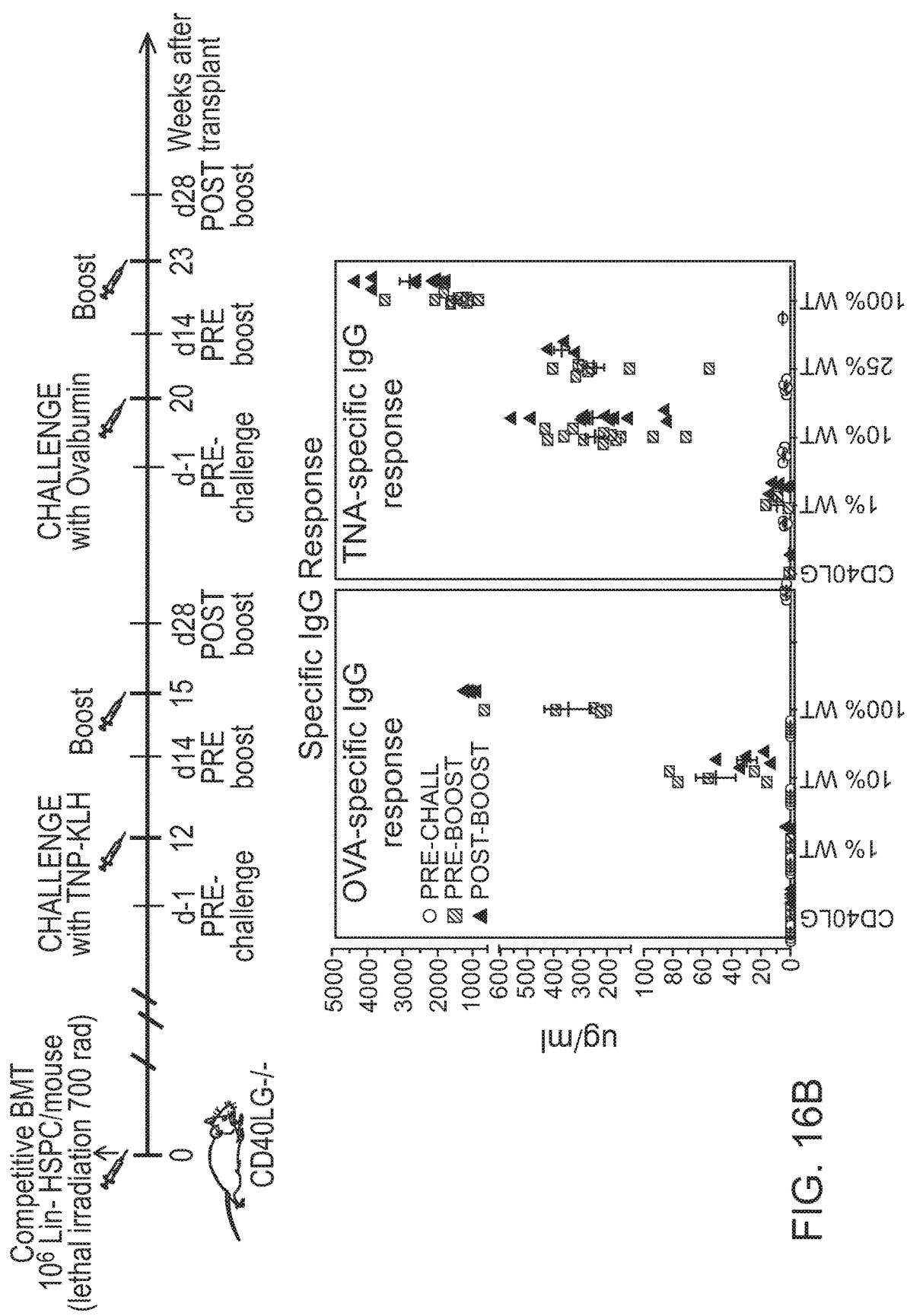
Figure 16C:
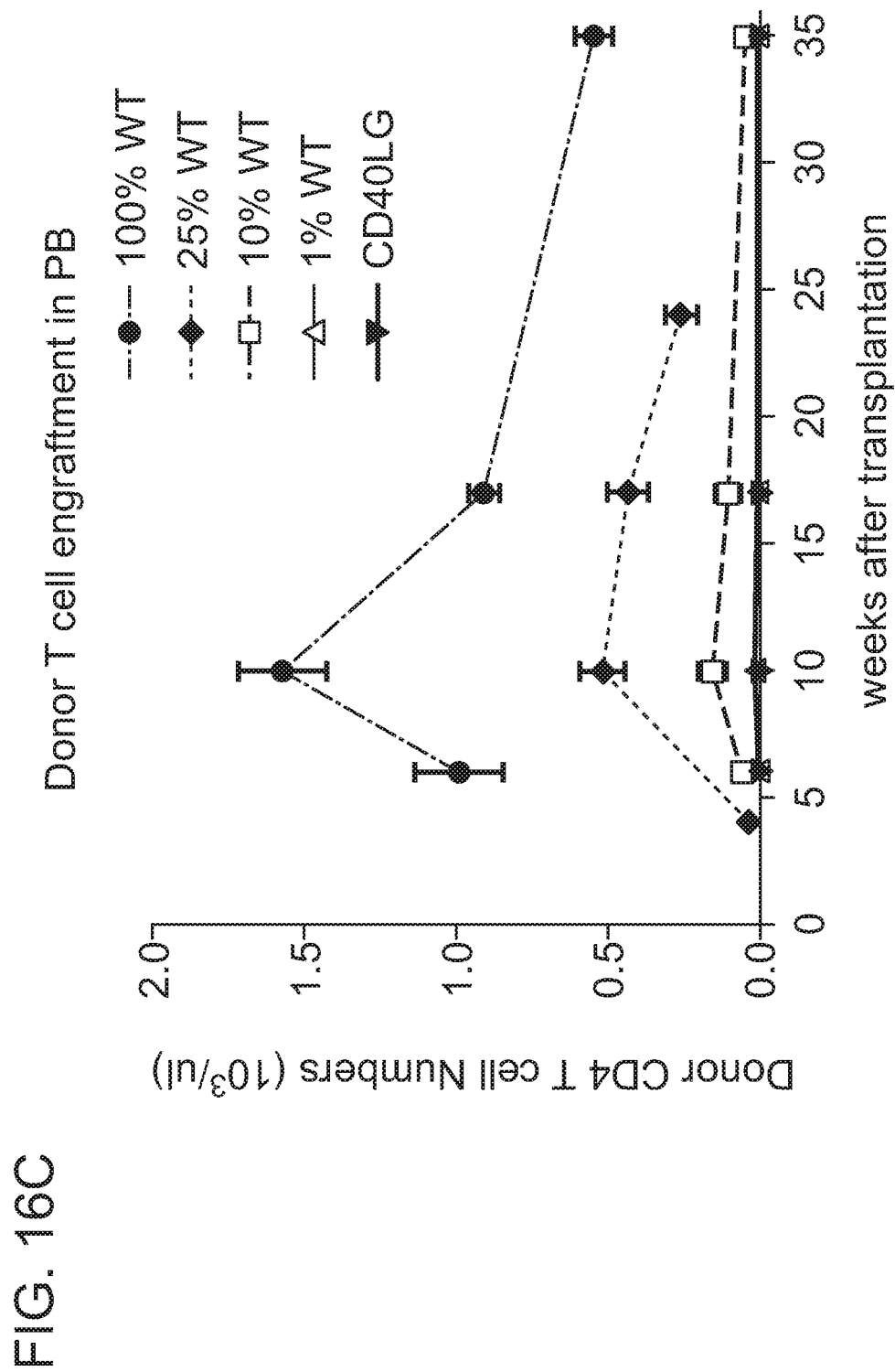

In a second experiment, mice were challenged with two antigens, TNP-KLH and Ovalbumin (OVA), as shown in FIG. 16B. CD40LG-negative mice were transplanted with different percentages of wild type HSPC on day 0. The mice were immunized with TNP-KLH at 12 and 15 weeks following transplantation, and were subsequently immunized with OVA at 20 and 23 weeks following transplantation. TNP-specific IgG response was assessed (i) prior to immunization with TNP-KLH (pre-challenge), (ii) 14 days following the initial immunization with TNP-KLH (day 14), and (iii) 28 days following the initial immunization with TNP-KLH (post-boost; day 28). OVA-specific IgG response was assessed (i) prior to immunization with OVA (pre-challenge), (ii) 14 days following the initial immunization with OVA (day 14), and (iii) 28 days following the initial immunization with OVA (post-boost; day 28). The results indicate that restoration of at least 10% of CD40LG positive HSPC allow partial restoration of immune response to different T cell dependent vaccinations. FIG. 16C depict the donor T cell engraftment in peripheral blood.

Figure 17:
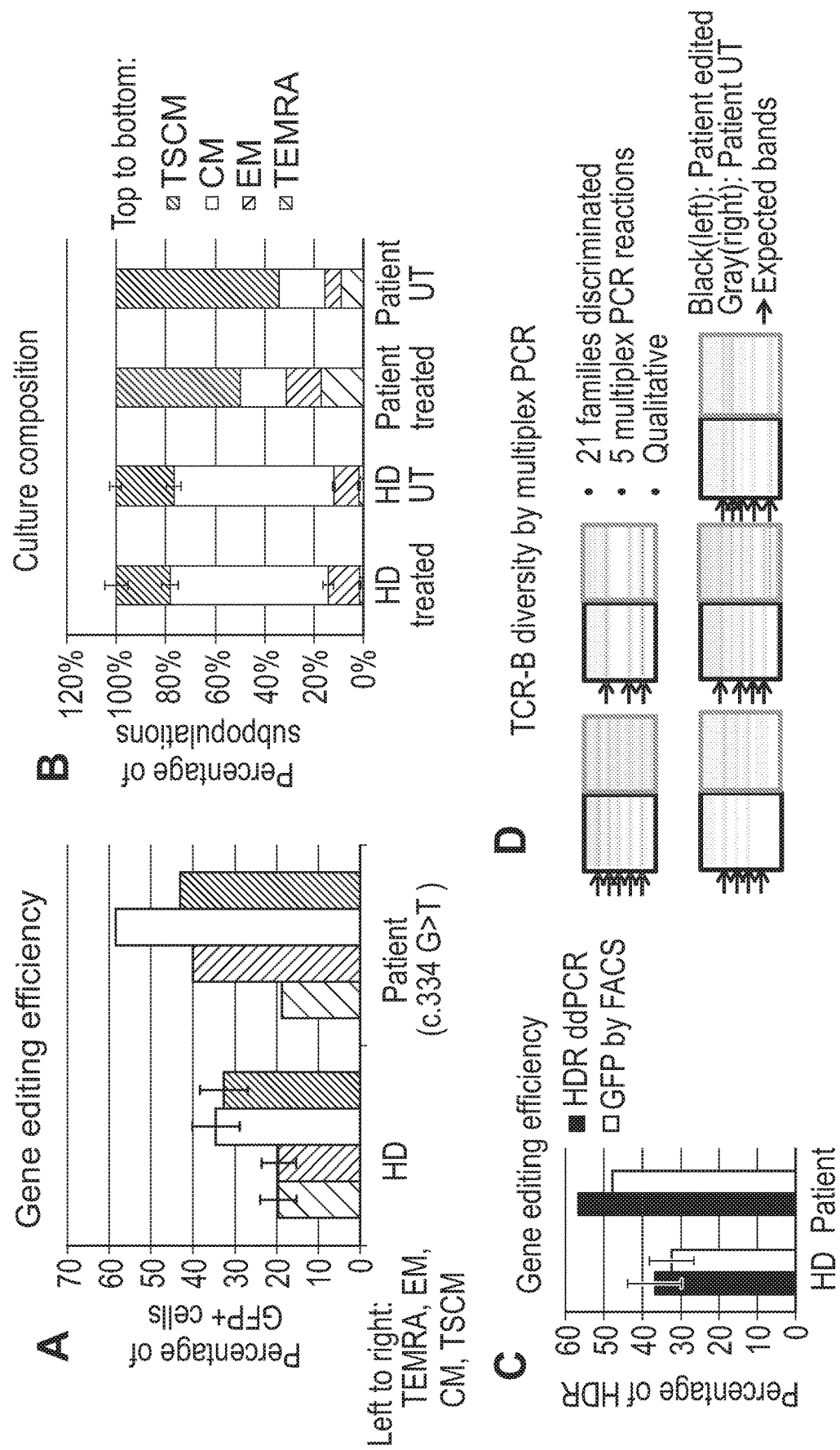
FIGS. 17A-17D depict high and polyclonal CD40L targeting in both healthy donor (HD) and patient derived T cells. CD4 T cells were collected from different healthy donors (HD, n=4) or from a patient carrying the indicated HIGM1 causing mutation into the exon 3 (Patient), stimulated in vitro and treated with 25 pmol RNP A (S.p.) and AAV6 at MOI: 5*10~4 vg/cell.
Figure 18:
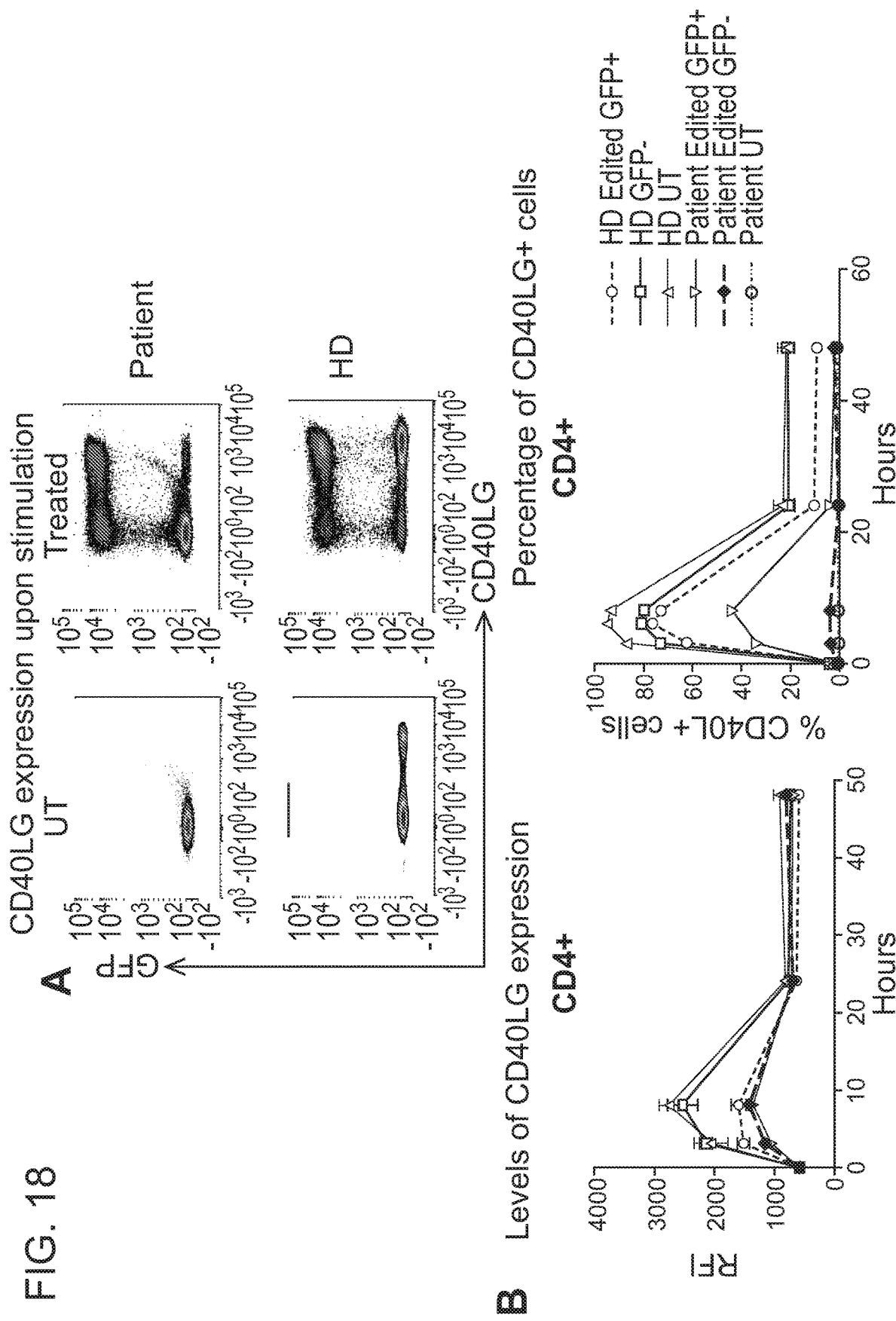
FIGS. 18A and 18B depict that targeted integration of the corrective construct restored CD40L expression and physiologic regulation.
Figure 19:
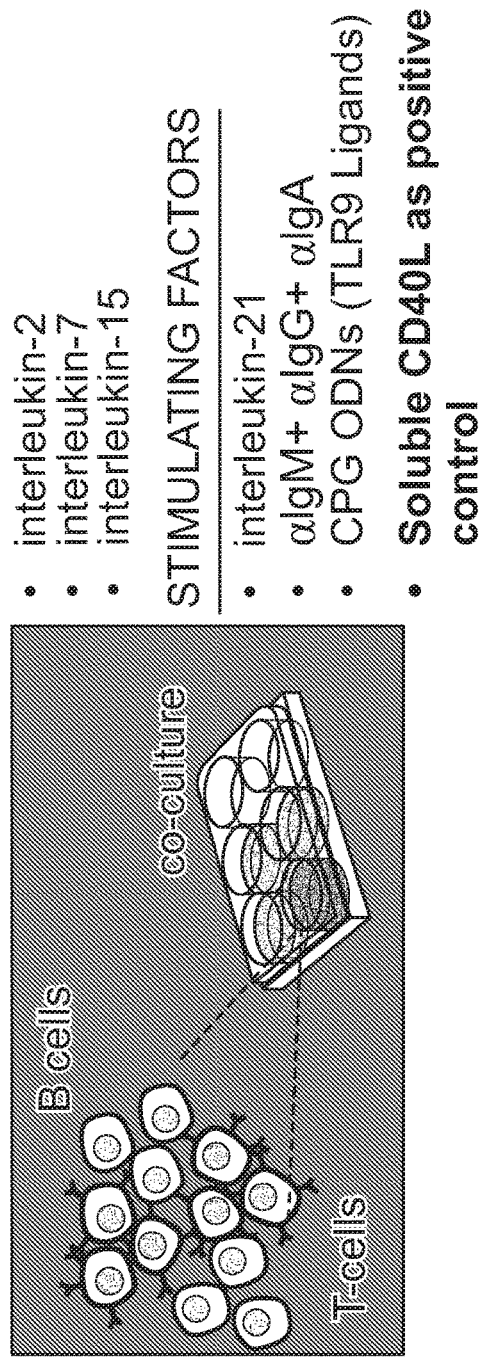
FIGS. 19A-19C depict the ability of CD40L edited T cells to restore B cell proliferation in a co-culture assay.
Figure 19:
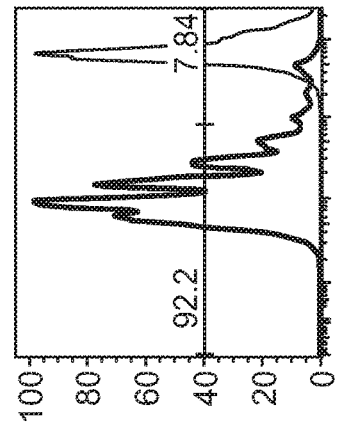
Figure 19:
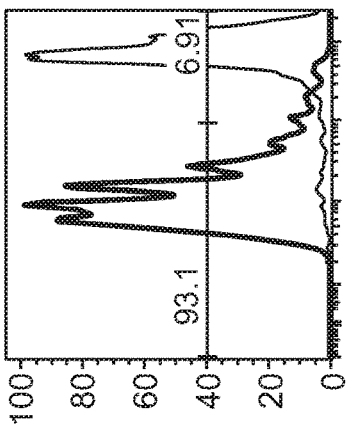
Figure 19:
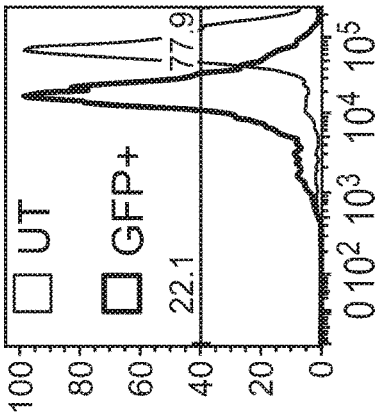
Figure 19C:
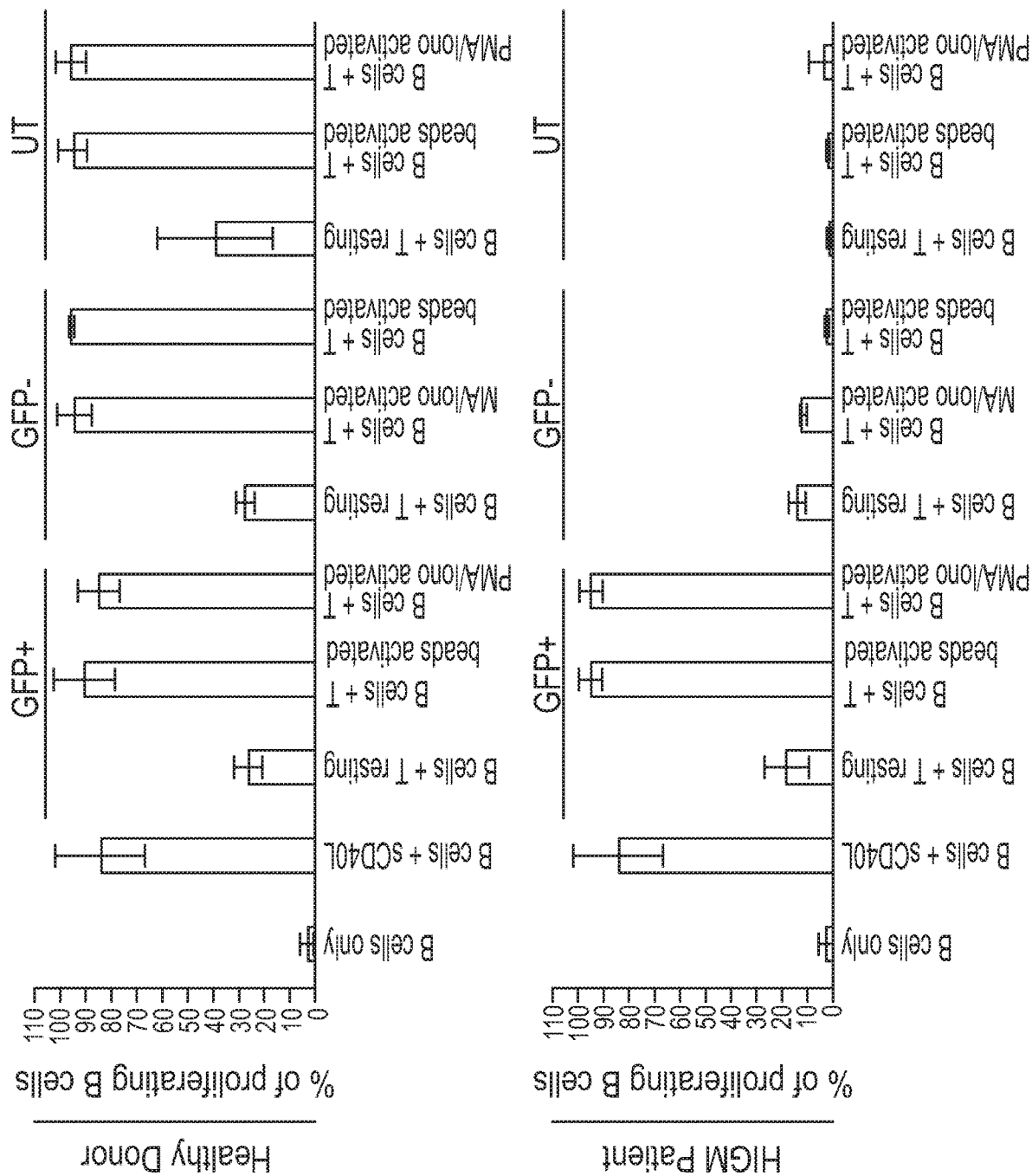
Figure 20:
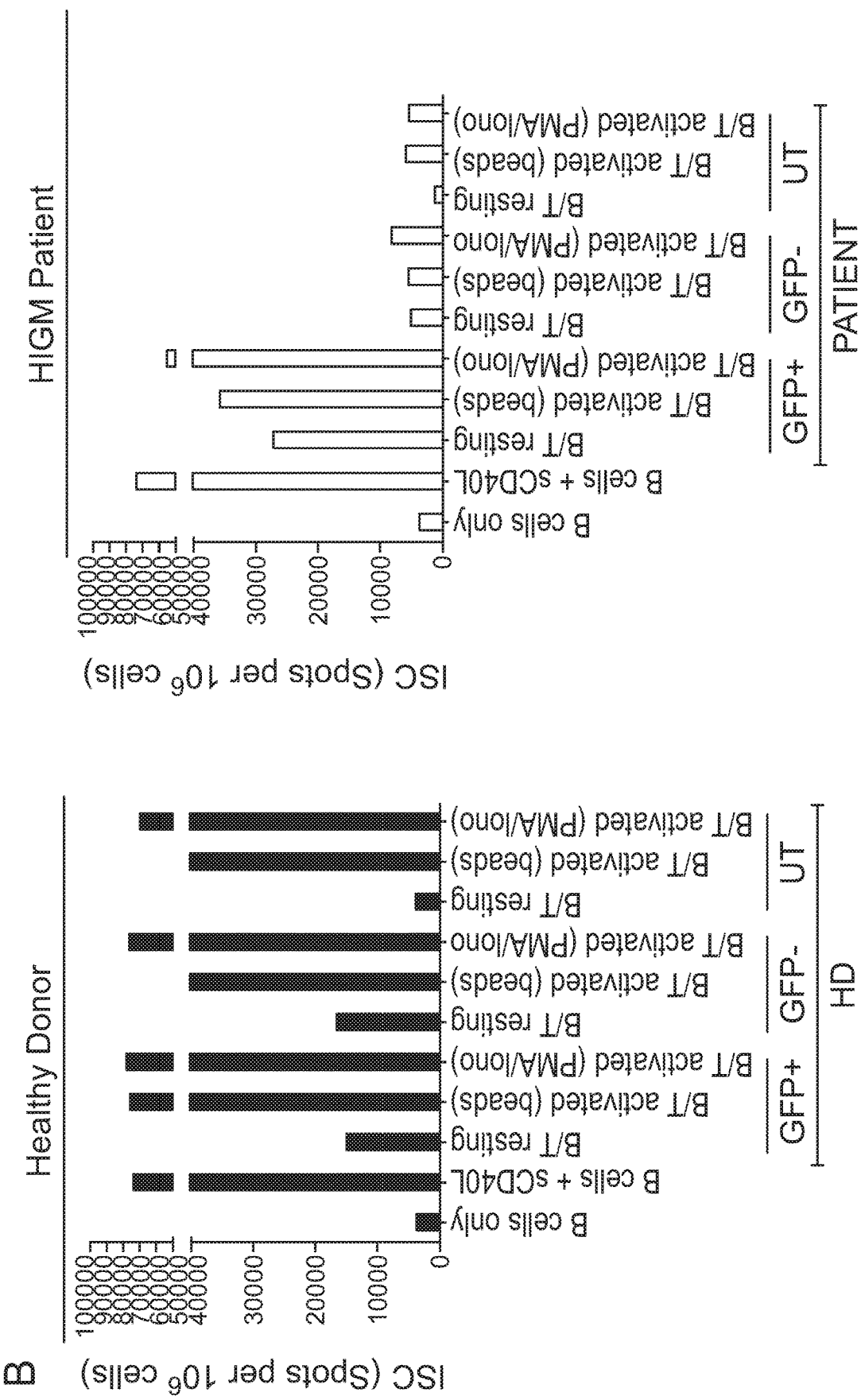
FIGS. 20A and 20B depict the ability of CD40L edited T cells to restore B cell class switching in a co-culture assay.

Example 6: Proof-of-Concept of CD40LG Correction on T Cells Derived from a HIGM1 Patient To confirm correction of mutations causative of HIGM1 by targeted integration of the corrective donor template, gene editing was performed on T cells harvested from a male subject with a genotyped inactivating mutation on exon 3 of the CD40L gene (c.334 G>T). CD4+ T cells derived from the patient and from healthy donors (HD) as control (n=4) were grown and nucleofected with RNP (gRNA A) and, 15 minutes later, transduced with an AAV6 vector carrying the corrective donor template depicted in FIG. 2A, at an MOI of 5e4. Targeted integration was measured by cytofluorimetric analysis scoring the percentage of GFP+ cells within the following CD4 T cell sub-populations: the T stem cell memory (TSCM, CD45RA+CD62L+), the central memory (CM, CD45RA−CD62L+), the effector memory (EM, CD45RA−CD62L−) and the effector memory RA (TEMRA, CD45RA+CD62L−; FIG. 17A, 17B). Targeted insertion was verified by digital droplet PCR analysis quantifying the 5' vector to genome junction, which confirmed similar amounts of homology directed repair as those measured by GFP expression (FIG. 17C). Polyclonal T cell targeting was confirmed by quantification of T-cell receptor diversity through TCR-beta spectratyping (FIG. 17D). Integration of the corrective construct restored expression and physiologic regulation of CD40L in edited patient T cells after PMA/Ionomycin stimulation (FIG. 18). To assess the functionality of the edited cells, sorted GFP+ cells were tested in a T-B cell co-culture assay (FIG. 19A), which confirmed the restoration of a T cell-dependent signal to B cells, inducing their proliferation (FIG. 19B,C) and production of class-switched IgG (FIG. 20).

Example 7: Selection of the CD40LG Edited Cells Before Transplantation

Figure 22F:
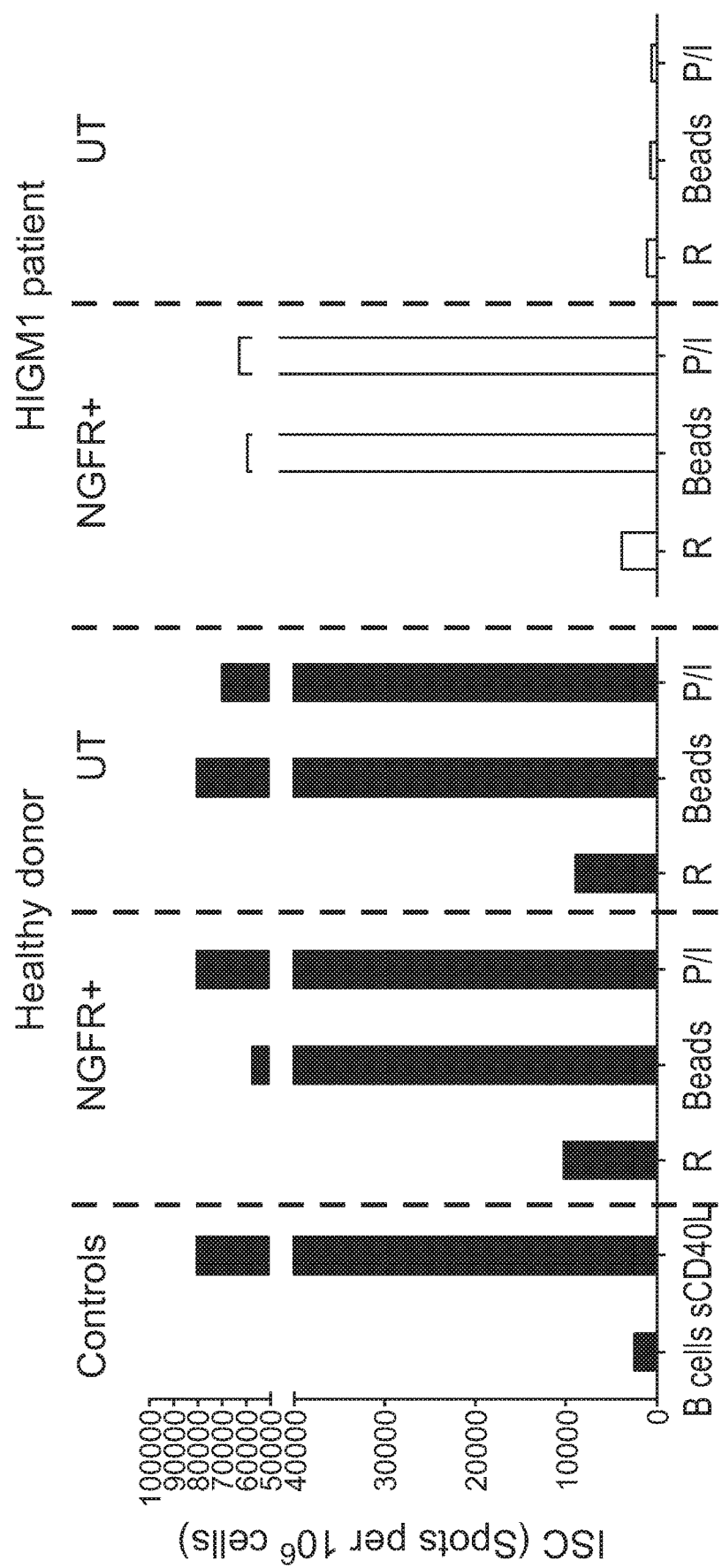
Figure 23:
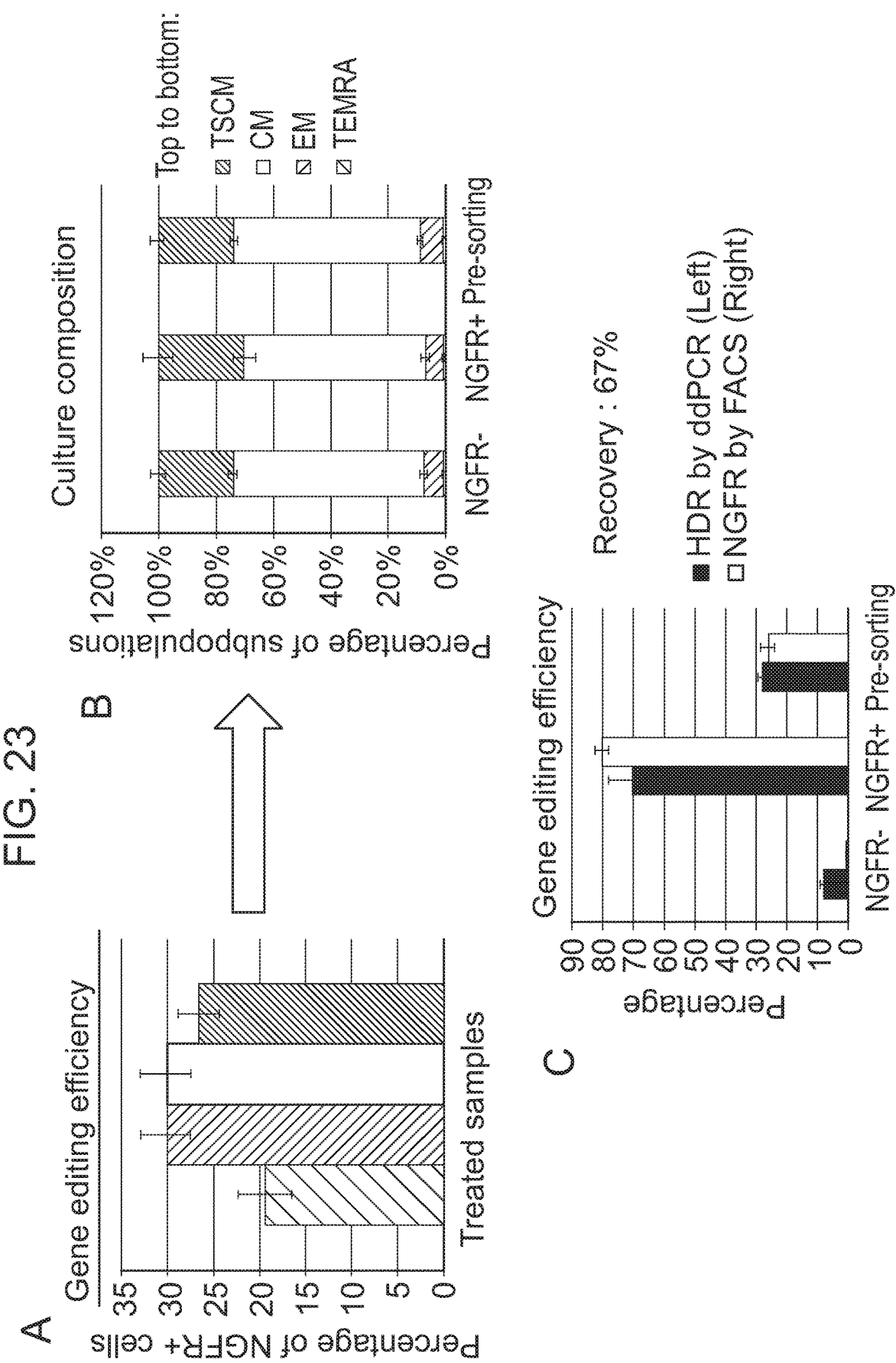
FIGS. 23A-23C depict the selection of CD40LG edited cells using a NGFR selection gene.
Figure 24A:
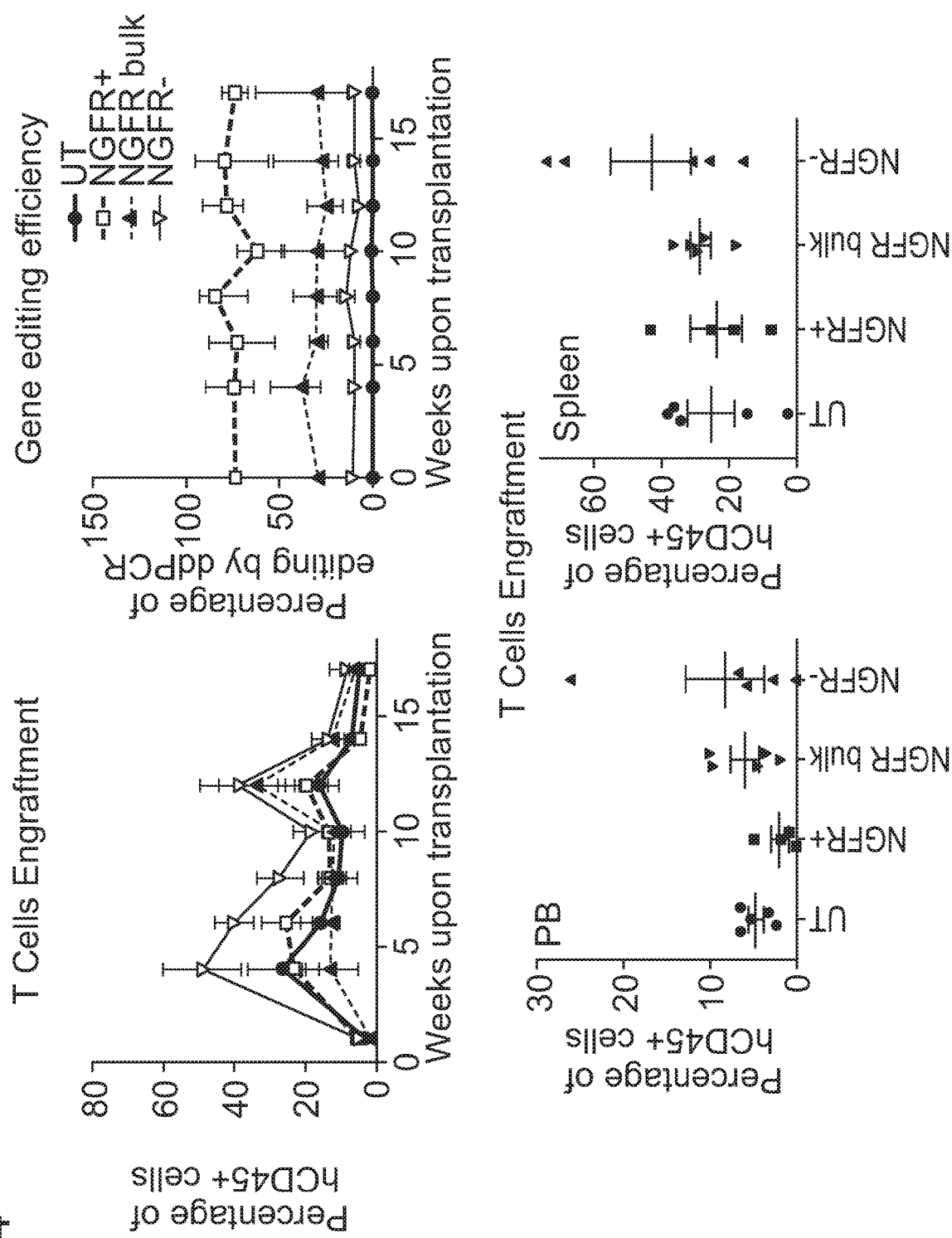
FIGS. 24A-24C depict the engraftment of CD40LG edited cells after xeno-transplantation in NSG mice.
Figure 24:
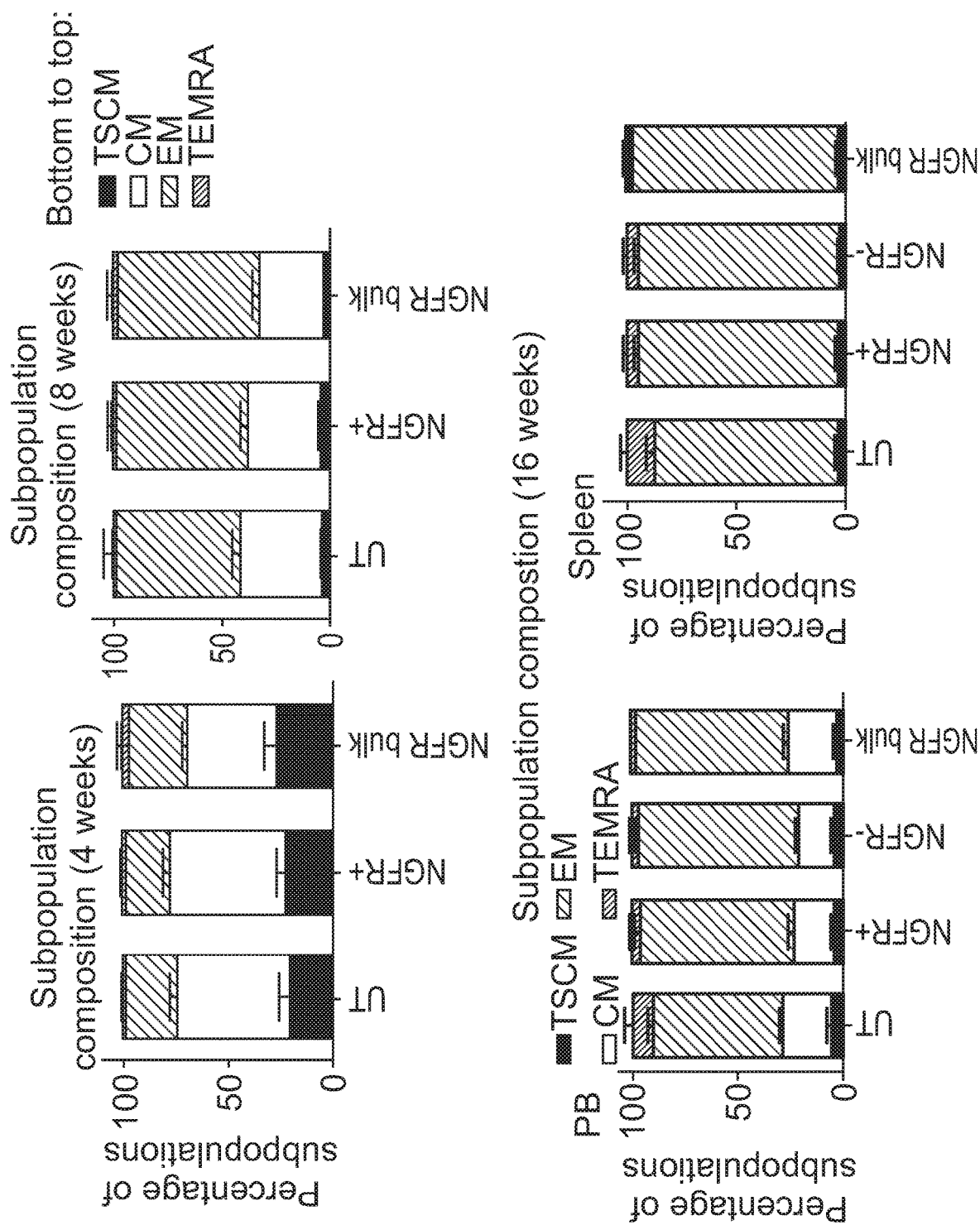
Figure 24C:
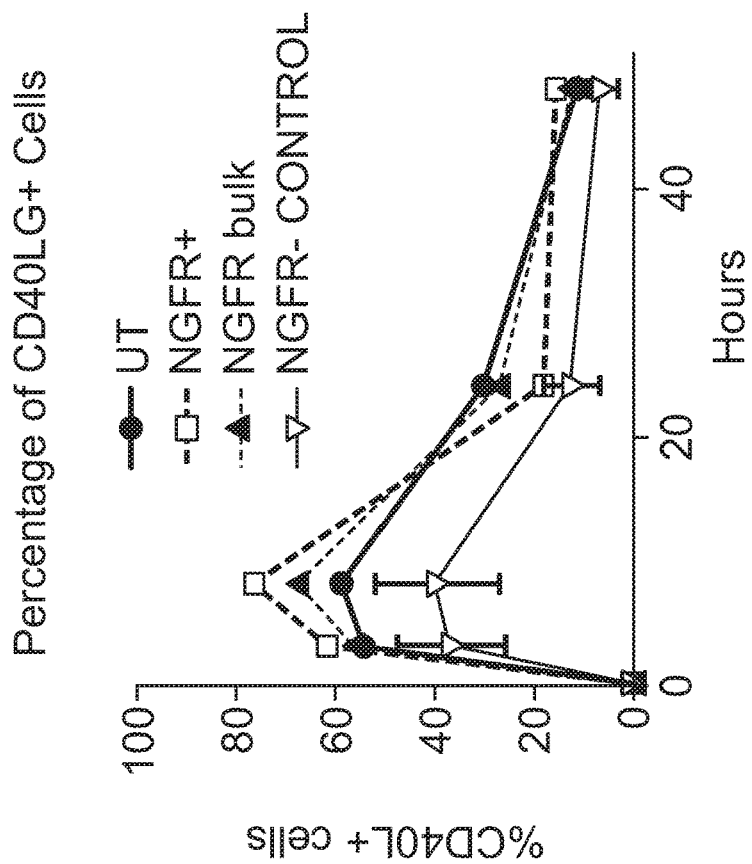
Figure 24C:
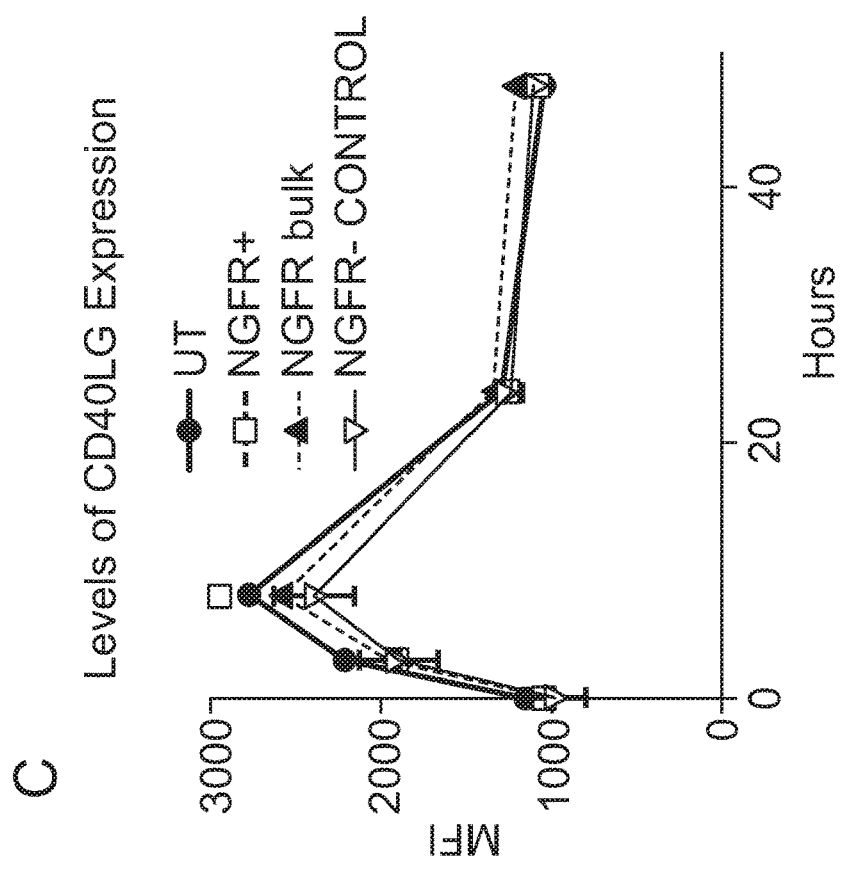

In addition to the methods described above, the corrective construct used for fixing CD40LG mutations can be equipped with a selection gene in order to enrich the edited cells before transplantation. By coupling the corrective CD40LG cDNA with a selection gene (e.g. nerve growth factor receptor (NGFR)) preceded by an Internal Ribosome entry site (IRES) sequence (FIG. 22A), it is possible to express the selection gene only in cells in which targeted integration occurred that are concomitantly expressing the CD40LG gene. While CD40LG needs strong stimulation in order to be exposed on the surface of T lymphocytes, basal levels of expression from the CD40LG promoter are sufficient to allow surface expression of the NGFR selection gene on the edited cells starting 6 days after gene editing, followed by antibody selection at day 13 (FIG. 22B and FIG. 22C). After PMA/ionomycin stimulation of the treated cells, the CD40LG promoter boosted the expression of both the CD40L and NGFR proteins (FIG. 22D). However, the kinetics of CD40L surface expression are comparable to those measured in the mock (unedited, UT) T cells (FIG. 22E). The NGFR expression cassette was used to obtain physiologic expression of the CD40LG gene in the edited cells, both in terms of the level of expression, and the percentage of CD40L+ cells (FIG. 22E). FIG. 22F depicts the ability of CD40L edited T cells to restore B cell class switching in a co-culture assay, showing the percentage of IgG switched B-cells in co-culture with resting, bead-activated (1:1 ratio) or PMA/Ionomycin stimulated T cells (untreated (UT) or edited (NGFR+)). Targeted integration efficiency of the corrective donor with the selection cassette (FIG. 23A) was similar to that measured with the original corrective donor template (FIG. 6A). Targeted cells that express CD40LG can be enriched by NGFR selection without any skew in the T cell culture composition (FIG. 23B), and molecular analysis confirmed the presence of targeted integration in the NGFR+ cells (FIG. 23C). NSG mice were transplanted with edited CD4+ T cells, that were either sorted or not sorted for NGFR expression. Levels of engraftment were comparable to those observed in mice transplanted with unedited T cells, and the fraction of edited cells remained stable over time (FIG. 24A). These data demonstrate that the CD40LG editing procedure and the NGFR selection do not impair the repopulation capacity of the treated T cells, which are normally able to engraft long-term and to physiologically differentiate into effector cells after transplant (FIG. 24B). FIG. 24C shows that the edited CD40LG is expressed by the edited T cells recovered from the NSG mice.

The selection strategy described herein can be exploited increase the fraction and the absolute number of therapeutically relevant corrected T cells that can be adoptively transplanted in a HIGM patient, while minimizing the number of uncorrected, in vitro-cultured, T cells which do not provide any therapeutic effect.

Example 8: Gene Editing of CD40L on Human Hematopoietic Stem Progenitor Cells

An adoptive immunotherapy approach based on gene corrected autologous T cells may be sufficient to induce the generation of protective immunity in recipient HIGM1 patients and possibly also the production of some long living memory B cells. However, multiple administrations of edited T-cells may be required to reconstitute a long-lasting and broad T cell repertoire that can mediate efficient T cell help in response to a wide range of pathogens. Moreover, while CD40LG has a critical function on CD4 T cells (Th0, Th1 and Th2), this molecule is also expressed on several other hematopoietic cell types, such as activated B cells, platelets, NK cells, monocytes, basophils and eosinophils. Therefore, it will be useful to expand the gene editing strategy from the correction of T-cells to the correction of autologous Hematopoietic stem/progenitor cells (HSPC), which can provide a much broader and prolonged therapeutic benefit.

Figure 25D:
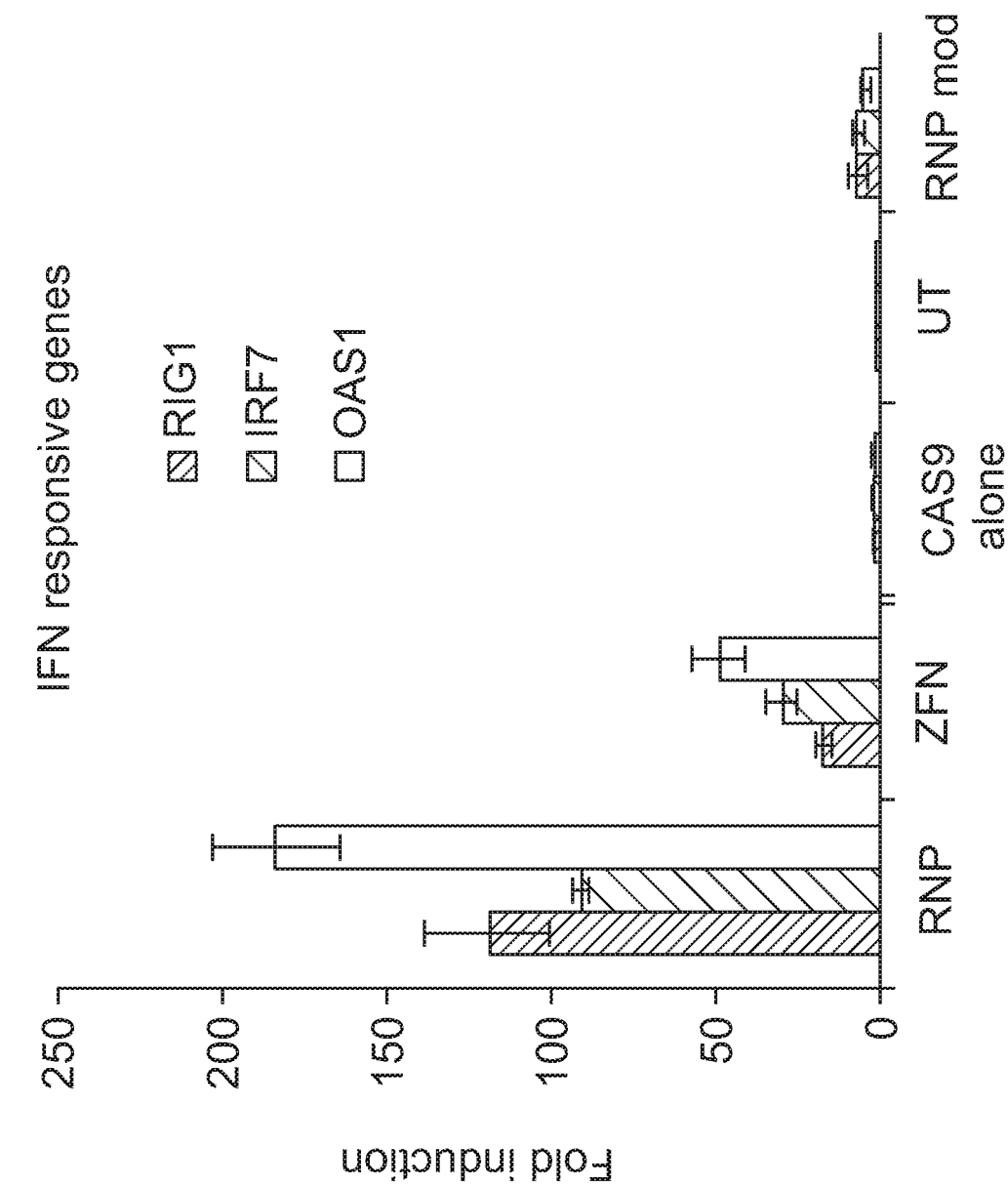

To demonstrate the portability of the described gene correction strategy on human HSPC, we first adapted the previously reported ZFN-based gene editing protocol to the CRISPR/Cas9 system. Briefly, CD34+ cells were isolated from cord blood and prestimulated for two days using SR1+dmPGE2, as shown in FIG. 25A. Cells were infected with IDLV donor on day 2, and were electroporated at day 3 with a ribonucleoprotein (RNP) complex composed by the Cas9 protein assembled with an in vitro transcribed gRNA or with a modified version in vitro transcribed gRNA (gRNAmod: HPLC purification, ARCA capping, 5' Phosphatase). Cells were then FACS analyzed for expression of GFP and cell surface markers on day 7. The targeted integration efficiency achieved with the two different RNPs and a reference ZFN in specified cell populations is shown in FIG. 25B. The culture composition following editing with ZFN and the RNPs, compared to untreated cells, is shown in FIG. 25C. The fold induction of the interferon (IFN) responsive genes RIG1, IRF7, and OAS1 in edited cells is shown in FIG. 25D. These results show that the delivery of a modified RNP allow levels of homology-mediated editing in human HSPCs comparable to our historical, gold-standard ZFN protocol, without inducing detrimental IFN response and without affecting the phenotype of the treated cells.

Figure 26:
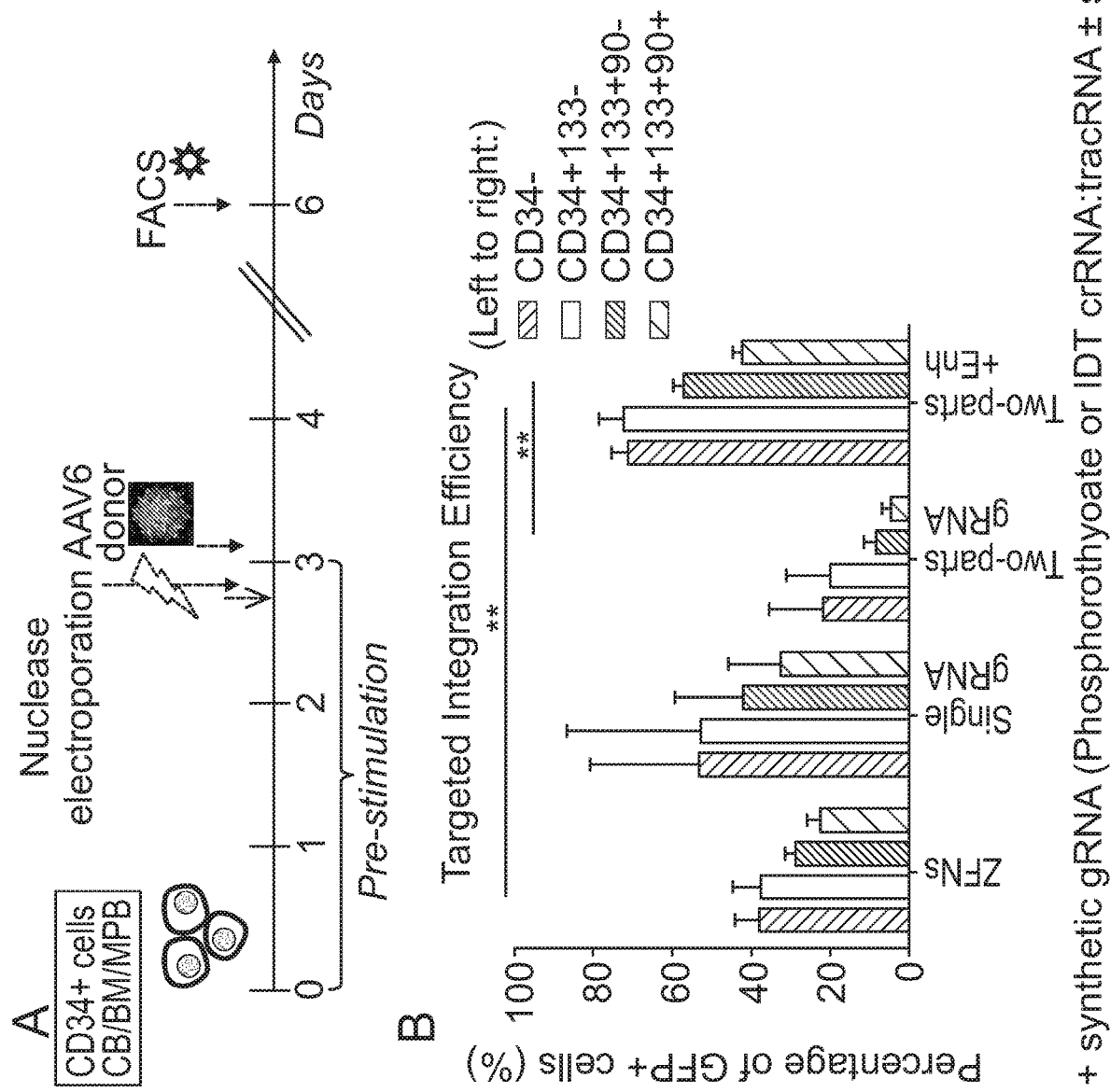
FIGS. 26A-26D depict additional experiments demonstrating that HSPC editing is portable to the CRISPR/Cas platform.
Figure 26:
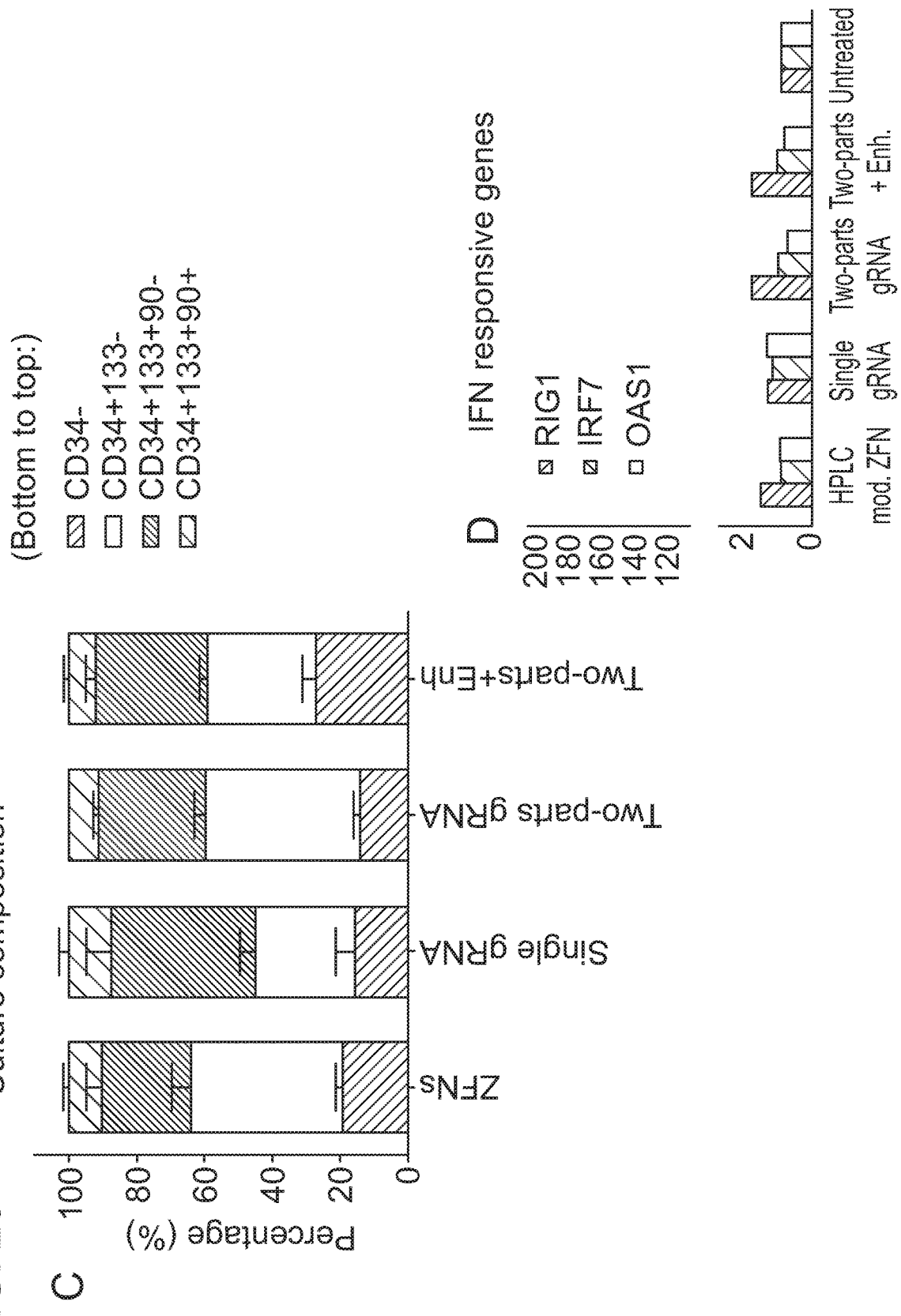

Additional experiments were performed using CD34+ cells obtained from cord blood (CB), bone marrow (BM), and mobilized peripheral blood (MPB). Briefly, Cells were pre-stimulated with SR1, dmPGE2 and UM171 for three days, at which time cells were electroporated with a RNP complex composed by the Cas9 protein assembled with a single or a two-part synthetic gRNA and infected with AAV6 donor, as shown in FIG. 26A. Cells were then FACS sorted for expression of GFP and cell surface markers on day 6. The targeted integration efficiency (expressed as the percentage of GFP+ cells) is shown in FIG. 26B. The cell culture composition after editing is shown in FIG. 26C. Expression of IFN-responsive genes is shown in FIG. 26D. These results confirmed that homology-mediated editing in human HSPCs can be achieved, without inducing detrimental IFN response and without affecting the phenotype of the treated cells, also with the use of AAV6 as delivery vehicles for the donor DNA or with RNP assembled with synthetic gRNAs.

Figure 27:
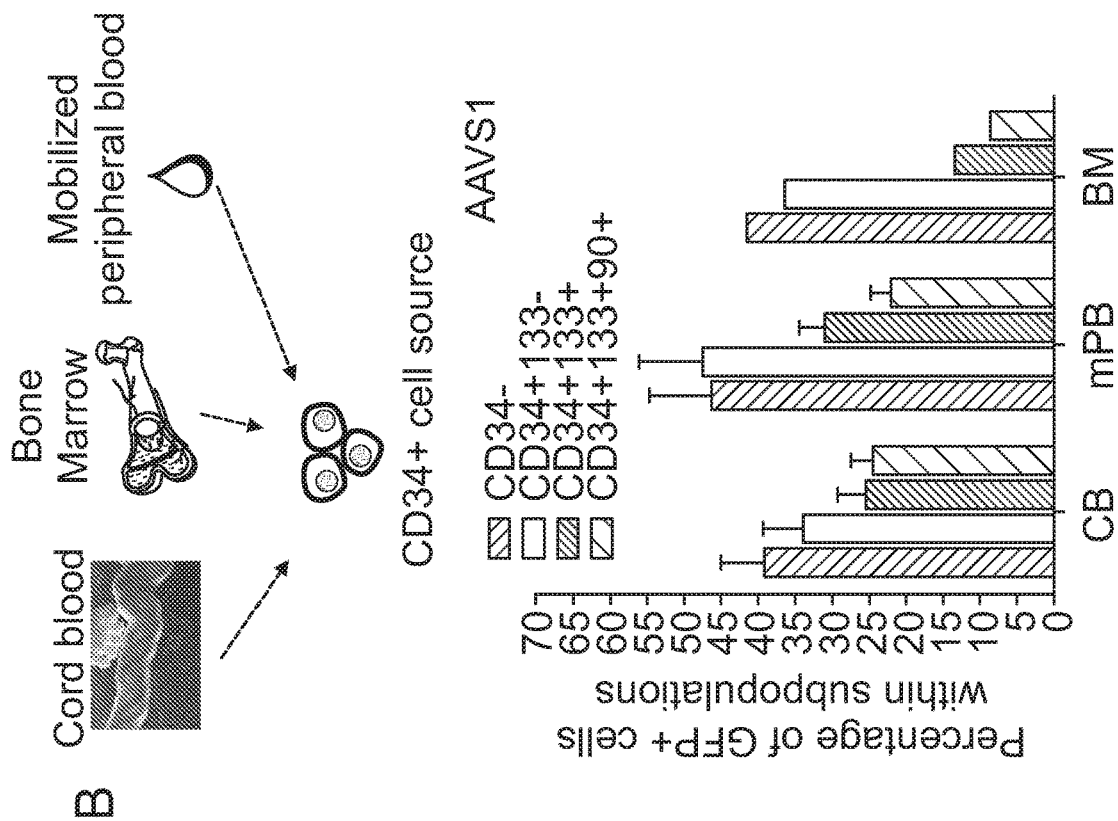
FIGS. 27A and 27B depict data indicating that human HSPCs from diverse sources can be efficiently edited using a variety of donor vehicles and nuclease configurations.
Figure 27:
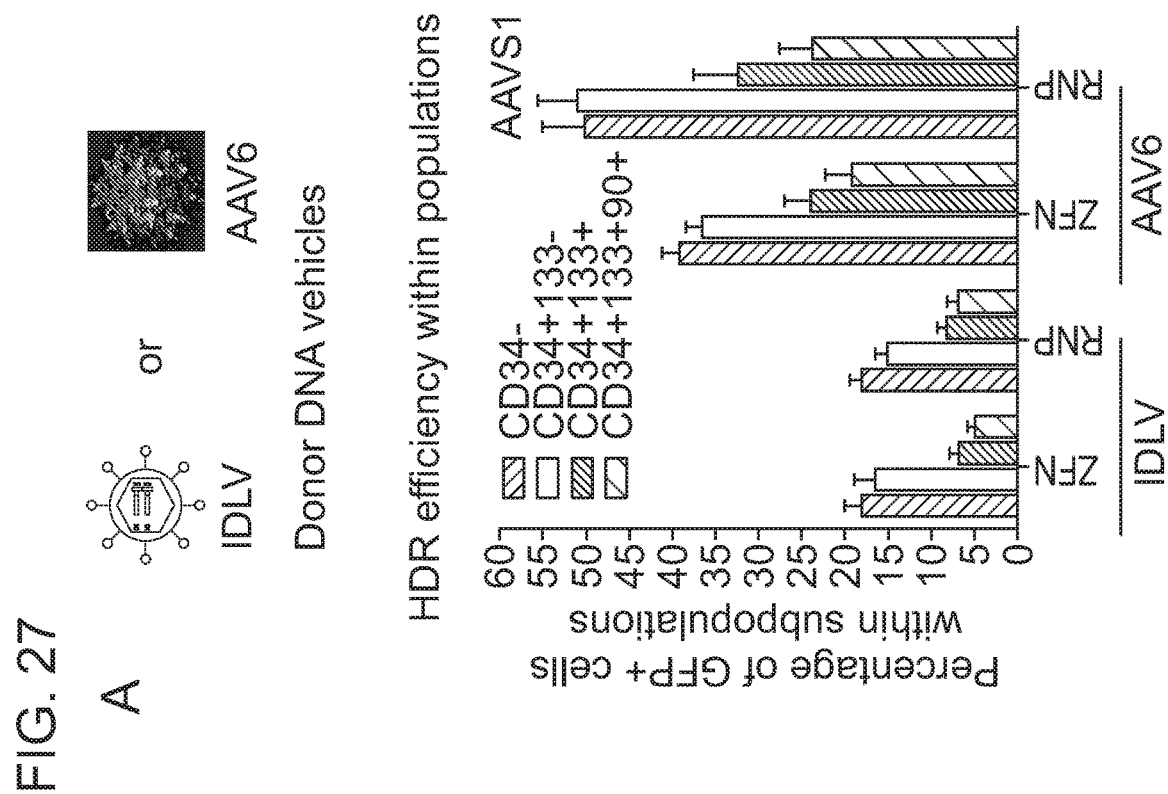

Human HSPCs from diverse sources can be efficiently edited using a variety of donor vehicles and nuclease configurations, as shown in FIG. 27. The indicated cell types were edited using either ZFN or RNP, with an IDLV or AAV6 donor template. The percentage of edited (GFP+)

cells in each subpopulation is shown in FIG. 27A. The percentage of edited (GFP+) cell populations derived from cord blood, bone marrow, and mobilized peripheral blood (mPB) is shown in FIG. 27B.

Figure 21:
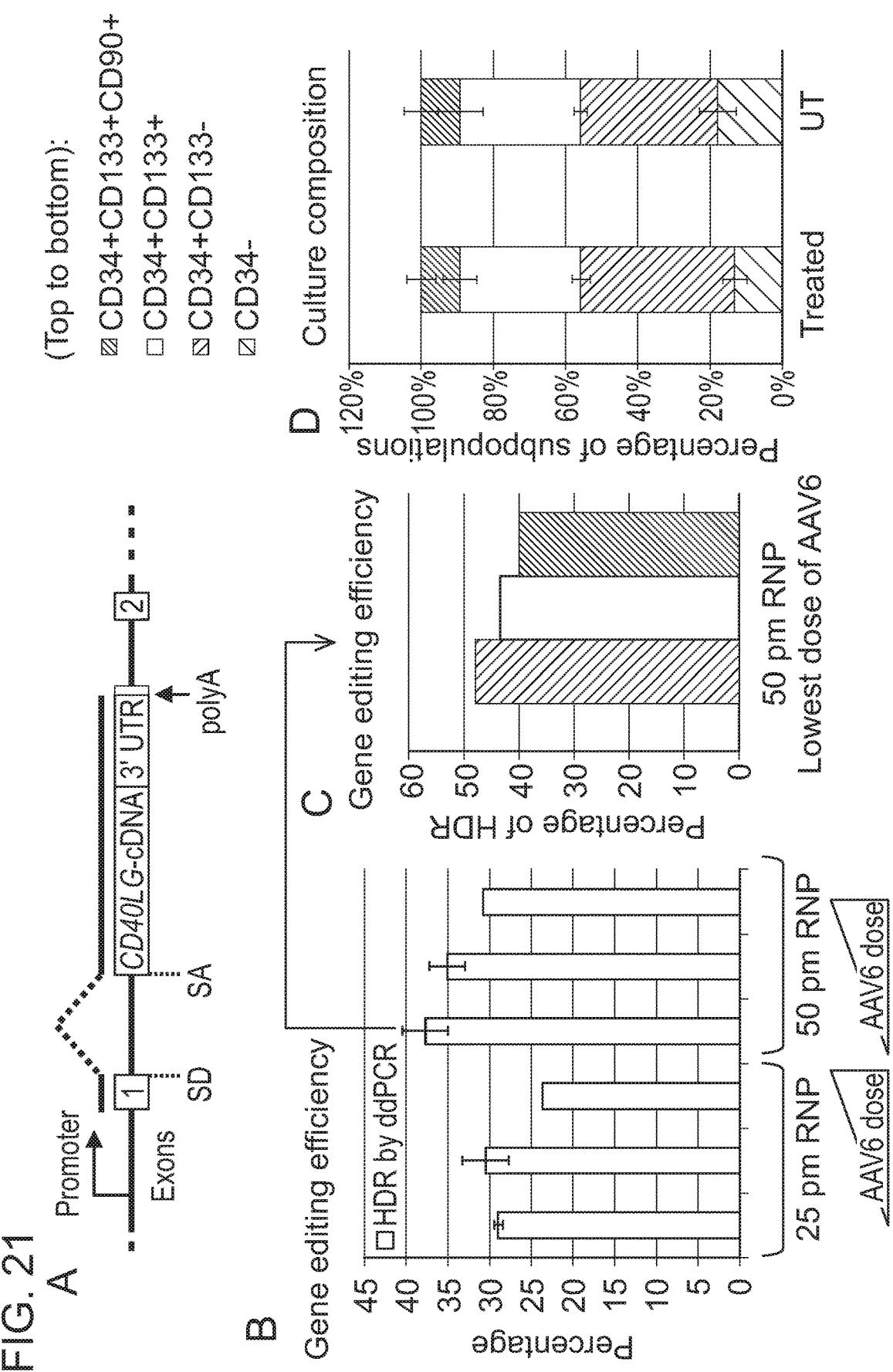
FIGS. 21A-21F depict that the genome editing systems described herein resulted in high levels of CD40LG gene editing in human hematopoietic stem/progenitor cells (HSPCs).
Figure 21:
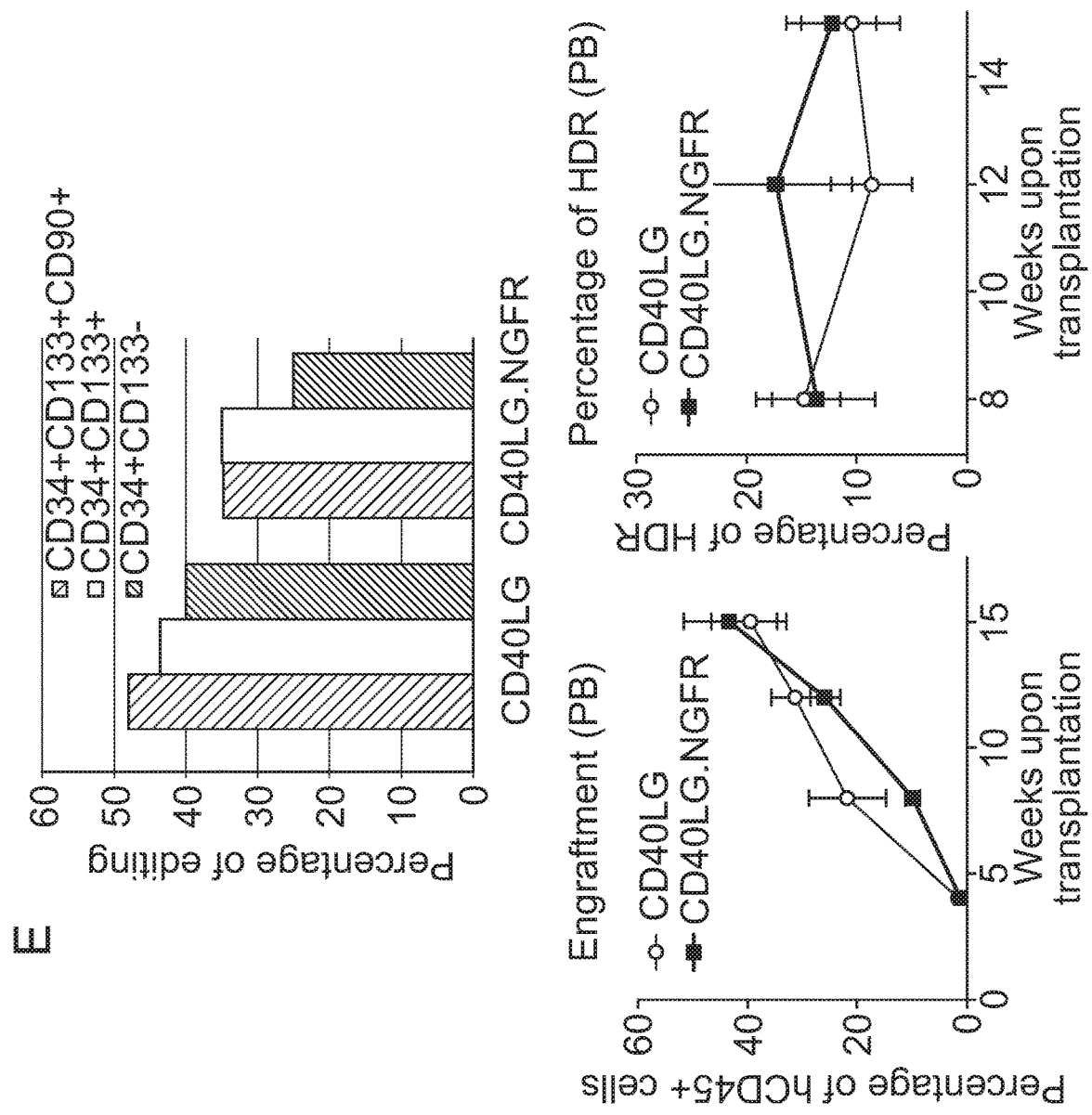

To confirm that the CD40L gene correction strategy is feasible in human HSPC, targeted integration of the corrective donor was performed on cord blood CD34+ cells harvested from healthy male donors. HSPC were grown and nucleofected with different RNP (gRNA A) doses and, 15 minutes later, transduced with different doses an AAV6 vector (MOI: 1e4, 5e4 and 1e5 vg/cell) carrying the corrective donor (FIG. 21A). Targeted integration was measured by digital droplet PCR analysis quantifying the 5' vector to genome junction. To confirm editing in all the different HSPC cell sub-populations, treated cells were sorted taking advantage of surface markers prospectively identifying the more primitive (CD34+CD133+CD90+), early (CD34+CD133+CD90−) and committed (CD34+CD133−) progenitors, and the differentiated cells (CD34−). High levels of targeted integration were measured both in the bulk and in the different sorted populations (FIGS. 21B, C and E), without altering the overall culture composition (FIG. 21D). Levels of engraftment were comparable to those observed in mice transplanted with unedited T cells, and the fraction of edited cells remained stable over time (FIG. 21F).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

The invention claimed is:

1. An isolated oligonucleotide donor template which comprises, from 5' to 3', A1-N-UTR-pA-A2, wherein
   A1 is a homology arm that is substantially identical to a first homology arm of a target CD40L nucleic acid;
   N is a cargo comprising one or more of exons 2-5 of a CD40L gene;
   UTR is a CD40L 3' untranslated region (UTR);
   pA is a polyA tail; and
   A2 is a homology arm that is substantially identical to a second homology arm of the target CD40L nucleic acid,
   and wherein the cargo does not comprise exon 1 of CD40L.

2. The isolated oligonucleotide donor template of claim 1, wherein the isolated oligonucleotide donor template comprises:
   (a) from 5' to 3', A1-S1-N-UTR-pA-S2-A2, wherein S1 is a first stuffer, wherein S2 is a second stuffer;
   (b) from 5' to 3', A1-N-UTR-pA-R-A2, wherein R is a reporter; or
   (c) from 5' to 3', A1-N-IRES-Sel/R-UTR-pA-A2, wherein IRES is an internal ribosome entry site, and wherein Sel/R is a selector gene or a reporter.

3. The isolated oligonucleotide donor template of claim 2, wherein the isolated oligonucleotide donor template comprises, from 5' to 3', A1-S1-N-UTR-pA-R-S2-A2, wherein R is a reporter.

4. The isolated oligonucleotide donor template of claim 1, wherein the cargo comprises: exon 2 of the CD40L gene; exon 3 of the CD40L gene; exon 4 of the CD40L gene; exon 5 of the CD40L gene; exons 2-5 of the CD40L gene; exons 2-4 of the CD40L gene; exons 2 and 3 of the CD40L gene; exons 3-5 of the CD40L gene; exons 3 and 4 of the CD40L gene; or exons 4 and 5 of the CD40L gene; optionally wherein the cargo comprises a codon optimized CD40L sequence.

5. The isolated oligonucleotide donor template of claim 2, wherein the reporter is a green fluorescence protein (GFP); a yellow fluorescence protein (YFB); DS-Red; luciferase; a low affinity nerve growth factor receptor (NGFR); truncated CD19; truncated epidermal growth factor receptor (EGFR); neomycin resistance protein; or puromycin resistance protein.

6. A composition comprising the isolated oligonucleotide donor template of claim 1 and, optionally, a pharmaceutically acceptable carrier.

7. A vector comprising the isolated oligonucleotide donor template of claim 1.

8. The vector of claim 7, wherein the vector is an AAV vector, a lentivirus vector, a naked DNA vector, or a lipid nanoparticle.

9. A genome editing system comprising the isolated oligonucleotide donor template of claim 1.

10. The genome editing system of claim 9, further comprising a RNA-guided nuclease and at least one guide RNA (gRNA) molecule.

11. The genome editing system of claim 9, further comprising an isolated gRNA molecule, comprising any one of SEQ ID NOs: 18-25.

12. A method of altering a cell comprising contacting the cell with the genome editing system of claim 9, thereby altering the cell.

13. A kit comprising the genome editing system of claim 9.

14. A method of altering a cell, comprising the steps of:
forming, in a target CD40L nucleic acid of the cell, at least one single- or double-strand break at a cleavage site, wherein the target CD40L nucleic acid comprises:
a first homology arm 5' to the cleavage site and a second homology arm 3' to the cleavage site, and
recombining an exogenous oligonucleotide donor template with the target CD40L nucleic acid by homologous recombination to produce an altered CD40L nucleic acid, wherein the exogenous oligonucleotide donor template comprises a first donor homology arm that is substantially identical to the first homology arm, a cargo comprising one or more of exons 2-5 of a CD40L gene, a 3' CD40L untranslated region (UTR), a polyA tail, and a second donor homology arm that is substantially identical to the second homology arm, and wherein the cargo does not comprise exon 1 of CD40L, thereby altering the cell.

15. The method of claim 14, wherein the exogenous oligonucleotide donor template comprises:
(a) the first donor homology arm that is substantially identical to the first homology arm, a first stuffer, the cargo comprising one or more of exons 2-5 of the CD40L gene, the 3' CD40L untranslated region (UTR), the polyA tail, a second stuffer, and the second donor homology arm that is substantially identical to the second homology arm; or
(b) the first donor homology arm that is substantially identical to the first homology arm, the cargo comprising one or more of exons 2-5 of the CD40L gene, the 3' CD40L untranslated region (UTR), the polyA tail, a reporter, and the second donor homology arm that is substantially identical to the second homology arm.

16. The method of claim 15, wherein the exogenous oligonucleotide donor template comprises the first donor homology arm that is substantially identical to the first homology arm, the first stuffer, the cargo comprising one or more of exons 2-5 of the CD40L gene, the 3' CD40L untranslated region (UTR), the polyA tail, a reporter, the second stuffer, and the second donor homology arm that is substantially identical to the second homology arm.

17. The method of claim 14, wherein the cargo comprises exon 2 of the CD40L gene; exon 3 of the CD40L gene; exon 4 of the CD40L gene; exon 5 of the CD40L gene; exons 2-5 of the CD40L gene; exons 2-4 of the CD40L gene; exons 2 and 3 of the CD40L gene; exons 3-5 of the CD40L gene; exons 3 and 4 of the CD40L gene; or exons 4 and 5 of the CD40L gene.

18. The method of claim 14, wherein the step of forming the at least one single- or double-strand break comprises contacting the cell with an RNA-guided nuclease.

19. The method of claim 14, further comprising introducing the cell into a subject after the recombining step or after the cleavage event is repaired by the at least one DNA repair pathway.

20. The method of claim 19, wherein:
(a) class switching is restored in the subject;
(b) levels of IgM are decreased in a subject; and/or
(c) levels of IgG are increased in a subject.

\* \* \* \* \*